(12) United States Patent
Shultz et al.

(10) Patent No.: US 7,943,652 B2
(45) Date of Patent: May 17, 2011

(54) HYDROXAMATE-BASED INHIBITORS OF DEACETYLASES B

(75) Inventors: Michael D. Shultz, Stow, MA (US); Christine Hiu-Tung Chen, Waltham, MA (US); Young Shin Cho, Cambridge, MA (US); Lei Jiang, Waltham, MA (US); Jianmei Fan, Newton, MA (US); Gang Liu, Waltham, MA (US); Dyuti Majumdar, Cambridge, MA (US); Jianke Li, Cambridge, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 12/411,715

(22) Filed: Mar. 26, 2009

(65) Prior Publication Data

US 2009/0247547 A1 Oct. 1, 2009

Related U.S. Application Data

(60) Provisional application No. 61/039,674, filed on Mar. 26, 2008.

(51) Int. Cl.
*A61K 31/4162* (2006.01)
*A61K 31/4155* (2006.01)
*C07D 487/04* (2006.01)
*C07D 231/10* (2006.01)

(52) U.S. Cl. ............... 514/403; 514/406; 548/360.1; 548/364.1

(58) Field of Classification Search ............ 514/254.09, 514/414, 378, 406, 300, 423, 343, 255.05; 548/504, 247, 364.1, 540; 435/375; 546/121, 546/276.4; 544/405, 373

See application file for complete search history.

(56) References Cited

U.S. PATENT DOCUMENTS

| | | |
|---|---|---|
| 2010/0069318 A1 | 3/2010 | Atadja |
| 2010/0179208 A1 | 7/2010 | Atadja et al. |

FOREIGN PATENT DOCUMENTS

| | | |
|---|---|---|
| WO | WO 02/22577 A2 | 3/2002 |
| WO | WO 2004/063169 A1 | 7/2004 |
| WO | WO 2005/013958 A1 | 2/2005 |
| WO | WO 2005/014004 A1 | 2/2005 |
| WO | WO 2007/030454 A2 | 3/2007 |
| WO | WO 2007/030455 A2 | 3/2007 |
| WO | WO 2008/014114 A1 | 11/2008 |

OTHER PUBLICATIONS

Vippagunta et al., Crystalline solids, 2001, Advanced Drug Delivery Reviews, 48, pp. 3 and 18.*
Golub et al., Molecular Classification of Cancer: Class Discovery and Class Prediction by Gene Expression Monitoring, 1999, Science, vol. 286, pp. 531-537.*
Lala et al., Role of nitric oxide in tumor progression: Lessons from experimental tumors, 1998, Cancer and Metastasis Reviews,17(1 ), pp. 91-106.*

* cited by examiner

*Primary Examiner* — Kamal A Saeed
*Assistant Examiner* — Kristin Bianchi

(57) ABSTRACT

The present teachings relate to compounds of Formula I:

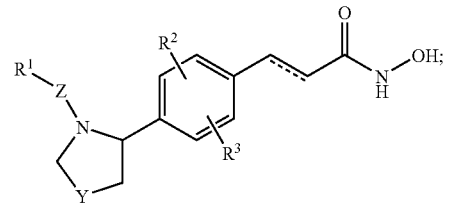

and pharmaceutically acceptable salts, hydrates, esters, and prodrugs thereof, wherein $R^1$, $R^2$, $R^3$, Y, Z, and ═══ are as defined herein.

The present teachings also provide methods of preparing compounds of Formula I and methods of using compounds of Formula I in treating, inhibiting, or preventing pathologic conditions or disorders mediated wholly or in part by deacetylases.

42 Claims, No Drawings

HYDROXAMATE-BASED INHIBITORS OF DEACETYLASES B

RELATED APPLICATIONS

This application claims priority to U.S. Provisional Application Ser. No. 61/039,674 filed Mar. 26, 2008, the contents of which are incorporated herein by reference in its entirety.

INTRODUCTION

Deacetylation, catalyzed by deacetylases, relates to transcriptional regulation of proteins involved in signal transduction. Accordingly, deacetylase inhibitors can be used for the therapy of pathological conditions or disorders wholly or in part mediated by one or more deacetylases. These conditions or disorders can include retinopathies, age-related macular degeneration, psoriasis, haemangioblastoma, haemangioma, arteriosclerosis, muscle wasting conditions such as muscular dystrophies, cachexia, Huntington's syndrome, inflammatory diseases such as rheumatoid or rheumatic inflammatory diseases, cardiovascular diseases such as cardiac hypertrophy and heart failure, renal disease and dysfunction, stroke autoimmune disorders and neoplastic diseases. More specifically, deacetylase inhibitors can be useful for treating arthritis and arthritic conditions (e.g., osteoarthritis, rheumatoid arthritis, and the like), other chronic inflammatory disorders (e.g., chronic asthma, arterial or post-transplantational atherosclerosis, endometriosis, and the like), solid tumors (e.g., cancers of the gastrointestinal tract, pancreas, breast, stomach, cervix, bladder, kidney, prostate, esophagus, ovaries, endometrium, lung, brain, melanoma, Kaposi's sarcoma, squamous cell carcinoma of head and neck, malignant pleural mesothelioma, lymphoma, multiple myeloma, and the like), and liquid tumors (e.g., leukemias).

More specifically, histone deacetylases remove an acetyl group from an N-acetyl lysine on a histone. In normal cells, histone deacetylase (HDAC) and histone acetyltransferase together control the level of acetylation of histones and non-histone proteins to maintain a balance. Reversible acetylation of histones is a major regulator of gene expression that acts by altering accessibility of transcription factors to DNA.

HDAC inhibitors have been studied for their therapeutic effect to proliferative diseases, including tumors, hyperproliferative conditions, neoplasias, immune diseases, cardiovascular diseases and central and peripheral nervous system diseases. More specifically, HDAC inhibitors can be useful for their antitumor activities. For example, butyric acid and its derivatives, including sodium phenylbutyrate, have been reported to induce apoptosis in vitro in human colon carcinoma, leukemia, and retinoblastoma cell lines. However, butyric acid and its derivatives are not useful as pharmacological agents because they tend to be metabolized rapidly and have a very short half-life in vivo. Other HDAC inhibitors that have been studied for their anti-cancer activities include trichostatin A and trapoxin. Trichostatin A, an antifungal and antibiotic agent, is a reversible inhibitor of mammalian HDAC and trapoxin, a cyclic tetrapeptide, is an irreversible inhibitor of mammalian HDAC. Although trichostatin and trapoxin have been studied for their anti-cancer activities, the in vivo instability of these compounds makes them less suitable as anti-cancer drugs.

SUMMARY

The present teachings relate to compounds of Formula I:

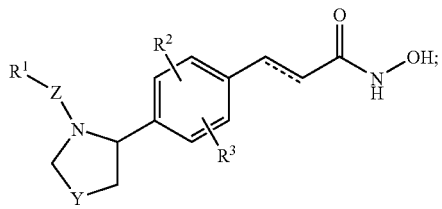

and pharmaceutically acceptable salts, hydrates, esters, and prodrugs thereof, wherein $R^1$, $R^2$, $R^3$, Y, Z, and ≗≗≗ are as defined herein.

The present teachings also relate to methods of preparing compounds of Formula I, including pharmaceutically acceptable salts, hydrates, esters and prodrugs thereof, and methods of using compounds of Formula I, including pharmaceutically acceptable salts, hydrates, esters and prodrugs thereof, in treating pathologic conditions or disorders mediated wholly or in part by deacetylases, for example, including administering a therapeutically effective amount of a compound of Formula I to a patient, for example, a patient in need thereof. Examples of the pathologic conditions or disorders include undesired proliferative conditions, neurodegenerative diseases, cardiovascular diseases, strokes, autoimmune diseases, inflammatory diseases, undesired immunological processes, and fungal infections.

The foregoing as well as other features and advantages of the present teachings will be more fully understood from the following description and claims.

DETAILED DESCRIPTION

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components.

The use of the term "include,", "includes," "including," "have," "has," or "having", should be generally understood as open-ended and non-limiting unless specifically stated otherwise.

The use of the singular herein includes the plural (and vice versa) unless specifically stated otherwise. In addition, where the use of the term "cabout" is before a quantitative value, the present teachings also include the specific quantitative value itself, unless specifically stated otherwise. As used herein, the term "about" refers to a ±5% variation from the nominal value.

It should be understood that the order of steps or order for performing certain actions is immaterial so long as the present teachings remain operable. Moreover, two or more steps or actions may be conducted simultaneously.

As used herein, a "compound" refers to the compound itself and its pharmaceutically acceptable salts, hydrates, and esters, unless otherwise understood from the context of the description or expressly limited to one particular form of the compound, i.e., the compound itself, or a pharmaceutically acceptable salt, hydrate, or ester thereof.

As used herein, "halo" or "halogen" refers to fluoro, chloro, bromo, and iodo.

As used herein, "oxo" refers to a double-bonded oxygen (i.e., =O).

As used herein, "alkyl" refers to a straight-chain or branched saturated hydrocarbon group. In some embodiments, an alkyl group can have from 1 to 10 carbon atoms (e.g., from 1 to 6 carbon atoms). Examples of alkyl groups include methyl (Me), ethyl (Et), propyl (e.g., n-propyl and isopropyl), butyl (e.g., n-butyl, isobutyl, s-butyl, t-butyl), pentyl groups (e.g., n-pentyl, isopentyl, neopentyl), and the like. In some embodiments, alkyl groups optionally can be substituted with up to four groups independently selected from -L'-$R^5$ and -L'-$R^{10}$, where L', $R^5$, and $R^{10}$ are as described herein. A lower alkyl group typically has up to 4 carbon atoms. Examples of lower alkyl groups include methyl, ethyl, propyl (e.g., n-propyl and isopropyl), and butyl groups (e.g., n-butyl, isobutyl, s-butyl, t-butyl).

As used herein, "alkenyl" refers to a straight-chain or branched alkyl group having one or more carbon-carbon double bonds. In some embodiments, an alkenyl group can have from 2 to 10 carbon atoms (e.g., from 2 to 6 carbon atoms). Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In some embodiments, alkenyl groups optionally can be substituted with up to groups independently selected from -L'-$R^5$ and -L'-$R^{10}$, where L', $R^5$, and $R^{10}$ are as described herein.

As used herein, "alkynyl" refers to a straight-chain or branched alkyl group having one or more carbon-carbon triple bonds. In some embodiments, an alkynyl group can have from 2 to 10 carbon atoms (e.g., from 2 to 6 carbon atoms). Examples of alkynyl groups include ethynyl, propynyl, butynyl, pentynyl, and the like. The one or more carbon-carbon triple bonds can be internal (such as in 2-butyne) or terminal (such as in 1-butyne). In some embodiments, alkynyl groups optionally can be substituted with up to four groups independently selected from -L'-$R^5$ and -L'-$R^{10}$, where L', $R^5$, and $R^{10}$ are as described herein.

As used herein, "alkoxy" refers to an —O-alkyl group. Examples of alkoxy groups include methoxy, ethoxy, propoxy (e.g., n-propoxy and isopropoxy), t-butoxy groups, and the like.

As used herein, "alkylthio" refers to an —S-alkyl group. Examples of alkylthio groups include methylthio, ethylthio, propylthio (e.g., n-propylthio and isopropylthio), t-butylthio groups, and the like.

As used herein, "haloalkyl" refers to an alkyl group having one or more halogen substituents. In some embodiments, a haloalkyl group can have 1 to 10 carbon atoms (e.g., from 1 to 6 carbon atoms). Examples of haloalkyl groups include $CF_3$, $C_2F_5$, $CHF_2$, $CH_2F$, $CCl_3$, $CHCl_2$, $CH_2Cl$, $C_2Cl_5$, and the like. Perhaloalkyl groups, i.e., alkyl groups wherein all of the hydrogen atoms are replaced with halogen atoms (e.g., $CF_3$ and $C_2F_5$), are included within the definition of "haloalkyl." For example, a $C_{1-10}$ haloalkyl group can have the formula —$C_iH_{2i+1-j}X_j$, wherein X is F, Cl, Br, or I, i is an integer in the range of 1 to 10, and j is an integer in the range of 0 to 21, provided that j is less than or equal to 2i+1.

As used herein, "cycloalkyl" refers to a non-aromatic carbocyclic group including cyclized alkyl, alkenyl, and alkynyl groups. A cycloalkyl group can be monocyclic (e.g., cyclohexyl) or polycyclic (e.g., containing fused, bridged, and/or spiro ring systems), wherein the carbon atoms are located inside or outside of the ring system. A cycloalkyl group, as a whole, can have from 3 to 14 ring atoms (e.g., from 3 to 8 carbon atoms for a monocyclic cycloalkyl group and from 7 to 14 carbon atoms for a polycyclic cycloalkyl group). Any suitable ring position of the cycloalkyl group can be covalently linked to the defined chemical structure. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcaryl, adamantyl, and spiro[4.5]decanyl groups, as well as their homologs, isomers, and the like. In some embodiments, cycloalkyl groups optionally can be substituted with up to four groups independently selected from -L'-$R^5$ and -L'-$R^{10}$, where L', $R^5$, and $R^{10}$ are as described herein. For example, cycloalkyl groups can be substituted with one or more oxo groups.

As used herein, "heteroatom" refers to an atom of any element other than carbon or hydrogen and includes, for example, nitrogen, oxygen, sulfur, phosphorus, and selenium.

As used herein, "cycloheteroalkyl" refers to a non-aromatic cycloalkyl group that contains at least one (e.g., one, two, three, four, or five) ring heteroatom selected from O, N, and S, and optionally contains one or more (e.g., one, two, or three) double or triple bonds. A cycloheteroalkyl group, as a whole, can have from 3 to 14 ring atoms and contains from 1 to 5 ring heteroatoms (e.g., from 3-6 ring atoms for a monocyclic cycloheteroalkyl group and from 7 to 14 ring atoms for a polycyclic cycloheteroalkyl group). The cycloheteroalkyl group can be covalently attached to the defined chemical structure at any heteroatom(s) or carbon atom(s) that results in a stable structure. One or more N or S atoms in a cycloheteroalkyl ring may be oxidized (e.g., morpholine N-oxide, thiomorpholine S-oxide, thiomorpholine S,S-dioxide). In some embodiments, nitrogen atoms of cycloheteroalkyl groups can bear a substituent, for example, a -L'-$R^5$ or -L'-$R^{10}$ group, where L', $R^5$, and $R^{10}$ are as described herein. Cycloheteroalkyl groups can also contain one or more oxo groups, such as phthalimidyl, piperidonyl, oxazolidinonyl, 2,4(1H,3H)-dioxo-pyrimidinyl, pyridin-2(1H)-onyl, and the like. Examples of cycloheteroalkyl groups include, among others, morpholinyl, thiomorpholinyl, pyranyl, imidazolidinyl, imidazolinyl, oxazolidinyl, pyrazolidinyl, pyrazolinyl, pyrrolidinyl, pyrrolinyl, tetrahydrofuranyl, tetrahydrothienyl, piperidinyl, piperazinyl, and the like. In some embodiments, cycloheteroalkyl groups optionally can be substituted with up to four groups independently selected from -L'-$R^5$ and -L'-$R^{10}$, where L', $R^5$, and $R^{10}$ are as described herein.

As used herein, "aryl" refers to an aromatic monocyclic hydrocarbon ring system or a polycyclic ring system where at least one of the rings in the ring system is an aromatic hydrocarbon ring and any other aromatic rings in the ring system include only hydrocarbons. In some embodiments, a monocyclic aryl group can have from 6 to 14 carbon atoms and a polycyclic aryl group can have from 8 to 14 carbon atoms. The aryl group can be covalently attached to the defined chemical structure at any carbon atom(s) that result in a stable structure. In some embodiments, an aryl group can have only aromatic carbocyclic rings, e.g., phenyl, 1-naphthyl, 2-naphthyl, anthracenyl, phenanthrenyl groups, and the like. In other embodiments, an aryl group can be a polycyclic ring system in which at least one aromatic carbocyclic ring is fused (i.e., having a bond in common with) to one or more cycloalkyl or cycloheteroalkyl rings. Examples of such aryl groups include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, each aryl group optionally can be substituted with up to four groups independently selected from -L'-$R^5$ and -L'-$R^{10}$, where L', $R^5$, and $R^{10}$ are as described herein.

As used herein, "heteroaryl" refers to an aromatic monocyclic ring system containing at least one ring heteroatom selected from O, N, and S or a polycyclic ring system where at least one of the rings in the ring system is aromatic and contains at least one ring heteroatom. A heteroaryl group, as a whole, can have from 5 to 14 ring atoms and contain 1-5 ring heteroatoms. In some embodiments, heteroaryl groups can include monocyclic heteroaryl rings fused to one or more aromatic carbocyclic rings, non-aromatic carbocyclic rings, or non-aromatic cycloheteroalkyl rings. The heteroaryl group can be covalently attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide, thiophene S-oxide, thiophene S,S-dioxide). Examples of heteroaryl groups include, for example, the 5-membered and 6-membered monocyclic and 5-6 bicyclic ring systems shown below:

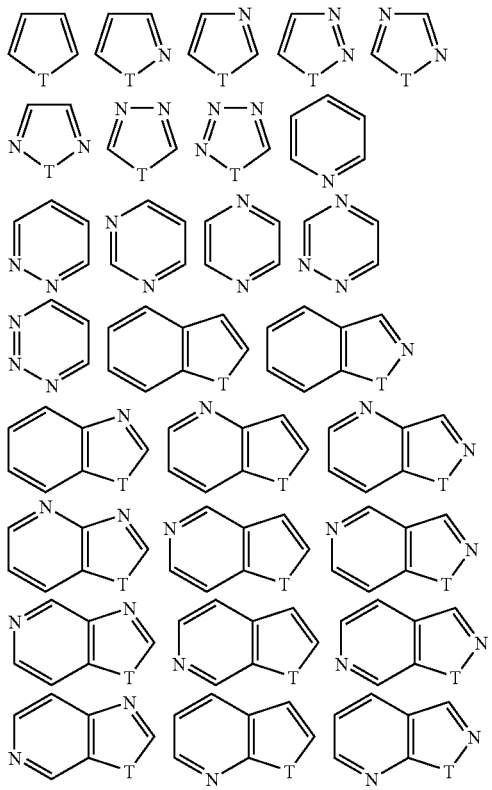

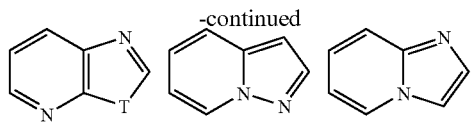

where T is O, S, NH, N-L'-$R^5$, or N-L'-$R^{10}$, where L', $R^5$, and $R^{10}$ are as defined herein. Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuryl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be substituted with up to four groups independently selected from -L'-$R^5$ or -L'-$R^{10}$, where L', $R^5$, and $R^{10}$ are as described herein.

The compounds of the present teachings can include a "divalent group" defined herein as a linking group capable of forming a covalent bond with two other moieties. For example, compounds described herein can include a divalent $C_{1-10}$ alkyl group, such as, for example, a methylene group.

As used herein, a "leaving group" ("LG") refers to a charged or uncharged atom (or group of atoms) that can be displaced as a stable species as a result of, for example, a substitution or elimination reaction. Examples of leaving groups include, but are not limited to, halide (e.g., Cl, Br, I), azide ($N_3$), thiocyanate (SCN), nitro ($NO_2$), cyanate (CN), tosylate (toluenesulfonate, OTs), mesylate (methanesulfonate, OMs), brosylate (p-bromobenzenesulfonate, OBs), nosylate (4-nitrobenzenesulfonate, ONs), water ($H_2O$), ammonia ($NH_3$), and triflate (trifluoromethanesulfonate, OTf).

At various places in the present specification, substituents of compounds are disclosed in groups or in ranges. It is specifically intended that the description includes each and every individual subcombination of the members of such groups and ranges. For example, the term "$C_{1-10}$ alkyl" is specifically intended to individually disclose $C_1$, $C_2$, $C_3$, $C_4$, $C_5$, $C_6$, $C_7$, $C_8$, $C_9$, $C_{10}$, $C_1$-$C_{10}$, $C_1$-$C_9$, $C_1$-$C_8$, $C_1$-$C_7$, $C_1$-$C_6$, $C_1$-$C_5$, $C_1$-$C_4$, $C_1$-$C_3$, $C_1$-$C_2$, $C_2$-$C_{10}$, $C_2$-$C_9$, $C_2$-$C_8$, $C_2$-$C_7$, $C_2$-$C_6$, $C_2$-$C_5$, $C_2$-$C_4$, $C_2$-$C_3$, $C_3$-$C_{10}$, $C_3$-$C_9$, $C_3$-$C_8$, $C_3$-$C_7$, $C_3$-$C_6$, $C_3$-$C_5$, $C_3$-$C_4$, $C_4$-$C_{10}$, $C_4$-$C_9$, $C_4$-$C_8$, $C_4$-$C_7$, $C_4$-$C_6$, $C_4$-$C_5$, $C_5$-$C_{10}$, $C_5$-$C_9$, $C_5$-$C_8$, $C_5$-$C_7$, $C_5$-$C_6$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$, and $C_9$-$C_{10}$ alkyl. By way of another example, the term "5-14 membered heteroaryl group" is specifically intended to individually disclose a heteroaryl group having 5, 6, 7, 8, 9, 10, 11, 12, 13, 14, 5-14, 5-13, 5-12, 5-11, 5-10, 5-9, 5-8, 5-7, 5-6, 6-14, 6-13, 6-12, 6-11, 6-10, 6-9, 6-8, 6-7, 7-14, 7-13, 7-12, 7-11, 7-10, 7-9, 7-8, 8-14, 8-13, 8-12, 8-11, 8-10, 8-9, 9-14, 9-13, 9-12, 9-11, 9-10, 10-14, 10-13, 10-12, 10-11, 11-14, 11-13, 11-12, 12-14, 12-13, or 13-14 ring atoms; and the phrase "optionally substituted with 1-4 groups" is specifically intended to individually disclose a chemical group that can include 0, 1, 2, 3, 4, 0-4, 0-3, 0-2, 0-1, 1-4, 1-3, 1-2, 2-4, 2-3, and 3-4 groups.

Compounds described herein can contain an asymmetric atom (also referred as a chiral center) and some of the compounds can contain one or more asymmetric atoms or centers, which can thus give rise to optical isomers (enantiomers) and diastereomers (geometric isomers). Compounds of the present teachings include such optical isomers and diastereomers in their respective enantiomerically pure forms (i.e., (+) and (−) stereoisomers), in racemic mixtures, and in other mixtures of the (+) and (−) stereoisomers, as well as pharmaceutically acceptable salts, hydrates, and esters thereof. Optical isomers in pure form or in enantiomerically enriched mixture can be obtained by standard procedures known to those skilled in the art, which include, but are not limited to, chiral separation, diastereomeric salt formation, kinetic resolution, and asymmetric synthesis. The present teachings also encompass cis and trans-isomers of compounds containing alkenyl moieties (e.g., alkenes and imines). It is also understood that the present teachings encompass all possible regioisomers and mixtures thereof, which can be obtained in pure form or in substantially enriched mixture by standard separation procedures known to those skilled in the art, including, but not limited to, column chromatography, thin-layer chromatography, simulated moving-bed chromatography, and high-performance liquid chromatography.

The present invention includes all pharmaceutically acceptable isotopically-labeled compounds of formula (I) wherein one or more atoms are replaced by atoms having the same atomic number, but an atomic mass or mass number different from the atomic mass or mass number usually found in nature.

Examples of isotopes suitable for inclusion in the compounds of the invention comprises isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Isotopically-labeled compounds of formula (I) can generally be prepared by conventional techniques known to those skilled in the art or by processes analogous to those described in the accompanying Examples and Preparations Sections using an appropriate isotopically-labeled reagent in place of the non-labeled reagent previously employed.

In one aspect, the present teachings provide compounds of Formula I:

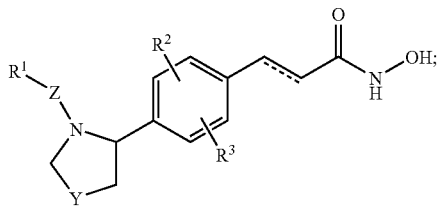

I and pharmaceutically acceptable salts, hydrates, esters, and prodrugs thereof, wherein:
⸺ is a) a single bond or b) a double bond;
Y and Z independently are a) -L-, b) -L-O-L-, c) -L-S(O)$_m$-L-, or d) -L-NR$^4$-L-;
L, at each occurrence, is a) a divalent C$_{1-10}$ alkyl group, b) a divalent C$_{2-10}$ alkenyl group, c) a divalent C$_{2-10}$ alkynyl group, or d) a covalent bond, wherein each of a)-c) optionally is substituted with 1-4 -L'-R$^5$;
R$^1$ is a) H, b) a C$_{1-10}$ alkyl group, c) a C$_{2-10}$ alkenyl group, d) a C$_{2-10}$ alkynyl group, e) a C$_{3-14}$ cycloalkyl group, f) a C$_{6-14}$ aryl group, g) a 3-14 membered cycloheteroalkyl group, or h) a 5-14 membered heteroaryl group, wherein each of b)-h) optionally is substituted with 1-4 L'-R$^5$ groups;
R$^2$ and R$^3$ independently are a) H, b) halogen, halogen c) —NO$_2$, d) —CN, e) a C$_{1-10}$ alkyl group, f) a C$_{2-10}$ alkenyl group, g) a C$_{2-10}$ alkynyl group, h) a C$_{3-14}$ cycloalkyl group, i) a C$_{6-14}$ aryl group, j) a 3-14 membered cycloheteroalkyl group, k) a 5-14 membered heteroaryl group, l) a C$_{1-10}$ alkoxy group, m) —NC$_{1-10}$ alkyl, n) C(O)C$_{1-10}$ alkyl, and o) C(O)OC$_{1-10}$ alkyl, wherein each of e)-o) optionally is substituted with 1-4 -L'-R$^7$ groups;
R$^4$ is a) H, b) —C(O)OR$^6$, or c) a C$_{1-10}$ alkyl group;
R$^5$, at each occurrence, is a) halogen, b) —CN, c) —NO$_2$, d) oxo, e) =N-L'-R$^6$, f) —O-L'-R$^6$, g) —S(O)$_m$R$^7$, h) a C$_{1-10}$ alkyl group, i) a C$_{2-10}$ alkenyl group, j) a C$_{2-10}$ alkynyl group, k) a C$_{3-14}$ cycloalkyl group, l) a C$_{6-14}$ aryl group, m) a 3-14 membered cycloheteroalkyl group, or n) a 5-14 membered heteroaryl group, wherein each of h)-n) optionally is substituted with 1-4 -L'-R$^{10}$ groups;
R$^6$, at each occurrence, is a) H, b) —OR$^8$, c) —S(O)$_m$R$^8$, or d) a C$_{1-10}$ alkyl group optionally substituted with 1-4 -L'-R$^{10}$ groups;
R$^7$ is a) H, b) —OR$^8$, c) —NR$^8$R$^9$, d) a C$_{1-10}$ alkyl group, e) a C$_{2-10}$ alkenyl group, f) a C$_{2-10}$ alkynyl group, g) a C$_{3-14}$ cycloalkyl group, h) a C$_{6-14}$ aryl group, i) a 3-14 membered cycloheteroalkyl group, or) a 5-14 membered heteroaryl group, wherein each of d)-j) optionally is substituted with 1-4 -L'-R$^{10}$ groups;
R$^8$ and R$^9$, at each occurrence, independently are a) H, b) a C$_{1-10}$ alkyl group, c) a C$_{2-10}$ alkenyl group, d) a C$_{2-10}$ alkynyl group, e) a C$_{3-14}$ cycloalkyl group, f) a C$_{6-14}$ aryl group, g) a 3-14 membered cycloheteroalkyl group, or h) a 5-14 membered heteroaryl group, wherein each of b)-h) optionally is substituted with 1-4 -L'-R$^{10}$ groups;
R$^{10}$, at each occurrence, is a) halogen, b) —CN, c) —NO$_2$, d) oxo, e) —OH, f) —NH$_2$, g) —NH(C$_{1-10}$ alkyl), h) —N(C$_{1-10}$ alkyl)$_2$, i) —CHO, j) —C(O)—C$_{1-10}$ alkyl, k) —C(O)OH, l) —C(O)—OC$_{1-10}$ alkyl, m) —C(O)SH, n) —C(O)—SC$_{1-10}$ alkyl, o) —C(O)NH$_2$, p) —C(O)NH(C$_{1-10}$ alkyl), q) —C(O)N(C$_{1-10}$ alkyl)$_2$, r) —C(S)H, s) —C(S)—C$_{1-10}$ alkyl, t) —C(S)NH$_2$, u) —C(S)NH(C$_{1-10}$ alkyl), v) —C(S)N(C$_{1-10}$ alkyl)$_2$, w) —C(NH)H, x) —C(NH)C$_{1-10}$ alkyl, y) —C(NH)NH$_2$, z) —C(NH)NH(C$_{1-10}$ alkyl), aa) —C(NH)N(C$_{1-10}$ alkyl)$_2$, ab) —C(NC$_{1-10}$ alkyl)H, ac) —C(NC$_{1-10}$ alkyl)-C$_{1-10}$ alkyl, ad) —C(NC$_{1-10}$ alkyl)NH(C$_{1-10}$ alkyl), ae) —C(NC$_{1-10}$ alkyl)N(C$_{1-10}$ alkyl)$_2$, af) —S(O)$_m$H, ag) —S(O)$_m$—C$_{1-10}$ alkyl, ah) —S(O)$_2$OH, ai) —S(O)$_m$—OC$_{1-10}$ alkyl, aj) —S(O)$_m$NH$_2$, ak) —S(O)$_m$NH(C$_{1-10}$ alkyl), al) —S(O)$_m$N(C$_{1-10}$ alkyl)$_2$, am) —Si(C$_{1-10}$ alkyl)$_3$, an) a C$_{1-10}$ alkyl group, ao) a C$_{2-10}$ alkenyl group, ap) a C$_{2-10}$ alkynyl group, aq) a C$_{1-10}$ alkoxy group, ar) a C$_{1-10}$ haloalkyl group, as) a C$_{3-14}$ cycloalkyl group, at) a C$_{6-14}$ aryl group, au) a 3-14 membered cycloheteroalkyl group, or av) a 5-14 membered heteroaryl group;
L', at each occurrence, is a) a divalent C$_{1-10}$ alkyl group, b) a divalent C$_{2-10}$ alkenyl group, c) a divalent C$_{2-10}$ alkynyl group, d) a divalent $C_{1-10}$ haloalkyl group, d) a divalent $C_{1-10}$ alkoxy group, or t) a covalent bond; and m, at each occurrence, is 0, 1, or 2.

In some embodiments, ═══ can be a single bond. In some embodiments, ═══ can be a double bond. For example, the double bond can be a cis-double bond (i.e., a Z-double bond) or a trans-double bond (i.e., a E-double bond). In certain embodiments, ═══ can be a trans-double bond. Accordingly, compound of the present teachings can have Formula Ia or Formula Ib:

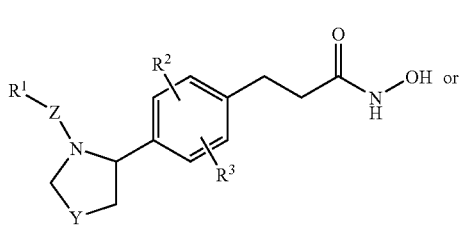

Ia

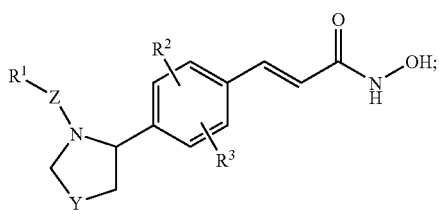

Ib where $R^1$, $R^2$, $R^3$, Y, and Z are as defined herein.

In various embodiments, $R^1$ can be H, a $C_{2-10}$ alkenyl group, a $C_{2-10}$ alkynyl group, a $C_{3-14}$ cycloalkyl group, a $C_{6-14}$ aryl group, a 3-14 membered cycloheteroalkyl group, or a 5-14 membered heteroaryl group, where each of the $C_{2-10}$ alkenyl group, the $C_{2-10}$ alkynyl group, the $C_{3-14}$ cycloalkyl group, the $C_{6-14}$ aryl group, the 3-14 membered cycloheteroalkyl group, and the 5-14 membered heteroaryl group optionally can be substituted with 1-4 -L'-$R^5$ groups, and L' and $R^5$ as defined herein. For example, $R^1$ can be H, a $C_{2-10}$ alkenyl group, a $C_{3-14}$ cycloalkyl group, or a 3-14 membered cycloheteroalkyl group, wherein each of the $C_{2-10}$ alkenyl group, the $C_{3-14}$ cycloalkyl group, and the 3-14 membered cycloheteroalkyl group optionally can be substituted with 1-4 -L'-$R^5$ groups, and L' and $R^5$ are as defined herein.

In some embodiments, $R^1$ can be a $C_{2-10}$ alkenyl group optionally substituted with 1-4 -L'-$R^5$ groups, where L' and $R^5$ as defined herein. For example, $R^1$ can be a $C_{2-10}$ alkenyl group optionally substituted with 1-4 groups independently selected from halogen, —CN, —NO$_2$, and a $C_{1-10}$ haloalkyl group. In certain embodiments, $R^1$ can be a $C_{2-10}$ alkenyl group optionally substituted with 1-4 groups independently selected from halogen, —CN, —NO$_2$, and —CF$_3$. In particular embodiments, $R^1$ can be 2,2-dichloroethenyl.

In some embodiments, $R^1$ can be a $C_{3-14}$ cycloalkyl group or a 3-14 membered cycloheteroalkyl group, each of which optionally can be substituted with 1-4 -L'-$R^5$ groups, where L' and $R^5$ are as defined herein. In certain embodiments, $R^1$ can be selected from a cyclopropyl group, a cyclobutyl group, a cyclopentyl group, a cyclohexyl group, and a cycloheptyl group, each of which optionally can be substituted with 1-4 -L'-$R^5$ groups, where L' and $R^5$ are as defined herein. In particular embodiments, $R^1$ can be cyclopropyl, cyclobutyl, cyclopentyl, cyclohexyl, or cycloheptyl. In certain embodiments, $R^1$ can be selected from a pyrrolidyl group, a piperidyl group, a tetrahydrofuranyl group, and a tetrahydropyranyl group, each of which optionally can be substituted with 1-4 -L'-$R^5$ groups, where L' and $R^5$ are as defined herein. In particular embodiments, $R^1$ can be tetrahydropyranyl.

In some embodiments, $R^1$ can be a $C_{6-14}$ aryl group or a 5-14 membered heteroaryl group, each of which optionally can be substituted with 1-4 -L'-$R^5$ groups, where L' and $R^5$ are as defined herein. In certain embodiments, $R^1$ can be a phenyl group optionally substituted with 1-4 groups independently selected from halogen, —CN, —NO$_2$, a $C_{1-10}$ alkyl group, a $C_{3-14}$ cycloalkyl group, and a $C_{6-14}$ aryl group, where each of the $C_{1-10}$ alkyl group, the $C_{3-14}$ cycloalkyl group, and the $C_{6-14}$ aryl group optionally can be substituted with 1-4 -L'-$R^{10}$ groups, and L' and $R^{10}$ are as defined herein. In particular embodiments, $R^1$ can be a phenyl group optionally substituted with 1-4 groups independently selected from F, Cl, —NO$_2$, —OH, —OCH$_3$, and methyl.

In various embodiments, $R^1$ can be a 5-14 membered heteroaryl group optionally substituted with 1-4 -L'-$R^5$ groups, where L' and $R^5$ are as defined herein. For example, the 5-14 membered heteroaryl group can be selected from:

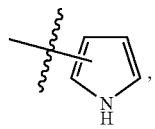

i

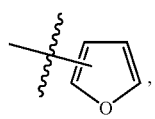

ii

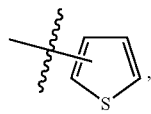

iii

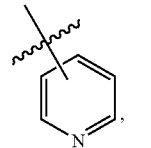

iv

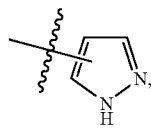

v

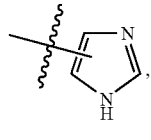

vi

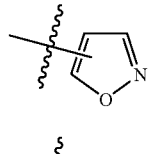

vii

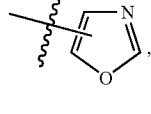

viii

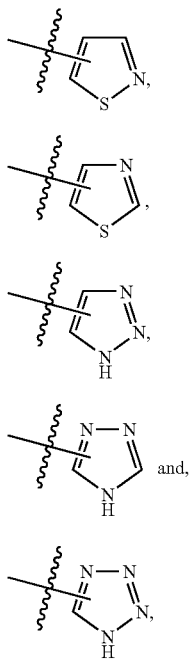

wherein each of i-xiii optionally can be fused to a phenyl group or a 5-6 membered heteroaryl group, and optionally can be substituted with 1-4 -L'-$R^5$ groups, where L' and $R^5$ are as defined herein.

In some embodiments, $R^1$ can be selected from i-xiii, each of which optionally can be substituted with 1-4 -L'-$R^5$ groups, where $R^5$ can be halogen, $NO_2$, $S(O)_mR^7$, a $C_{1-10}$ alkyl group, a $C_{2-10}$ alkenyl group, a $C_{2-10}$ alkynyl group, a $C_{3-14}$ cycloalkyl group, a $C_{6-14}$ aryl group, a 3-14 membered cycloheteroalkyl group, and a 5-14 membered heteroaryl group, where each of the $C_{1-10}$ alkyl groups, the $C_{2-10}$ alkenyl group, the $C_{2-10}$ alkynyl group, the $C_{3-14}$ cycloalkyl group, the $C_{6-14}$ aryl group, the 3-14 membered cycloheteroalkyl group, and the 5-14 membered heteroaryl group optionally can be substituted with 1-4 -L'-$R^{10}$ groups, and L', $R^7$, and $R^{10}$ are as defined herein. In certain embodiments, $R^1$ can be selected from i-xiii, each of which optionally can be substituted with 1-4 groups independently selected from halogen, $-NO_2$, $-S(O)_mR^7$, $-(C_{1-10}$ alkyl)-$(C_{3-14}$ cycloalkyl), $-(C_{1-10}$ alkyl)-$(C_{6-14}$ aryl), $-(C_{1-10}$ alkyl)-(3-14 membered cycloheteroalkyl), $-(C_{1-10}$ alkyl)-(5-14 heteroaryl), $-(C_{1-10}$ alkoxy)-$(C_{3-14}$ cycloalkyl), $-(C_{1-10}$ alkoxy)-$(C_{6-14}$ aryl), $-(C_{1-10}$ alkoxy)-(3-14 membered cycloheteroalkyl), $-(C_{1-10}$ alkoxy)-(5-14 heteroaryl), a $C_{1-10}$ alkyl group, a $C_{2-10}$ alkenyl group, a $C_{2-10}$ alkynyl group, a $C_{3-14}$ cycloalkyl group, a $C_{6-14}$ aryl group, a 3-14 membered cycloheteroalkyl group, and a 5-14 membered heteroaryl group, where each of the $C_{1-10}$ alkyl groups, the $C_{2-10}$ alkenyl group, the $C_{2-10}$ alkynyl group, the $C_{1-10}$ alkoxy groups, the $C_{3-14}$ cycloalkyl groups, the $C_{6-14}$ aryl groups, the 3-14 membered cycloheteroalkyl groups, and the 5-14 membered heteroaryl groups optionally can be substituted with 1-4 -L'-$R^{10}$ groups, and L', $R^7$, and $R^{10}$ are as defined herein. In particular embodiments, $R^1$ can be a pyrazolyl group optionally substituted with 1-4 groups independently selected from F, Cl, Br, $-OH$, $-CF_3$, methyl, ethyl, n-propyl, i-propyl, n-butyl, t-butyl, 2-methyl-propyl, 2,2-dimethyl-propyl, propynyl, cyanomethyl, 2-cyanoethyl, 3-cyanopropyl, cyclopropylmethyl, tetrahydropyranylmethyl, phenyl, and trifluorophenyl. In particular embodiments, $R^1$ can be a thienyl group, a pyridyl group, an imidazolyl group, an oxazolyl group, an isoxazolyl group, a triazolyl group, or a tetrazolyl group, each of which optionally can be substituted with 1-4 groups independently selected from F, Cl, Br, $-CF_3$, methyl, ethyl, i-propyl, t-butyl, (trimethylsilyl)methyl, benzyl, 2-benzoxyethyl, phenyl, and 4-aminophenyl.

In an embodiment, $R^1$ can be

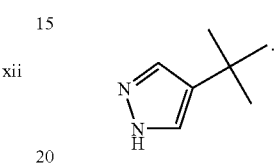

In another embodiment, $R^1$ can be disubstituted with methyl.

In some embodiments, $R^1$ can be a bicyclic heteroaryl group optionally substituted with 1-4 -L'-$R^5$ groups, where L' and $R^5$ are as defined herein. For example, the bicyclic heteroaryl group can be selected from an indolyl group, a pyrazolopyridyl group, a pyrrolopyridinyl group, an imidazopyridyl group, a benzoisoxazolyl group, an indazolyl group and an imidazothiazolyl group. In certain embodiments, $R^1$ can be an indolyl group, a pyrazolo[1,5-a]pyridyl group, a pyrrolo[2,3-b]pyridyl group, or an imidazo[1,2-a]pyridyl group, each of which optionally can be substituted with 1-4 groups independently selected from F, Cl, Br, $-NO_2$, $-CF_3$, methyl, ethyl, i-propyl, t-butyl, 1-hydroxy-1-methylethyl, phenyl, pyridyl, and pyrazinyl.

In various embodiments, $R^2$ and $R^3$ can independently be H or halogen. In some embodiments, $R^2$ can be selected from H, F, Cl, and Br. In some embodiments, $R^3$ can be selected from H, F, Cl, and Br.

In various embodiments, Y can be -L- or -L-$NR^4$-L-, and L and $R^4$ are as defined in herein. In some embodiments, Y can be -L-$NR^4$-L-, where $R^4$ can be selected from H, $-C(O)OR^6$, and a $C_{1-10}$ alkyl group, and L and $R^6$ are as defined herein. In particular embodiments, Y can be selected from $-CH_2-$, $-CH_2CH_2-$, $-CH_2CH_2CH_2-$, $-NHCH_2-$, $-N(CH_3)CH_2-$, and $-N(C(O)O-t-Bu)CH_2-$. In a preferred embodiment, Y can be $-CH_2-$.

In various embodiments, Z can be a divalent $C_{1-10}$ alkyl group optionally substituted with 1-4 groups independently selected from oxo, $=N-R^6$, and $-OH$, where $R^6$ is as defined herein. For example, Z can be selected from $-CH_2-$, $-CH_2CH_2-$, $-CH_2CH_2CH_2-$, $-C(O)CH_2-$, $-CH_2CH(OH)-$, $-CH_2CH_2CH(CH_3)-$, and $-CH_2C(=NOH)-$. In a further embodiment, Z can be $-CH_2CH_2-$.

In some embodiments, compounds of the present teachings can have Formula II' or Formula II":

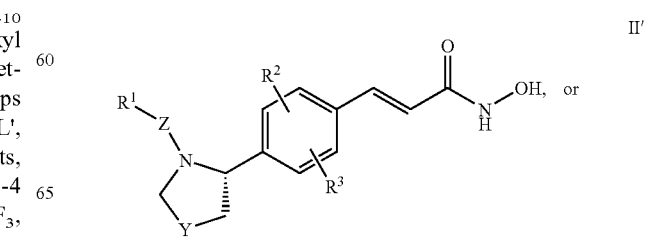

II'

-continued

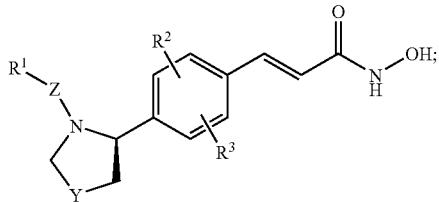

II'' including pharmaceutically acceptable salts, hydrates, esters, and prodrugs thereof, wherein $R^1$, $R^2$, $R^3$, L, Y, and Z are as defined herein.

In another embodiment, the present invention includes compounds of Formula Ia:

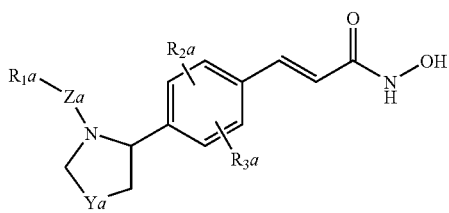

Ia or a pharmaceutically acceptable salt, hydrate, or ester thereof,
wherein:
Ya is a) —CH$_2$—;
Za is a) —CH$_2$—, b) —CH$_2$CH$_2$—, or c) —CH$_2$CH$_2$CH$_2$—;
$R^{1a}$ is a C$_{6-14}$ aryl group, a 3-14 membered cycloheteroalkyl group, or a 5-14 membered heteroaryl group, wherein $R^{1a}$ is optionally is substituted with 1-4 -La-R$^{5a}$ groups;
La is a) a divalent C$_{1-10}$ alkyl group, b) a divalent C$_{2-10}$ alkenyl group, c) a divalent C$_{2-10}$ alkynyl group, or d) a covalent bond, wherein each of a)-c) optionally is substituted with 1-4 -La'-R$^{5a}$;
$R^{2a}$ and $R^{3a}$ independently are a) H or b) halogen c) —NO$_2$, d) —CN, e) a C$_{1-10}$ alkyl group, f) a C$_{2-10}$ alkenyl group, g) a C$_{2-10}$ alkynyl group, h) a C$_{3-14}$ cycloalkyl group, i) a C$_{6-14}$ aryl group, j) a 3-14 membered cycloheteroalkyl group, k) a 5-14 membered heteroaryl group, l) a C$_{1-10}$ alkoxy group, m) —NC$_{1-10}$ alkyl, n) C(O)C$_{1-10}$ alkyl, and o) C(O)OC$_{1-10}$ alkyl, wherein each of e)-o) optionally is substituted with 1-4 -La-R$^{7a}$ groups;

$R^{5a}$, at each occurrence, is a) halogen, b) —CN, c) —NO$_2$, d) oxo, e) =N—La—R$^{6a}$, f) —O-L'—R$^{6a}$, g) —S(O)$_m$R$^{7a}$, h) a C$_{1-10}$ alkyl group, i) a C$_{2-10}$ alkenyl group, j) a C$_{2-10}$ alkynyl group, k) a C$_{3-14}$ cycloalkyl group, l) a C$_{6-14}$ aryl group, m) a 3-14 membered cycloheteroalkyl group, or n) a 5-14 membered heteroaryl group, wherein each of h)-n) optionally is substituted with 1-4 —La—R$^{10a}$ groups;

$R^{6a}$, at each occurrence, is a) H, b) —OR$^{8a}$, c) —S(O)$_m$R$^{8a}$, or d) a C$_{1-10}$ alkyl group optionally substituted with 1-4 La R$^{10a}$ groups;

$R^{7a}$ is a) H, b) —OR$^{8a}$, c) —NR$^{8a}$R$^{9a}$, d) a C$_{1-10}$ alkyl group, e) a C$_{2-10}$ alkenyl group, f) a C$_{2-10}$ alkynyl group, g) a C$_{3-14}$ cycloalkyl group, h) a C$_{6-14}$ aryl group, i) a 3-14 membered cycloheteroalkyl group, or j) a 5-14 membered heteroaryl group, wherein each of d)-j) optionally is substituted with 1-4 —La—R$^{10a}$ groups;

$R^{8a}$ and $R^{9a}$, at each occurrence, independently are a) H, b) a C$_{1-10}$ alkyl group, c) a C$_{2-10}$ alkenyl group, d) a C$_{2-10}$ alkynyl group, e) a C$_{3-14}$ cycloalkyl group, f) a C$_{6-14}$ aryl group, g) a 3-14 membered cycloheteroalkyl group, or h) a 5-14 membered heteroaryl group, wherein each of b)-h) optionally is substituted with 1-4 —La—R$^{10a}$ groups;

$R^{10a}$, at each occurrence, is a) halogen, b) —CN, c) —NO$_2$, d) oxo, e) —OH, f) —NH$_2$, g) —NH(C$_{1-10}$ alkyl), h) —N(C$_{1-10}$ alkyl)$_2$, i) —CHO, j) —C(O)—C$_{1-10}$ alkyl, k) —C(O)OH, l) —C(O)—OC$_{1-10}$ alkyl, m) —C(O)SH, n) —C(O)—SC$_{1-10}$ alkyl, o) —C(O)NH$_2$, p) —C(O)NH(C$_{1-10}$ alkyl), q) —C(O)N(C$_{1-10}$ alkyl)$_2$, r) —C(S)H, s) —C(S)—C$_{1-10}$ alkyl, t) —C(S)NH$_2$, u) —C(S)NH(C$_{1-10}$ alkyl), v) —C(S)N(C$_{1-10}$ alkyl)$_2$, w) —C(NH)H, x) —C(NH)C$_{1-10}$ alkyl, y) —C(NH)NH$_2$, z) —C(NH)NH(C$_{1-10}$ alkyl), aa) —C(NH)N(C$_{1-10}$ alkyl)$_2$, ab) —C(NC$_{1-10}$ alkyl)H, ac) —C(NC$_{1-10}$ alkyl)-C$_{1-10}$ alkyl, ad) —C(NC$_{1-10}$ alkyl)NH(C$_{1-10}$ alkyl), ae) —C(NC$_{1-10}$ alkyl)N(C$_{1-10}$ alkyl)$_2$, af) —S(O)$_m$H, ag) —S(O)$_m$—C$_{1-10}$ alkyl, ah) —S(O)$_2$OH, ai) —S(O)$_m$—OC$_{1-10}$ alkyl, aj) —S(O)$_m$NH$_2$, ak) —S(O)$_m$NH(C$_{1-10}$ alkyl), al) —S(O)$_m$N(C$_{1-10}$ alkyl)$_2$, am) —Si(C$_{1-10}$ alkyl)$_3$, an) a C$_{1-10}$ alkyl group, ao) a C$_{2-10}$ alkenyl group, ap) a C$_{2-10}$ alkynyl group, aq) a C$_{1-10}$ alkoxy group, ar) a C$_{1-10}$ haloalkyl group, as) a C$_{3-14}$ cycloalkyl group, at) a C$_{6-14}$ aryl group, au) a 3-14 membered cycloheteroalkyl group, or av) a 5-14 membered heteroaryl group;

La, at each occurrence, is a) a divalent C$_{1-10}$ alkyl group, b) a divalent C$_{2-10}$ alkenyl group, c) a divalent C$_{2-10}$ alkynyl group, d) a divalent C$_{1-10}$ haloalkyl group, d) a divalent C$_{1-10}$ alkoxy group, or f) a covalent bond; and
m, at each occurrence, is 0, 1, or 2.

Compounds of the present teachings can be selected from the compounds in Table 1.

TABLE 1

| Cpd # | Structure | Name |
|---|---|---|
| 1 | 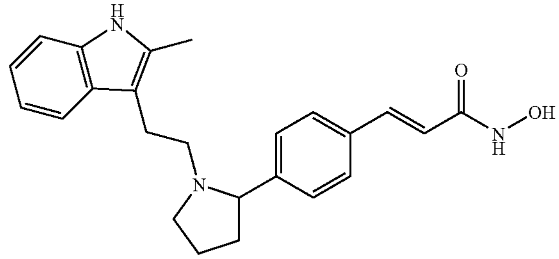 | (E)-N-Hydroxy-3-(4-{1-[2-(2-methyl-1H-indol-3-yl)-ethyl]-pyrrolidin-2-yl}-phenyl)-acrylamide |

TABLE 1-continued

| Cpd # | Structure | Name |
|---|---|---|
| 2 | 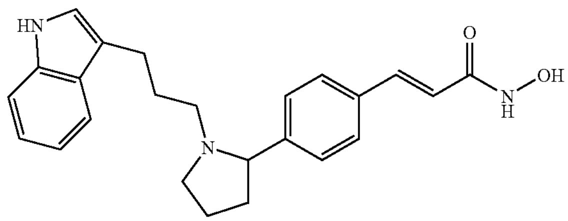 | (E)-N-Hydroxy-3-(4-{1-[3-(1H-indol-3-yl)-propyl]-pyrrolidin-2-yl}-phenyl)-acrylamide |
| 3 | 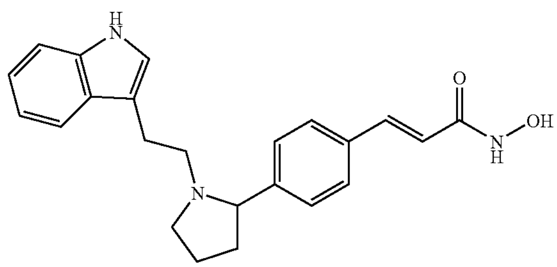 | (E)-N-Hydroxy-3-(4-{1-[2-(1H-methyl-3-yl)-ethyl]-pyrrolidin-2-yl}-phenyl)-acrylamide |
| 4 | 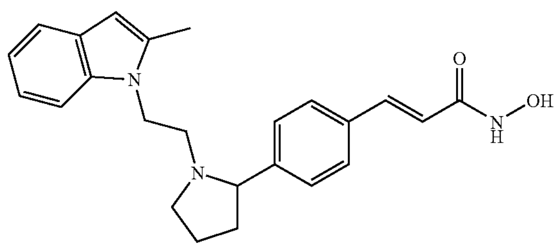 | (E)-N-Hydroxy-3-(4-{1-[2-(2-methyl-indol-1-yl)-ethyl]-pyrrolidin-2-yl}-phenyl)-acrylamide |
| 5 | 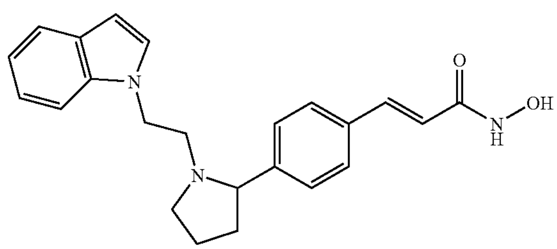 | (E)-N-Hydroxy-3-{4-[1-(2-indol-1-yl-ethyl)-pyrrolidin-2-yl]-phenyl}-acrylamide |
| 6 | 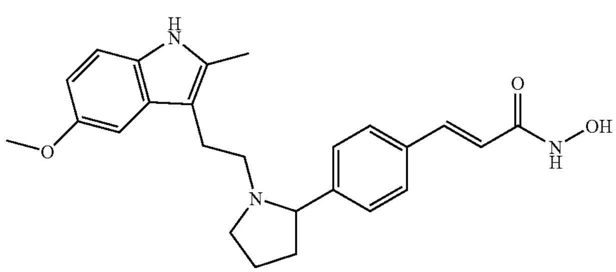 | (E)-N-Hydroxy-3-(4-{1-[2-(5-methoxy-2-methyl-1H-indol-3-yl)-ethyl]-pyrrolidin-2-yl}-phenyl)-acrylamide |
| 7 | 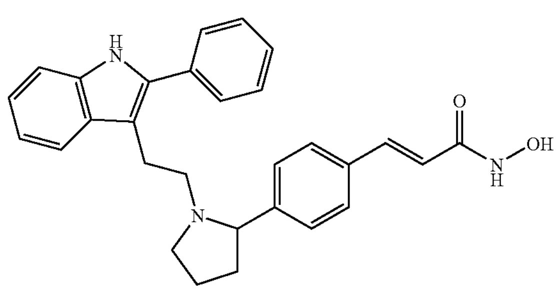 | (E)-N-Hydroxy-3-(4-{1-[2-(2-phenyl-1H-indol-3-yl)-ethyl]-pyrrolidin-2-yl}-phenyl)-acrylamide |

TABLE 1-continued

| Cpd # | Structure | Name |
|---|---|---|
| 8 | 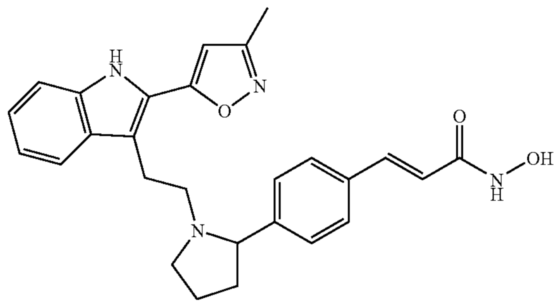 | (E)-N-Hydroxy-3-[4-(1-{2-[2-(5-methyl-isoxazol-3-yl)-1H-indol-3-yl]-ethyl}-pyrrolidin-2-yl)-phenyl]-acrylamide |
| 9 | 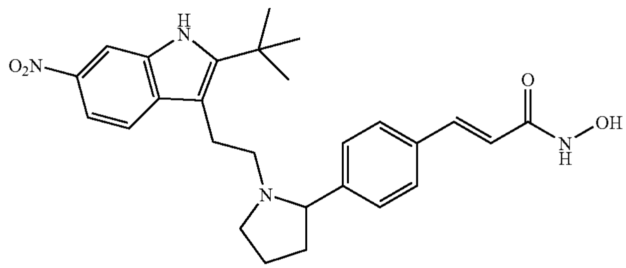 | (E)-3-(4-{1-[2-(2-tert-Butyl-6-nitro-1H-indol-3-yl)-ethyl]-pyrrolidin-2-yl}-phenyl)-N-hydroxy-acrylamide |
| 10 | 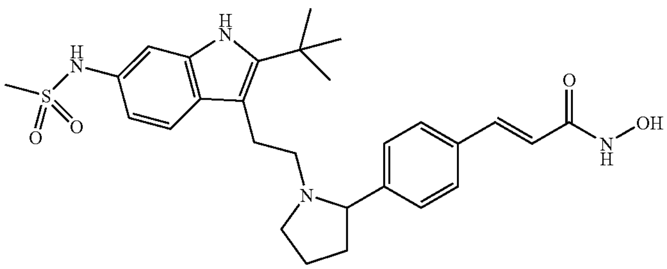 | (E)-3-(4-{1-[2-(2-tert-Butyl-6-methanesulfonylamino-1H-indol-3-yl)-ethyl]-pyrrolidin-2-yl}-phenyl)-N-hydroxy-acrylamide |
| 11 | 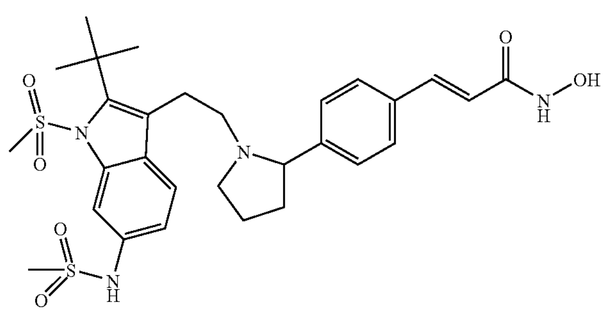 | (E)-3-(4-{1-[2-(2-tert-Butyl-1-methanesulfonyl-6-methanesulfonylamino-1H-indol-3-yl)-ethyl]-pyrrolidin-2-yl}-phenyl)-N-hydroxy-acrylamide |
| 12 | 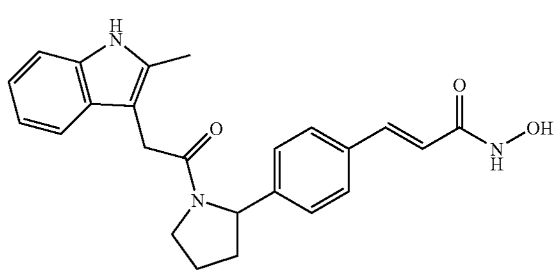 | (E)-N-Hydroxy-3-(4-{1-[2-(2-methyl-1H-indol-3-yl)-acetyl]-pyrrolidin-2-yl}-phenyl)-acrylamide |

TABLE 1-continued

| Cpd # | Structure | Name |
|---|---|---|
| 13 | 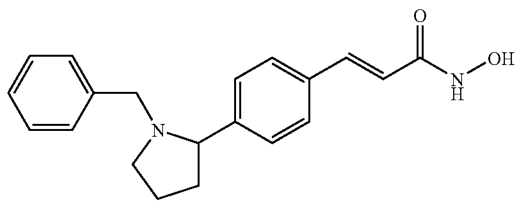 | (E)-3-[4-(1-Benzyl-pyrrolidin-2-yl)-phenyl]-N-hydroxy-acrylamide |
| 14 | 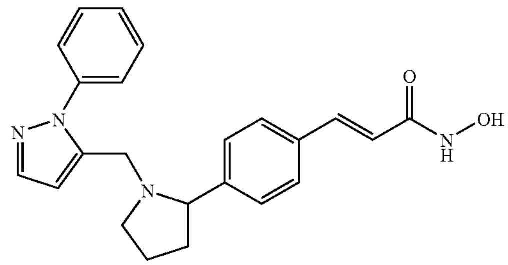 | (E)-N-Hydroxy-3-{4-[1-(2-phenyl-2H-pyrazol-3-ylmethyl)-pyrrolidin-2-yl]-phenyl}-acrylamide |
| 15 | 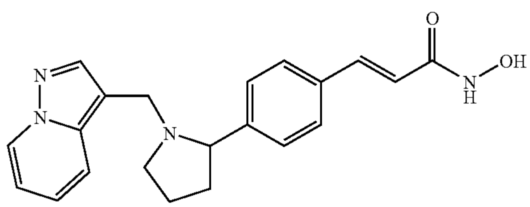 | (E)-N-Hydroxy-3-[4-(1-pyrazolo[1,5-a]pyridin-3-ylmethyl-pyrrolidin-2-yl)-phenyl]-acrylamide |
| 16 | 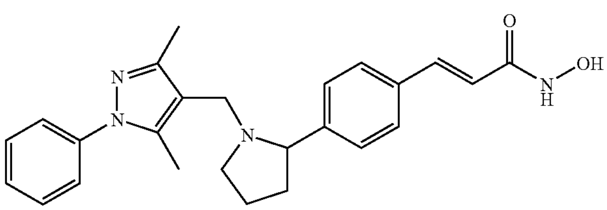 | (E)-3-{4-[1-(3,5-Dimethyl-1-phenyl-1H-pyrazol-4-ylmethyl)-pyrrolidin-2-yl]-phenyl}-N-hydroxy-acrylamide |
| 17 | 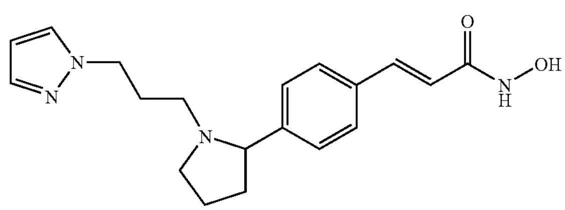 | (E)-N-Hydroxy-3-{4-[(S)-1-(3-pyrazol-1-yl-propyl)-pyrrolidin-2-yl]-phenyl}-acrylamide |
| 18 | 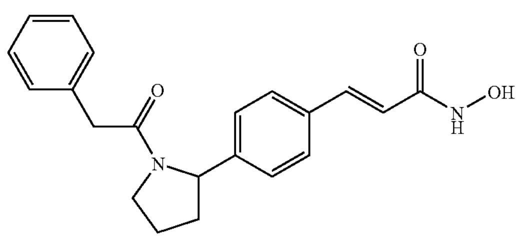 | (E)-N-Hydroxy-3-[4-((S)-1-phenylacetyl-pyrrolidin-2-yl)-phenyl]-acrylamide |
| 19 | 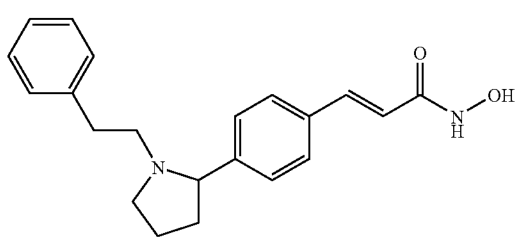 | (E)-N-Hydroxy-3-[4-(1-phenethyl-pyrrolidin-2-yl)-phenyl]-acrylamide |

TABLE 1-continued

| Cpd # | Structure | Name |
|---|---|---|
| 20 | 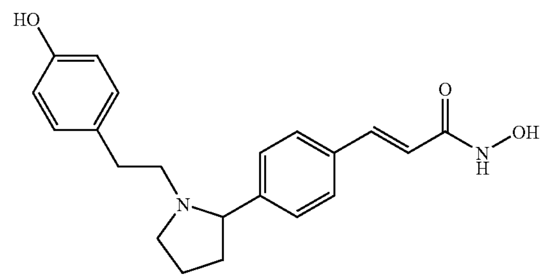 | (E)-N-Hydroxy-3-(4-{1-[2-(4-hydroxy-phenyl)-ethyl]-pyrrolidin-2-yl}-phenyl)-acrylamide |
| 21 | 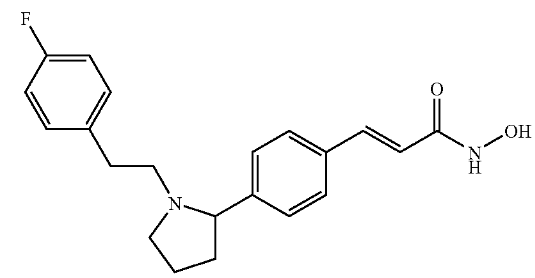 | (E)-3-(4-{(S)-1-[2-(4-Fluoro-phenyl)-ethyl]-pyrrolidin-2-yl}-phenyl)-N-hydroxy-acrylamide |
| 22 | 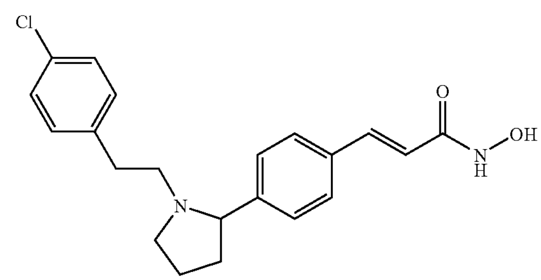 | (E)-3-(4-{(S)-1-[2-(4-Chloro-phenyl)-ethyl]-pyrrolidin-2-yl}-phenyl)-N-hydroxy-acrylamide |
| 23 | 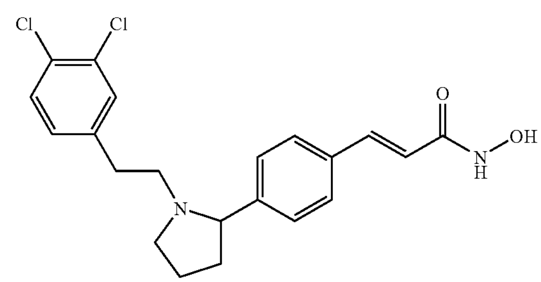 | (E)-3-(4-{1-[2-(3,4-Dichloro-phenyl)-ethyl]-pyrrolidin-2-yl}-phenyl)-N-hydroxy-acrylamide |
| 24 | 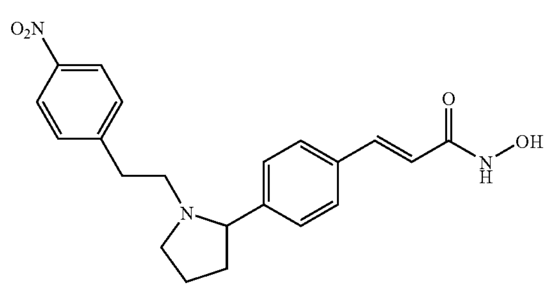 | (E)-N-Hydroxy-3-(4-{1-[2-(4-nitro-phenyl)-ethyl]-pyrrolidin-2-yl}-phenyl)-acrylamide |

TABLE 1-continued

| Cpd # | Structure | Name |
|---|---|---|
| 25 | 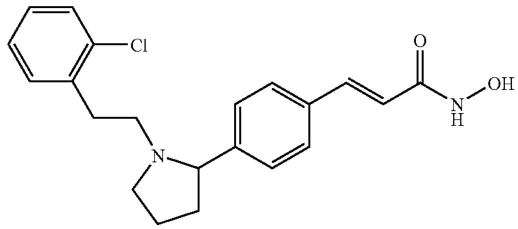 | (E)-3-(4-{1-[2-(2-Chloro-phenyl)-ethyl]-pyrrolidin-2-yl}-phenyl)-N-hydroxy-acrylamide |
| 26 | 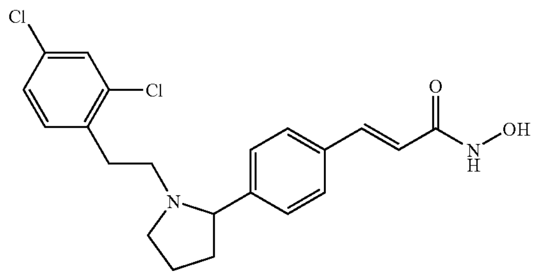 | (E)-3-(4-{1-[2-(2,4-Dichloro-phenyl)-ethyl]-pyrrolidin-2-yl}-phenyl)-N-hydroxy-acrylamide |
| 27 | 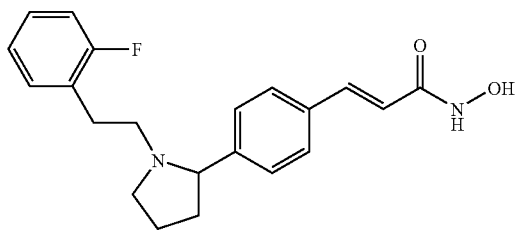 | (E)-3-(4-{1-[2-(2-Fluoro-phenyl)-ethyl]-pyrrolidin-2-yl}-phenyl)-N-hydroxy-acrylamide |
| 28 | 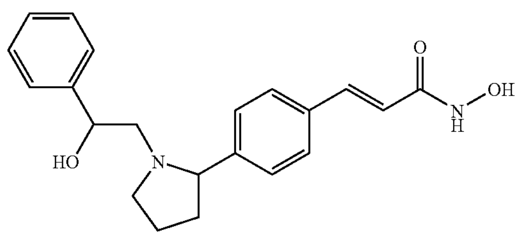 | (E)-N-Hydroxy-3-{4-[1-(2-hydroxy-2-phenyl-ethyl)-pyrrolidin-2-yl]-phenyl}-acrylamide |
| 29 | 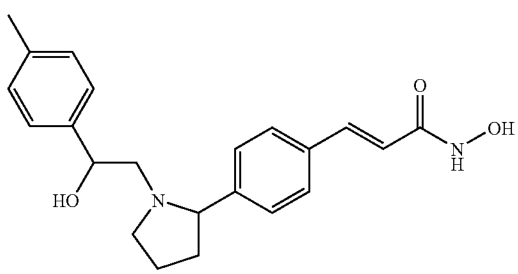 | (E)-N-Hydroxy-3-{4-[1-(2-hydroxy-2-p-tolyl-ethyl)-pyrrolidin-2-yl]-phenyl}-acrylamide |
| 30 | 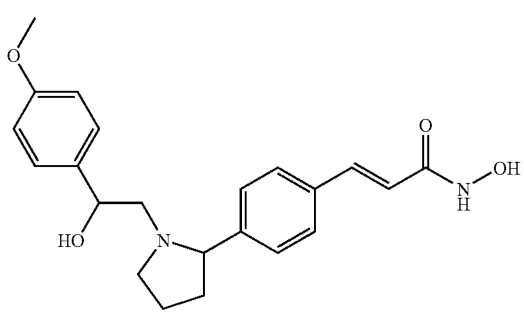 | (E)-N-Hydroxy-3-(4-{1-[2-hydroxy-2-(4-methoxy-phenyl)-ethyl]-pyrrolidin-2-yl}-phenyl)-acrylamide |

TABLE 1-continued

| Cpd # | Structure | Name |
|---|---|---|
| 31 | 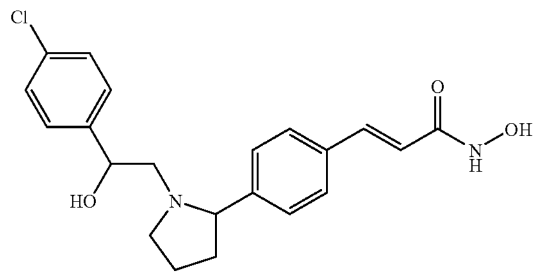 | (E)-3-(4-{1-[2-(4-Chloro-phenyl)-2-hydroxy-ethyl]-pyrrolidin-2-yl}-phenyl)-N-hydroxy-acrylamide |
| 32 | 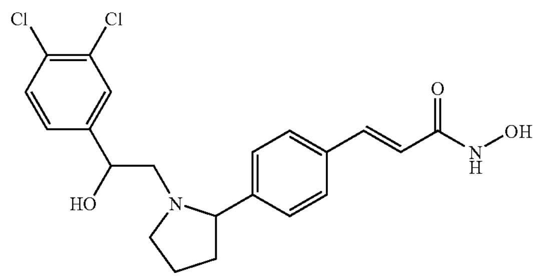 | (E)-3-(4-{1-[2-(3,4-Dichloro-phenyl)-2-hydroxy-ethyl]-pyrrolidin-2-yl}-phenyl)-N-hydroxy-acrylamide |
| 33 | 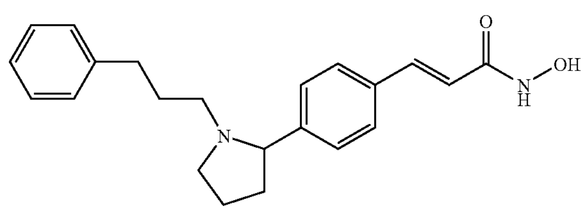 | (E)-N-Hydroxy-3-{4-[1-(3-phenyl-propyl)-pyrrolidin-2-yl]-phenyl}-acrylamide |
| 34 | 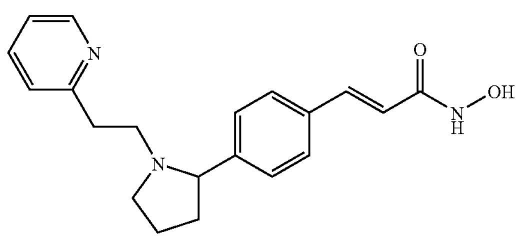 | (E)-N-Hydroxy-3-{4-[1-(2-pyridin-2-yl-ethyl)-pyrrolidin-2-yl]-phenyl}-acrylamide |
| 35 | 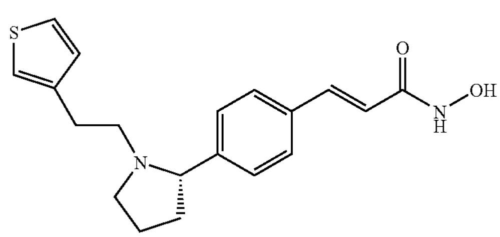 | (E)-N-Hydroxy-3-{4-[(S)-1-(2-thiophen-3-yl-ethyl)-pyrrolidin-2-yl]-phenyl}-acrylamide |
| 36 | 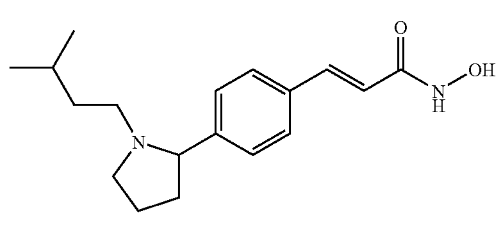 | (E)-N-Hydroxy-3-{4-[1-(3-methyl-butyl)-pyrrolidin-2-yl]-phenyl}-acrylamide |

TABLE 1-continued

| Cpd # | Structure | Name |
|---|---|---|
| 37 | 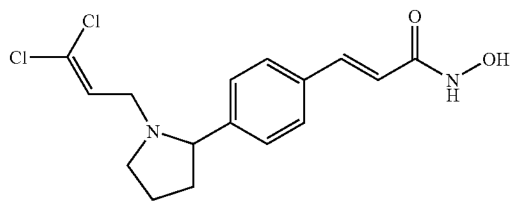 | (E)-3-{4-[1-(3,3-Dichloro-allyl)-pyrrolidin-2-yl]-phenyl}-N-hydroxy-acrylamide |
| 38 | 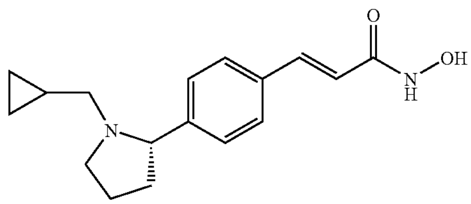 | (E)-3-[4-((S)-1-Cyclopropylmethyl-pyrrolidin-2-yl)-phenyl]-N-hydroxy-acrylamide |
| 39 | 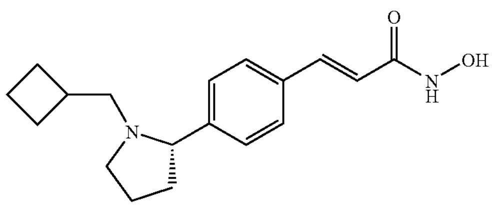 | (E)-3-[4-((S)-1-Cyclobutylmethyl-pyrrolidin-2-yl)-phenyl]-N-hydroxy-acrylamide |
| 40 | 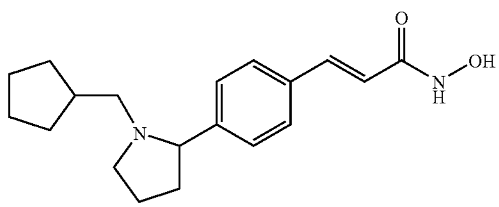 | (E)-3-[4-(1-Cyclopentylmethyl-pyrrolidin-2-yl)-phenyl]-N-hydroxy-acrylamide |
| 41 | 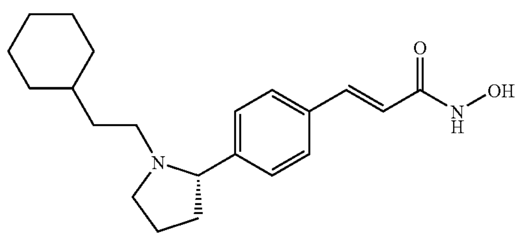 | (E)-3-{4-[(S)-1-(2-Cyclohexyl-ethyl)-pyrrolidin-2-yl]-phenyl}-N-hydroxy-acrylamide |
| 42 | 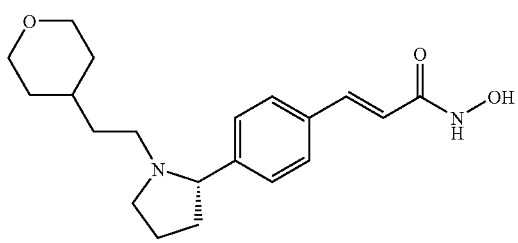 | (E)-N-Hydroxy-3-(4-{(S)-1-[2-(tetrahydro-pyran-4-yl)-ethyl]-pyrrolidin-2-yl}-phenyl-acrylamide |
| 43 | 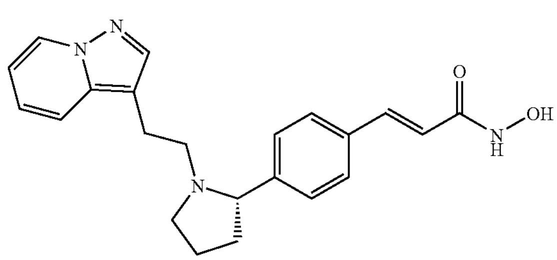 | (E)-N-Hydroxy-3-{4-[(S)-1-(2-pyrazolo[1,5-a]pyridin-3-yl-ethyl)-pyrrolidin-2-yl]-phenyl}-acrylamide |

TABLE 1-continued

| Cpd # | Structure | Name |
|---|---|---|
| 44 | 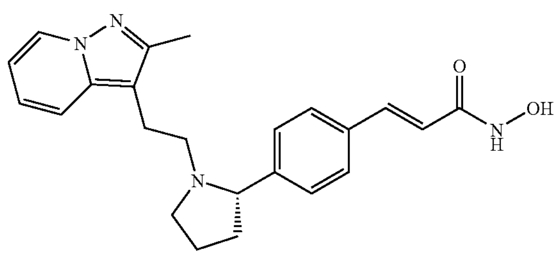 | (E)-N-Hydroxy-3-(4-{(S)-1-[2-(2-methyl-pyrazolo[1,5-a]pyridin-3-yl)-ethyl]-pyrrolidin-2-yl}-phenyl)-acrylamide |
| 45 | 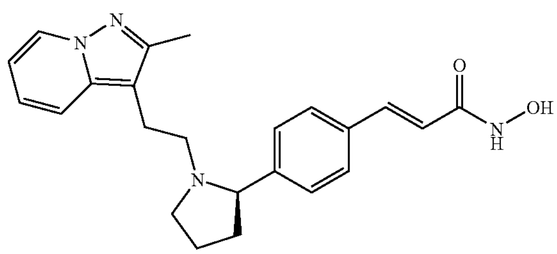 | (E)-N-Hydroxy-3-(4-{(R)-1-[2-(2-methyl-pyrazolo[1,5-a]pyridin-3-yl)-ethyl]-pyrrolidin-2-yl}-phenyl)-acrylamide |
| 46 | 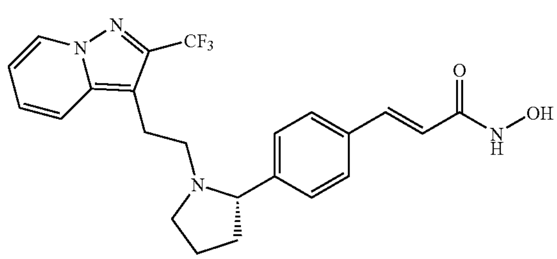 | (E)-N-Hydroxy-3-(4-{(S)-1-[2-(2-trifluoromethyl-pyrazolo[1,5-a]pyridin-3-yl)-ethyl]-pyrrolidin-2-yl}-phenyl)-acrylamide |
| 47 | 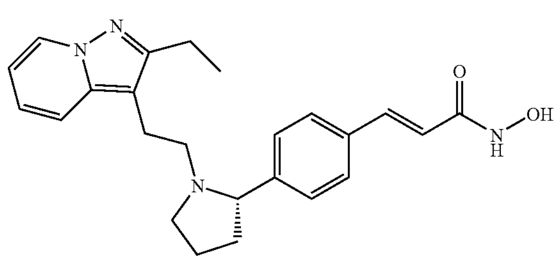 | (E)-3-{(S)-1-[2-(2-Ethyl-pyrazolo[1,5-a]pyridin-3-yl)-ethyl]-pyrrolidin-2-yl}-phenyl)-N-hydroxy-acrylamide |
| 48 | 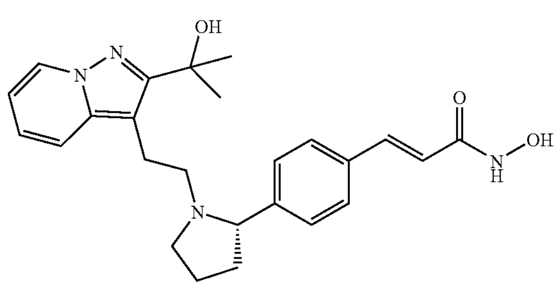 | (E)-N-Hydroxy-3-[4-((S)-1-{2-[2-(1-hydroxy-1-methyl-ethyl)-pyrazolo[1,5-a]pyridin-3-yl]-ethyl}-pyrrolidin-2-yl)-phenyl]-acrylamide |

TABLE 1-continued

| Cpd # | Structure | Name |
|---|---|---|
| 49 | 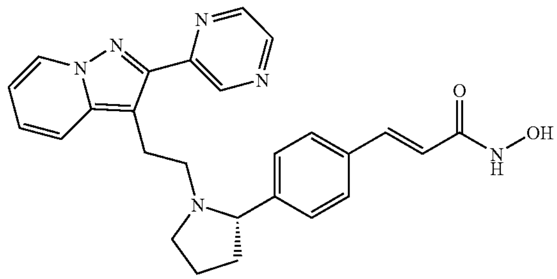 | (E)-N-Hydroxy-3-(4-{(S)-1-[2-(2-pyrazin-2-yl-pyrazolo[1,5-a]pyridin-3-yl)-ethyl]-pyrrolidin-2-yl}-phenyl)-acrylamide |
| 50 | 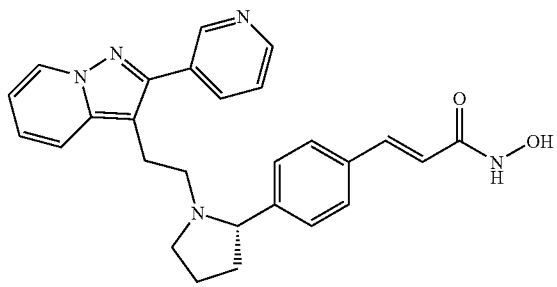 | (E)-N-Hydroxy-3-(4-{(S)-1-[2-(2-pyridin-3-yl-pyrazolo[1,5-a]pyridin-3-yl)-ethyl]-pyrrolidin-2-yl}-phenyl)-acrylamide |
| 51 | 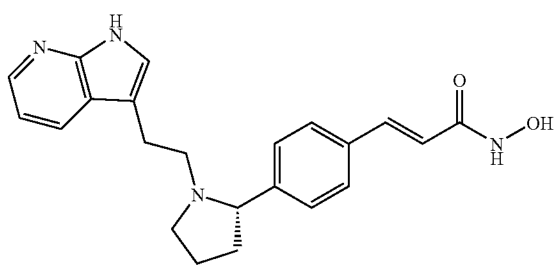 | (E)-N-Hydroxy-3-(4-{(S)-1-[2-(1H-pyrrolo[2,3-b]pyridin-3-yl)-ethyl]-pyrrolidin-2-yl}-phenyl)-acrylamide |
| 52 | 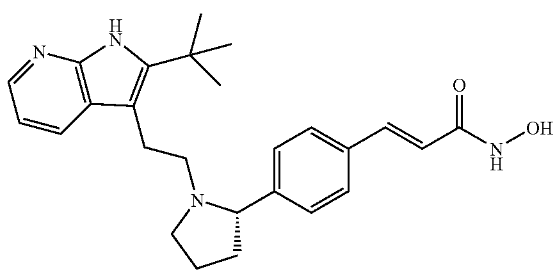 | (E)-3-(4-{(S)-1-[2-(2-tert-Butyl-1H-pyrrolo[2,3-b]pyridin-3-yl)-ethyl]-pyrrolidin-2-yl}-phenyl)-N-hydroxy-acrylamide |
| 53 | 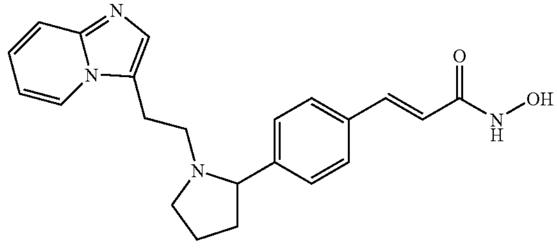 | (E)-N-Hydroxy-3-{4-[1-(2-imidazo[1,2-a]pyridin-3-yl-ethyl)-pyrrolidin-2-yl]-phenyl}-acrylamide |

TABLE 1-continued

| Cpd # | Structure | Name |
|---|---|---|
| 54 | 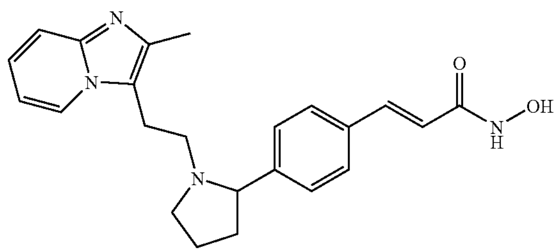 | (E)-N-Hydroxy-3-(4-{(S)-1-[2-(2-methyl-imidazo[1,2-a]pyridin-3-yl)-ethyl]-pyrrolidin-2-yl}-phenyl)-acrylamide |
| 55 | 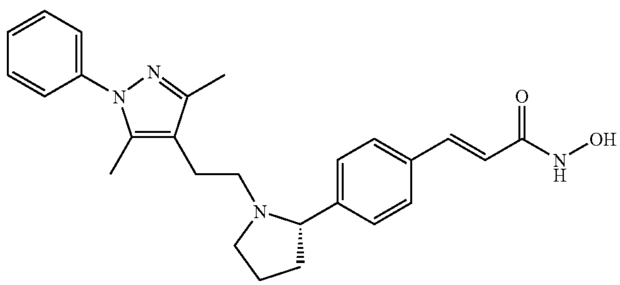 | (E)-3-(4-{(S)-1-[2-(3,5-Dimethyl-1-phenyl-1H-pyrazol-4-yl)-ethyl]-pyrrolidin-2-yl}-phenyl)-N-hydroxy-acrylamide |
| 56 | 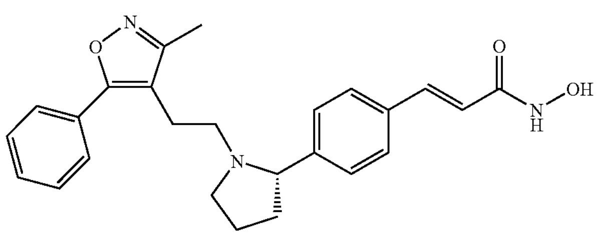 | (E)-N-Hydroxy-3-(4-{(S)-1-[2-(3-methyl-5-phenyl-isoxazol-4-yl)-ethyl]-pyrrolidin-2-yl}-phenyl)-acrylamide |
| 57 | 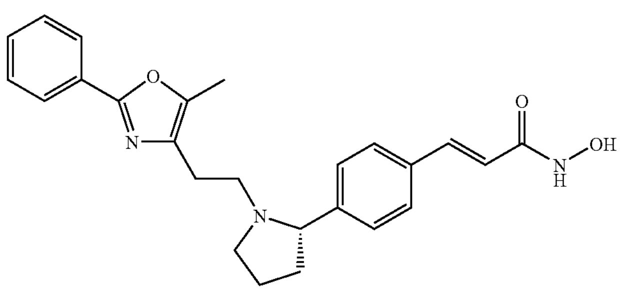 | (E)-N-Hydroxy-3-(4-{(S)-1-[2-(5-methyl-2-phenyl-oxazol-4-yl)-ethyl]-pyrrolidin-2-yl}-phenyl)-acrylamide |
| 58 | 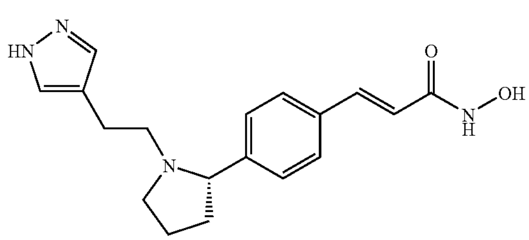 | (E)-N-Hydroxy-3-(4-{(S)-1-[2-(1H-pyrazol-4-yl)-ethyl]-pyrrolidin-2-yl}-phenyl)-acrylamide |
| 59 | 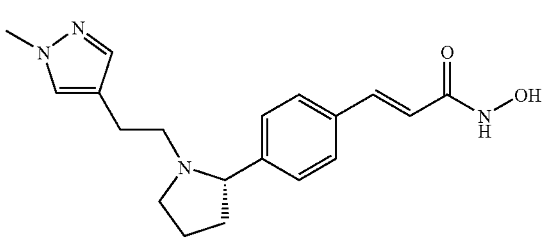 | (E)-N-Hydroxy-3-(4-{(S)-1-[2-(1-methyl-1H-pyrazol-4-yl)-ethyl]-pyrrolidin-2-yl}-phenyl)-acrylamide |

TABLE 1-continued

| Cpd # | Structure | Name |
|---|---|---|
| 60 | 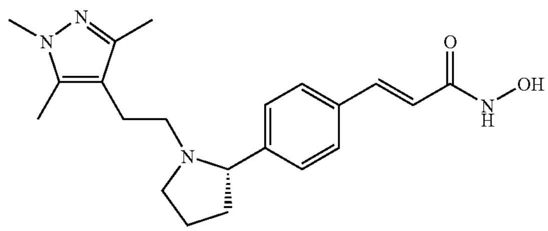 | (E)-N-Hydroxy-3-(4-{(S)-1-[2-(1,3,5-trimethyl-1H-pyrazol-4-yl)-ethyl]-pyrrolidin-2-yl}-phenyl)-acrylamide |
| 61 | 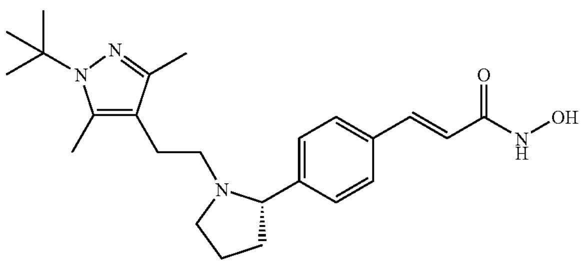 | (E)-3-(4-{(S)-1-[2-(1-tert-Butyl-3,5-dimethyl-1H-pyrazol-4-yl)-ethyl]-pyrrolidin-2-yl}-phenyl)-N-hydroxy-acrylamide |
| 62 | 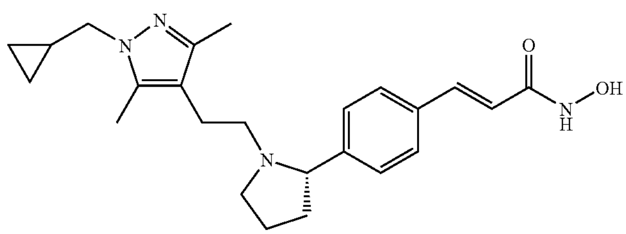 | (E)-3-(4-{(S)-1-[2-(1-Cyclopropylmethyl-3,5-dimethyl-1H-pyrazol-4-yl)-ethyl]-pyrrolidin-2-yl}-phenyl)-N-hydroxy-acrylamide |
| 63 | 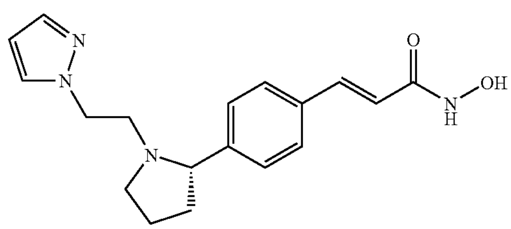 | (E)-N-Hydroxy-3-{4-[(S)-1-(2-pyrazol-1-yl-ethyl)-pyrrolidin-2-yl]-phenyl}-acrylamide |
| 64 | 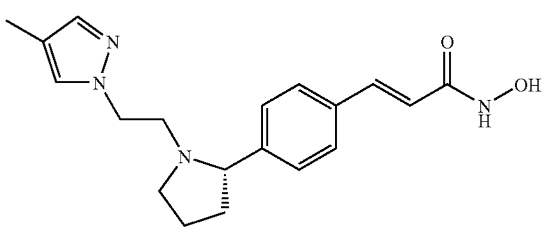 | (E)-N-Hydroxy-3-(4-{(S)-1-[2-(4-methyl-pyrazol-1-yl)-ethyl]-pyrrolidin-2-yl}-phenyl)-acrylamide |
| 65 | 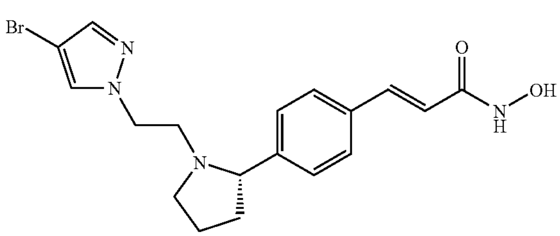 | (E)-3-(4-{(S)-1-[2-(4-Bromo-pyrazol-1-yl)-ethyl]-pyrrolidin-2-yl}-phenyl)-N-hydroxy-acrylamide |

TABLE 1-continued

| Cpd # | Structure | Name |
|---|---|---|
| 66 | 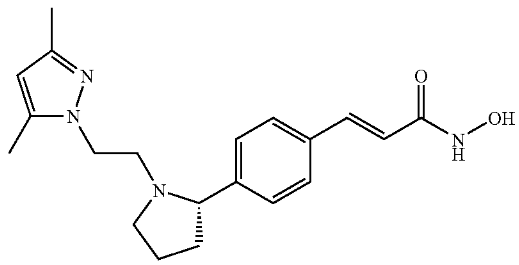 | (E)-3-(4-{(S)-1-[2-(3,5-Dimethyl-pyrazol-1-yl)-ethyl]-pyrrolidin-2-yl}-phenyl)-N-hydroxy-acrylamide |
| 67 | 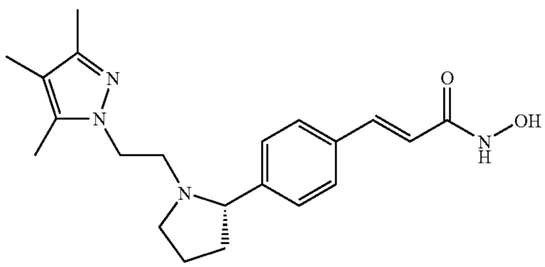 | (E)-N-Hydroxy-3-(4-{1-[2-(3,4,5-trimethyl-pyrazol-1-yl)-ethyl]-pyrrolidin-2-yl}-phenyl)-acrylamide |
| 68 | 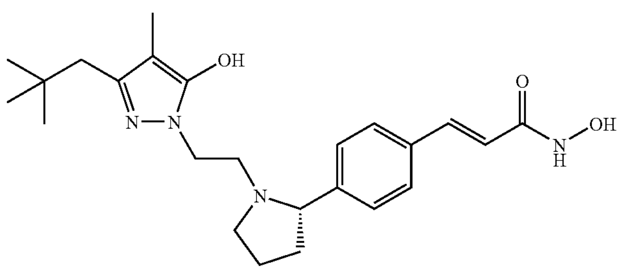 | (E)-3-[4-((S)-1-{2-[3-(2,2-Dimethyl-propyl)-5-hydroxy-4-methyl-pyrazol-1-yl]-ethyl}-pyrrolidin-2-yl)-phenyl]-N-hydroxy-acrylamide |
| 69 | 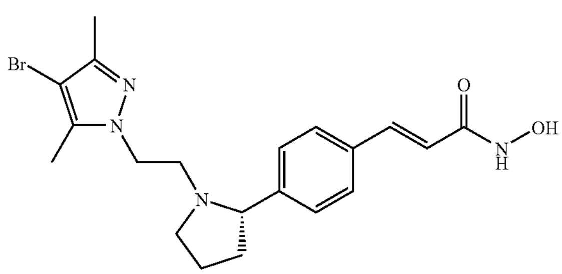 | (E)-3-(4-{(S)-1-[2-(4-Bromo-3,5-dimethyl-pyrazol-1-yl)-ethyl]-pyrrolidin-2-yl}-phenyl)-N-hydroxy-acrylamide |
| 70 | 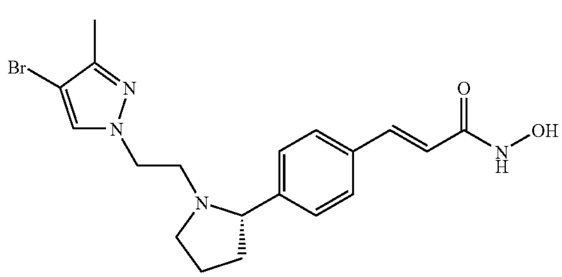 | (E)-3-(4-{(S)-1-[2-(4-Bromo-3-methyl-pyrazol-1-yl)-ethyl]-pyrrolidin-2-yl}-phenyl)-N-hydroxy-acrylamide |

TABLE 1-continued

| Cpd # | Structure | Name |
|---|---|---|
| 71 | 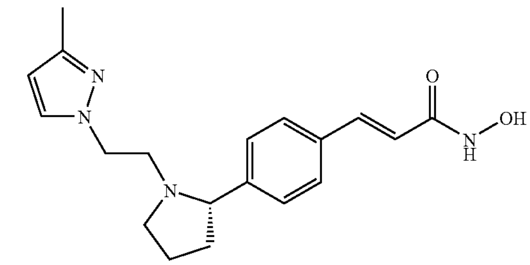 | (E)-N-Hydroxy-3-(4-{(S)-1-[2-(3-methyl-pyrazol-1-yl)-ethyl]-pyrrolidin-2-yl}-phenyl)-acrylamide |
| 72 | 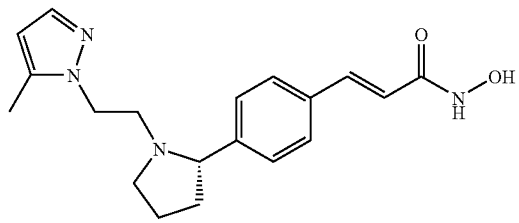 | (E)-N-Hydroxy-3-(4-{(S)-1-[2-(5-methyl-pyrazol-1-yl)-ethyl]-pyrrolidin-2-yl}-phenyl)-acrylamide |
| 73 | 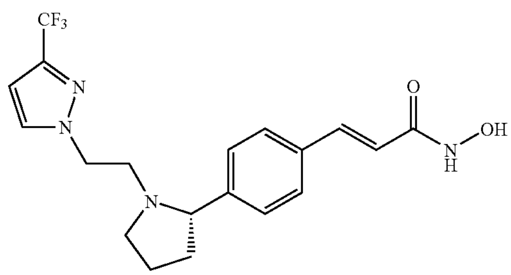 | (E)-N-Hydroxy-3-(4-{(S)-1-[2-(3-trifluoromethyl-pyrazol-1-yl)-ethyl]-pyrrolidin-2-yl}-phenyl)-acrylamide |
| 74 | 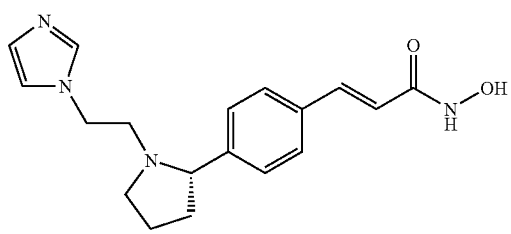 | (E)-N-Hydroxy-3-{4-[1-(2-imidazol-1-yl-ethyl)-pyrrolidin-2-yl]-phenyl}-acrylamide |
| 75 | 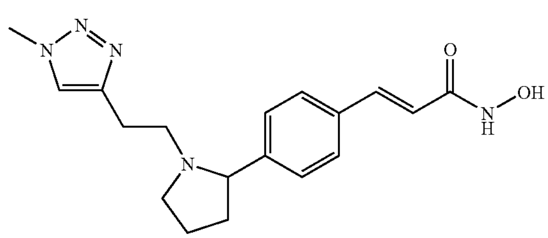 | (E)-N-Hydroxy-3-(4-{(S)-1-[2-(1-methyl-1H-[1,2,3]triazol-4-yl)-ethyl]-pyrrolidin-2-yl}-phenyl)-acrylamide |
| 76 | 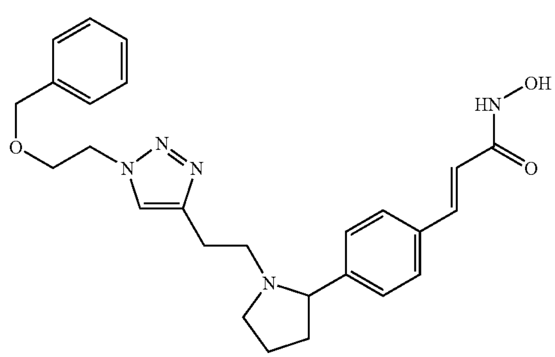 | (E)-3-[4-((S)-1-{2-[1-(2-Benzyloxy-ethyl)-1H-[1,2,3]triazol-4-yl]-ethyl}-pyrrolidin-2-yl)-phenyl]N-hydroxy-acrylamide |

TABLE 1-continued

| Cpd # | Structure | Name |
|---|---|---|
| 77 | 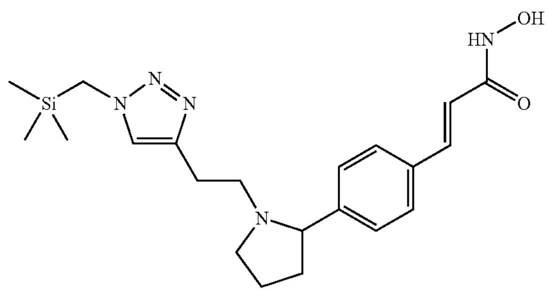 | (E)-N-Hydroxy-3-(4-{(S)-1-[2-(1-trimethylsilanylmethyl-1H-[1,2,3]triazol-4-yl)-ethyl]pyrrolidin-2-yl}-phenyl)-acrylamide |
| 78 | 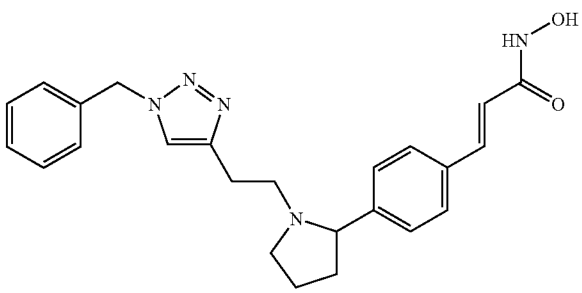 | (E)-3-(4-{(S)-1-[2-(1-Benzyl-1H-[1,2,3]triazol-4-yl)-ethyl]-pyrrolidin-2-yl}-phenyl)-N-hydroxy-acrylamide |
| 79 | 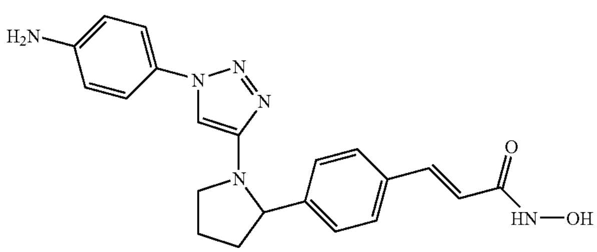 | (E)-3-[4-((S)-1-{2-[1-(4-Amino-phenyl)-1H-[1,2,3]triazol-4-yl]-ethyl}-pyrrolidin-2-yl)-phenyl]-N-hydroxy-acrylamide |
| 80 | 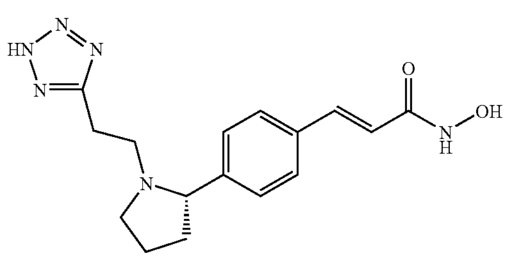 | (E)-N-Hydroxy-3-(4-{(S)-1-[2-(2H-tetrazol-5-yl)-ethyl]-pyrrolidin-2-yl}-phenyl)-acrylamide |
| 81 | 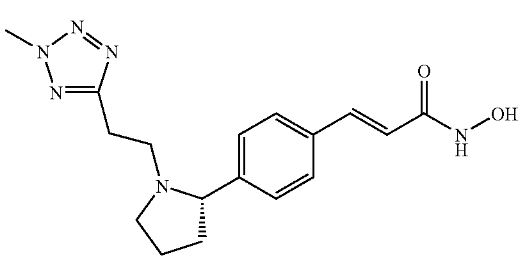 | (E)-N-Hydroxy-3-(4-{(S)-1-[2-(2-methyl-2H-tetrazol-5-yl)-ethyl]-pyrrolidin-2-yl}-phenyl)-acrylamide |

TABLE 1-continued

| Cpd # | Structure | Name |
|---|---|---|
| 82 | 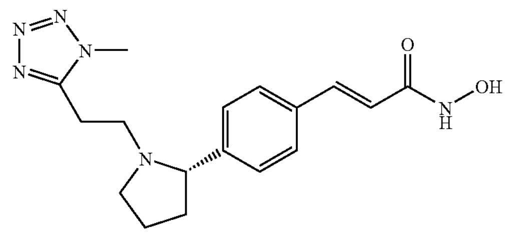 | (E)-N-Hydroxy-3-(4-{(S)-1-[2-(1-methyl-1H-tetrazol-5-yl)-ethyl]-pyrrolidin-2-yl}-phenyl)-acrylamide |
| 83 | 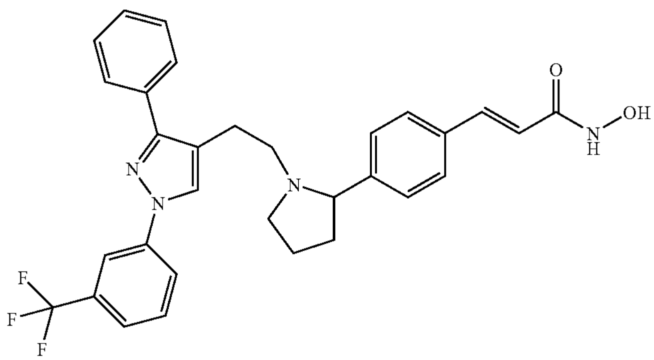 | (E)-N-Hydroxy-3-[4-(1-{2-[3-phenyl-1-(3-trifluoromethyl-phenyl)-1H-pyrazol-4-yl]-ethyl}-pyrrolidin-2-yl)-phenyl]-acrylamide |
| 84 | 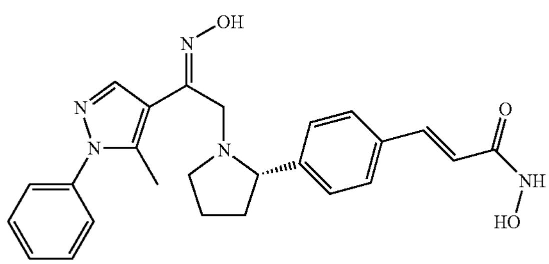 | (E)-N-Hydroxy-3-(4-{(S)-1-[2-[(Z)-hydroxyimino]-2-(5-methyl-1-phenyl-1H-pyrazol-4-yl)-ethyl]-pyrrolidin-2-yl}-phenyl)-acrylamide |
| 85 | 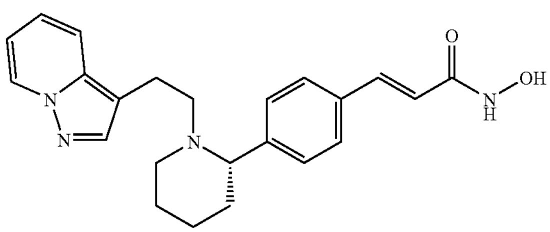 | (E)-N-Hydroxy-3-{4-[(S)-1-(2-pyrazolo[1,5-a]pyridin-3-yl-ethyl)-piperidin-2-yl]-phenyl}-acrylamide |
| 86 | 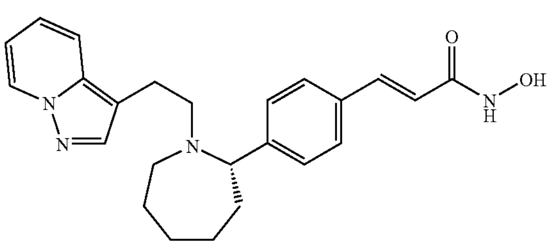 | (E)-N-Hydroxy-3-{4-[(S)-1-(2-pyrazolo[1,5-a]pyridin-3-yl-ethyl)-azepan-2-yl]-phenyl}-acrylamide |

TABLE 1-continued

| Cpd # | Structure | Name |
|---|---|---|
| 87 | 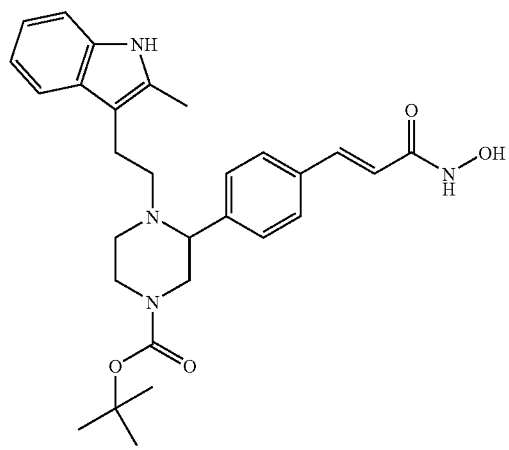 | 3-[4-((E)-2-Hydroxycarbamoyl-vinyl)-phenyl]-4-[2-(2-methyl-1H-indol-3-yl)-ethyl]-piperazine-1-carboxylic acid tert-butyl ester |
| 88 | 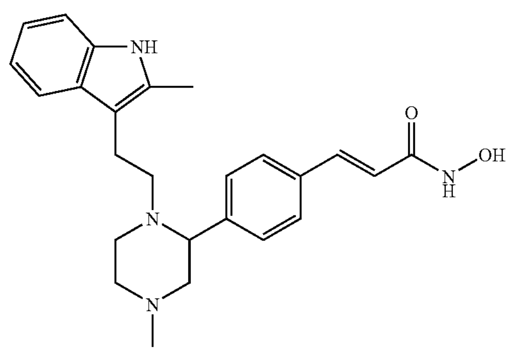 | (E)-N-Hydroxy-3-(4-{4-methyl-1-[2-(2-methyl-1H-indol-3-yl)-ethyl]-piperazin-2-yl}-phenyl)-acrylamide |
| 89 | 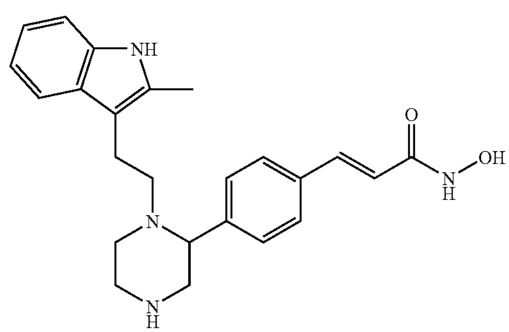 | (E)-N-Hydroxy-3-(4-{1-[2-(2-methyl-1H-indol-3-yl)-ethyl]-piperazin-2-yl}-phenyl)-acrylamide |
| 90 | 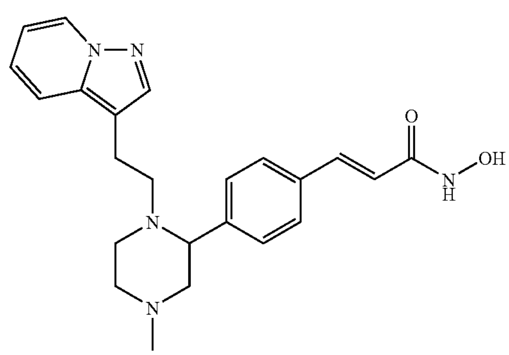 | (E)-N-Hydroxy-3-{4-[4-methyl-1-(2-pyrazolo[1,5-a]pyridin-3-yl-ethyl)-piperazin-2-yl]-phenyl}-acrylamide |

TABLE 1-continued

| Cpd # | Structure | Name |
|---|---|---|
| 91 | 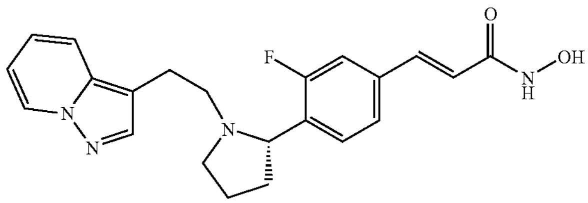 | (E)-3-{3-Fluoro-4-[(S)-1-(2-pyrazolo[1,5-a]pyridin-3-yl-ethyl)-pyrrolidin-2-yl]-phenyl}-N-hydroxy-acrylamide |
| 92 | 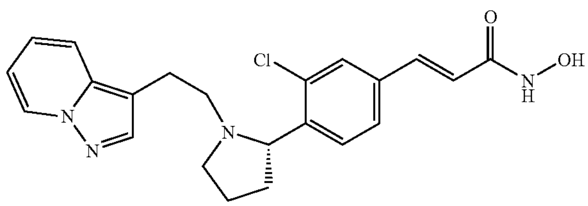 | (E)-3-{3-Chloro-4-[(S)-1-(2-pyrazolo[1,5-a]pyridin-3-yl-ethyl)-pyrrolidin-2-yl]-phenyl}-N-hydroxy-acrylamide |
| 93 | 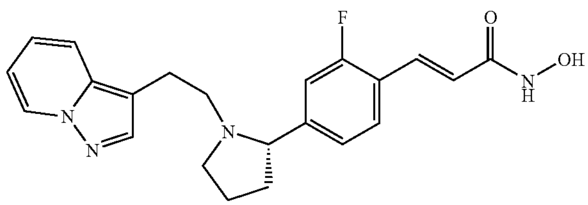 | (E)-3-{2-Fluoro-4-[(S)-1-(2-pyrazolo[1,5-a]pyridin-3-yl-ethyl)-pyrrolidin-2-yl]-phenyl}-N-hydroxy-acrylamide |
| 94 | 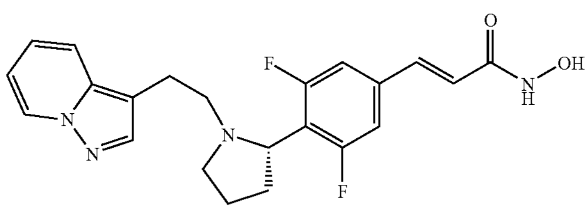 | (E)-3-{3,5-Difluoro-4-[(S)-1-(2-pyrazolo[1,5-a]pyridin-3-yl-ethyl)-pyrrolidin-2-yl]-phenyl}-N-hydroxy-acrylamide |
| 95 | 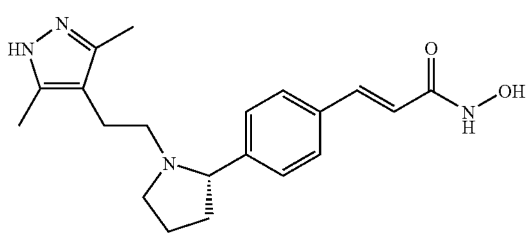 | (E)-3-(4-{(S)-1-[2-(3,5-Dimethyl-1H-pyrazol-4-yl)-ethyl]-pyrrolidin-2-yl}-phenyl)-N-hydroxy-acrylamide |
| 96 | 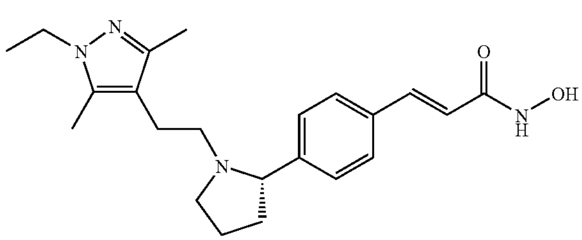 | (E)-3-(4-{(S)-1-[2-(1-Ethyl-3,5-dimethyl-1H-pyrazol-4-yl)-ethyl]-pyrrolidin-2-yl}-phenyl)-N-hydroxy-acrylamide |
| 97 | 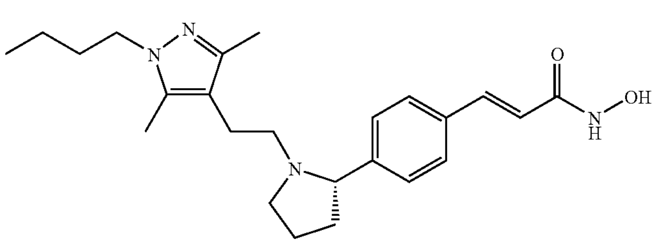 | (E)-3-(4-{(S)-1-[2-(1-Butyl-3,5-dimethyl-1H-pyrazol-4-yl)-ethyl]-pyrrolidin-2-yl}-phenyl)-N-hydroxy-acrylamide |

TABLE 1-continued

| Cpd # | Structure | Name |
|---|---|---|
| 98 | 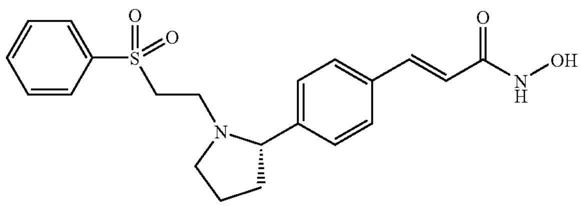 | (E)-3-{4-[(S)-1-(2-Benzenesulfonyl-ethyl)-pyrrolidin-2-yl]-phenyl}-N-hydroxy-acrylamide |
| 99 | 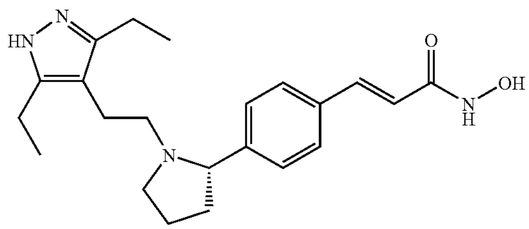 | (E)-3-(4-{(S)-1-[2-(3,5-Diethyl-1H-pyrazol-4-yl)-ethyl]-pyrrolidin-2-yl}-phenyl)-N-hydroxy-acrylamide |
| 100 | 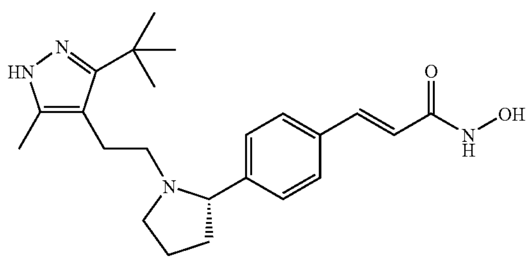 | (E)-3-(4-{(S)-1-[2-(3-tert-Butyl-5-methyl-1H-pyrazol-4-yl)-ethyl]-pyrrolidin-2-yl}-phenyl)-N-hydroxy-acrylamide |
| 101 | 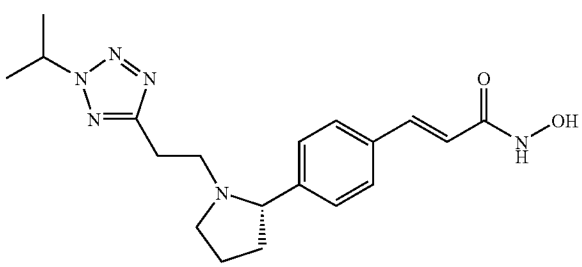 | (E)-N-Hydroxy-3-(4-{(S)-1-[2-(2-isopropyl-2H-tetrazol-5-yl)-ethyl]-pyrrolidin-2-yl}-phenyl)-acrylamide |
| 102 | 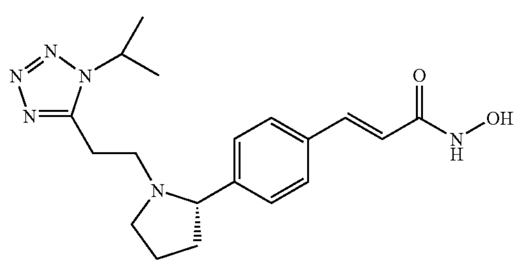 | (E)-N-Hydroxy-3-(4-{(S)-1-[2-(1-isopropyl-1H-tetrazol-5-yl)-ethyl]-pyrrolidin-2-yl}-phenyl)-acrylamide |
| 103 | 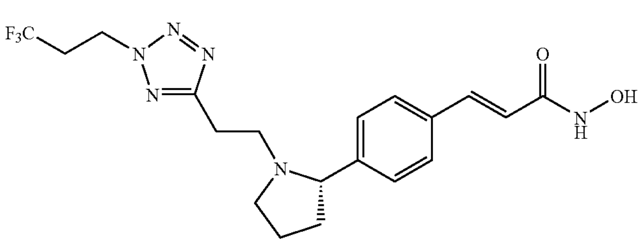 | (E)-N-Hydroxy-3-[4-(1-{2-[2-(3,3,3-trifluoro-propyl)-2H-tetrazol-5-yl]-ethyl}-pyrrolidin-2-yl)-phenyl]-acrylamide |

TABLE 1-continued

| Cpd # | Structure | Name |
|---|---|---|
| 104 | 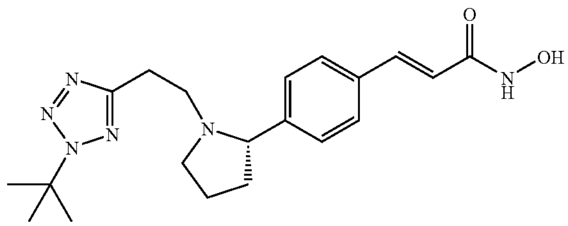 | (E)-3-(4-{(S)-1-[2-(2-tert-Butyl-2H-tetazol-5-yl)-ethyl]-pyrrolidin-2-yl}-phenyl)-N-hydroxy-acrylamide |
| 105 | 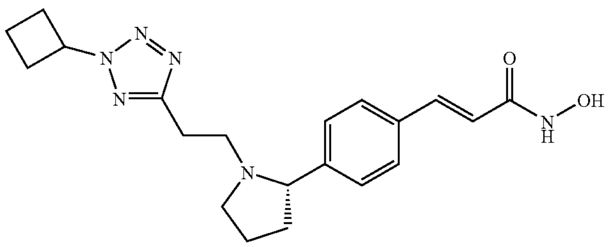 | (E)-3-(4-{(S)-1-[2-(2-Cyclobutyl-2H-tetrazol-5-yl)-ethyl]-pyrrolidin-2-yl}-phenyl)-N-hydroxy-acrylamide |
| 106 | 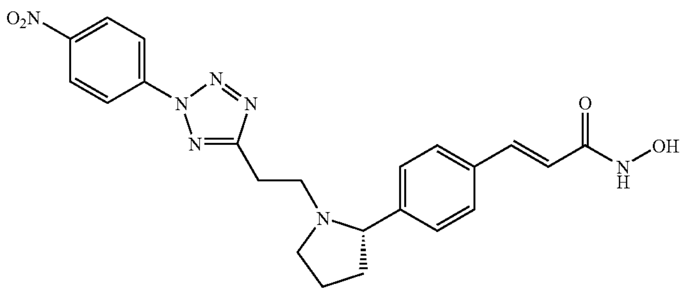 | (E)-N-Hydroxy-3-[4-((S)-1-{2-[2-(4-nitro-phenyl)-2H-tetrazol-5-yl]-ethyl}-pyrrolidin-2-yl)-phenyl]-acrylamide |
| 107 | 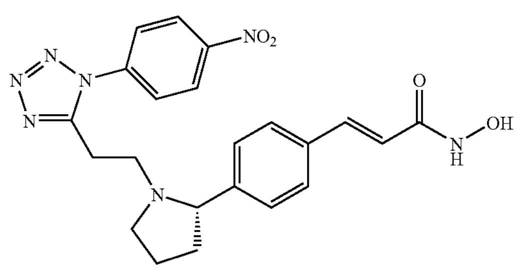 | (E)-N-Hydroxy-3-[4-((S)-1-{2-[1-(4-nitro-phenyl)-1H-tetrazol-5-yl]-ethyl}-pyrrolidin-2-yl)-phenyl]-acrylamide |
| 108 | 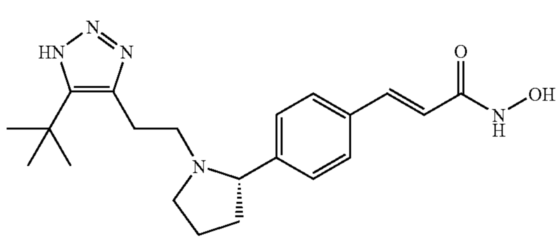 | (E)-3-(4-{(S)-1-[2-(5-tert-Butyl-1H-[1,2,3]triazol-4-yl)-ethyl]-pyrrolidin-2-yl}-phenyl)-N-hydroxy-acrylamide |

TABLE 1-continued

| Cpd # | Structure | Name |
|---|---|---|
| 109 | 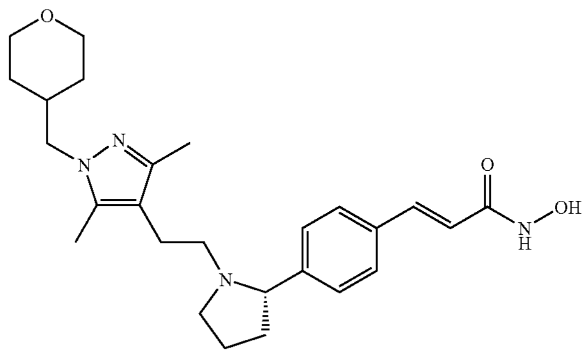 | (E)-3-[4-((S)-1-{2-[3,5-Dimethyl-1-(tetrahydro-pyran-4-ylmethyl)-1H-pyrazol-4-yl]-ethyl}-pyrrolidin-2-yl)-phenyl]-N-hydroxy-acrylamide |
| 110 | 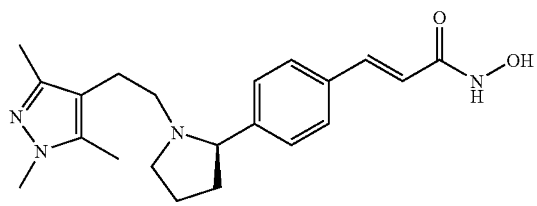 | (E)-N-Hydroxy-3-(4-{(R)-1-[2-(1,3,5-trimethyl-1H-pyrazol-4-yl)-ethyl]-pyrrolidin-2-yl}-phenyl)-acrylamide |
| 111 | 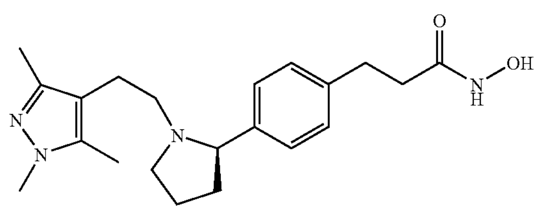 | N-Hydroxy-3-(4-{(R)-1-[2-(1,3,5-trimethyl-1H-pyrazol-4-yl)-ethyl]-pyrrolidin-2-yl}-phenyl)-propionamide |
| 112 | 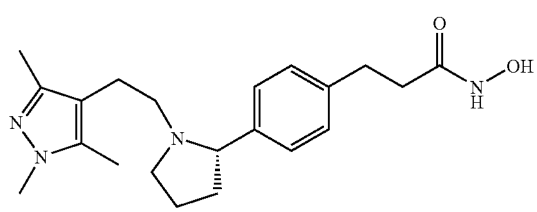 | N-Hydroxy-3-(4-{(S)-1-[2-(1,3,5-trimethyl-1H-pyrazol-4-yl)-ethyl]-pyrrolidin-2-yl}-phenyl)-propionamide |
| 113 | 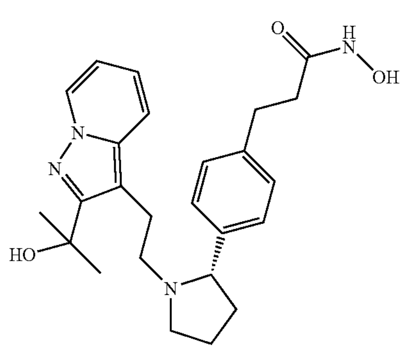 | N-Hydroxy-3-[4-((S)-1-{2-[2-(1-hydroxy-1-methyl-ethyl)-pyrazolo[1,5-a]pyridin-3-yl]-ethyl}-pyrrolidin-2-yl)-phenyl]-propionamide |

| Cpd # | Structure | Name |
|---|---|---|
| 114 | 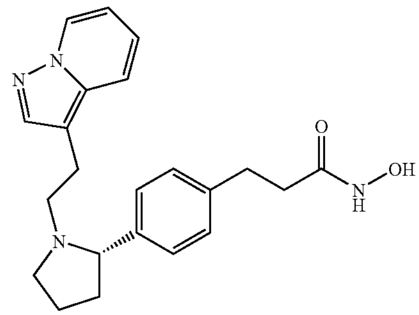 | N-Hydroxy-3-{4-[(S)-1-(2-pyrazolo[1,5-a]pyridin-3-yl]-ethyl)-pyrrolidin-2-yl]-phenyl}-propionamide |
| 115 | 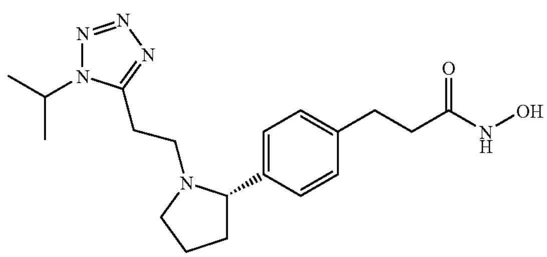 | N-Hydroxy-3-(4-{(S)-1-[2-(1-isopropyl-1H-tetrazol-5-yl)-ethyl]-pyrrolidin-2-yl}-phenyl)-propionamide |
| 116 | 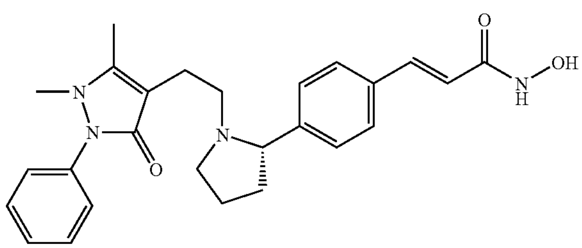 | (E)-3-(4-{(S)-1-[2-(1,5-Dimethyl-3-oxo-2-phenyl-2,3-dihydro-1H-pyrazol-4-yl)-ethyl]-pyrrolidin-2-yl}-phenyl)-N-hydroxy-acrylamide |
| 117 | 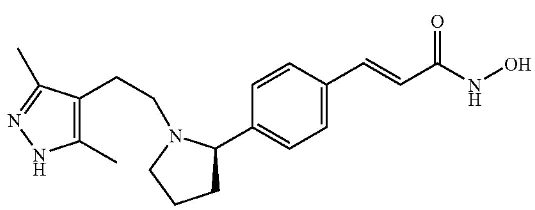 | (E)-3-(4-{(R)-1-[2-(3,5-Dimethyl-1H-pyrazol-4-yl)-ethyl]-pyrrolidin-2-yl}-phenyl)-N-hydroxy-acrylamide |
| 118 | 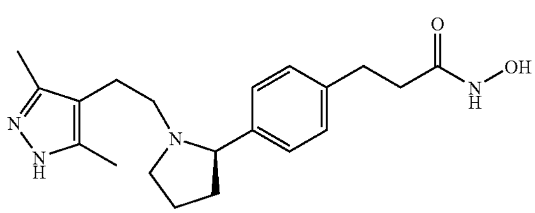 | 3-(4-{(R)-1-[2-(3,5-Dimethyl-1H-pyrazol-4-yl)-ethyl]-pyrrolidin-2-yl}-phenyl)-N-hydroxy-propionamide |
| 119 | 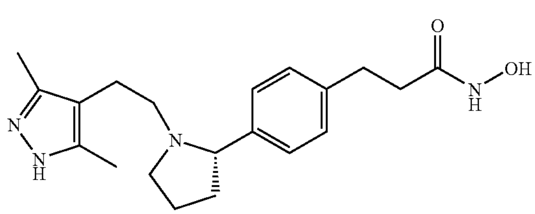 | 3-(4-{(S)-1-[2-(3,5-Dimethyl-1H-pyrazol-4-yl)-ethyl]-pyrrolidin-2-yl}-phenyl)-N-hydroxy-propionamide |

TABLE 1-continued

| Cpd # | Structure | Name |
|---|---|---|
| 120 | 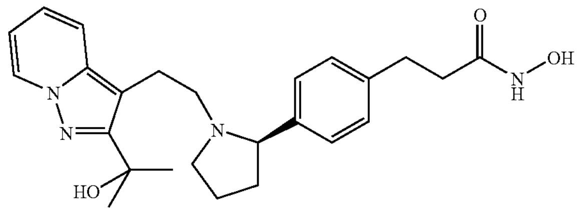 | N-Hydroxy-3-[4-((R)-1-{2-[2-(1-hydroxy-1-methyl-ethyl)-pyrazolo[1,5-a]pyridin-3-yl]-ethyl}-pyrrolidin-2-yl)-phenyl]-propionamide |
| 121 | 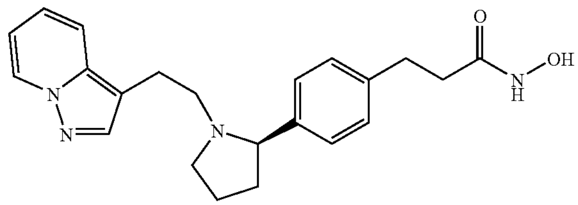 | N-Hydroxy-3-{4-[(R)-1-(2-pyrazolo[1,5-a]pyridin-3-yl-ethyl)-pyrrolidin-2-yl]-phenyl}-propionamide |

Also provided in accordance with the present teachings are prodrugs of the compounds disclosed herein. As used herein, "prodrug" refers to a compound ("parent compound") having a moiety that produces, generates, or releases a compound of the present teachings ("active compound") when administered to a mammalian subject. Prodrugs can be prepared by modifying functional groups present in the active compounds in such a way that the modifications can be removed, either by routine manipulation or in vivo, from the parent compounds. Examples of prodrugs include compounds that contain one or more molecular moieties that are appended to a hydroxyl, amino, sulfhydryl, or carboxyl group of the active compounds, and that, when administered to a mammalian subject, is/are cleaved in vivo to form the free hydroxyl, amino, sulfhydryl, or carboxyl group, respectively, and to release the active compound. Examples of prodrugs can include acetate, formate, and benzoate derivatives of hydroxy and amino functional groups in the compounds of the present teachings. Preparation and use of prodrugs is discussed in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, the entire disclosures of which are incorporated by reference herein for all purposes.

Ester forms of the compounds according to the present teachings include pharmaceutically acceptable esters known in the art that can be metabolized into the free acid form, such as a free carboxylic acid form, in a mammal body. Examples of such esters include alkyl esters (e.g., alkyls of 1 to 10 carbon atoms), cycloalkyl esters (e.g., cycloalkyls of 3-10 carbon atoms), aryl esters (e.g., aryls of 6-14 carbon atoms, including of 6-10 carbon atoms), and heterocyclic analogues thereof (e.g., heterocyclics of 3-14 ring atoms, 1-3 of which can be selected from O, N, and S) and the alcoholic residue can carry further substituents. In some embodiments, esters of the compounds disclosed herein can be $C_{1-10}$ alkyl esters, such as methyl esters, ethyl esters, propyl esters, isopropyl esters, butyl esters, isobutyl esters, t-butyl esters, pentyl esters, isopentyl esters, neopentyl esters, hexyl esters, cyclopropylmethyl esters, and benzyl esters, $C_{3-10}$ cycloalkyl esters, such as cyclopropyl esters, cyclobutyl esters, cyclopentyl esters, and cyclohexyl esters, or aryl esters, such as phenyl esters and tolyl ester.

Pharmaceutically acceptable salts of compounds of the present teachings, which can have an acidic moiety, can be formed using organic or inorganic bases. Both mono and polyanionic salts are contemplated, depending on the number of acidic hydrogens available for deprotonation. Suitable salts formed with bases include metal salts, such as alkali metal or alkaline earth metal salts, for example sodium, potassium, or magnesium salts; ammonia salts and organic amine salts, such as those formed with morpholine, thiomorpholine, piperidine, pyrrolidine, a mono-, di-, or tri-lower alkylamine (e.g., ethyl-tert-butylamine, diethylamine, diisopropylamine, triethylamine, tributylamine, or dimethylpropylamine), or a mono-, di-, or trihydroxy lower alkylamine (e.g., mono-, di- or triethanolamine). Non-limiting examples of inorganic bases include $NaHCO_3$, $Na_2CO_3$, $KHCO_3$, $K_2CO_3$, $Cs_2CO_3$, LiOH, NaOH, KOH, $NaH_2PO_4$, $Na_2HPO_4$, and $Na_3PO_4$. Internal salts also can be formed. Similarly, when a compound disclosed herein contains a basic moiety, salts can be formed using organic and inorganic acids. For example, salts can be formed from any of the following acids: acetic, benzenesulfonic, benzoic, camphorsulfonic, citric, dichloroacetic, ethenesulfonic, formic, fumaric, gluconic, glutamic, hippuric, hydrobromic, hydrochloric, isethionic, lactic, maleic, malic, malonic, mandelic, methanesulfonic, mucic, napthalenesulfonic, nitric, oxalic, pamoic, pantothenic, phosphoric, phthalic, propionic, succinic, sulfuric, tartaric, toluenesulfonic, as well as other known pharmaceutically acceptable acids.

In another aspect, the present teachings provide pharmaceutical compositions including at least one compound described herein and one or more pharmaceutically acceptable carriers, excipients, or diluents. Examples of such carriers are well known to those skilled in the art and can be prepared in accordance with acceptable pharmaceutical procedures, such as, for example, those described in *Remington: The Science and Practice of Pharmacy*, 20th edition, Alfonoso R. Gennaro (ed.), Lippincott Williams & Wilkins, Baltimore, Md. (2000), the entire disclosure of which is incorporated by reference herein for all purposes. As used herein, "pharmaceutically acceptable" refers to a substance that is acceptable for use in pharmaceutical applications from a toxicological perspective and does not adversely interact with the active ingredient. Accordingly, pharmaceutically acceptable carriers are those that are compatible with the other ingredients in the formulation and are biologically acceptable. Supplementary active ingredients can also be incorporated into the pharmaceutical compositions.

Compounds of the present teachings can be useful for inhibiting a deacetylase in a cell. Accordingly, another aspect of the present teachings includes a method of contacting a cell with one or more compounds of the present teachings (or a salt, hydrate, or ester thereof) or a composition that includes one or more compounds of the present teachings. In certain embodiments, the composition can further include one or more pharmaceutically acceptable carrier or excipients.

Compounds of the present teachings can be useful for the treatment, inhibition, prevention, or diagnosis of a pathological condition or disorder in a mammal, for example, a human. Accordingly, another aspect of the present teachings includes a method of providing to a mammal a compound of the present teachings (or its pharmaceutically acceptable salt, hydrate, or ester) or a pharmaceutical composition that includes one or more compounds of the present teachings in combination or association with a pharmaceutically acceptable carrier. Compounds of the present teachings can be administered alone or in combination with other therapeutically effective compounds or therapies for the treatment, inhibition, prevention, or diagnosis of the pathological condition or disorder. As used herein, "therapeutically effective" refers to a substance or an amount that elicits a desirable biological activity or effect.

In various embodiments, the present teachings can further include use of the compounds disclosed herein as active therapeutic substances for the treatment or inhibition of a pathological condition or disorder, for example, a condition mediated wholly or in part by one or more deacetylases, such as an undesired proliferative condition; a neurodegenerative disease, including Alzheimer's disease, Hungtington's disease, Rubenstein-Taybis syndrome, Parkinson's disease, muscular dystrophy, spinal muscular atrophy, Rett's syndrome, and the like; a cardiovascular disease, including heart failure, cardiac hypertrophy, thrombosis, and the like; an autoimmune disease, including Lupus, atherosclerosis, scleroderma, and the like; an inflammatory disorder, including arthritis and arthritic conditions (e.g., osteoarthritis, rheumatoid arthritis, and the like), and other chronic inflammatory disorders (e.g., chronic asthma, arterial or post-transplantational atherosclerosis, endometriosis, and the like); an undesired immunological process; stroke; and an fungal infection. In some embodiments, the undesired proliferative condition includes a cancer (e.g., brain cancer, kidney cancer, liver cancer, adrenal gland cancer, bladder cancer, breast tumor, stomach cancer including gastric tumors, esophagus cancer, ovarian cancer, colon cancer, rectum cancer, prostate cancer, pancreas cancer, lung cancer including small cell lung cancer, vagina cancer, thyroid cancer, sarcoma, glioblastomas, multiple myeloma, gastrointestinal cancer, lung cancer, colon cancer, breast cancer, ovarian cancer, bladder cancer), a tumor, a fibrosis, and the like; a neoplasia, including mammary carcinoma, leukemia, and the like; and an epidermal hyperproliferation, including psoriasis, prostate hyperplasia, and the like. In certain embodiments, the present teachings can provide methods of treating these pathological conditions and disorders using the compounds described herein. As used herein, "treating" refers to partially or completely alleviating and/or ameliorating the condition or symptoms thereof. In particular embodiments, the methods can include identifying a mammal having a pathological condition or disorder mediated by deacetylases, and providing to the mammal a therapeutically effective amount of a compound as described herein. In some embodiments, the method can include administering to a mammal a pharmaceutical composition that can include a compound disclosed herein in combination or association with a pharmaceutically acceptable carrier.

In certain embodiments, compounds of formula (I) may be used in treating the following cancers. Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, inesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinorna, glucagonoma, gastrinoma, carcinoid tumors, vipoma), small bowel (adenocarcinorna, lymphoma, carcinoid tumors, Karposis sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nepbroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocareinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lyinphoma (reticulum cell sarcoma), multiple myeloma, malignant giant cell tumor chordoma, osteoclironfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformians), meninges (meningioma, meningiosarcoma, gliomatosis), brain (astrocytoma, medulloblastoma, glioma, ependymoma, germinoma [pinealoma], glioblastorna multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal Glands: neuroblastoma.

Cardiac hypertrophy in response to an increased workload imposed on the heart is a fundamental adaptive mechanism. It is a specialized process reflecting a quantitative increase in cell size and mass (rather than cell number) as the result of any or a combination of neural, endocrine or mechanical stimuli. Hypertension, another factor involved in cardiac hypertrophy, is a frequent precursor of congestive heart failure. When heart failure occurs, the left ventricle usually is hypertrophied and dilated and indices of systolic function, such as ejection fraction, are reduced. Clearly, the cardiac hypertrophic response is a complex syndrome and the elucidation of the pathways leading to cardiac hypertrophy will be beneficial in the treatment of heart disease resulting from a various stimuli.

In an embodiment, there is provided a method of preventing pathologic cardiac hypertrophy and heart failure with the compounds of the present invention. The method includes administering to the patient a histone deacetylase inhibitor. Administration may comprise intravenous, oral, transdermal, sustained release, suppository, or sublingual administration. The patient at risk may exhibit one or more of long standing uncontrolled hypertension, uncorrected valvular disease, chronic angina and/or recent myocardial infarction.

In one embodiment of the present invention, methods for the treatment of cardiac hypertrophy utilizing HDAC inhibitors are provided. For the purposes of the present application, treatment comprises reducing one or more of the symptoms of cardiac hypertrophy, such as reduced exercise capacity, reduced blood ejection volume, increased left ventricular end diastolic pressure, increased pulmonary capillary wedge pressure, reduced cardiac output, cardiac index, increased pulmonary artery pressures, increased left ventricular end systolic and diastolic dimensions, and increased left ventricular wall stress, wall tension and wall thickness-same for right ventricle. In addition, use of HDAC inhibitors may prevent cardiac hypertrophy and its associated symptoms from arising.

Treatment regimens would vary depending on the clinical situation. However, long term maintenance would appear to be appropriate in most circumstances. It also may be desirable treat hypertrophy with HDAC inhibitors intermittently, such as within brief window during disease progression. At present, testing indicates that the optimal dosage for an HDAC inhibitor will be the maximal dose before significant toxicity occurs.

In another embodiment, it is envisioned to use an HDAC inhibition in combination with other therapeutic modalities. Thus, in addition to the therapies described above, one may also provide to the patient more "standard" pharmaceutical cardiac therapies. Examples of standard therapies include, without limitation, so-called "beta blockers," anti-hypertensives, cardiotonics, anti-thrombotics, vasodilators, hormone antagonists, iontropes, diuretics, endothelin antagonists, calcium channel blockers, phosphodiesterase inhibitors, ACE inhibitors, angiotensin type 2 antagonists and cytokine blockers/inhibitors.

A HDAC inhibitor of the present invention may be usefully combined with another pharmacologically active compound, or with two or more other pharmacologically active compounds, particularly in the treatment of cancer. For example, a compound of the formula (I), or a pharmaceutically acceptable salt thereof, as defined above, may be administered simultaneously, sequentially or separately in combination with one or more agents selected from chemotherapy agents, e.g. mitotic inhibitors such as a taxane, a vinca alkaloid, paclitaxel, docetaxel, vincristine, vinblastine, vinorelbine or vinflunine, and other anticancer agents, e.g. cisplatin, 5-fluorouracil or 5-fluoro-2-4(1H,3H)-pyrimidinedione (5FU), flutamide or gemcitabine.

Such combinations may offer significant advantages, including synergistic activity, in therapy.

A compound of the formula (I) may also be used to advantage in combination with other antiproliferative compounds. Such antiproliferative compounds include, but are not limited to aromatase inhibitors; antiestrogens; topoisomerase I inhibitors; topoisomerase II inhibitors; microtubule active compounds; alkylating compounds; compounds which induce cell differentiation processes; cyclooxygenase inhibitors; MMP inhibitors; mTOR inhibitors; antineoplastic antimetabolites; platin compounds; compounds targeting decreasing a protein or lipid kinase activity and further antiangiogenic compounds; compounds which target, decrease or inhibit the activity of a protein or lipid phosphatase; gonadorelin agonists; anti-androgens; methionine aminopeptidase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylamino-geldanamycin, NSC330507), 17-DMAG (17-dimethylaminoethylamino-17-demethoxy-geldanamycin, NSC707545), IPI-504, CNF 1010, CNF2024, CNF1010 from Conforma Therapeutics; temozolomide (TEMODAL); kinesin spindle protein inhibitors, such as SB715992 or SB743921 from GlaxoSmithKline, or pentamidine/chlorpromazine from CombinatoRx; PI3K inhibitors; RAF inhibitors; EDG binders, antileukemia compounds, ribonucleotide reductase inhibitors, S-adenosylmethionine decarboxylase inhibitors, antiproliferative anti-bodies or other chemotherapeutic compounds. Further, alternatively or in addition they may be used in combination with other tumor treatment approaches, including surgery, ionizing radiation, photodynamic therapy, implants, e.g. with corticosteroids, hormones, or they may be used as radiosensitizers. Also, in anti-inflammatory and/or antiproliferative treatment, combination with anti-inflammatory drugs is included. Combination is also possible with antihistamine drug substances, bronchodilatatory drugs, NSA/D or antagonists of chemokine receptors.

The term "aromatase inhibitor" as used herein relates to a compound which inhibits the estrogen production, i.e. the conversion of the substrates androstenedione and testosterone to estrone and estradiol, respectively. The term includes, but is not limited to steroids, especially atame-stane, exemestane and formestane and, in part-icular, non-steroids, especially aminoglutethimide, roglethimide, pyridoglutethimide, trilostane, testolactone, ketokonazole, vorozole, fadrozole, anastrozole and letrozole. Exemestane can be administered, e.g., in the form as it is marketed, e.g. under the trademark AROMASIN. Formestane can be administered, e.g., in the form as it is marketed, e.g. under the trademark LENTARON. Fadrozole can be administered, e.g., in the form as it is marketed, e.g. under the trademark AFEMA. Anastrozole can be administered, e.g., in the form as it is marketed, e.g. under the trademark ARIMIDEX. Letrozole can be administered, e.g., in the form as it is marketed, e.g. under the trademark FEMARA or FEMAR. Amino glutethimide can be administered, e.g., in the form as it is marketed, e.g. under the trademark, ORIMETEN. A combination of the invention comprising a chemotherapeutic agent which is an aromatase inhibitor is particularly useful for the treatment of hormone receptor positive tumors, e.g., breast tumors.

The term "anti-estrogen" as used herein relates to a compound which antagonizes the effect of estrogens at the estrogen receptor level. The term includes, but is not limited to tamoxifen, fulvestrant, raloxifene and raloxifene hydrochloride. Tamoxifen can be administered, e.g., in the form as it is marketed, e.g. under the trademark NOLVADEX. Raloxifene hydrochloride can be administered, e.g., in the form as it is marketed, e.g. under the trademark EVISTA. Fulvestrant can be formulated as disclosed in U.S. Pat. No. 4,659,516 or it can be administered, e.g., in the form as it is marketed, e.g. under the trademark FASLODEX. A combination of the invention comprising a chemotherapeutic agent which is an anti-estrogen is particularly useful for the treatment of estrogen receptor positive tumors, e.g. breast tumors.

The term "anti-androgen" as used herein relates to any substance which is capable of inhibiting the biological effects of androgenic hormones and includes, but is not limited to, bicalutamide (CASODEX), which can be formulated, e.g. as disclosed in U.S. Pat. No. 4,636,505.

The term "gonadorelin agonist" as used herein includes, but is not limited to abarelix, goserelin and goserelin acetate. Goserelin is disclosed in U.S. Pat. No. 4,100,274 and can be administered, e.g., in the form as it is marketed, e.g. under the trademark ZOLADEX. Abarelix can be formulated, e.g. as disclosed in U.S. Pat. No. 5,843,901.

The term "topoisomerase I inhibitor" as used herein includes, but is not limited to topotecan, gimatecan, irinotecan, camptothecin and its analogues, 9-nitrocamptothecin and the macromolecular camptothecin conjugate PNU-166148 (compound A1 in WO99/17804). Irinotecan can be administered, e.g. in the form as it is marketed, e.g. under the trademark CAMPTOSAR. Topotecan can be administered, e.g., in the form as it is marketed, e.g. under the trademark HYCAMTIN.

The term "topoisomerase II inhibitor" as used herein includes, but is not limited to the anthracyclines such as doxorubicin (including liposomal formulation, e.g. CAELYX), daunorubicin, epirubicin, idarubicin and nemorubicin, the anthraquinones mitoxantrone and losoxantrone, and the podophillotoxines etoposide and teniposide. Etoposide can be administered, e.g. in the form as it is marketed, e.g. under the trademark ETOPOPHOS. Teniposide can be administered, e.g. in the form as it is marketed, e.g. under the trademark VM 26-BRISTOL. Doxorubicin can be administered, e.g. in the form as it is marketed, e.g. under the trademark ADRIBLASTIN or ADRIAMYCIN. Epirubicin can be administered, e.g. in the form as it is marketed, e.g. under the trademark FARMORUBICIN. Idarubicin can be administered, e.g. in the form as it is marketed, e.g. under the trademark ZAVEDOS. Mitoxantrone can be administered, e.g. in the form as it is marketed, e.g. under the trademark NOVANTRON.

The term "microtubule active compound" relates to microtubule stabilizing, microtubule destabilizing compounds and microtublin polymerization inhibitors including, but not limited to taxanes, e.g. paclitaxel and docetaxel, vinca alkaloids, e.g., vinblastine, especially vinblastine sulfate, vincristine especially vincristine sulfate, and vinorelbine, discodermolides, cochicine and epothilones and derivatives thereof, e.g. epothilone B or D or derivatives thereof. Paclitaxel may be administered e.g. in the form as it is marketed, e.g. TAXOL. Docetaxel can be administered, e.g., in the form as it is marketed, e.g. under the trademark TAXOTERE. Vinblastine sulfate can be administered, e.g., in the form as it is marketed, e.g. under the trademark VINBLASTIN R.P. Vincristine sulfate can be administered, e.g., in the form as it is marketed, e.g. under the trademark FARMISTIN. Discodermolide can be obtained, e.g., as disclosed in U.S. Pat. No. 5,010,099. Also included are Epothilone derivatives which are disclosed in WO 98/10121, U.S. Pat. No. 6,194,181, WO 98/25929, WO 98/08849, WO 99/43653, WO 98/22461 and WO 00/31247. Especially preferred are Epothilone A and/or B.

The term "alkylating compound" as used herein includes, but is not limited to, cyclophosphamide, ifosfamide, melphalan or nitrosourea (BCNU or Gliadel). Cyclophosphamide can be administered, e.g., in the form as it is marketed, e.g. under the trademark CYCLOSTIN. Ifosfamide can be administered, e.g., in the form as it is marketed, e.g., under the trademark HOLOXAN.

The term "antineoplastic antimetabolite" includes, but is not limited to, 5-Fluorouracil or 5-FU, capecitabine, gemcitabine, DNA demethylating compounds, such as 5-azacy-tidine and decitabine, methotrexate and edatrexate, and folic acid antagonists such as pemetrexed. Capecitabine can be administered, e.g., in the form as it is marketed, e.g. under the trademark XELODA. Gemcitabine can be administered, e.g., in the form as it is marketed, e.g. under the trademark GEMZAR. The term "platin compound" as used herein includes, but is not limited to, carboplatin, cis-platin, cisplatinum and oxaliplatin. Carboplatin can be administered, e.g., in the form as it is marketed, e.g. under the trademark CARBOPLAT. Oxaliplatin can be administered, e.g., in the form as it is marketed, e.g. under the trademark ELOXATIN.

The term "compounds targeting decreasing a protein or lipid kinase activity"; or a "protein or lipid phosphatase activity"; or "further anti-angiogenic compounds" as used herein includes, but is not limited to, protein tyrosine kinase and/or serine and/or threonine kinase inhibitors or lipid kinase inhibitors, e.g., a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, e.g. a N-phenyl-2-pyrimidine-amine derivative, e.g. imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, such as those compounds disclosed in WO 02/092599, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the Axl receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, i.e C-kit receptor tyrosine kinases—(part of the PDGFR family), such as compounds which target, decrease or inhibit the activity of the c-Kit receptor tyrosine kinase family, especially compounds which inhibit the c-Kit receptor, e.g. imatinib; h) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, e.g. a N-phenyl-2-pyrimidine-amine derivative, e.g. imatinib or nilotinib (AMN107); PD180970; AG957; NSC 680410; PD173955 from ParkeDavis; or dasatinib (BMS-354825); i) compounds targeting, decreasing or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK) and are especially those staurosporine derivatives disclosed in U.S. Pat. No. 5,093,330, e.g. midostaurin; examples offurther compounds include e.g. UCN-01, safingol, BAY 43-9006, Bryostatin 1, Perifosine; Ilmofosine; RO 318220 and RO 320432; GO 6976; Isis 3521; LY333531/LY379196; isochinoline compounds such as those disclosed in WO 00/09495; FTIs; BEZ235 (a PI3K inhibitor) or AT7519 (CDK inhibitor); j) compounds targeting, decreasing or inhibiting the activity of protein-tyrosine kinase inhibitors, such as compounds which target, decrease or inhibit the activity of protein-tyrosine kinase inhibitors include imatinib mesylate (GLEEVEC) or tyrphostin. A tyrphostin is preferably a low molecular weight (mw<1500) compound, or a pharmaceutically acceptable salt thereof, especially a compound selected from the benzylidenemalonitrile class or the S-arylbenzenemalonirile or bisubstrate quinoline class of compounds, more especially any compound selected from the group consisting of Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); k) compounds targeting, decreasing or inhibiting the activity of the epidermal growth factor family of receptor tyrosine kinases (EGFR, ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, e.g. EGF receptor, ErbB2, ErbB3 and ErbB4 or bind to EGF or EGF related ligands, and are in particular those compounds, proteins or monoclonal antibodies generically and specifically disclosed in WO 97/02266, e.g. the compound of ex. 39, or in EP 0 564 409, WO 99/03854, EP 0520722, EP 0 566 226, EP 0 787 722, EP 0 837 063, U.S. Pat. No. 5,747,498, WO 98/10767, WO 97/30034, WO 97/49688, WO 97/38983 and, especially, WO 96/30347 (e.g. compound known as CP 358774), WO 96/33980 (e.g. compound ZD 1839) and WO 95/03283 (e.g. compound ZM105180); e.g. trastuzumab (Herceptin), cetuximab (Erbitux), Iressa, Tarceva, OSI-774, CI-1033, EKB-569, GW-2016, E1.1, E2.4, E2.5, E6.2, E6.4, E2.11, E6.3 or E7.6.3, and 7H-pyrrolo-[2,3-d]pyrimidine derivatives which are disclosed in WO 03/013541; and l) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF.

Further anti-angiogenic compounds include compounds having another mechanism for their activity, e.g. unrelated to protein or lipid kinase inhibition e.g. thalidomide (THALOMID) and TNP-470.

Compounds which target, decrease or inhibit the activity of a protein or lipid phosphatase are e.g., inhibitors of phosphatase 1, phosphatase 2A or CDC25, e.g. okadaic acid or a derivative thereof.

Compounds which induce cell differentiation processes are e.g. retinoic acid, or tocopherol or tocotrienol.

The term cyclooxygenase inhibitor as used herein includes, but is not limited to, e.g. Cox-2 inhibitors, 5-alkyl substituted 2-arylaminophenylacetic acid and derivatives, such as celecoxib (CELEBREX), rofecoxib (VIOXX), etoricoxib, valdecoxib or a 5-alkyl-2-arylaminophenylacetic acid, e.g. 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. "Etridonic acid" can be administered, e.g., in the form as it is marketed, e.g. under the trademark DIDRONEL. "Clodronic acid" can be administered, e.g., in the form as it is marketed, e.g. under the trademark BONEFOS. "Tiludronic acid" can be administered, e.g., in the form as it is marketed, e.g. under the trademark SKELID. "Pamidronic acid" can be administered, e.g. in the form as it is marketed, e.g. under the trademark AREDIA. "Alendronic acid" can be administered, e.g., in the form as it is marketed, e.g. under the trademark FOSAMAN. "Ibandronic acid" can be administered, e.g., in the form as it is marketed, e.g. under the trademark BONDRANAT. "Risedronic acid" can be administered, e.g., in the form as it is marketed, e.g. under the trademark ACTONEL. "Zoledronic acid" can be administered, e.g. in the form as it is marketed, e.g. under the trademark ZOMETA.

The term "mTOR inhibitors" relates to compounds which inhibit the mammalian target of rapamycin (mTOR) and which possess antiproliferative activity such as sirolimus (Rapamune), everolimus (CerticanO), CCI-779 and ABT578.

The term "heparanase inhibitor" as used herein refers to compounds which target, decrease or inhibit heparin sulfate degradation. The term includes, but is not limited to, PI-88.

The term "biological response modifier" as used herein refers to a lymphokine or interferons, e.g. interferon.

The term "inhibitor of Ras oncogenic isoforms", e.g. H-Ras, K-Ras, or N-Ras, as used herein refers to compounds which target, decrease or inhibit the oncogenic activity of Ras e.g. a "farnesyl transferase inhibitor" e.g. L-744832, DKSG557 or R115777 (Zarnestra).

The term "telomerase inhibitor" as used herein refers to compounds which target, decrease or inhibit the activity of telomerase. Compounds which target, decrease or inhibit the activity of telomerase are especially compounds which inhibit the telomerase receptor, e.g. telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase are e.g. bengamide or a derivative thereof.

The term "proteasome inhibitor" as used herein refers to compounds which target, decrease or inhibit the activity of the proteasome. Compounds which target, decrease or inhibit the activity of the proteasome include e.g. Bortezomid (Velcade) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TA 211, MMI270B or AAJ996.

The term "compounds used in the treatment of hematologic malignancies" as used herein includes, but is not limited to, FMS-like tyrosine kinase inhibitors e.g. compounds targeting, decreasing or inhibiting the activity of FMS-like tyrosine kinase receptors (Flt-3R); interferon, 1-b-D-arabinofuransylcytosine (ara-c) and bisulfan; and ALK inhibitors e.g. compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, e.g. PKC412, TKI258, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90 e.g., 17-ally-lamino, 17-demethoxygeldanamycin (17AAG), a geldanamycin derivative; other geldanamycin related compounds; radicicol and HDAC inhibitors. An example HSP90 inhibitor is AUY922.

The term "antiproliferative antibodies" as used herein includes, but is not limited to, trastuzumab (Herceptin), Trastuzumab-DM1, erbitux, bevacizumab (Avastin), rituximab (Rituxan), PRO64553 (anti-CD40) and 2C4 Antibody. By antibodies is meant e.g. intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of formula (I) can be used in combination with standard leukemia therapies, especially in combination with therapies used for the treatment of AML. In particular, compounds of formula (I) can be administered in combination with, e.g., farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

The term "antileukemic compounds" includes, for example, Ara-C, a pyrimidine analog, which is the 2-alpha-hydroxy ribose (arabinoside) derivative of deoxycytidine. Also included is the purine analog of hypoxanthine, 6-mercaptopurine (6-MP) and fludarabine phosphate.

Somatostatin receptor antagonists as used herein refers to compounds which target, treat or inhibit the somatostatin receptor such as octreotide, and SOM230 (pasireotide).

Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in *Principles and Practice of Oncology*, Devita et al., Eds., $4^{th}$ Edition, Vol. 1, pp. 248-275 (1993).

The term "EDG binders" as used herein refers a class of immunosuppressants that modulates lymphocyte recirculation, such as FTY720.

The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives, such as PL-1, PL-2, PL-3, PL-4, PL-5, PL-6, PL-7 or PL-8 mentioned in Nandy et al., *Acta Oncologica*, Vol. 33, No. 8, pp. 953-961 (1994).

The term "S-adenosylmethionine decarboxylase inhibitors" as used herein includes, but is not limited to the compounds disclosed in U.S. Pat. No. 5,461,076.

Also included are in particular those compounds, proteins or monoclonal antibodies of VEGF disclosed in WO 98/35958, e.g. 1-(4-chloroanilino)-4-(4-pyridylmethyl)phthalazine or a pharmaceutically acceptable salt thereof, e.g. the succinate, or in WO 00/09495, WO 00/27820, WO 00/59509, WO 98/11223, WO 00/27819 and EP 0 769 947; those as described by Prewett et al, *Cancer Res*, Vol. 59, pp. 5209-5218 (1999); Yuan et al., *Proc Natl Acad Sci USA*, Vol. 93, pp. 14765-14770 (1996); Zhu et al., *Cancer Res*, Vol. 58, pp. 3209-3214 (1998); and Mordenti et al., *Toxicol Pathol*, Vol. 27, No. 1, pp. 14-21 (1999); in WO 00/37502 and WO 94/10202; ANGIOSTATIN, described by O'Reilly et al., *Cell*, Vol. 79, pp. 315-328 (1994); ENDOSTATIN, described by O'Reilly et al., *Cell*, Vol. 88, pp. 277-285 (1997); anthranilic acid amides; ZD4190; ZD6474; SU5416; SU6668; bevacizumab; or anti-VEGF antibodies or anti-VEGF receptor antibodies, e.g. rhuMAb and RHUFab, VEGF aptamer e.g. Macugon; FLT-4 inhibitors, FLT-3 inhibitors, VEGFR-2 IgG1 antibody, Angiozyme (RPI 4610) and Bevacizumab (Avastin).

Photodynamic therapy as used herein refers to therapy which uses certain chemicals known as photosensitizing compounds to treat or prevent cancers. Examples of photodynamic therapy includes treatment with compounds, such as e.g. VISUDYNE and porfimer sodium.

Angiostatic steroids as used herein refers to compounds which block or inhibit angiogenesis, such as, e.g., anecortave, triamcinolone, hydrocortisone, 11-epihydrocotisol, cortexolone, 17-hydroxyprogesterone, corticosterone, desoxycorticosterone, testosterone, estrone and dexamethasone.

Implants containing corticosteroids refers to compounds, such as e.g. fluocinolone, dexamethasone.

"Other chemotherapeutic compounds" include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The structure of the active compounds identified by code nos., generic or trade names may be taken from the actual edition of the standard compendium "The Merck Index" or from databases, e.g. Patents International (e.g. IMS World Publications).

In an embodiment, the cardiovascular indications for which the HDAC inhibitors may be used include: diastolic dysfunction, myocardial Infarction (systolic dysfunction), inhibition of overall cardiac remodeling in both acute and chronic heart failure conditions, adriamycin induced cardiotoxicity, inducing cardioprotection from ischemic events, and for the use of hemorrhagic shock and resuscitation.

Compounds of the present teachings can be administered orally or parenterally, neat or in combination with conventional pharmaceutical carriers. Applicable solid carriers can include one or more substances which can also act as flavoring agents, lubricants, solubilizers, suspending agents, fillers, glidants, compression aids, binders, tablet-disintegrating agents, or encapsulating materials. The compounds can be formulated in conventional manner, for example, in a manner similar to that used for known HDAC inhibitors. Oral formulations containing an active compound disclosed herein can include any conventionally used oral form, including tablets, capsules, buccal forms, troches, lozenges and oral liquids, suspensions, and solutions. In powders, the carrier can be a finely divided solid, which is an admixture with a finely divided active compound. In tablets, an active compound can be mixed with a carrier having the necessary compression properties in suitable proportions and compacted in the shape and size desired. The powders and tablets may contain up to 99% of the active compound.

Capsules can contain mixtures of active compound(s) optionally with inert filler(s) and/or diluent(s) such as the pharmaceutically acceptable starches (e.g., corn, potato or tapioca starch), sugars, artificial sweetening agents, powdered celluloses (e.g., crystalline and microcrystalline celluloses), flours, gelatins, gums, and the like.

Useful tablet formulations can be made by conventional compression, wet granulation or dry granulation methods and utilize pharmaceutically acceptable diluents, binding agents, lubricants, disintegrants, surface modifying agents (including surfactants), suspending agents, or stabilizing agents, including magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes, and ion exchange resins. Preferred surface modifying agents include nonionic and anionic surface modifying agents. Representative examples of surface modifying agents include poloxamer 188, benzalkonium chloride, calcium stearate, cetostearl alcohol, cetomacrogol emulsifying wax, sorbitan esters, colloidal silicon dioxide, phosphates, sodium dodecylsulfate, magnesium aluminum silicate, and triethanolamine. Oral formulations herein can utilize standard delay or time-release formulations to alter the absorption of the active compound(s). The oral formulation can also consist of administering an active compound in water or fruit juice, containing appropriate solubilizers or emulsifiers as needed.

Liquid carriers can be used in preparing solutions, suspensions, emulsions, syrups, and elixirs. An active compound described herein can be dissolved or suspended in a pharmaceutically acceptable liquid carrier such as water, an organic solvent, a mixture thereof, or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, and osmo-regulators. Examples of liquid carriers for oral and parenteral administration include water (particularly containing additives as described above, e.g., cellulose derivatives such as a sodium carboxymethyl cellulose solution), alcohols (including monohydric alcohols and polyhydric alcohols, e.g., glycols) and their derivatives, and oils (e.g., fractionated coconut oil and arachis oil). For parenteral administration, the carrier can be an oily ester such as ethyl oleate and isopropyl myristate. Sterile liquid carriers are used in sterile liquid form compositions for parenteral administration. The liquid carrier for pressurized compositions can be a halogenated hydrocarbon or other pharmaceutically acceptable propellants.

Liquid pharmaceutical compositions, which are sterile solutions or suspensions, can be utilized by, for example, intramuscular, intraperitoneal, or subcutaneous injection. Sterile solutions can also be administered intravenously. Compositions for oral administration can be in either liquid or solid form.

The pharmaceutical composition can be in unit dosage form, for example, as tablets, capsules, powders, solutions, suspensions, emulsions, granules, or suppositories. In such form, the pharmaceutical composition can be sub-divided in unit dose(s) containing appropriate quantities of the active compound. The unit dosage forms can be packaged compositions, for example, packeted powders, vials, ampoules, prefilled syringes or sachets containing liquids. Alternatively, the unit dosage form can be a capsule or tablet itself, or it can be the appropriate number of any such compositions in package form. Such unit dosage form may contain from about 1 mg/kg of active compound to about 500 mg/kg of active compound, and can be given in a single dose or in two or more doses. Such doses can be administered in any manner useful in directing the active compound(s) to the recipient's bloodstream, including orally, via implants, parenterally (including intravenous, intraperitoneal and subcutaneous injections), rectally, vaginally, and transdermally. Such administrations can be carried out using the compounds of the present teachings including pharmaceutically acceptable salts, hydrates, and esters thereof, in lotions, creams, foams, patches, suspensions, solutions, and suppositories (rectal and vaginal).

When administered for the treatment or inhibition of a particular pathologic condition or disorder, it is understood that an effective dosage can vary depending upon the particular compound utilized, the mode of administration, and/or severity of the condition being treated, as well as the various physical factors related to the individual being treated. In therapeutic applications, a compound of the present teachings can be provided to a patient already suffering from a disease in an amount sufficient to cure or at least partially ameliorate the symptoms of the disease and its complications. In preventive applications, a compound of the present teachings can be provided to a patient that can suffer from a disease in an amount sufficient to prevent or at least delay the symptoms of the disease and its complications. The dosage to be used in the treatment of a specific individual typically must be subjectively determined by the attending physician. The variables involved include the specific condition and its state as well as the size, age and response pattern of the patient.

In some cases, for example, those in which the lung is the targeted organ, it may be desirable to administer a compound directly to the airways of the patient, using devices such as metered dose inhalers, breath-operated inhalers, multidose dry-powder inhalers, pumps, squeeze-actuated nebulized spray dispensers, aerosol dispensers, and aerosol nebulizers. For administration by intranasal or intrabronchial inhalation, the compounds of the present teachings can be formulated into a liquid composition, a solid composition, or an aerosol composition. The liquid composition can include, by way of illustration, one or more compounds of the present teachings dissolved, partially dissolved, or suspended in one or more pharmaceutically acceptable solvents and can be administered by, for example, a pump or a squeeze-actuated nebulized spray dispenser. The solvents can be, for example, isotonic saline or bacteriostatic water. The solid composition can be, by way of illustration, a powder preparation including one or more compounds of the present teachings intermixed with lactose or other inert powders that are acceptable for intrabronchial use, and can be administered by, for example, an aerosol dispenser or a device that breaks or punctures a capsule encasing the solid composition and delivers the solid composition for inhalation. The aerosol composition can include, by way of illustration, one or more compounds of the present teachings, propellants, surfactants, and co-solvents, and can be administered by, for example, a metered device. The propellants can be a chlorofluorocarbon (CFC), a hydrofluoroalkane (HFA), or other propellants that are physiologically and environmentally acceptable.

Compounds described herein can be administered parenterally or intraperitoneally. Solutions or suspensions of these active compounds or pharmaceutically acceptable salts, hydrates, or esters thereof can be prepared in water mixed with a suitable surfactant such as hydroxyl-propylcellulose. Dispersions can also be prepared in glycerol, liquid polyethylene glycols, and mixtures thereof in oils. Under ordinary conditions of storage and use, these preparations typically contain a preservative to inhibit the growth of microorganisms.

The pharmaceutical forms suitable for injection can include sterile aqueous solutions or dispersions and sterile powders for the extemporaneous preparation of sterile injectable solutions or dispersions. In preferred embodiments, the form is sterile and its viscosity permits it to flow through a syringe. The form preferably is stable under the conditions of manufacture and storage and can be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Compounds of the present teachings can be administered transdermally, i.e., administered across the surface of the body and the inner linings of bodily passages including epithelial and mucosal tissues. Such administration can be carried out using the compounds of the present teachings including pharmaceutically acceptable salts, hydrates, or esters thereof, in lotions, creams, foams, patches, suspensions, solutions, and suppositories (rectal and vaginal). Topical formulations that deliver active compound(s) through the epidermis can be useful for localized treatment of a pathologic condition or disorder.

Transdermal administration can be accomplished through the use of a transdermal patch containing an active compound and a carrier that can be inert to the active compound, can be non-toxic to the skin, and can allow delivery of the active compound for systemic absorption into the blood stream via the skin. The carrier can take any number of forms such as creams, ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the active compound can also be suitable. A variety of occlusive devices can be used to release the active compound into the blood stream, such as a semi-permeable membrane covering a reservoir containing the active compound with or without a carrier, or a matrix containing the active compound. Other occlusive devices known in the literature are also contemplated.

Compounds described herein can be administered rectally or vaginally in the form of a conventional suppository. Suppository formulations can be made from traditional materials, including cocoa butter, with or without the addition of waxes to alter the suppository's melting point, and glycerin. Water-soluble suppository bases, such as polyethylene glycols of various molecular weights, can also be used.

Lipid formulations or nanocapsules can also be used to introduce compounds of the present teachings into host cells either in vitro or in vivo. Lipid formulations and nanocapsules can be prepared by methods known in the art.

To increase the effectiveness of compounds of the present teachings, it can be desirable to combine a compound disclosed herein with other agents effective in the treatment of the target disease. For proliferative diseases, other active compounds (i.e., other active ingredients or agents) effective in their treatment, and particularly in the treatment of cancers and tumors, can be administered with active compounds of the present teachings. The other agents can be administered at the same time or at different times than the compounds disclosed herein.

The compounds of the present teachings can be prepared in accordance with the procedures outlined in the scheme below, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures. Those skilled in the art of organic synthesis will recognize that the nature and order of the synthetic steps presented may be varied for the purpose of optimizing the preparation of the compounds described herein.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), or mass spectrometry, or by chromatography such as high performance liquid chromatography (HPLC), gas chromatograph (GC), or thin layer chromatography.

Preparation of Compounds can Involve the Protection and Deprotection of Various chemical groups. The need for protection and deprotection and the selection of appropriate protecting groups can be readily determined by one skilled in the art. The chemistry of protecting groups can be found, for example, in Greene, et al., *Protective Groups in Organic Synthesis,* 4th Ed., Wiley & Sons, 2006, the entire disclosure of which is incorporated by reference herein for all purposes.

The reactions described herein can be carried out in suitable solvents which can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

Example 1

Preparation of (E)-3-((S)-4-pyrrolidin-2-yl-phenyl)-acrylic acid methyl ester hydrochloride Step a: Preparation of(S)-2-(4-bromo-phenyl)-pyrrolidine-1-carboxylic acid tert-butyl ester

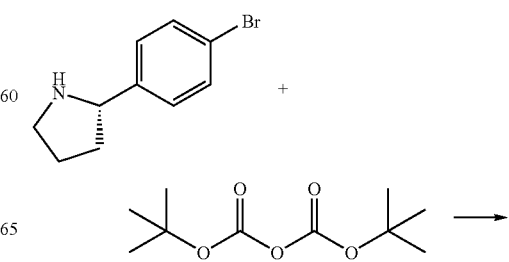

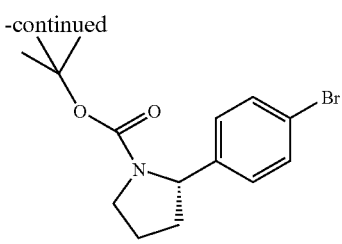

To a stirred suspension of (S)-2-(4-bromo-phenyl)-pyrrolidine (66.5 g, 168 mmol as tartaric acid salt) and N-methyl morpholine (46.2 mL, 420 mmol) in dichloromethane (400 mL) and N,N-dimethylformamide (40 mL) was added di-tert-butyldicarbonate (40.5 g, 185 mmol) in dichloromethane (100 mL). The reaction was stirred at room temperature for 4 hours (h). Ethyl acetate (1.5 L) was added and the resulting solution was washed twice with water (200 mL), saturated aqueous solution of sodium chloride (50 mL), four times with 10% citric acid until aqueous layer was acidic, twice with saturated sodium bicarbonate, and a saturated aqueous solution of sodium chloride. The organic solution was dried with sodium sulfate, filtered and concentrated in vacuo to yield 49.6 g (91%) of the title compound as an off-white solid.

Step b: Preparation of (S)-2-[4-((E)-2-methoxycarbonyl-vinyl)-phenyl]-pyrrolidine-1-carboxylic acid tert-butyl ester

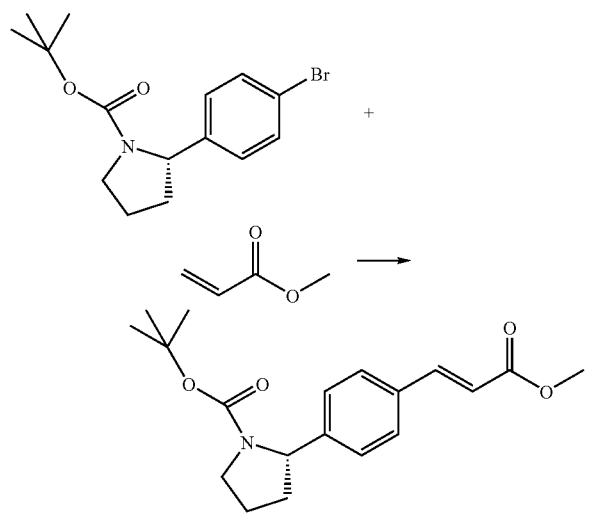

To a degassed solution of (S)-2-(4-bromo-phenyl)-pyrrolidine-1-carboxylic acid tert-butyl ester (44.0 g, 128 mmol) in 1,4-dioxane (500 mL) in a sealed pressure vessel was sequentially added N-methyldicyclohexylamine (32.9 mL, 154 mmol), (t-Bu)$_3$HBF$_4$ (1.19 g, 4.10 mmol), methyl acrylate (34.8 mL, 385 mmol) and Pd$_2$(dba)$_3$ (1.19 g, 1.29 mmol). The reaction mixture was heated to 150° C. in a sealed pressure vessel for 4.5 h then cooled in ice bath and placed in refrigerator for 16 h. The reaction mixture was filtered through a Celite pad, the filter cake was washed with 250 mL ethyl acetate, and the combined organics were concentrated in vacuo to a yellow oil. The oil was taken up in 20% ethyl acetate in heptane, sonicated and filtered, and the filtrate was concentrated again in vacuo. The residue was dissolved in ethyl acetate and the organic solution was washed sequentially with 10% citric acid, sodium bicarbonate solution and saturated sodium chloride solution, dried over sodium sulfate, filtered and concentrated in vacuo. The residue was purified via silica gel column chromatography (ethyl acetate/heptane) or recrystallized from 20% ethyl acetate in heptane. Total recovery is 42.1 g (99% yield).

Step c: Preparation of (E)-3-((S)-4-pyrrolidin-2-yl-phenyl)-acrylic acid methyl ester hydrochloride To a stirred solution of (S)-2-[4-((E)-2-methoxycarbonyl-vinyl)-phenyl]-pyrrolidine-1-carboxylic acid tert-butyl ester (40.2 g, 115 mmol) was added 120 mL of 4 N hydrochloric acid in dioxane and the reaction mixture was stirred for 16 h. Diethyl ether (500 mL) was added to the suspension and the resulting solid was filtered and washed twice with diethyl ether to yield 29.0 g (94%) of the title compound as a white solid.

Example 2

Typical Procedure for Conversion of Esters to Hydroxamic Acids

To a stirred solution of (E)-3-((S)-4-pyrrolidin-2-yl-phenyl)-acrylic acid methyl ester (4 mmol) in methanol (5 mL) at 0° C. was added sodium methoxide (5 equivalents, 20 mmol of a 25% solution in methanol) and 10 equivalents of hydroxylamine (50% solution in water). The reaction was monitored by LCMS and, upon completion, was brought to pH 7-8 with 1 N hydrochloric acid whereupon a precipitate formed. The solid was filtered, washed with water, and dried in vacuo to yield the desired hydroxamic acid.

Example 3

Typical Procedure for Alkylation of (E)-3-((S)-4-pyrrolidin-2-yl-phenyl)-acrylic acid methyl ester Via Reductive Amination To a solution of (E)-3-((S)-4-pyrrolidin-2-yl-phenyl)-acrylic acid methyl ester (892 mg, 3.33 mmol) in tetrahydrofuran were added triethylamine (0.93 mL, 6.66 mmol), the corresponding aldehyde (4.99 mmol), and sodium triacetoxyborohydride (1.64 g, 7.35 mol). The resulting mixture was stirred for about 3-24 hours. The reaction mixture was diluted with ethyl acetate, washed sequentially with a saturated aqueous sodium bicarbonate solution and a saturated aqueous sodium chloride solution, dried over sodium sulfate, filtered, and concentrated in vacuo to produce a crude product, which as purified via chromatography to provide the alkylated (E)-3-((S)-4-pyrrolidin-2-yl-phenyl)-acrylic acid methyl ester.

Example 4

Typical Procedure for Alkylation of (E)-3-((S)-4-Pyrrolidin-2-yl-phenyl)-acrylic acid methyl ester with Alkyl Bromides or Alkyl Mesylates

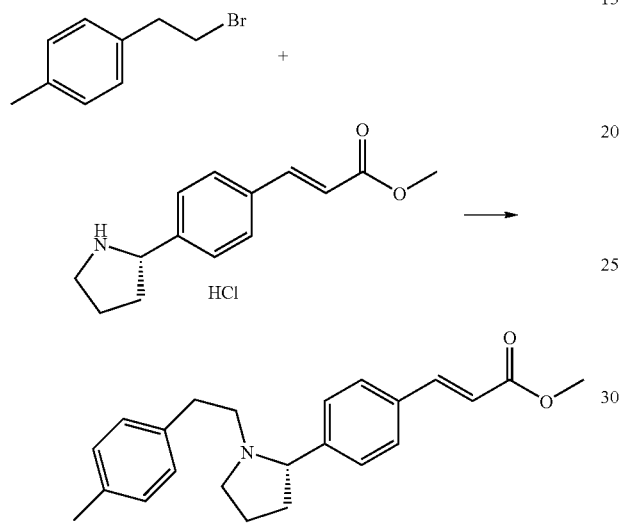

To a suspension of (E)-3-((S)-4-pyrrolidin-2-yl-phenyl)-acrylic acid methyl ester hydrochloride (0.3 g, 1.1 mmol) and potassium carbonate (0.4 g, 2.9 mmol) in acetonitrile (20 mL) was added 4-methylphenethyl bromide (0.2 mL, 1.3 mmol). The mixture was heated at the reflux temperature for 16 h, cooled to room temperature, filtered and concentrated in vacuo. The residue was dissolved in ethyl acetate, washed with water and saturated aqueous sodium chloride, dried over anhydrous sodium sulfate, filtered, and concentrated in vacuo to produce a crude product which was purified via silica gel column chromatography (ethyl acetate/heptanes) to provide the title compound (0.32 g, 82% yield) as a light yellow oil.

Example 5

Typical Procedure for Alkylation of (E)-3-((S)-4-pyrrolidin-2-yl-phenyl)-acrylic acid methyl ester with Epoxides

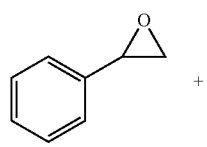

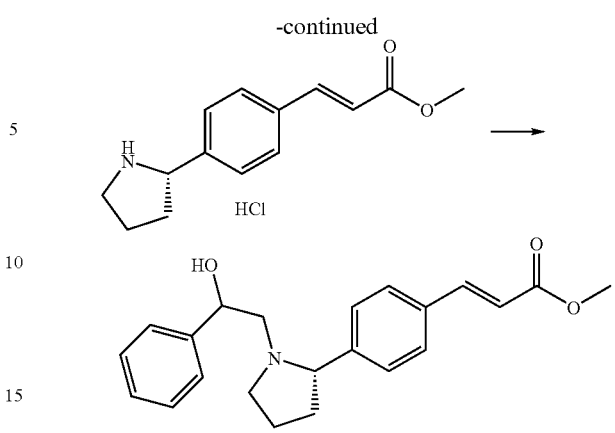

To a solution of (E)-3-((S)-4-pyrrolidin-2-yl-phenyl)-acrylic acid methyl ester hydrochloride (0.2 g, 0.75 mmol) and triethylamine (0.15 mL, 1.1 mmol) in isopropanol (5 mL) was added styrene oxide (0.12 mL, 1.05 mmol) and the reaction mixture was stirred at 90° C. for 16 h. The reaction mixture was concentrated under reduced pressure and the residue was purified via silica gel column chromatography (0-25% ethyl acetate in petroleum ether) to obtain the title compound as a brown oil (0.19 g, 0.54 mmol).

Example 6

Typical Procedure for Homologation of Aryl Aldehydes

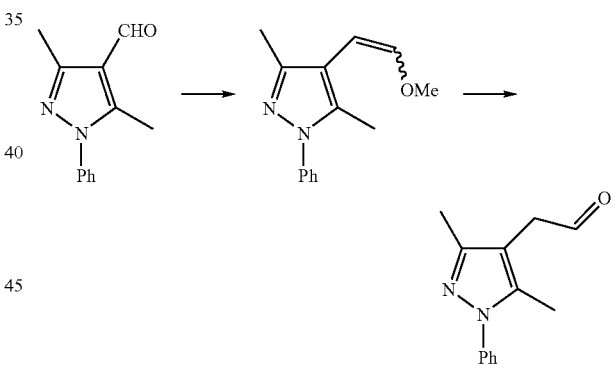

Step a: Preparation of 4-(2-methoxy-vinyl)-3,5-dimethyl-1-phenyl-1H-pyrazole

To an ice-cold suspension of methoxymethyltriphenylphosphonium chloride (26.2 g, 74.9 mmol) in 300 mL tetrahydrofuran was added n-butyllithium (31 mL, 2.5 M in hexane). The mixture was stirred at 0° C. for 15 minutes and treated with 3,5-dimethyl-1-phenyl-1H-pyrazole-4-carbaldehyde (7.5 g, 37.5 mmol, suspended in 150 mL tetrahydrofuran). The mixture was slowly warmed to room temperature over 2 hours and quenched by slow addition of a saturated aqueous sodium chloride solution. The resulting white precipitate was removed by filtration and the filtrate was extracted several times with ethyl acetate. The combined organic layers were dried over magnesium sulfate and concentrated in vacuo to an oil, which was purified via silica gel column chromatography (0-20% ethyl acetate in heptane) to provide the title compound as a yellow oil (7.09 g, 31.1 mmol, 83% yield) as a mixture of E:Z isomers.

Step b: Preparation of (3,5-dimethyl-1-phenyl-1H-pyrazol-4-yl)-acetaldehyde

To a stirred solution of 4-(2-methoxy-vinyl)-3,5-dimethyl-1-phenyl-1H-pyrazole (7.09 g, 31.1 mmol) in 100 mL isopropanol-water (1:1 v/v) was added p-toluenesulfonic acid monohydrate (1.5 g, 7.76 mmol). After the reaction was heated at 60° C. for 16 h, 1.9 mL concentrated hydrochloric acid was added and the reaction mixture was heated at 60° C. for 20 h. The organic solvent was removed in vacuo and the remaining aqueous suspension was neutralized with an aqueous sodium bicarbonate solution and extracted several times with a dichloromethane-ethyl acetate mixture. The combined organic extracts were dried over magnesium sulfate and concentrated in vacuo to produce a residue, which was purified via silica gel column chromatography (0-50% ethyl acetate in heptane) to give the title compound as a yellow solid (4.02 g, 18.8 mmol, 60% yield).

Example 7

Typical Procedure for Formation of 1-(2-bromoethyl)-1H-pyrazoles from 1-H-pyrazoles

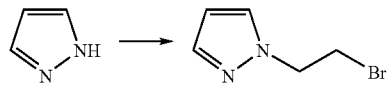

A stirred suspension of pyrazole (2 g, 29.4 mmol), 1,2-dibromoethane (25.3 mL, 294 mmol), tetrabutylammonium bromide (159 mg, 2.94 mmol), and 40% aqueous sodium hydroxide (9 mL, 88 mmol) was heated at 30° C. for 16 hours. The resulting material was washed twice with water, dried over sodium sulfate, filtered and concentrated in vacuo to produce an oil, which was purified by silica gel column chromatography (ethyl acetate/heptanes) to yield the desired alkyl bromide.

Example 8

Typical Procedure for Reduction of Ketones to Hydroxy Analogs

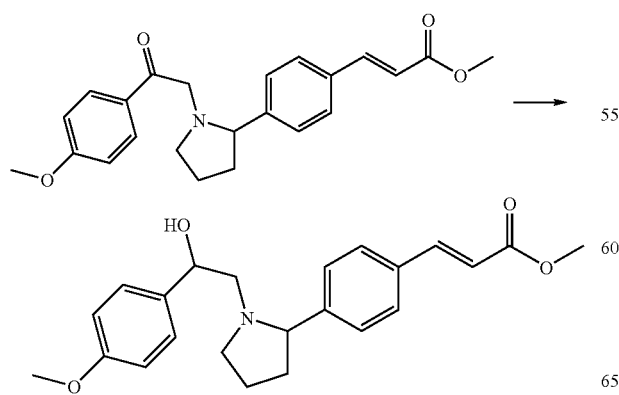

To a solution of (E)-3-(4-{1-[2-(4-methoxy-phenyl)-2-oxo-ethyl]-pyrrolidin-2-yl}-phenyl)-acrylic acid methyl ester (0.4 g, 1.05 mmol) (prepared from 2-bromo-4'-methoxyacetophenone following procedures analogous to those described in Example 4) in methanol (20 mL) at 0° C. was added sodium borohydride (0.04 g, 1.06 mmol). The resulting mixture was warmed to room temperature over one hour. The mixture was concentrated and purified by silica gel column chromatography (0-20% ethyl acetate in petroleum ether) to obtain the product as brown oil (0.35 g, 0.92 mmol, 88% yield) as a mixture of diastereomers.

Example 9

Typical Procedure for Formation of Aryl and Heteroaryl Acetaldehydes

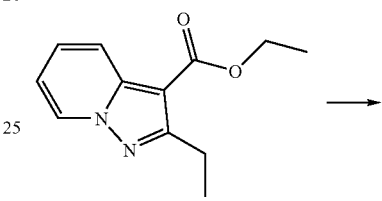

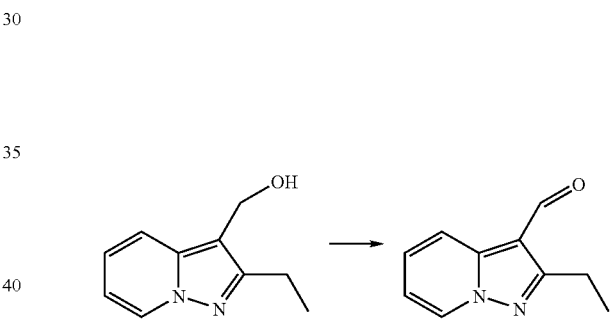

Step a: Preparation of (2-ethyl-pyrazolo[1,5-a]pyridin-3-yl)-methanol

A solution of 2-ethyl-pyrazolo[1,5-a]pyridine-3-carboxylic acid ethyl ester (15 g, 68.7 mmol) in tetrahydrofuran (300 mL) was cooled in an ice bath and lithium aluminum hydride (2.6 g, 68.7 mmol) was added. The reaction mixture was stirred at room temperature for 16 h. Water was added until bubbling stopped. Silica gel was added and the solvent was evaporated in vacuo. The resulting residue was purified via silica chromatography (20-100% ethyl acetate/heptane) to yield the title compound as a yellow/brown oil (9.67 g, 80% yield).

Step b: Preparation of 2-ethyl-pyrazolo[1,5-a]pyridine-3-carbaldehyde

To a solution of (2-ethyl-pyrazolo[1,5-a]pyridin-3-yl)-methanol (9.67 g, 54.9 mmol) in tetrahydrofuran (500 mL) was added MnO$_2$ (23.88 g, 274.5 mmol, 85%, dried in oven at 120° C. for 16 h) and stirred at the reflux temperature for 1.5 h. The reaction mixture was filtered through a Celite pad, and concentrated under reduced pressure to give 9.4 g (98%) of product, which was used without further purification.

Example 10

Preparation of 2-ethyl-pyrazolo[1,5-a]pyridine-3-carboxylic acid ethyl ester

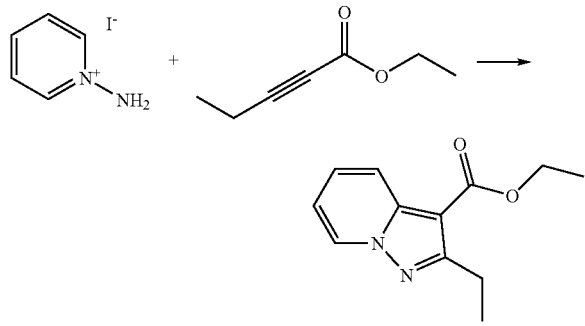

To a solution of amino-pyridinium iodide (22 g, 99 mmol) and anhydrous potassium carbonate (17.8 g, 128.7 mmol) in dimethylformamide (225 mL) was added ethyl-2-pentynoate (24.98 g, 198 mmol). The solution was stirred at room temperature for 24 h. The reaction mixture was poured into 1.2 L of ice water. The resulting light brown precipitate was collected by vacuum filtration and air-dried for 16 h to yield crude product (1.9 g, 55%), which was used without further purification.

Example 11

Preparation of (E)-N-hydroxy-3-(4-{1-[2-(2-methyl-1H-indol-3-yl)-ethyl]-pyrrolidin-2-yl}-phenyl)-acrylamide (1)

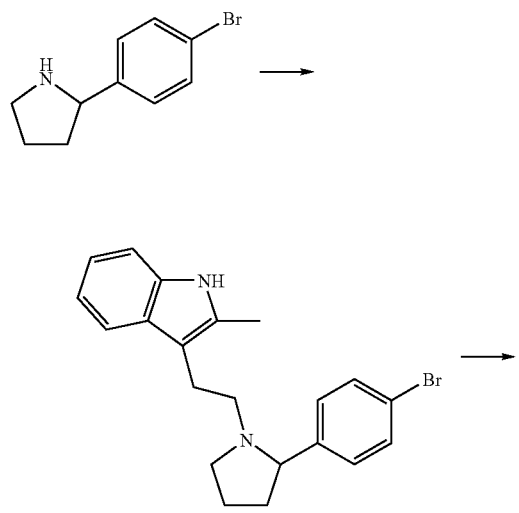

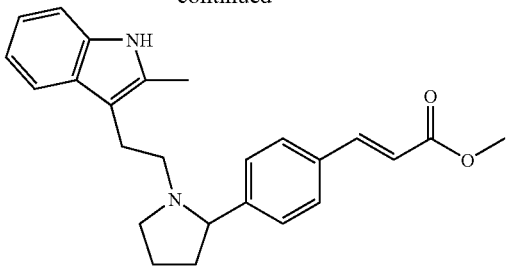

To a solution of 2-(4-bromo-phenyl)-pyrrolidine (326 mg, 1.44 mmol) in dichloromethane (20 mL) were added (2-methyl-1H-indol-3-yl)-acetaldehyde (250 mg, 1.44 mmol), triethylamine (0.603 mL, 4.33 mmol) and a solution of titanium (IV) chloride in dichloromethane (0.720 mL, 1 M, 0.72 mmol), and the resulting mixture was stirred at room temperature. The reaction mixture was treated with sodium cyanoborohydride (286 mg, 4.32 mmol), stirred for 2 h, basified to pH 13 with an aqueous 5 N sodium hydroxide solution, and extracted with ethyl acetate. The organic layers were combined, dried over magnesium sulfate, filtered and concentrated to provide a crude product, which was purified on silica gel column chromatography to give 3-{2-[2-(4-bromo-phenyl)-pyrrolidin-1-yl]-ethyl}-2-methyl-1H-indole (630 mg, 99% yield). LCMS (m/z): 384.84 (M+1).

A solution of 3-{2-[2-(4-bromo-phenyl)-pyrrolidin-1-yl]-ethyl}-2-methyl-1H-indole (630 mg, 1.63 mmol), methyl acrylate (286 mg, 3.26 mmol), Pd$_2$(dba)$_3$ (14.9 mg, 0.0162 mmol), P(t-Bu)$_3$HBF$_4$ (18.9 mg, 0.0652 mmol) and Cy$_2$NMe (414 µL, 1.95 mmol) in dioxane (10 mL) was heated at 100° C. by microwave for 60 minutes. The mixture was diluted with ethyl acetate, washed with water and brine, dried over magnesium sulfate, filtered, and concentrated to provide a crude product, which was purified on silica gel column chromatography to give (E)-3-(4-{1-[2-(2-Methyl-1H-indol-3-yl)-ethyl]-pyrrolidin-2-yl}-phenyl)-acrylic acid methyl ester (400 mg, 63%). LCMS (m/z): 388.97 (M+1).

Following procedures analogous to those described in Example 2 and using (E)-3-(4-{1-[2-(2-methyl-1H-indol-3-yl)-ethyl]-pyrrolidin-2-yl}-phenyl)-acrylic acid methyl ester (400 mg), (E)-N-hydroxy-3-(4-{1-[2-(2-methyl-1H-indol-3-yl)-ethyl]-pyrrolidin-2-yl}-phenyl)-acrylamide (1, 26 mg, 6.5%) was prepared. LCMS (m/z): 389.9 (M+1).

Example 12

Preparation of (E)-N-hydroxy-3-(4-{1-[3-(1H-indol-3-yl)-propyl]-pyrrolidin-2-yl}-phenyl)-acrylamide (2)

Following procedures analogous to those described in Example 11, (E)-3-(4-{1-[3-(1H-indol-3-yl)-propyl]-pyrrolidin-2-yl}-phenyl)-acrylic acid methyl ester was prepared. LCMS (m/z): 389.18 (M+1).

Following procedures analogous to those described in Example 2 and using (E)-3-(4-{1-[3-(1H-indol-3-yl)-propyl]-pyrrolidin-2-yl}-phenyl)-acrylic acid methyl ester (200 mg), (E)-N-hydroxy-3-(4-{1-[3-(1H-indol-3-yl)-propyl]-pyrrolidin-2-yl}-phenyl)-acrylamide (2, 16 mg, 8.1%) was prepared. LCMS (m/z): 390.2166 (M+1).

Example 13

Preparation of (E)-N-hydroxy-3-(4-{1-[2-(1H-indol-3-yl)-ethyl]-pyrrolidin-2-yl}-phenyl)-acrylamide (3)

Following procedures analogous to those described in Example 11, (E)-3-(4-{1-[2-(1H-indol-3-yl)-ethyl]-pyrrolidin-2-yl}-phenyl)-acrylic acid methyl ester was prepared. LCMS (m/z): 375.15 (M+1).

Following procedures analogous to those described in Example 2 and using (E)-3-(4-{1-[2-(1H-indol-3-yl)-ethyl]-pyrrolidin-2-yl}-phenyl)-acrylic acid methyl ester (180 mg), (E)-N-hydroxy-3-(4-{1-[2-(1H-indol-3-yl)-ethyl]-pyrrolidin-2-yl}-phenyl)-acrylamide (3, 117 mg, 65%) was prepared. LCMS (m/z): 376.1 (M+1).

Example 14

Preparation of (E)-N-hydroxy-3-(4-{(S)-1-[2-(2-methyl-indol-1-yl)-ethyl]-pyrrolidin-2-yl}-phenyl)-acrylamide (4)

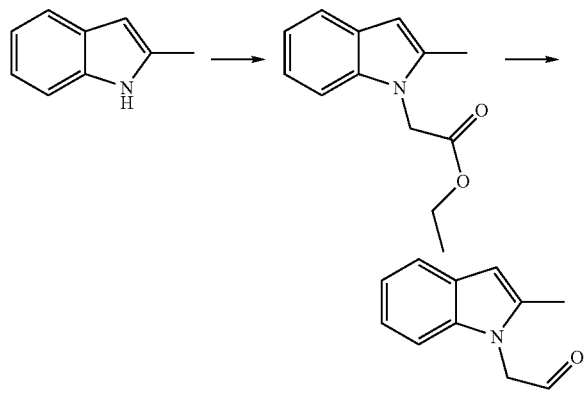

A solution of 2-methyl-1H-indole (1.0 g, 7.6 mmol) in acetonitrile (25 mL) was treated with 2-bromoacetate (2.54 mL, 22.9 mmol), cesium carbonate (2.10 g, 11.4 mmol) and potassium iodide (253 mg, 1.52 mmol) and the resulting mixture was stirred at room temperature for 16 h. The mixture was diluted with ethyl acetate, washed with water and brine, dried over sodium sulfate, filtered, and concentrated, and the residue was purified to give (2-methyl-indol-1-yl)-acetic acid ethyl ester (1.36 g, 82% yield). LCMS (m/z): 218.1 (M+1).

A solution of (2-methyl-indol-1-yl)-acetic acid ethyl ester (400 mL, 1.97 mmol) in dimethoxyethane-dichloromethane (1:1, 30 mL) was cooled to −70° C. and treated with a solution of diisobutyl aluminum hydride in cyclohexane (3.9 mL, 1.0 M). The reaction was stirred at −70° C. for 4 h, quenched with an aqueous solution of hydrochloric acid (80 mL, 1 N) and extracted with ethyl acetate. The organic layers were combined, dried over sodium sulfate, filtered and concentrated, and the residue was purified to give (2-methyl-indol-1-yl)-acetaldehyde (234 mg, 75% yield). LCMS (m/z): 206.1 (M+1).

Following procedures analogous to those described in Example 3, (E)-3-(4-{1-[2-(2-methyl-1H-indol-3-yl)-ethyl]-pyrrolidin-2-yl}-phenyl)-acrylic acid methyl ester (72 mg, 50%) was prepared from (2-methyl-indol-1-yl)-acetaldehyde (100 mg). LCMS (m/z): 389.2 (M+1).

Following procedures analogous to those described in Example 2, (E)-N-hydroxy-3-(4-{(S)-1-[2-(2-methyl-indol-1-yl)-ethyl]-pyrrolidin-2-yl}-phenyl)-acrylamide (4, 76 mg, 67%) was prepared from (E)-3-(4-{1-[2-(2-methyl-1H-indol-3-yl)-ethyl]-pyrrolidin-2-yl}-phenyl)-acrylic acid methyl ester (113 mg). LCMS (m/z): 390.33 (M+1).

Example 15

Preparation of (E)-N-hydroxy-3-{4-[(S)-1-(2-indol-1-yl-ethyl)-pyrrolidin-2-yl]-phenyl}-acrylamide (5)

Following procedures analogous to those described in Example 14, indol-1-yl-acetaldehyde was prepared. LCMS (m/z): 158.1 (M−1).

Following procedures analogous to those described in Example 3, (E)-3-{4-[(S)-1-(2-indol-1-yl-ethyl)-pyrrolidin-2-yl]-phenyl}-acrylic acid methyl ester (125 mg, 50%) was prepared from indol-1-yl-acetaldehyde (180 mg). LCMS (m/z): 375.3 (M+1).

Following procedures analogous to those described in Example 2, (E)-N-hydroxy-3-{4-[(S)-1-(2-indol-1-yl-ethyl)-pyrrolidin-2-yl]-phenyl}-acrylamide (5, 36 mg, 18%) was prepared from (E)-3-{4-[(S)-1-(2-indol-1-yl-ethyl)-pyrrolidin-2-yl]-phenyl}-acrylic acid methyl ester (197 mg). LCMS (m/z): 376.2026 (M+1).

Example 16

Preparation of (E)-N-hydroxy-3-(4-{(S)-1-[2-(5-methoxy-2-methyl-1H-indol-3-yl)-ethyl]-pyrrolidin-2-yl}-phenyl)-acrylamide (6)

Following procedures analogous to those described in Example 3, (E)-3-(4-{(S)-1-[2-(5-methoxy-2-methyl-1H-indol-3-yl)-ethyl]-pyrrolidin-2-yl}-phenyl)-acrylic acid methyl ester (140 mg, 50%) was prepared. LCMS (m/z): 418.8 (M+).

Following procedures analogous to those described in Example 2, (E)-N-hydroxy-3-(4-{(S)-1-[2-(5-methoxy-2-methyl-1H-indol-3-yl)-ethyl]-pyrrolidin-2-yl}-phenyl)-acrylamide (6, 101 mg, 72%) was prepared from (E)-3-(4-{(S)-1-[2-(5-methoxy-2-methyl-1H-indol-3-yl)-ethyl]-pyrrolidin-2-yl}-phenyl)-acrylic acid methyl ester (140 mg). LCMS (m/z): 420.2 (M+1).

Example 17

Preparation of (E)-N-hydroxy-3-(4-{1-[2-(2-phenyl-1H-indol-3-yl)-ethyl]-pyrrolidin-2-yl}-phenyl)-acrylamide (7)

Following procedures analogous to those described in Example 11, (E)-3-(4-{1-[2-(2-phenyl-1H-indol-3-yl)-ethyl]-pyrrolidin-2-yl}-phenyl)-acrylic acid methyl ester was prepared. LCMS (m/z): 451.15 (M+1).

Following procedures analogous to those described in Example 2, (E)-N-hydroxy-3-(4-{1-[2-(2-phenyl-1H-indol-3-yl)-ethyl]-pyrrolidin-2-yl}-phenyl)-acrylamide (7, 74 mg, 21%) was prepared from (E)-3-(4-{1-[2-(2-phenyl-1H-indol-3-yl)-ethyl]-pyrrolidin-2-yl}-phenyl)-acrylic acid methyl ester (360 mg). LCMS (m/z): 451.86 (M+1).

Example 18

Preparation of (E)-N-hydroxy-3-[4-(1-{2-[2-(5-methyl-isoxazol-3-yl)-1H-indol-3-yl]-ethyl}-pyrrolidin-2-yl)-phenyl]-acrylamide (8)

With vigorous stirring, POCl$_3$ (1.4 mL, 15 mmol) was added slowly to dimethylformamide (2 mL) at 0° C. 2-(5-

Methyl-isoxazol-3-yl)-1H-indole (1.0 g, 5.04 mmol) dissolved in N,N-dimethylformamide (8 mL) was added. The reaction mixture was allowed to come to room temperature, stirred for 4 h, and quenched with ice cold water followed by a 10% sodium hydroxide solution. The resulting precipitate was washed with water, dried in vacuo, and purified via silica gel column chromatography (30% ethyl acetate in petroleum ether) to obtain 2-(5-methyl-isoxazol-3-yl)-1H-indole-3-carbaldehyde (0.6 g, 2.65 mmol) as a white solid.

Following procedures analogous to those described in Example 6, [2-(5-methyl-isoxazol-3-yl)-1H-indol-3-yl]-acetaldehyde (0.4 g) was prepared from the aldehyde above.

Following procedures analogous to those described in Example 3, (E)-3-[4-((S)-1-{2-[2-(5-methyl-isoxazol-3-yl)-1H-indol-3-yl]-ethyl}-pyrrolidin-2-yl)-phenyl]-acrylic acid methyl ester (0.16 g, 0.35 mmol) was prepared from the aldehyde above (0.3 g, 1.12 mmol, 31% yield).

Following procedures analogous to those described in Example 2, (E)-N-hydroxy-3-[4-(1-{2-[2-(5-methyl-isoxazol-3-yl)-1H-indol-3-yl]-ethyl}-pyrrolidin-2-yl)-phenyl]-acrylamide was prepared (8, 0.12 g) as a pale brown solid. LCMS (m/z): 457.2 (M+1).

Example 19

Preparation of (E)-3-(4-{(S)-1-[2-(2-tert-butyl-6-nitro-1H-indol-3-yl)-ethyl]-pyrrolidin-2-yl}-phenyl)-N-hydroxy-acrylamide (9)

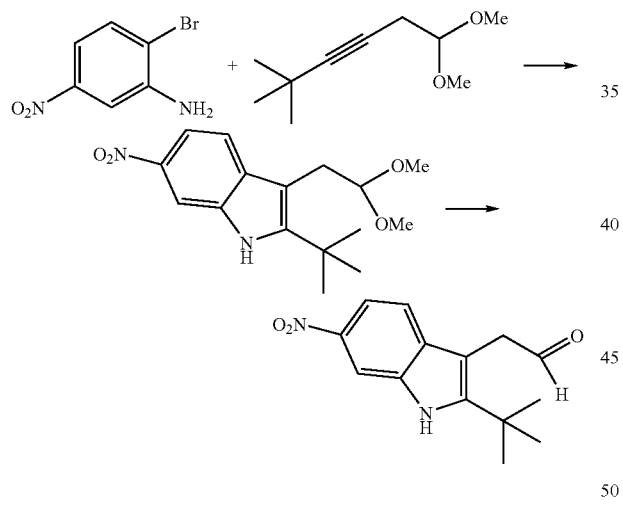

Step a: Preparation of 2-tert-butyl-3-(2,2-dimethoxy-ethyl)-6-nitro-1H-indole

2-Bromo-5-nitro-phenylamine (4.9 g, 22.6 mol), Pd$_2$(dba)$_3$ (207 mg, 0.226 mmol), and 2-dicyclohexylphosphino-2',4',6'-triisopropylbiphenyl (431 mg, 0.904 mmol) was added in a dry 500 mL round-bottom flask. The flask was evacuated and purged with nitrogen three times. 1,1-Dimethoxy-5,5-dimethyl-hex-3-yne (4.61 g, 27.1 mmol), dicyclohexyl-methyl-amine (14.5 mL, 67.8 mmol) and N,N-dimethylformamide (56.5 mL) was added. The reaction mixture was stirred at 100° C. for 24 h, cooled to room temperature, and filtered through a pad of Celite, which was rinsed with ethyl acetate. The filtrate and wash were combined, washed with water and a saturated sodium chloride solution, dried over magnesium sulfate, filtered and concentrated in vacuo. The crude product was purified by silica gel column chromatography to give the title compound as an orange powder (1.41 g, 20%). LCMS (m/z): 307.1 (M+1).

Step b: Preparation of (2-tert-butyl-5-nitro-1H-indol-3-yl)-acetaldehyde

To a solution of 2-tert-butyl-3-(2,2-dimethoxy-ethyl)-6-nitro-1H-indole (1.08 g, 3.54 mmol) in dichloromethane (11.8 mL) was added trifluoroacetic acid (5.9 mL, 50% aqueous) dropwise at 0° C. After stirred for 1 h, the reaction was warmed to room temperature and quenched with a saturated sodium bicarbonate solution until neutral pH was reached. The mixture was separated and the aqueous phase was extracted three times with dichloromethane (75 mL). The combined organic phases were washed with saturated sodium chloride solution, dried over magnesium sulfate, filtered, and concentrated in vacuo to give the title compound as an orange powder (546 mg, 59%). LCMS (m/z): 261.0 (M+1).

Following procedures analogous to those described in Example 3, (E)-3-(4-{(S)-1-[2-(2-tert-butyl-6-nitro-1H-indol-3-yl)-ethyl]-pyrrolidin-2-yl}-phenyl)-acrylic acid methyl ester (0.11 g, 0.231 mmol, 40% yield) was prepared from (2-tert-butyl-6-nitro-1H-indol-3-yl)-acetaldehyde (0.15 g, 0.576 mmol).

Following procedures analogous to those described in Example 2, (E)-3-(4-{(S)-1-[2-(2-tert-butyl-6-nitro-1H-indol-3-yl)-ethyl]-pyrrolidin-2-yl}-phenyl)-N-hydroxy-acrylamide was prepared (9, 41 mg, 0.086 mmol, 37% yield) as a yellow solid. LCMS (m/z): 477.2 (M+1).

Example 20

Preparation of (E)-3-(4-{1-[2-(2-tert-butyl-6-methanesulfonylamino-1H-indol-3-yl)-ethyl]-pyrrolidin-2-yl}-phenyl)-N-hydroxy-acrylamide (10)

Step a: Preparation of (2-tert-butyl-6-nitro-1H-indol-3-yl)-acetaldehyde

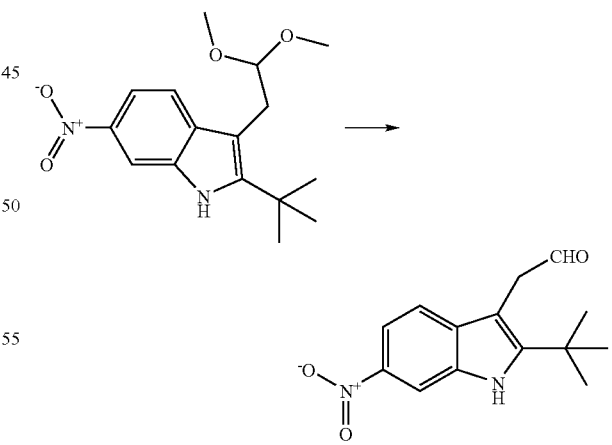

To a solution of 2-tert-butyl-3-(2,2-dimethoxy-ethyl)-6-nitro-1H-indole (0.80 g, 2.6 mmol) in methylene chloride (10 mL) was added trifluoroacetic acid (5 mL, 50%) at 0° C. and the resulting solution was stirred at room temperature for 6 h. Saturated sodium bicarbonate was added until pH>7. The aqueous layer was extracted with methylene chloride several times. The combined organic layers were dried over sodium sulfate, filtrated, and concentrated in vacuo. The residue was purified via silica gel column chromatography to give the title compound (0.62 g, 91%). LCMS (m/z): 261.0 (M+1).

Step b: Preparation of (E)-3-(4-{1-[2-(2-tert-butyl-6-nitro-1H-indol-3-yl)-ethyl]-pyrrolidin-2-yl}-phenyl)-acrylic acid methyl ester

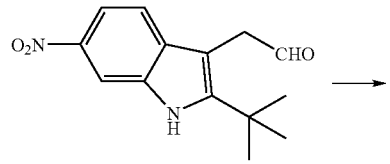

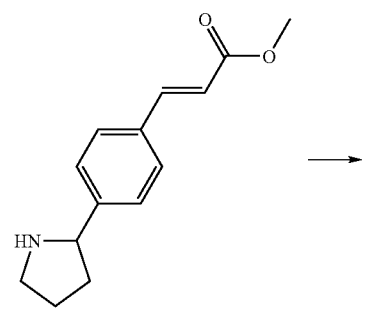

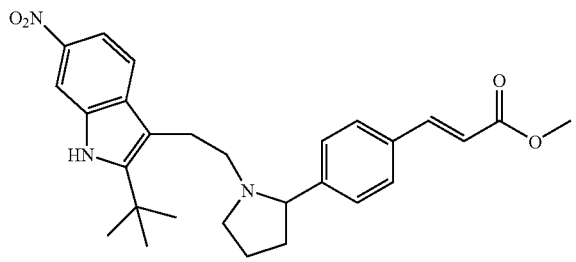

To a solution of (2-tert-butyl-6-nitro-1H-indol-3-yl)-acetaldehyde (0.74 g, 2.8 mmol) in tetrahydrofuran (20 mL) was added (E)-3-(4-pyrrolidin-2-yl-phenyl)-acrylic acid methyl ester hydrochloride (0.91 g, 3.4 mmol) and triethylamine (871 μL, 6.26 mmol). The resulting mixture was stirred at room temperature for 1 h and sodium triacetoxyborohydride (0.88 g, 4.0 mmol) was added. The mixture was stirred at room temperature for 16 h, diluted with ethyl acetate, and washed with a saturated sodium bicarbonate and a saturated aqueous solution of sodium chloride. The organic layer was dried over sodium sulfate, filtered, and concentrated in vacuo. The residue was purified via silica gel column chromatography to give the title compound (0.77 g, 57%). LCMS (m/z): 476.2539 (M+1).

Step c: Preparation of (E)-3-(4-{1-[2-(6-amino-2-tert-butyl-1H-indol-3-yl)-ethyl]-pyrrolidin-2-yl}-phenyl)-acrylic acid methyl ester

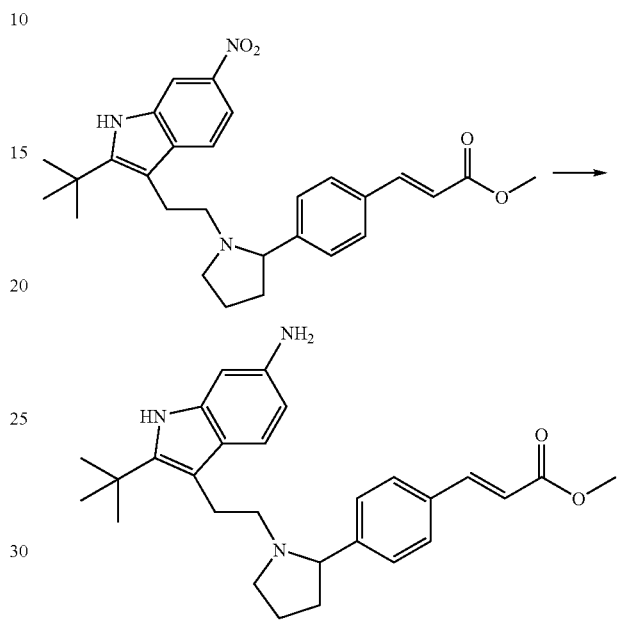

To a solution of (E)-3-(4-{1-[2-(2-tert-butyl-6-nitro-1H-indol-3-yl)-ethyl]-pyrrolidin-2-yl}-phenyl)-acrylic acid methyl ester (0.70 g, 1.5 mmol) in ethanol (14 mL) and water (7 mL) was added iron powder (0.74 g, 13 mmol) and ammonium chloride (87 mg, 1.6 mmol) and the resulting mixture was stirred at 85° C. for 1 h. Additional iron powder (820 mg, 14.7 mmol), ethanol (6 mL) and water (3 mL) were added and the reaction was stirred at 85° C. for 50 h. The reaction mixture was filtered and concentrated in vacuo, and the residue was taken up in water. A brown solid precipitate was recovered via vacuum filtration to yield the title compound (0.40 g, 49% yield). LCMS (m/z): 446.0 (M+1).

Step d: Preparation of (E)-3-(4-{1-[2-(2-tert-butyl-6-methanesulfonylamino-1H-indol-3-yl)-ethyl]-pyrrolidin-2-yl}-phenyl)-acrylic acid methyl ester

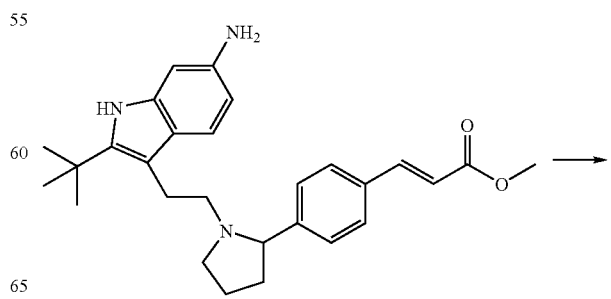

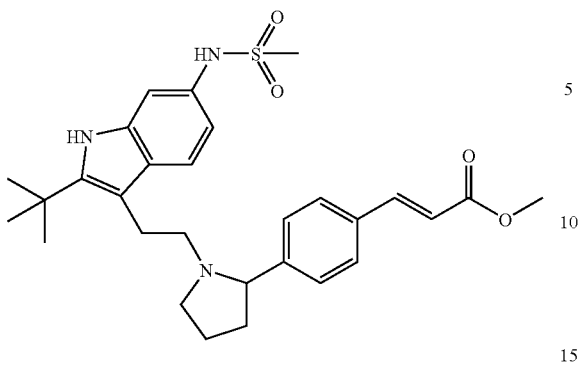

To a solution of (E)-3-(4-{1-[2-(6-amino-2-tert-butyl-1H-indol-3-yl)-ethyl]-pyrrolidin-2-yl}-phenyl)-acrylic acid methyl ester (0.70 g, 1.6 mmol) in dichloromethane (7 mL) was added methanesulfonyl chloride (0.198 g, 1.73 mmol), triethylamine (241 μL, 1.73 mmol). The resulting solution was stirred at room temperature for 1 h, diluted with ethyl acetate, and washed with 1 N hydrochloric acid, a saturated sodium bicarbonate solution, and a saturated aqueous solution of sodium chloride. The organic layer was dried over sodium sulfate, filtered and concentrated in vacuo. The residue was purified via silica gel column chromatography to give the title compound (0.21 g, 26% yield). LCMS (m/z): 523.9 (M+1).

Following procedures analogous to those described in Example 2, (E)-3-(4-{1-[2-(2-tert-butyl-6-methanesulfonylamino-1H-indol-3-yl)-ethyl]-pyrrolidin-2-yl}-phenyl)-acrylic acid methyl ester (200 mg) was converted to (E)-3-(4-{1-[2-(2-tert-butyl-6-methanesulfonylamino-1H-indol-3-yl)-ethyl]-pyrrolidin-2-yl}-phenyl)-N-hydroxy-acrylamide (10, 83 mg, 41% yield). LCMS (m/z): 525.2535 (M+1).

Example 21

Preparation of (E)-3-(4-{1-[2-(2-tert-butyl-1-methanesulfonyl-6-methanesulfonylamino-1H-indol-3-yl)-ethyl]-pyrrolidin-2-yl}-phenyl)-N-hydroxy-acrylamide (11)

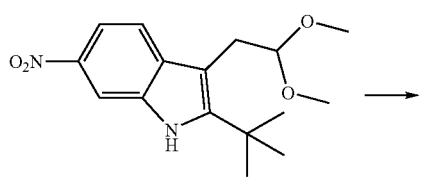

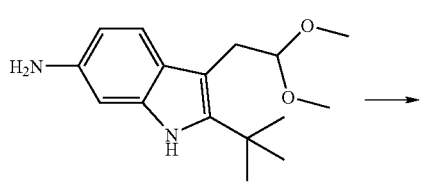

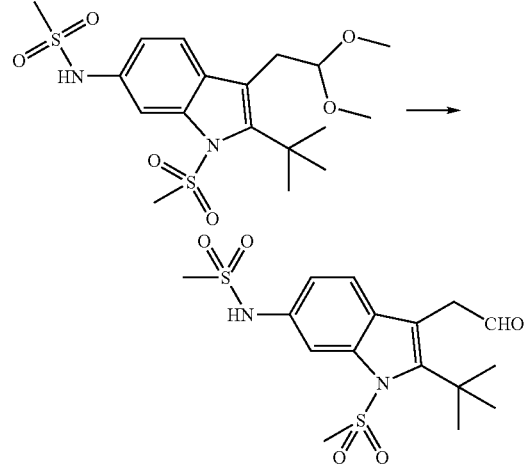

Step a: Preparation of 2-tert-butyl-3-(2,2-dimethoxy-ethyl)-1H-indol-6-ylamine

To a solution of 2-tert-butyl-3-(2,2-dimethoxy-ethyl)-6-nitro-1H-indole (611 mg, 2 mmol) in methanol was added palladium hydroxide on carbon (100 mg). The flask was evacuated and purged with hydrogen gas three times. The reaction was stirred under hydrogen for 16 h and filtered through a pad of Celite, which was rinsed with methanol. The organic solution was combined and concentrated in vacuo and the residue was purified via flash chromatography to give the desired product (347 mg, 63% yield).

Step b: Preparation of N-[2-tert-butyl-3-(2,2-dimethoxy-ethyl)-1-methanesulfonyl-1H-indol-6-yl]-methanesulfonamide To a solution of 2-tert-butyl-3-(2,2-dimethoxy-ethyl)-1H-indol-6-ylamine (347 mg, 1.25 mmol) and triethylamine (0.350 mL, 2.5 mmol) in dichloromethane (6 mL) was added methanesulfonyl chloride (0.291 mL, 3.75 mmol) at 0° C. After stirred for 16 h, the mixture was poured into water and the aqueous layer was extracted with dichloromethane. The organic layers were combined, washed with a saturated aqueous solution of sodium chloride, dried over magnesium sulfate, filtered, and concentrated in vacuo. The crude product was purified by a silica gel column chromatography to give the title compound (40 mg, 7% yield). LCMS (m/z): found 431 (M−1).

Step c: Preparation of N-[2-tert-butyl-1-methanesulfonyl-3-(2-oxo-ethyl)-1H-indol-6-yl]-methanesulfonamide To a solution of N-[2-tert-butyl-3-(2,2-dimethoxy-ethyl)-1-methanesulfonyl-1H-indol-6-yl]-methanesulfonamide (110 mg, 0.25 mmol) in dichloromethane (1 mL) was added trifluoroacetic acid (1 mL, 50% aqueous) dropwise at 0° C. After 1 h, the solution was warmed to room temperature and quenched with a saturated sodium bicarbonate solution until neutral pH was reached. The mixture was separated and the aqueous phase was extracted three times with dichloromethane (10 mL). The combined organic phases were washed with a saturated sodium chloride solution, dried over magnesium sulfate, filtered, and concentrated in vacuo to obtain the crude product in quantitative yield which was used directly to next step without further purification. LCMS (m/z): 385.1 (M−1).

Following procedures analogous to those described in Example 3, (E)-3-(4-{1-[2-(2-tert-butyl-1-methanesulfonyl-6-methanesulfonylamino-1H-indol-3-yl)-ethyl]-pyrrolidin-2-yl}-phenyl)-acrylic acid methyl ester was prepared from N-[2-tert-butyl-1-methanesulfonyl-3-(2-oxo-ethyl)-1H-indol-6-yl]-methanesulfonamide in 40% yield.

Following procedures analogous to those described in Example 2, (E)-3-(4-{1-[2-(2-tert-butyl-1-methanesulfonyl-6-methanesulfonylamino-1H-indol-3-yl)-ethyl]-pyrrolidin-2-yl}-phenyl)-N-hydroxy-acrylamide was prepared and isolated from preparative HPLC (11, 2.6 mg, 4%) as a light yellow solid. LCMS (m/z): 603 (M+1)

Example 22

Preparation of (E)-N-hydroxy-3-(4-{(S)-1-[2-(2-methyl-1H-indol-3-yl)-acetyl]-pyrrolidin-2-yl}-phenyl)-acrylamide (12)

To a stirred solution of (E)-3-((S)-4-pyrrolidin-2-yl-phenyl)-acrylic acid methyl ester hydrochloride (0.3 g, 1.12 mmol) in N,N-dimethylformamide (20 mL) was added sequentially triethylamine (0.5 mL, 3.58 mmol), 1-ethyl-3-(3-dimethylaminopropyl)carbodiimide hydrochloride (0.24 g, 1.25 mmol), 1-hydroxybenzotriazole (0.17 g, 1.25 mmol) and 2-methylindole-3-acetic acid (0.235 g, 1.24 mmol). The reaction was stirred for 16 h and diluted with dichloromethane, and the solution was washed with a saturated aqueous solution of sodium chloride, dried over sodium sulfate, filtered, and concentrated under reduced pressure. The crude product was purified by silica gel column chromatography (2% methanol in dichloromethane) to obtain (E)-3-(4-{(S)-1-[2-(2-methyl-1H-indol-3-yl)-acetyl]-pyrrolidin-2-yl}-phenyl)-acrylic acid methyl ester as a colorless oil (0.42 g, 1.03 mmol, 93% yield).

Following procedures analogous to those described in Example 2, (E)-N-hydroxy-3-(4-{(S)-1-[2-(2-methyl-1H-indol-3-yl)-acetyl]-pyrrolidin-2-yl}-phenyl)-acrylamide was prepared (12, 0.31 g, 0.768 mmol, 78% yield) as an off-white solid. LCMS (m/z): 404.1 (M+1).

Example 23

Preparation of (E)-3-[4-((S)-1-benzyl-pyrrolidin-2-yl)-phenyl]-N-hydroxy-acrylamide (13)

Following procedures analogous to those described in Example 3, (E)-3-[4-((S)-1-benzyl-pyrrolidin-2-yl)-phenyl]-acrylic acid methyl ester (0.28 g, 0.87 mmol) was prepared from benzaldehyde (0.3 mL, 3.2 mmol, 27% yield).

Following procedures analogous to those described in Example 2, (E)-3-[4-((S)-1-benzyl-pyrrolidin-2-yl)-phenyl]-N-hydroxy-acrylamide was prepared (13, 0.12 g) as an off-white solid. LCMS (m/z): 323.3 (M+1).

Example 24

Preparation of (E)-N-hydroxy-3-{4-[(S)-1-(2-phenyl-2H-pyrazol-3-ylmethyl)-pyrrolidin-2-yl]-phenyl}-acrylamide (14)

Following procedures analogous to those described in Example 3, (E)-3-{4-[(S)-1-(2-phenyl-2H-pyrazol-3-ylmethyl)-pyrrolidin-2-yl]-phenyl}-acrylic acid methyl ester (0.347 g, 0.896 mmol) was prepared from 2-phenyl-2H-pyrazole-3-carbaldehyde (0.2 g, 1.16 mmol, 77% yield).

Following procedures analogous to those described in Example 2, (E)-N-hydroxy-3-{4-[(S)-1-(2-phenyl-2H-pyrazol-3-ylmethyl)-pyrrolidin-2-yl]-phenyl}-acrylamide was prepared (14, 0.246 g, 0.633 mmol, 72% yield) as a brown solid. LCMS (m/z): 389.0 (M+1).

Example 25

Preparation of (E)-N-hydroxy-3-[4-((S)-1-pyrazolo[1,5-a]pyridin-3-ylmethyl-pyrrolidin-2-yl)-phenyl]-acrylamide (15)

Following procedures analogous to those described in Example 3, (E)-3-[4-((S)-1-pyrazolo[1,5-a]pyridin-3-ylmethyl-pyrrolidin-2-yl)-phenyl]-acrylic acid methyl ester (0.249 g, 0.689 mmol, 50% yield) was prepared from pyrazolo[1,5-a]pyridine-3-carbaldehyde (0.2 g, 1.37 mmol).

Following procedures analogous to those described in Example 2, (E)-N-hydroxy-3-[4-((S)-1-pyrazolo[1,5-a]pyridin-3-ylmethyl-pyrrolidin-2-yl)-phenyl]-acrylamide was prepared (15, 0.159 g, 0.439 mmol, 66% yield) as an off-white solid. LCMS (m/z): 363.2 (M+1).

Example 26

Preparation of (E)-3-{4-[1-(3,5-dimethyl-1-phenyl-1H-pyrazol-4-ylmethyl)-pyrrolidin-2-yl]-phenyl}-N-hydroxy-acrylamide (16)

Following procedures analogous to those described in Example 3, (E)-3-{4-[(S)-1-(3,5-dimethyl-1-phenyl-1H-pyrazol-4-ylmethyl)-pyrrolidin-2-yl]-phenyl}-acrylic acid methyl ester (0.079 g, 0.19 mmol, 31% yield) was prepared from 3,5-dimethyl-1-phenyl-1H-pyrazole-4-carbaldehyde (0.125 g, 0.624 mmol).

Following procedures analogous to those described in Example 2, (E)-3-{4-[1-(3,5-dimethyl-1-phenyl-1H-pyrazol-4-ylmethyl)-pyrrolidin-2-yl]-phenyl}-N-hydroxy-acrylamide was prepared (16, 10 mg, 0.024 mmol, 15% yield) as a solid. LCMS (m/z): 417.2 (M+1).

Example 27

Preparation of (E)-N-hydroxy-3-{4-[(S)-1-(3-pyrazol-1-yl-propyl)-pyrrolidin-2-yl]-phenyl}-acrylamide (17)

Following procedures analogous to those described in Example 3, (E)-3-{4-[(S)-1-(3-pyrazol-1-yl-propyl)-pyrrolidin-2-yl]-phenyl}-acrylic acid methyl ester (0.29 g, 0.85 mmol, 76% yield) was prepared from 3-pyrazol-1-yl-propionaldehyde (0.15 g, 1.2 mmol).

Following procedures analogous to those described in Example 2, (E)-N-hydroxy-3-{4-[(S)-1-(3-pyrazol-1-yl-propyl)-pyrrolidin-2-yl]-phenyl}-acrylamide was prepared (17, 0.11 g, 0.323 mmol, 44% yield) as a pale brown solid. LCMS (m/z): 341.1 (M+1).

Example 28

Preparation of (E)-N-hydroxy-3-[4-((S)-1-phenylacetyl-pyrrolidin-2-yl)-phenyl]-acrylamide (18)

In an oven-dried flask under nitrogen were suspended (E)-3-((S)-4-pyrrolidin-2-yl-phenyl)acrylic acid methyl ester hydrochloride (0.312 g, 1.16 mmol) and triethylamine (0.3 mL, 2.16 mmol) in dry dichloromethane and the mixture was sonicated for 30 seconds. Phenylacetyl chloride (0.13 mL, 0.98 mmol) was added and the mixture was slowly warmed to room temperature over 16 h. The reaction was quenched by addition of an aqueous ammonium chloride solution. Ethyl acetate was added, the layers were separated, and the aqueous layer was washed with ethyl acetate. The combined organic layers were dried over magnesium sulfate, filtered, and concentrated in vacuo to give an oil that was purified via silica gel column chromatography (0-40% ethyl acetate in heptane) to give (E)-3-[4-((S)-1-phenylacetyl-pyrrolidin-2-yl)-phenyl]-acrylic acid methyl ester as a colorless oil (0.262 g, 0.75 mmol, 76% yield).

Following procedures analogous to those described in Example 2, (E)-N-hydroxy-3-[4-((S)-1-phenylacetyl-pyrrolidin-2-yl)-phenyl]-acrylamide was prepared (18, 0.177 g, 0.505 mmol, 78% yield) as an off-white solid. LCMS (m/z): 351.2 (M+1).

Example 29

Preparation of (E)-N-hydroxy-3-[4-((S)-1-phenethyl-pyrrolidin-2-yl)-phenyl]-acrylamide (19)

Following procedures analogous to those described in Example 4, (E)-3-[4-((S)-1-phenethyl-pyrrolidin-2-yl)-phenyl]-acrylic acid methyl ester was prepared from phenethyl-bromide.

Following procedures analogous to those described in Example 2, (E)-N-hydroxy-3-[4-((S)-1-phenethyl-pyrrolidin-2-yl)-phenyl]-acrylamide was prepared (19). LCMS (m/z): 337.1919 (M+).

Example 30

Preparation of (E)-N-hydroxy-3-(4-{1-[2-(4-hydroxy-phenyl)-ethyl]-pyrrolidin-2-yl}-phenyl)-acrylamide (20)

Following procedures analogous to those described in Example 4, (E)-3-(4-{(S)-1-[2-(4-hydroxy-phenyl)-ethyl]-pyrrolidin-2-yl}-phenyl)-acrylic acid methyl ester (0.22 g, 0.63 mmol, 56% yield) was prepared from 4-hydroxyphenethylbromide (0.23 g, 1.1 mmol).

Following procedures analogous to those described in Example 2, (E)-N-hydroxy-3-(4-{1-[2-(4-hydroxy-phenyl)-ethyl]-pyrrolidin-2-yl}-phenyl)-acrylamide was prepared (20, 0.04 g, 0.11 mmol, 19% yield) as an off-white solid. LCMS (m/z): 353.1 (M+1).

Example 31

Preparation of (E)-3-(4-{(S)-1-[2-(4-fluoro-phenyl)-ethyl]-pyrrolidin-2-yl}-phenyl)-N-hydroxy-acrylamide (21)

Following procedures analogous to those described in Example 6, (4-fluoro-phenyl)-acetaldehyde (1.2 g, 8.69 mmol) was prepared from 4-fluoro-benzaldehyde (2 g, 16 mmol).

Following procedures analogous to those described in Example 3, (E)-3-(4-{(S)-1-[2-(4-fluoro-phenyl)-ethyl]-pyrrolidin-2-yl}-phenyl)-acrylic acid methyl ester (0.25 g, 0.71 mmol, 63% yield) was prepared from the acetaldehyde above (0.3 g, 2.17 mmol).

Following procedures analogous to those described in Example 2, (E)-3-(4-{(S)-1-[2-(4-fluoro-phenyl)-ethyl]-pyrrolidin-2-yl}-phenyl)-N-hydroxy-acrylamide was prepared (21, 0.19 g, 0.54 mmol, 83% yield) as an off-white solid. LCMS (m/z): 355.1 (M+1).

Example 32

Preparation of (E)-3-(4-{(S)-1-[2-(4-chloro-phenyl)-ethyl]-pyrrolidin-2-yl}-phenyl)-N-hydroxy-acrylamide (22)

Following procedures analogous to those described in Example 6, (4-chloro-phenyl)-acetaldehyde (0.49 g, 3.17 mmol) was prepared from 4-chloro-benzaldehyde (2 g, 14 mmol).

Following procedures analogous to those described in Example 3, (E)-3-(4-{(S)-1-[2-(4-chloro-phenyl)-ethyl]-pyrrolidin-2-yl}-phenyl)-acrylic acid methyl ester (0.18 g, 0.54 mmol, 44% yield) was prepared from the acetaldehyde above (0.25 g, 1.6 mmol).

Following procedures analogous to those described in Example 2, (E)-3-(4-{(S)-1-[2-(4-chloro-phenyl)-ethyl]-pyrrolidin-2-yl}-phenyl)-N-hydroxy-acrylamide was prepared (22, 0.12 g, 60% yield) as an off-white solid. LCMS (m/z): 371.1 (M+1).

Example 33

Preparation of (E)-3-(4-{1-[2-(3,4-dichloro-phenyl)-ethyl]-pyrrolidin-2-yl}-phenyl)-N-hydroxy-acrylamide (23)

Following procedures analogous to those described in Example 6, (3,4-dichloro-phenyl)-acetaldehyde (0.62 g, 3.28 mmol) was prepared from 3,4-dichlorobenzaldehyde (1.5 g, 8.57 mmol).

Following procedures analogous to those described in Example 3, (E)-3-(4-{(S)-1-[2-(3,4-dichloro-phenyl)-ethyl]-pyrrolidin-2-yl}-phenyl)-acrylic acid methyl ester (0.22 g, 0.54 mmol, 87% yield) was prepared from the acetaldehyde above.

Following procedures analogous to those described in Example 2, (E)-3-(4-{1-[2-(3,4-dichloro-phenyl)-ethyl]-pyrrolidin-2-yl}-phenyl)-N-hydroxy-acrylamide was prepared (23, 0.12 g, 60% yield) as a pale yellow solid. LCMS (m/z): 405.1 (M+1).

Example 34

Preparation of (E)-N-hydroxy-3-(4-{1-[2-(4-nitro-phenyl)-ethyl]-pyrrolidin-2-yl}-phenyl)-acrylamide (24)

Following procedures analogous to those described in Example 4, (E)-3-(4-{(S)-1-[2-(4-nitro-phenyl)-ethyl]-pyrrolidin-2-yl}-phenyl)-acrylic acid methyl ester (0.2 g, 0.657 mmol, 57% yield) was prepared from 4-nitrophenethyl bromide (0.28 g, 1.22 mmol).

Following procedures analogous to those described in Example 2, (E)-N-hydroxy-3-(4-{1-[2-(4-nitro-phenyl)-ethyl]-pyrrolidin-2-yl}-phenyl)-acrylamide was prepared (24, 0.04 g) as a pale yellow solid. LCMS (m/z): 382.1 (M+1).

Example 35

Preparation of (E)-3-(4-{1-[2-(2-chloro-phenyl)-ethyl]-pyrrolidin-2-yl}-phenyl)-N-hydroxy-acrylamide (25)

Following procedures analogous to those described in Example 6, (2-chloro-phenyl)-acetaldehyde (1.2 g, 7.7 mmol) was prepared from 2-chlorobenzaldehyde (2 g, 14 mmol).

Following procedures analogous to those described in Example 3, (E)-3-(4-{(S)-1-[2-(2-chloro-phenyl)-ethyl]-pyrrolidin-2-yl}-phenyl)-acrylic acid methyl ester (0.23 g, 0.62 mmol, 55% yield) was prepared from the acetaldehyde above.

Following procedures analogous to those described in Example 2, (E)-3-(4-{1-[2-(2-chloro-phenyl)-ethyl]-pyrrolidin-2-yl}-phenyl)-N-hydroxy-acrylamide was prepared (25, 0.05 g, 0.135 mmol, 25% yield) as a pale yellow solid. LCMS (m/z): 371.0 (M+1).

Example 36

Preparation of (E)-3-(4-{1-[2-(2,4-dichloro-phenyl)-ethyl]-pyrrolidin-2-yl}-phenyl)-N-hydroxy-acrylamide (26)

Following procedures analogous to those described in Example 4, (E)-3-(4-{(S)-1-[2-(2,4-dichloro-phenyl)-ethyl]-pyrrolidin-2-yl}-phenyl)-acrylic acid methyl ester (0.21 g, 0.52 mmol) was prepared from 1-(2-bromo-ethyl)-2,4-dichloro-benzene (0.2 g, 0.75 mmol).

Following procedures analogous to those described in Example 2, (E)-3-(4-{1-[2-(2,4-dichloro-phenyl)-ethyl]-pyrrolidin-2-yl}-phenyl)-N-hydroxy-acrylamide was prepared (26, 0.09 g, 47% yield) as an off-white solid. LCMS (m/z): 405.1 (M+1).

Example 37

Preparation of (E)-3-(4-{1-[2-(2-fluoro-phenyl)-ethyl]-pyrrolidin-2-yl}-phenyl)-N-hydroxy-acrylamide (27)

Following procedures analogous to those described in Example 6, (2-fluoro-phenyl)-acetaldehyde was prepared from 2-fluoro-benzaldehyde.

Following procedures analogous to those described in Example 3, (E)-3-(4-{(S)-1-[2-(2-fluoro-phenyl)-ethyl]-pyrrolidin-2-yl}-phenyl)-acrylic acid methyl ester (0.18 g, 0.51 mmol, 45% yield) was prepared from (2-fluoro-phenyl)-acetaldehyde (0.2 g, 1.45 mmol).

Following procedures analogous to those described in Example 2, (E)-3-(4-{1-[2-(2-fluoro-phenyl)-ethyl]-pyrrolidin-2-yl}-phenyl)-N-hydroxy-acrylamide was prepared (27, 0.12 g, 60% yield) as a pale yellow solid. LCMS (m/z): 355.1 (M+1).

Example 38

Preparation of (E)-N-hydroxy-3-{4-[1-(2-hydroxy-2-phenyl-ethyl)-pyrrolidin-2-yl]-phenyl}-acrylamide (28)

Following procedures analogous to those described in Example 2, (E)-N-hydroxy-3-{4-[1-(2-hydroxy-2-phenyl-ethyl)-pyrrolidin-2-yl]-phenyl}-acrylamide was prepared (28, 0.15 g, 0.43 mmol, 83% yield) as an off-white solid. LCMS (m/z): 353.1 (M+1).

Example 39

Preparation of (E)-N-hydroxy-3-{4-[1-(2-hydroxy-2-p-tolyl-ethyl)-pyrrolidin-2-yl]-phenyl}-acrylamide (29)

Following procedures analogous to those described in Examples 4 and 8, (E)-3-{4-[(S)-1-(2-hydroxy-2-p-tolyl-ethyl)-pyrrolidin-2-yl]-phenyl}-acrylic acid methyl ester (0.31 g, 0.85 mmol) was prepared from 2-bromo-1-p-tolyl-ethanone (0.35 g, 1.31 mmol).

Following procedures analogous to those described in Example 2, (E)-3-{4-[(S)-1-(2-hydroxy-2-p-tolyl-ethyl)-pyrrolidin-2-yl]-phenyl}-acrylic acid methyl ester (0.33 g, 0.86 mmol) was converted to (E)-N-hydroxy-3-{4-[1-(2-hydroxy-2-p-tolyl-ethyl)-pyrrolidin-2-yl]-phenyl}-acrylamide (29, 0.28 g, 0.76 mmol, 89% yield) as a pale yellow solid. LCMS (m/z): 367.1 (M+1).

Example 40

Preparation of (E)-N-hydroxy-3-(4-{(S)-1-[2-hydroxy-2-(4-methoxy-phenyl)-ethyl]-pyrrolidin-2-yl}-phenyl)-acrylamide (30)

Following procedures analogous to those described in Example 2, (E)-3-(4-{(S)-1-[2-hydroxy-2-(4-methoxy-phenyl)-ethyl]-pyrrolidin-2-yl}-phenyl)-acrylic acid methyl ester (0.33 g, 0.86 mmol) was converted to (E)-N-hydroxy-3-(4-{(S)-1-[2-hydroxy-2-(4-methoxy-phenyl)-ethyl]-pyrrolidin-2-yl}-phenyl)-acrylamide (30, 0.19 g, 0.5 mmol, 58% yield) as a pale brown solid. LCMS (m/z): 383.1 (M+1).

Example 41

Preparation of (E)-3-(4-{1-[2-(4-chloro-phenyl)-2-hydroxy-ethyl]-pyrrolidin-2-yl}-phenyl)-N-hydroxy-acrylamide (31)

Following procedures analogous to those described in Examples 4 and 8, (E)-3-(4-{(S)-1-[2-(4-chloro-phenyl)-2-oxo-ethyl]-pyrrolidin-2-yl}-phenyl)-acrylic acid methyl ester (0.28 g, 0.73 mmol) was prepared from 2-bromo-1-(4-chloro-phenyl)-ethanone (0.3 g, 1.12 mmol).

Following procedures analogous to those described in Example 2, (E)-3-(4-{(S)-1-[2-(4-chloro-phenyl)-2-oxo-ethyl]-pyrrolidin-2-yl}-phenyl)-acrylic acid methyl ester (0.27 g, 0.70 mmol) was converted to (E)-3-(4-{1-[2-(4-chloro-phenyl)-2-hydroxy-ethyl]-pyrrolidin-2-yl}-phenyl)-N-hydroxy-acrylamide (31, 0.22 g, 0.57 mmol, 81% yield) as a pale brown solid. LCMS (m/z): 387.2 (M+1).

Example 42

Preparation of (E)-3-(4-{1-[2-(3,4-dichloro-phenyl)-2-hydroxy-ethyl]-pyrrolidin-2-yl}-phenyl)-N-hydroxy-acrylamide (32)

Following procedures analogous to those described in Examples 4 and 8, (E)-3-(4-{(S)-1-[2-(3,4-dichloro-phenyl)-2-hydroxy-ethyl]-pyrrolidin-2-yl}-phenyl)-acrylic acid methyl ester (0.29 g, 0.69 mmol) was prepared from 2-bromo-3',4'-dichloroacetophenone (0.3 g, 1.12 mmol).

Following procedures analogous to those described in Example 2, (E)-3-(4-{(S)-1-[2-(3,4-dichloro-phenyl)-2-hydroxy-ethyl]-pyrrolidin-2-yl}-phenyl)-acrylic acid methyl ester (0.28 g, 0.66 mmol) was converted to (E)-3-(4-{1-[2-(3,4-dichloro-phenyl)-2-hydroxy-ethyl]-pyrrolidin-2-yl}-phenyl)-N-hydroxy-acrylamide (32, 0.25 g, 0.59 mmol, 89% yield) as an off-white solid. LCMS (m/z): 421.1 (M+1).

Example 43

Preparation of (E)-N-hydroxy-3-{4-[1-(3-phenyl-propyl)-pyrrolidin-2-yl]-phenyl}-acrylamide (33)

Following procedures analogous to those described in Example 4, (E)-3-{4-[(S)-1-(3-phenyl-propyl)-pyrrolidin-2-yl]-phenyl}-acrylic acid methyl ester (0.23 g, 0.66 mmol, 61% yield) was prepared from (3-bromo-propyl)-benzene (0.24 mL, 1.6 mmol).

Following procedures analogous to those described in Example 2, (E)-N-hydroxy-3-{4-[1-(3-phenyl-propyl)-pyrrolidin-2-yl]-phenyl}-acrylamide was prepared (33, 0.043 g, 0.12 mmol, 27% yield) as a white solid. LCMS (m/z): 353.36 (M+1).

Example 44

Preparation of (E)-N-hydroxy-3-{4-[1-(2-pyridin-2-yl-ethyl)-pyrrolidin-2-yl]-phenyl}-acrylamide (34)

Following procedures analogous to those described in Example 4, (E)-3-{4-[(S)-1-(2-pyridin-2-yl-ethyl)-pyrrolidin-2-yl]-phenyl}-acrylic acid methyl ester (0.19 g, 0.57 mmol) was prepared from 2-(2-bromo-ethyl)-pyridine (0.3 g, 1.1 mmol).

Following procedures analogous to those described in Example 2, (E)-N-hydroxy-3-{4-[1-(2-pyridin-2-yl-ethyl)-pyrrolidin-2-yl]-phenyl}-acrylamide was prepared (34, 0.12 g, 67% yield) as a pale yellow solid. LCMS (m/z): 338.1 (M+1).

Example 45

Preparation of (E)-N-hydroxy-3-{4-[(S)-1-(2-thiophen-3-yl-ethyl)-pyrrolidin-2-yl]-phenyl}-acrylamide (35)

Following procedures analogous to those described in Example 4, (E)-3-{4-[(S)-1-(2-thiophen-3-yl-ethyl)-pyrrolidin-2-yl]-phenyl}-acrylic acid methyl ester (0.15 g, 0.44 mmol) was prepared from methanesulfonic acid 2-thiophen-3-yl-ethyl ester (0.64 g, 3.1 mmol).

Following procedures analogous to those described in Example 2, (E)-N-hydroxy-3-{4-[(S)-1-(2-thiophen-3-yl-ethyl)-pyrrolidin-2-yl]-phenyl}-acrylamide was prepared (35, 0.011 g, 9% yield) as a pale yellow solid. LCMS (m/z): 343.1476 (M+1).

Example 46

Preparation of (E)-N-hydroxy-3-{4-[1-(3-methyl-butyl)-pyrrolidin-2-yl]-phenyl}-acrylamide (36)

Following procedures analogous to those described in Example 4, (E)-3-{4-[(S)-1-(3-methyl-butyl)-pyrrolidin-2-yl]-phenyl}-acrylic acid methyl ester (0.17 g, 0.56 mmol) was prepared from 1-bromo-3-methylbutane (0.3 g, 1.1 mmol).

Following procedures analogous to those described in Example 2, (E)-N-hydroxy-3-{4-[1-(3-methyl-butyl)-pyrrolidin-2-yl]-phenyl}-acrylamide was prepared (36, 0.16 g, 88% yield) as an off-white solid. LCMS (m/z): 303.1 (M+1).

Example 47

Preparation of (E)-3-{4-[1-(3,3-dichloro-allyl)-pyrrolidin-2-yl]-phenyl}-N-hydroxy-acrylamide (37)

Following procedures analogous to those described in Example 4, (E)-3-{4-[(S)-1-(3,3-dichloro-allyl)-pyrrolidin-2-yl]-phenyl}-acrylic acid methyl ester (0.34 g) was prepared from 3-bromo-1,1,1-trichloropropane (0.17 mL, 1.3 mmol).

Following procedures analogous to those described in Example 2, (E)-3-{4-[1-(3,3-dichloro-allyl)-pyrrolidin-2-yl]-phenyl}-N-hydroxy-acrylamide was prepared (37, 0.29 g, 0.85 mmol, 88% yield) as a pale yellow solid. LCMS (m/z): 341.1 (M+1).

Example 48

Preparation of (E)-3-[4-((5)-1-cyclopropylmethyl-pyrrolidin-2-yl)-phenyl]-N-hydroxy-acrylamide (38)

Following procedures analogous to those described in Example 4, (E)-3-[4-((S)-1-cyclopropylmethyl-pyrrolidin-2-yl)-phenyl]-acrylic acid methyl ester (0.18 µg 0.63 mmol) was prepared from bromomethylcyclopropane (0.16 g, 1.2 mmol).

Following procedures analogous to those described in Example 2, (E)-3-[4-((S)-1-cyclopropylmethyl-pyrrolidin-2-yl)-phenyl]-N-hydroxy-acrylamide was prepared (38, 0.15 g, 0.52 mmol, 87% yield) as an off-white solid. LCMS (m/z): 387.0 (M+1).

Example 49

Preparation of (E)-3-[4-((S)-1-cyclobutylmethyl-pyrrolidin-2-yl)-phenyl]-N-hydroxy-acrylamide (39)

Following procedures analogous to those described in Example 4, (E)-3-[4-((S)-1-cyclobutylmethyl-pyrrolidin-2-yl)-phenyl]-acrylic acid methyl ester (0.33 g, 1.1 mmol) was prepared from bromomethylcyclobutane (0.15 mL, 1.33 mmol).

Following procedures analogous to those described in Example 2, (E)-3-[4-((S)-1-cyclobutylmethyl-pyrrolidin-2-yl)-phenyl]-N-hydroxy-acrylamide was prepared (39, 0.23 g, 72% yield) as a pale yellow solid. LCMS (m/z): 301.1 (M+1).

Example 50

Preparation of (E)-3-[4-(1-cyclopentylmethyl-pyrrolidin-2-yl)-phenyl]-N-hydroxy-acrylamide (40)

Following procedures analogous to those described in Example 4, (E)-3-[4-((S)-1-cyclopentylmethyl-pyrrolidin-2-yl)-phenyl]-acrylic acid methyl ester (0.32 g, 1.0 mmol) was prepared from bromomethyl-cyclopentane (0.3 g, 1.4 mmol).

Following procedures analogous to those described in Example 2, (E)-3-[4-(1-cyclopentylmethyl-pyrrolidin-2-yl)- phenyl]-N-hydroxy-acrylamide was prepared (40, 0.24 g, 76% yield) as a white solid. LCMS (m/z): 315.1 (M+1).

Example 51

Preparation of (E)-3-{4-[(S)-1-(2-cyclohexyl-ethyl)-pyrrolidin-2-yl]-phenyl}-N-hydroxy-acrylamide (41)

Following procedures analogous to those described in Examples 4 and 2, (E)-3-{4-[(S)-1-(2-cyclohexyl-ethyl)-pyrrolidin-2-yl]-phenyl}-N-hydroxy-acrylamide (41) was prepared from (2-bromo-ethyl)-cyclohexane. LCMS (m/z): 343.2 (M+1).

Example 52

Preparation of (E)-N-hydroxy-3-(4-{(S)-1-[2-(tetrahydro-pyran-4-yl)-ethyl]-pyrrolidin-2-yl}-phenyl)-acrylamide (42)

Following procedures analogous to those described in Example 3, (E)-3-(4-{(S)-1-[2-(tetrahydro-pyran-4-yl)-ethyl]-pyrrolidin-2-yl}-phenyl)-acrylic acid methyl ester (0.14 g, 0.41 mmol, 35% yield) was prepared from (tetrahydro-pyran-4-yl)-acetaldehyde (0.15 g, 1.17 mmol) as a yellow oil.

Following procedures analogous to those described in Example 2, (E)-N-hydroxy-3-(4-{(S)-1-[2-(tetrahydro-pyran-4-yl)-ethyl]-pyrrolidin-2-yl}-phenyl)-acrylamide was prepared (42, 0.044 g, 0.128 mmol, 36% yield) as a solid. LCMS (m/z): 345.2 (M+1).

Example 53

Preparation of (E)-N-hydroxy-3-{4-[(s)-1-(2-pyrazolo[1,5-a]pyridin-3-yl-ethyl)-pyrrolidin-2-yl]-phenyl}-acrylamide (43)

Following procedures analogous to those described in Examples 2, 3, 6, 9, and 10, (E)-N-hydroxy-3-{4-[(S)-1-(2-pyrazolo[1,5-a]pyridin-3-yl-ethyl)-pyrrolidin-2-yl]-phenyl}-acrylamide (43) was prepared from (E)-3-((S)-4-Pyrrolidin-2-yl-phenyl)-acrylic acid methyl ester and propynoic acid ethyl ester. LCMS (m/z): 377.1972 (M+1).

Example 54

Preparation of (E)-N-hydroxy-3-(4-{(S)-1-[2-(2-methyl-pyrazolo[1,5-a]pyridin-3-yl)-ethyl]-pyrrolidin-2-yl}-phenyl)-acrylamide (44)

Following procedures analogous to those described in Examples 2, 3, 6, 9, and 10, (E)-N-hydroxy-3-(4-{(S)-1-[2-(2-methyl-pyrazolo[1,5-a]pyridin-3-yl)-ethyl]-pyrrolidin-2-yl}-phenyl)-acrylamide (44) was prepared from (E)-3-((S)-4-Pyrrolidin-2-yl-phenyl)-acrylic acid methyl ester and but-2-ynoic acid ethyl ester. LCMS (m/z): 391.2126 (M+1). $^1$H NMR (400 MHz, CD$_3$OD) δ 8.21 (d, J=7.0 Hz, 1 H), 7.41 (d, J=15.8 Hz, 1 H), 7.27 (d, J=8.0 Hz, 2 H), 7.16 (d, J=8.8 Hz, 1 H), 7.07 (d, J=8.0 Hz, 2 H), 6.91 (dd, J=7.8, 6.9 Hz, 1H), 6.61 (t, J=7.8 Hz, 1 H), 6.30 (d, J=15.8 Hz, 1 H), 3.44 (dt, J=9.0, 2.8 Hz, 1H), 3.26 (t, J=8.3 Hz, 1H), 2.74-2.51 (m, 3 H), 2.40-2.22 (m, 2 H), 2.17 (s, 3 H), 2.12-2.01 (m, 1 H), 1.93-1.75 (m, 2 H), 1.62-1.49 (m, 1 H); $^{13}$C NMR (400 MHz, CD$_3$OD) δ166.44, 150.68, 141.41, 140.54, 135.13, 129.17, 128.77, 128.61, 124.10, 117.94, 117.23, 112.36, 71.12, 55.56, 54.79, 35.54, 23.52, 23.01, 11.78

Example 55

Preparation of (E)-N-hydroxy-3-(4-{(R)-1-[2-(2-methyl-pyrazolo[1,5-a]pyridin-3-yl)-ethyl]-pyrrolidin-2-yl}-phenyl)-acrylamide (45)

Following procedures analogous to those described in Examples 2 and 3, (E)-N-hydroxy-3-(4-{(R)-1-[2-(2-methyl-pyrazolo[1,5-a]pyridin-3-yl)-ethyl]-pyrrolidin-2-yl}-phenyl)-acrylamide (45) was prepared from (R)-2-(4-bromo-phenyl)-pyrrolidine-1-carboxylic acid tert-butyl ester and but-2-ynoic acid ethyl ester. LCMS (m/z): 391.2134 (M+1).

Example 56

Preparation of (E)-N-hydroxy-3-(4-{(S)-1-[2-(2-trifluoromethyl-pyrazolo[1,5-a]pyridin-3-yl)-ethyl]-pyrrolidin-2-yl}-phenyl)-acrylamide (46)

Following procedures analogous to those described in Examples 2 and 3, (E)-N-hydroxy-3-(4-{(S)-1-[2-(2-trifluoromethyl-pyrazolo[1,5-a]pyridin-3-yl)-ethyl]-pyrrolidin-2-yl}-phenyl)-acrylamide (46) was prepared from (E)-3-((S)-4-pyrrolidin-2-yl-phenyl)-acrylic acid methyl ester and 4,4,4-trifluoro-but-2-ynoic acid ethyl ester. LCMS (m/z): 445.183 (M+1).

Example 57

Preparation of (E)-3-(4-{(S)-1-[2-(2-ethyl-pyrazolo[1,5-a]pyridin-3-yl)-ethyl]-pyrrolidin-2-yl}-phenyl)-N-hydroxy-acrylamide (47)

Following procedures analogous to those described in Examples 2 and 3, (E)-3-(4-{(S)-1-[2-(2-ethyl-pyrazolo[1,5-a]pyridin-3-yl)-ethyl]-pyrrolidin-2-yl}-phenyl)-N-hydroxy-acrylamide (47) was prepared from (E)-3-((S)-4-pyrrolidin-2-yl-phenyl)-acrylic acid methyl ester and pent-2-ynoic acid ethyl ester. LCMS (m/z): 405.2275 (M+1).

Example 58

Preparation of (E)-N-hydroxy-3-[4-((S)-1-{2-[2-(1-hydroxy-1-methyl-ethyl)-pyrazolo[1,5-a]pyridin-3-yl]-ethyl}-pyrrolidin-2-yl)-phenyl]-acrylamide (48)

Step a: Preparation of 4-hydroxy-4-methyl-pent-2-ynoic acid ethyl ester

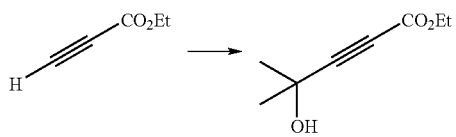

To a stirred solution of propynoic acid ethyl ester (20 mL, 197 mmol) in a mixture of 300 mL tetrahydrofuran:ether:pentane (4:1:1 by volume) cooled in a dry ice/isopropanol bath was added n-butyllithium (79 mL, 197 mmol, 2.5 M in hexanes) dropwise. After 15 minutes, anhydrous acetone (13.1 mL, 197 mmol) was slowly added. The reaction was kept below −78° C. for 8 h and quenched with an aqueous ammonium chloride solution, and the resulting mixture was stirred for 5 min. The reaction was warmed up to room temperature and extracted repeatedly with ethyl acetate. The combined organic layers were dried over magnesium sulfate, filtered and concentrated in vacuo, and the residue was purified via silica gel column chromatography (0-15% ethyl acetate in heptane) to give the title compound (10.75 g, 68.8 mmol) as a yellow oil.

Step b: Preparation of 2-(1-hydroxy-1-methyl-ethyl)-pyrazolo[1,5-a]pyridine-3-carboxylic acid ethyl ester

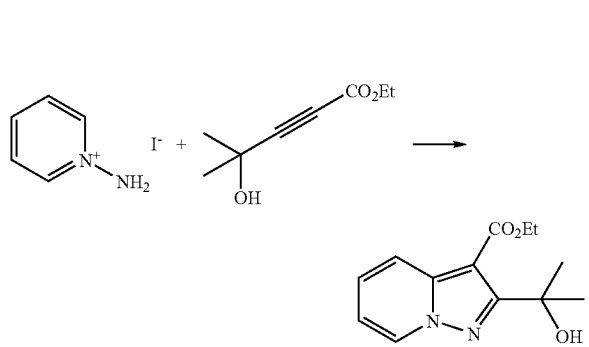

To a suspension of 1-amino-pyridinium iodide (0.343 g, 1.54 mmol) and potassium carbonate (0.278 g, 2.01 mmol) in 2 mL N,N-dimethylformamide was added 4-hydroxy-4-methyl-pent-2-ynoic acid ethyl ester (0.262 g, 1.70 mmol) in 1 mL N,N-dimethylformamide dropwise. The mixture was stirred at room temperature for 24 h under nitrogen atmosphere, poured on to ice and filtered, and the solid was washed with water to provide the crude product as a brown solid. The filtrate was extracted with ethyl acetate and the previously filtered solid was combined with the organic extracts, which was dried over magnesium sulfate, filtered and concentrated in vacuo and the residue was purified via silica gel column chromatography (0-50% ethyl acetate in heptane) to obtain the product as a yellow solid (0.296 g, 1.19 mmol, 77% yield).

Step c: Preparation of 2-(3-hydroxymethyl-pyrazolo[1,5-a]pyridin-2-yl)-propan-2-ol

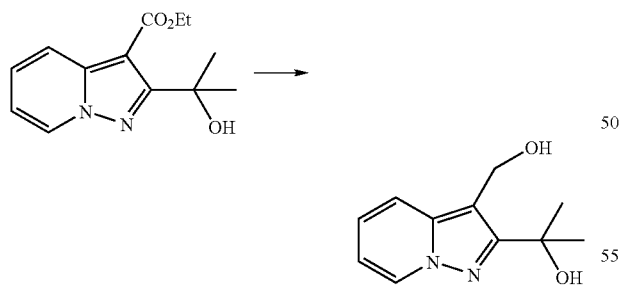

To a solution of 2-(1-hydroxy-1-methyl-ethyl)-pyrazolo[1,5-a]pyridine-3-carboxylic acid ethyl ester (1.54 g, 6.20 mmol) in tetrahydrofuran (25 mL) at 0° C. was added lithium aluminum hydride (0.27 g, 6.88 mmol). The mixture was allowed to warm to room temperature and stirred for 16 h. The reaction was cooled in an ice bath and 0.27 mL of water, 0.27 mL of 15% aqueous sodium hydroxide and 0.81 mL of water were sequentially added. The mixture was filtered through a plug of Celite, which was washed with methanol. The filtrate and washes were combined and concentrated in vacuo to give 1.5 g of the title compound as a yellow oil that was used directly in the next step.

Step d: Preparation of 2-(1-hydroxy-1-methyl-ethyl)-pyrazolo[1,5-a]pyridine-3-carbaldehyde

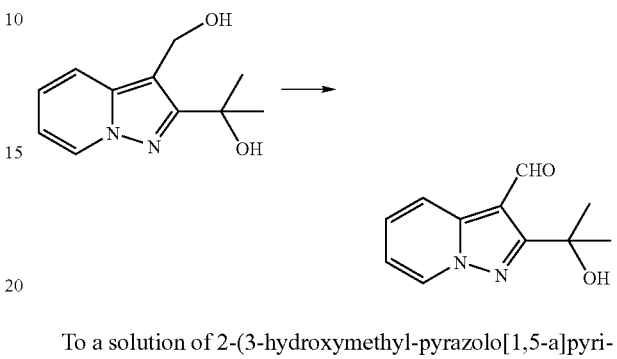

To a solution of 2-(3-hydroxymethyl-pyrazolo[1,5-a]pyridin-2-yl)-propan-2-ol (1.8 g, 7.42 mmol) in tetrahydrofuran (60 mL) under nitrogen atmosphere was added manganese (IV) oxide (5.22 g, 60 mmol) and the mixture was heated to 65° C. for 40 h. The mixture was filtered through a Celite pad, which was washed with excess dichloromethane. The filtrates were combined and concentrated in vacuo and the residue was purified via silica gel column chromatography (0-40% ethyl acetate in heptane) to give the title compound (1.01 g, 4.95 mmol, 67% yield) as a light yellow solid.

Following procedures analogous to those described in Example 6 step a, 2-(1-hydroxy-1-methyl-ethyl)-pyrazolo[1,5-a]pyridine-3-carbaldehyde (3.70 g, 18.1 mmol) was converted to 2-[3-(2-methoxy-vinyl)-pyrazolo[1,5-a]pyridin-2-yl]-propan-2-ol (3.01 g, 13.0 mmol, 72% yield).

Following procedures analogous to those described in Example 6 Step b, using concentrated hydrochloric acid (0.5 mL, 6 mmol) in lieu of p-toluenesulfonic acid, 2-[3-(2-methoxy-vinyl)-pyrazolo[1,5-a]pyridin-2-yl]-propan-2-ol (1.23 g, 5.30 mmol) was converted to 1,1-dimethyl-3,4-dihydro-1H-2-oxa-8a,9-diaza-fluoren-3-ol (0.697 g, 3.19 mmol, 60% yield) as a light yellow solid.

Following procedures analogous to those described in Examples 4 and 2, 1,1-dimethyl-3,4-dihydro-1H-2-oxa-8a,9-diaza-fluoren-3-ol was converted to (E)-N-hydroxy-3-[4-((S)-1-{2-[2-(1-hydroxy-1-methyl-ethyl)-pyrazolo[1,5-a]pyridin-3-yl]-ethyl}-pyrrolidin-2-yl)-phenyl]-acrylamide (48). LCMS (m/z): 435.2 (M+1).

Example 59

Preparation of (E)-N-hydroxy-3-(4-{(S)-1-[2-(2-pyrazin-2-yl-pyrazolo[1,5-a]pyridin-3-yl)-ethyl]-pyrrolidin-2-yl}-phenyl)-acrylamide (49)

Step a: Preparation of pyrazin-2-yl-propynoic acid ethyl ester

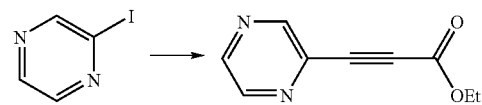

To a dry solution of zinc bromide (6.49 g, 28.8 mmol) in tetrahydrofuran (60 mL) was added triethylamine (16 mL, 115.2 mmol), iodopyrazine (4.95 g, 24 mmol), ethyl propionate (3.66 mL, 36 mmol) and tetrakis(triphenylphosphine) palladium (832 mg, 0.72 mmol). The reaction mixture was allowed to stir at ambient temperature for 16 h, diluted with diethyl ether, washed with saturated aqueous ammonium chloride and saturated aqueous sodium chloride, dried with anhydrous magnesium sulfate, filtered and concentrated in vacuo. The residue was purified via silica gel column chromatography (40% ethyl acetate in heptane) to yield the title compound as an orange oil (2.19 g, 52% yield). LCMS (m/z): 176.97 (M+).

Step b: Preparation of (E)-N-hydroxy-3-(4-{(S)-1-[2-(2-pyrazin-2-yl-pyrazolo[1,5-a]pyridin-3-yl)-ethyl]-pyrrolidin-2-yl}-phenyl)-acrylamide Following procedures analogous to those described in Example 58, (E)-N-hydroxy-3-(4-{(S)-1-[2-(2-pyrazin-2-yl-pyrazolo[1,5-a]pyridin-3-yl)-ethyl]-pyrrolidin-2-yl}-phenyl)-acrylamide (49) was prepared. LCMS (m/z): 455.2202 (M+1).

Example 60

Preparation of (E)-N-hydroxy-3-(4-{(S)-1-[2-(2-pyridin-3-yl-pyrazolo[1,5-a]pyridin-3-yl)-ethyl]-pyrrolidin-2-yl}-phenyl)-acrylamide (50)

Starting with 3-iodopyridine, (E)-N-hydroxy-3-(4-{(S)-1-[2-(2-pyridin-3-yl-pyrazolo[1,5-a]pyridin-3-yl)-ethyl]-pyrrolidin-2-yl}-phenyl)-acrylamide (50) was prepared following procedures analogous to those described in Example 69. LCMS (m/z): 454.2242 (M+1).

Example 61

Preparation of (E)-N-hydroxy-3-(4-{(S)-1-[2-(1H-pyrrolo[2,3-b]pyridin-3-yl)-ethyl]-pyrrolidin-2-yl}-phenyl)-acrylamide (51)

Following procedures analogous to those described in Example 4, (E)-3-(4-{(S)-1-[2-(1H-pyrrolo[2,3-b]pyridin-3-yl)-ethyl]-pyrrolidin-2-yl}-phenyl)-acrylic acid methyl ester (1.0 g, 2.7 mmol) was prepared from methanesulfonic acid 2-(1H-pyrrolo[2,3-b]pyridin-3-yl)-ethyl ester (1.06 g, 4.41 mmol).
Following procedures analogous to those described in Example 2, (E)-N-hydroxy-3-(4-{(S)-1-[2-(1H-pyrrolo[2,3-b]pyridin-3-yl)-ethyl]-pyrrolidin-2-yl}-phenyl)-acrylamide was prepared (51, 0.84 g, 85% yield) as a pale yellow solid. LCMS (m/z): 377.1971 (M+1).

Example 62

Preparation of (E)-3-(4-{(S)-1-[2-(2-tert-butyl-1H-pyrrolo[2,3-b]pyridin-3-yl)-ethyl]-pyrrolidin-2-yl}-phenyl)-N-hydroxy-acrylamide (52)

Phosphorous oxychloride (4.01 mL, 43 mmol) was added drop-wise to N,N-dimethylformamide (9.96 mL, 129 mmol) at 0° C. and the mixture was stirred for 20 min. A solution of 2-tert-butyl-1H-pyrrolo[2,3-b]pyridine (5.0 g, 28.7 mmol) dissolved in N,N-dimethylformamide (30 mL) was added and the resulting mixture was slowly warmed up to room temperature. The mixture was stirred at room temperature for 2 h then at 40° C. for 3 h, and cooled in an ice bath, and 0.5 mL water was added. The reaction mixture was slowly warmed to 40° C. and stirred for 20 h. The mixture was poured onto approximately 100 mL ice, neutralized with an aqueous sodium hydroxide (5%) and extracted with dichloromethane. The organic layers were combined, dried over magnesium sulfate, filtered and concentrated in vacuo, and the residue was purified via silica gel column chromatography (0-30% ethyl acetate in heptane) to obtain 2-tert-butyl-1H-pyrrolo[2,3-b]pyridine-3-carbaldehyde (2.4 g, 11.9 mmol, 41% yield) as an off white solid.

Following procedures analogous to those described in Example 6, 2-tert-butyl-1H-pyrrolo[2,3-b]pyridine-3-carbaldehyde was converted to (2-tert-butyl-1H-pyrrolo[2,3-b]pyridin-3-yl)-acetaldehyde.

Following procedures analogous to those described in Example 3, (E)-3-(4-{(S)-1-[2-(2-tert-butyl-1H-pyrrolo[2,3-b]pyridin-3-yl)-ethyl]-pyrrolidin-2-yl}-phenyl)-acrylic acid methyl ester (0.072 g, 0.167 mmol, 18% yield) was prepared from (2-tert-butyl-1H-pyrrolo[2,3-b]pyridin-3-yl)-acetaldehyde (0.285 g, 0.92 mmol).

Following procedures analogous to those described in Example 2, (E)-3-(4-{(S)-1-[2-(2-tert-butyl-1H-pyrrolo[2,3-b]pyridin-3-yl)-ethyl]-pyrrolidin-2-yl}-phenyl)-N-hydroxy-acrylamide was prepared (52, 0.044 g, 0.102 mmol, 61% yield) as a solid. LCMS (m/z): 433.3 (M+1).

Example 63

Preparation of (E)-N-hydroxy-3-{4-[1-(2-Imidazo[1,2-a]pyridin-3-yl-ethyl)-pyrrolidin-2-yl]-phenyl}-acrylamide (53)

Following procedures analogous to those described in Example 4, (E)-3-{4-[1-(2-imidazo[1,2-a]pyridin-3-yl-ethyl)-pyrrolidin-2-yl]-phenyl}-acrylic acid methyl ester (0.46 g, 0.95 mmol) was prepared from methanesulfonic acid 2-imidazo[1,2-a]pyridin-3-yl-ethyl ester (1.05 g, 4.37 mmol).

Following procedures analogous to those described in Example 2, (E)-N-hydroxy-3-{4-[1-(2-imidazo[1,2-a]pyridin-3-yl-ethyl)-pyrrolidin-2-yl]-phenyl}-acrylamide was prepared (53, 0.20 g, 58% yield) as a pale yellow solid. LCMS (m/z): 377.1982 (M+1).

Example 64

Preparation of (E)-N-hydroxy-3-(4-{(S)-1-[2-(2-methyl-imidazo[1,2-a]pyridin-3-yl)-ethyl]-pyrrolidin-2-yl}-phenyl)-acrylamide (54)

Following procedures analogous to those described in Example 6 and use triphenyl-(2-trimethylsilanyl-ethoxymethyl) phosphonium chloride, 2-methyl-imidazo[1,2-a]pyridine-3-carbaldehyde was converted into 2-methyl-3-[2-(2-trimethylsilanyl-ethoxy)-vinyl]-imidazo[1,2-a]pyridine (96% yield).

To a solution of 2-methyl-3-[2-(2-trimethylsilanyl-ethoxy)-vinyl]-imidazo[1,2-a]pyridine (1.8 g, 6.56 mmol) in a mixture of acetonitrile and water (1:1 by volume, 16 mL) in a 100 mL plastic bottle was added HF (8 mL, 48% solution in water). The reaction mixture was stirred at room temperature for 96 h and solid sodium bicarbonate was added in batches until the mixture reached pH 6. The mixture was washed twice with ether, basified to pH 8 with solid sodium hydroxide, and extracted three times with dichloromethane. The combined dichloromethane extracts were dried over magnesium sulfate and concentrated in vacuo to give (2-methyl-imidazo[1,2-a]pyridin-3-yl)-acetaldehyde (922 mg) as a deep brown semi-solid that was used directly in the next step without further purification.

Following procedures analogous to those described in Example 3, (E)-3-(4-{1-[2-(2-methyl-imidazo[1,2-a]pyridin-3-yl)-ethyl]-pyrrolidin-2-yl}-phenyl)-acrylic acid methyl ester (0.096 g, 0.246 mmol, 12% yield) was prepared from the (2-methyl-imidazo[1,2-a]pyridin-3-yl)-acetaldehyde.

Following procedures analogous to those described in Example 2, (E)-N-hydroxy-3-(4-{(S)-1-[2-(2-methyl-imidazo[1,2-a]pyridin-3-yl)-ethyl]-pyrrolidin-2-yl}-phenyl)-acrylamide was prepared (54, 0.037 g, 0.095 mmol, 43% yield) as a yellow solid. LCMS (m/z): 391.1 (M+1).

Example 65

Preparation of (E)-3-(4-{(S)-1-[2-(3,5-dimethyl-1-phenyl-1H-pyrazol-4-yl)-ethyl]-pyrrolidin-2-yl}-phenyl)-N-hydroxy-acrylamide (55)

Following procedures analogous to those described in Example 6, (3,5-dimethyl-1-phenyl-1H-pyrazol-4-yl)-acetaldehyde was prepared from 3,5-dimethyl-1-phenyl-1H-pyrazole-4-carbaldehyde.

Following procedures analogous to those described in Example 3, (E)-3-(4-{(S)-1-[2-(3,5-dimethyl-1-phenyl-1H-pyrazol-4-yl)-ethyl]-pyrrolidin-2-yl}-phenyl)-acrylic acid methyl ester (0.071 g, 0.165 mmol, 35% yield) was prepared from the above aldehyde (0.1 g, 0.467 mmol) as a yellow oil.

Following procedures analogous to those described in Example 2, (E)-3-(4-{(S)-1-[2-(3,5-dimethyl-1-phenyl-1H-pyrazol-4-yl)-ethyl]-pyrrolidin-2-yl}-phenyl)-N-hydroxy-acrylamide was prepared (55, 0.01 g, 0.021 mmol, 21% yield) as a white solid. LCMS (m/z): 431.2 (M+1).

Example 66

Preparation of (E)-N-hydroxy-3-(4-{(S)-1-[2-(3-methyl-5-phenyl-isoxazol-4-yl)-ethyl]-pyrrolidin-2-yl}-phenyl)-acrylamide (56)

Following procedures analogous to those described in Example 3, (E)-3-(4-{(S)-1-[2-(3-methyl-5-phenyl-isoxazol-4-yl)-ethyl]-pyrrolidin-2-yl}-phenyl)-acrylic acid methyl ester (0.20 g, 0.48 mmol, 22% yield) was prepared from (3-methyl-5-phenyl-isoxazol-4-yl)-acetaldehyde (0.5 g, 2.5 mmol).

Following procedures analogous to those described in Example 2, (E)-N-hydroxy-3-(4-{(S)-1-[2-(3-methyl-5-phenyl-isoxazol-4-yl)-ethyl]-pyrrolidin-2-yl}-phenyl)-acrylamide was prepared (56, 0.11 g, 0.26 mmol, 58% yield) as a pale yellow solid. LCMS (m/z): 418.1 (M+1).

Example 67

Preparation of (E)-N-hydroxy-3-(4-{(S)-1-[2-(5-methyl-2-phenyl-oxazol-4-yl)-ethyl]-pyrrolidin-2-yl}-phenyl)-acrylamide (57)

Following procedures analogous to those described in Example 4, (E)-3-(4-{(S)-1-[2-(5-methyl-2-phenyl-oxazol-4-yl)-ethyl]-pyrrolidin-2-yl}-phenyl)-acrylic acid methyl ester (0.21 g, 0.05 mmol) was prepared from methanesulfonic acid 2-(5-methyl-2-phenyl-oxazol-4-yl)-ethyl ester (0.80 g, 0.28 mmol).

Following procedures analogous to those described in Example 2, the title compound was prepared (57, 1.5 mg, 6.1% yield). LCMS (m/z): 418.2122 (M+1).

Example 68

Preparation of (E)-N-hydroxy-3-(4-{(S)-1-[2-(1H-pyrazol-4-yl)-ethyl]-pyrrolidin-2-yl}-phenyl)-acrylamide (58)

Following procedures analogous to those described in Example 4, (E)-3-(4-{(S)-1-[2-(1H-pyrazol-4-yl)-ethyl]-pyrrolidin-2-yl}-phenyl)-acrylic acid methyl ester (1.2 g, 3.0 mmol) was prepared from methanesulfonic acid 2-(1H-pyrazol-4-yl)-ethyl ester (1.2 g, 4.3 mmol).

Following procedures analogous to those described in Example 2, (E)-N-hydroxy-3-(4-{(S)-1-[2-(5-methyl-2-phenyl-oxazol-4-yl)-ethyl]-pyrrolidin-2-yl}-phenyl)-acrylamide was prepared (58, 0.52 g, 39% yield). LCMS (m/z): 327.1823 (M+1).

Example 69

Preparation of (E)-N-hydroxy-3-(4-{(S)-1-[2-(1-methyl-1H-pyrazol-4-yl)-ethyl]-pyrrolidin-2-yl}-phenyl)-acrylamide (59)

Following procedures analogous to those described in Example 4, ((E)-3-(4-{(S)-1-[2-(1-methyl-1H-pyrazol-4-yl)-ethyl]-pyrrolidin-2-yl}-phenyl)-acrylic acid methyl ester (0.54 g, 1.6 mmol) was prepared from methanesulfonic acid 2-(1-methyl-1H-pyrazol-4-yl)-ethyl ester (0.52 g, 2.6 mmol).

Following procedures analogous to those described in Example 2, (E)-N-hydroxy-3-(4-{(S)-1-[2-(1-methyl-1H-pyrazol-4-yl)-ethyl]-pyrrolidin-2-yl}-phenyl)-acrylamide was prepared (59, 0.57 g, 81% yield). 341.1975 (M+1).

Example 70

Preparation of (E)-N-hydroxy-3-(4-{(S)-1-[2-(1,3,5-trimethyl-1H-pyrazol-4-yl)-ethyl]-pyrrolidin-2-yl}-phenyl)-acrylamide (60)

Following procedures analogous to those described in Example 6, (1,3,5-trimethyl-1H-pyrazol-4-yl)-acetaldehyde was prepared from 1,3,5-trimethyl-1H-pyrazole-4-carbaldehyde.

Following procedures analogous to those described in Example 3, (E)-3-(4-{(S)-1-[2-(1,3,5-trimethyl-1H-pyrazol-4-yl)-ethyl]-pyrrolidin-2-yl}-phenyl)-acrylic acid methyl ester (0.41 g, 1.12 mmol) was prepared from the acetaldehyde above (0.35 g, 2.3 mmol, 52% yield).

Following procedures analogous to those described in Example 2, (E)-N-hydroxy-3-(4-{(S)-1-[2-(1,3,5-trimethyl-1H-pyrazol-4-yl)-ethyl]-pyrrolidin-2-yl}-phenyl)-acrylamide was prepared (60, 0.09 g, 0.24 mmol, 22% yield) as a pale yellow solid. LCMS (m/z): 369.0 (M+1). $^1$H NMR (400 MHz, DMSO-$d_6$) δ 10.73 (s, 1 H), 9.01 (s, 1 H), 7.45 (d, J=8.2 Hz, 2 H), 7.42 (d, J=17.4 Hz, 1 H), 7.28 (d, J=7.7 Hz, 2 H), 6.43 (d, J=15.8 Hz, 1 H), 3.54 (s, 3 H), 3.43-3.23 (m, 2 H), 2.45-2.23 (m, 4 H), 2.18-2.02 (m, 2 H), 1.96 (s, 3 H), 1.89 (s, 3 H), 1.86-1.73 (m, 2 H), 1.57-1.43 (m, 1 H); $^{13}$C NMR (400 MHz, DMSO-$d_6$) δ162.66, 145.58, 143.62, 137.99, 135.29, 133.26, 127.49, 127.26, 118.26, 113.36, 68.48, 54.44, 52.85, 35.34, 34.62, 22.52, 22.14, 11.32, 8.84; HRMS calcd for $C_{21}H_{28}N_4O_2$ [M+1]$^+$ 369.2291, found 369.2289.

Example 71

Preparation of (E)-3-(4-{(S)-1-[2-(1-tert-butyl-3,5-dimethyl-1H-pyrazol-4-yl)-ethyl]-pyrrolidin-2-yl}-phenyl)-N-hydroxy-acrylamide (61)

Following procedures analogous to those described in Examples 6, 3, and 2, (E)-3-(4-{(S)-1-[2-(1-tert-butyl-3,5-dimethyl-1H-pyrazol-4-yl)-ethyl]-pyrrolidin-2-yl}-phenyl)-N-hydroxy-acrylamide (61) was prepared. LCMS (m/z): 411.2761 (M+).

Example 72

Preparation of (E)-3-(4-{(S)-1-[2-(1-cyclopropylmethyl-3,5-dimethyl-1H-pyrazol-4-yl)-ethyl]-pyrrolidin-2-yl}-phenyl)-N-hydroxy-acrylamide (62)

Following procedures analogous to those described in Example 4, (E)-3-(4-{(S)-1-[2-(1-cyclopropylmethyl-3,5-dimethyl-1H-pyrazol-4-yl)-ethyl]-pyrrolidin-2-yl}-phenyl)-acrylic acid methyl ester (0.143 g, 0.351 mmol) was prepared from methanesulfonic acid 2-(1-cyclopropylmethyl-3,5-dimethyl-1H-pyrazol-4-yl)-ethyl ester (400 mg, 1.47 mmol, 24% yield) as a yellow oil.

Following procedures analogous to those described in Example 2, (E)-3-(4-{(S)-1-[2-(1-cyclopropylmethyl-3,5-dimethyl-1H-pyrazol-4-yl)-ethyl]-pyrrolidin-2-yl}-phenyl)-N-hydroxy-acrylamide was prepared (62, 0.078 g, 0.191 mmol, 78% yield) as a brown solid. LCMS (m/z): 409.3 (M+1).

Example 73

Preparation of (E)-N-hydroxy-3-{4-[(S)-1-(2-pyrazol-1-yl-ethyl)-pyrrolidin-2-yl]-phenyl}-acrylamide (63)

Following procedures analogous to those described in Example 7,1-(2-bromo-ethyl)-1H-pyrazole was prepared from 1H-pyrazole.

Following procedures analogous to those described in Example 4, (E)-3-{4-[(S)-1-(2-pyrazol-1-yl-ethyl)-pyrrolidin-2-yl]-phenyl}-acrylic acid methyl ester (0.27 g, 0.83 mmol) was prepared from 1-(2-bromo-ethyl)-1H-pyrazole (0.3 g, 1.1 mmol).

Following procedures analogous to those described in Example 2, (E)-N-hydroxy-3-{4-[(S)-1-(2-pyrazol-1-yl-ethyl)-pyrrolidin-2-yl]-phenyl}-acrylamide was prepared (63, 0.11 g, 44% yield) as a pale yellow solid. LCMS (m/z): 327.1 (M+1).

Example 74

Preparation of (E)-N-hydroxy-3-(4-{(S)-1-[2-(4-methyl-pyrazol-1-yl)-ethyl]-pyrrolidin-2-yl}-phenyl)-acrylamide (64)

Following procedures analogous to those described in Examples 7, 4, and 2, (E)-N-hydroxy-3-(4-{(S)-1-[2-(4-methyl-pyrazol-1-yl)-ethyl]-pyrrolidin-2-yl}-phenyl)-acrylamide (64) was prepared from 4-methyl-1H-pyrazole. LCMS (m/z): 341.1 (M+1).

Example 75

Preparation of (E)-3-(4-{(S)-1-[2-(4-bromo-pyrazol-1-yl)-ethyl]-pyrrolidin-2-yl}-phenyl)-N-hydroxy-acrylamide (65)

Following procedures analogous to those described in Examples 7, 4, and 2, (E)-3-(4-{(S)-1-[2-(4-bromo-pyrazol-1-yl)-ethyl]-pyrrolidin-2-yl}-phenyl)-N-hydroxy-acrylamide (65) was prepared from 4-bromo-pyrazole. LCMS (m/z): 406.8 (M+1).

Example 76

Preparation of (E)-3-(4-{(S)-1-[2-(3,5-dimethyl-pyrazol-1-yl)-ethyl]-pyrrolidin-2-yl}-phenyl)-N-hydroxy-acrylamide (66)

Following procedures analogous to those described in Examples 7, 4, and 2, (E)-3-(4-{(S)-1-[2-(3,5-dimethyl-pyrazol-1-yl)-ethyl]-pyrrolidin-2-yl}-phenyl)-N-hydroxy-acrylamide (66) was prepared from 3,5-dimethyl-pyrazole. LCMS (m/z): 355.0 (M+1).

Example 77

Preparation of (E)-N-hydroxy-3-(4-{1-[2-(3,4,5-trimethyl-pyrazol-1-yl)-ethyl]-pyrrolidin-2-yl}-phenyl)-acrylamide (67)

Following procedures analogous to those described in Example 7,1-(2-bromo-ethyl)-3,4,5-trimethyl-1H-pyrazole was prepared from 3,4,5-trimethyl-1H-pyrazole.

Following procedures analogous to those described in Example 4, (E)-3-(4-{(S)-1-[2-(3,4,5-trimethyl-pyrazol-1-yl)-ethyl]-pyrrolidin-2-yl}-phenyl)-acrylic acid methyl ester (0.39 g, 1.1 mmol) was prepared from 1-(2-bromo-ethyl)-3,4,5-trimethyl-1H-pyrazole (0.3 g, 1.12 mmol) as a yellow oil.

Following procedures analogous to those described in Example 2, (E)-N-hydroxy-3-(4-{1-[2-(3,4,5-trimethyl-pyrazol-1-yl)-ethyl]-pyrrolidin-2-yl}-phenyl)-acrylamide was prepared (67, 0.11 g, 44% yield) as a pale yellow solid. LCMS (m/z): 369.2 (M+1).

Example 78

Preparation of (E)-3-[4-((S)-1-{2-[3-(2,2-dimethyl-propyl)-5-hydroxy-4-methyl-pyrazol-1-yl]-ethyl}-pyrrolidin-2-yl)-phenyl]-N-hydroxy-acrylamide (63)

Following procedures analogous to those described in Example 4, methanesulfonic acid 5-(2,2-dimethyl-propyl)-1-(2-{(S)-2-[4-((E)-3-methoxy-buta-1,3-dienyl)-phenyl]-pyrrolidin-1-yl}-ethyl)-4-methyl-1H-pyrazol-3-yl ester (0.69 g, 1.38 mmol) was prepared from methanesulfonic acid 2-[5-(2,2-dimethyl-propyl)-3-methanesulfonyloxy-4-methyl-pyrazol-1-yl]-ethyl ester (0.62 g, 1.7 mmol).

Following procedures analogous to those described in Example 2, after preparative HPLC purification (0.1% trifluoroacetic acid in acetonitrile and water), (E)-3-[4-((S)-1-{2-[3-(2,2-dimethyl-propyl)-5-hydroxy-4-methyl-pyrazol- 1-yl]-ethyl}-pyrrolidin-2-yl)-phenyl]-N-hydroxy-acrylamide was obtained (68, 0.31 g, 43% yield). LC-MS (m/z): 427.2711 (M+1).

Example 79

Preparation of (E)-3-(4-{(S)-1-[2-(4-bromo-3,5-dimethyl-pyrazol-1-yl)-ethyl]-pyrrolidin-2-yl}-phenyl)-N-hydroxy-acrylamide (69)

Following procedures analogous to those described in Examples 7, 4, and 2, (E)-3-(4-{(S)-1-[2-(4-bromo-3,5-dimethyl-pyrazol-1-yl)-ethyl]-pyrrolidin-2-yl}-phenyl)-N-hydroxy-acrylamide (69) was prepared from 4-bromo-3,5-dimethyl-pyrazole. LCMS (m/z): 434.8 (M+1).

Example 80

Preparation of (E)-3-(4-{(S)-1-[2-(4-bromo-3-methyl-pyrazol-1-yl)-ethyl]-pyrrolidin-2-yl}-phenyl)-N-hydroxy-acrylamide (70)

Following procedures analogous to those described in Example 4, (E)-3-(4-{(S)-1-[2-(4-bromo-3-methyl-pyrazol-1-yl)-ethyl]-pyrrolidin-2-yl}-phenyl)-acrylic acid methyl ester (0.69 g, 1.7 mmol) was prepared from 4-bromo-1-(2-bromo-ethyl)-3-methyl-1H-pyrazole (0.69 g, 1.9 mmol).

Following procedures analogous to those described in Example 2, (E)-3-(4-{(S)-1-[2-(4-bromo-3-methyl-pyrazol-1-yl)-ethyl]-pyrrolidin-2-yl}-phenyl)-N-hydroxy-acrylamide was prepared (70, 0.57 g, 91% yield). LCMS (m/z): 420.1048 (M+1).

Example 81

Preparation of (E)-N-hydroxy-3-(4-{(s)-1-[2-(3-methyl-pyrazol-1-yl)-ethyl]-pyrrolidin-2-yl}-phenyl)-acrylamide (71)

Following procedures analogous to those described in Example 4, (E)-3-(4-{(S)-1-[2-(3-methyl-pyrazol-1-yl)-ethyl]-pyrrolidin-2-yl}-phenyl)-acrylic acid methyl ester (0.81 g, 2.4 mmol) was prepared from 1-(2-bromo-ethyl)-3-methyl-1H-pyrazole (0.65 g, 3.4 mmol).

Following procedures analogous to those described in Example 2, (E)-N-hydroxy-3-(4-{(S)-1-[2-(3-methyl-pyrazol-1-yl)-ethyl]-pyrrolidin-2-yl}-phenyl)-acrylamide was prepared (71, 0.63 g, 87% yield). LCMS (m/z): 341.1987 (M+1).

Example 82

Preparation of (E)-N-hydroxy-3-(4-{(S)-1-[2-(5-methyl-pyrazol-1-yl)-ethyl]-pyrrolidin-2-yl}-phenyl)-acrylamide (72)

Following procedures analogous to those described in Example 4, (E)-3-(4-{(S)-1-[2-(5-methyl-pyrazol-1-yl)-ethyl]-pyrrolidin-2-yl}-phenyl)-acrylic acid methyl ester (0.54 g, 1.6 mmol) was prepared from 1-(2-bromo-ethyl)-5-methyl-1H-pyrazole (0.52 g, 2.6 mmol).

Following procedures analogous to those described in Example 2, (E)-N-hydroxy-3-(4-{(S)-1-[2-(5-methyl-pyrazol-1-yl)-ethyl]-pyrrolidin-2-yl}-phenyl)-acrylamide was prepared (72, 0.57 g, 81% yield). LCMS (m/z): 341.1976 (M+1).

Example 83

Preparation of (E)-N-hydroxy-3-(4-{(S)-1-[2-(3-trifluoromethyl-pyrazol-1-yl)-ethyl]-pyrrolidin-2-yl}-phenyl)-acrylamide (73)

Following procedures analogous to those described in Example 4, (E)-3-(4-{(S)-1-[2-(3-trifluoromethyl-pyrazol-1-yl)-ethyl]-pyrrolidin-2-yl}-phenyl)-acrylic acid methyl ester (0.77 g, 2.3 mmol) was prepared from 1-(2-bromo-ethyl)-3-trifluoromethyl-1H-pyrazole (0.50 g, 2.6 mmol).

Following procedures analogous to those described in Example 2, (E)-N-hydroxy-3-(4-{(S)-1-[2-(3-trifluoromethyl-pyrazol-1-yl)-ethyl]-pyrrolidin-2-yl}-phenyl)-acrylamide was prepared (73, 0.62 g, 89% yield). LCMS (m/z): 395.1703 (M+1).

Example 84

Preparation of (E)-N-hydroxy-3-{4-[1-(2-imidazol-1-yl-ethyl)-pyrrolidin-2-yl]-phenyl}-acrylamide (74)

Following procedures analogous to those described in Example 4, where potassium carbonate was replaced with cesium carbonate and 0.5 equivalent of tetrabutyl-ammonium bromide, (E)-3-{4-[(S)-1-(2-imidazol-1-yl-ethyl)-pyrrolidin-2-yl]-phenyl}-acrylic acid methyl ester (0.16 g, 0.49 mmol) was prepared from 1-(2-chloro-ethyl)-1H-imidazole hydrochloride salt (0.30 g, 1.8 mmol).

Following procedures analogous to those described in Example 2, (E)-N-hydroxy-3-{4-[1-(2-imidazol-1-yl-ethyl)-pyrrolidin-2-yl]-phenyl}-acrylamide was prepared (74, 0.011 g, 6.3% yield). LCMS (m/z): 327.1821 (M+1).

Example 85

Typical Procedure for Synthesis of Triazole Analogs

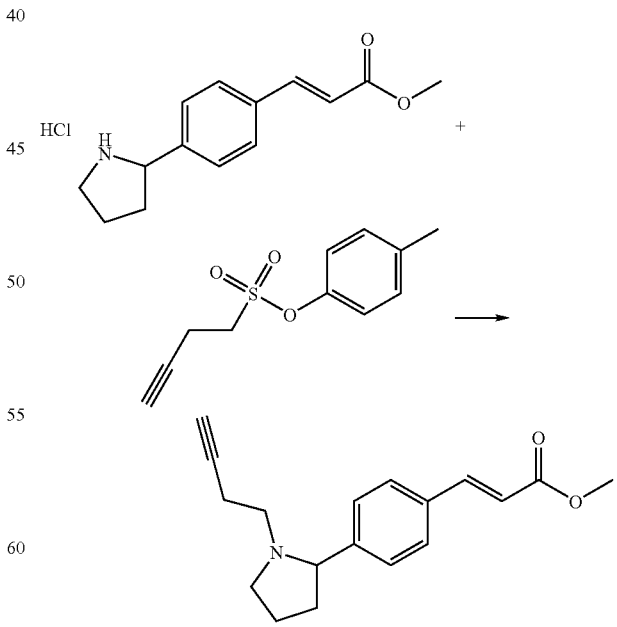

A mixture of (E)-3-(4-pyrrolidin-2-yl-phenyl)-acrylic acid methyl ester (5.52 g, 20.6 mmol), 3-butynyl p-toluenesulfonate (4.55 mL, 24.7 mmol) and potassium carbonate (5.98 g, 43.3 mmol) in acetonitrile (15 mL) was heated at 65° C. for 9 h. After cooled to room temperature, the reaction mixture was filtered, concentrated, and purified via silica gel column chromatography, and the residue was recrystallized from heptane to provide (E)-3-[4-(1-but-3-ynyl-pyrrolidin-2-yl)-phenyl]-acrylic acid methyl ester (3.68 g, 63% yield). LCMS (m/z): 284.2 (M+1).

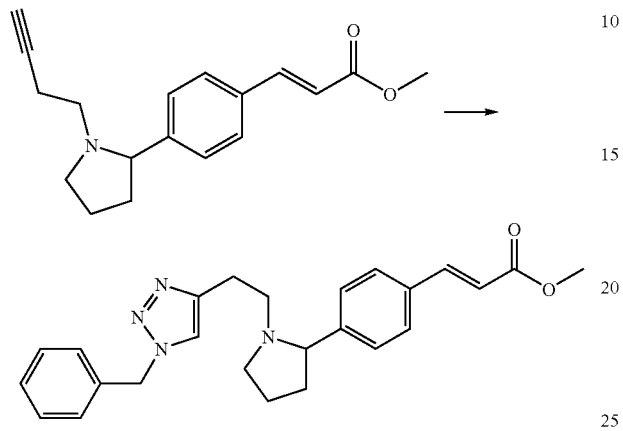

To a suspension of (E)-3-[4-(1-but-3-ynyl-pyrrolidin-2-yl)-phenyl]-acrylic acid methyl ester (50 mg, 0.176 mmol) and benzyl azide (23.5 mg, 0.176 mmol) in a mixture of water (0.7 mL) and tert-butanol (0.7 mL) were added a solution of sodium ascorbate (1 M in water, 18 µL) and copper sulfate pentahydrate (4.4 mg). The resulting mixture was stirred vigorously for 16 h, diluted with water, cooled to 0° C., and filtered, and the solid was washed with cold water and dried in vacuo to give (E)-3-(4-{1-[2-(1-benzyl-1H-[1,2,3]triazol-4-yl)-ethyl]-pyrrolidin-2-yl}-phenyl)-acrylic acid methyl ester (53 mg, 72% yield). LCMS (m/z): 417.2 (M+1).

Example 86

Preparation of (E)-N-hydroxy-3-(4-{(S)-1-[2-(1-methyl-1H-[1,2,3]triazol-4-yl)-ethyl]-pyrrolidin-2-yl}-phenyl)-acrylamide (75)

Following procedures analogous to those described in Examples 85 and 2, (E)-N-hydroxy-3-(4-{(S)-1-[2-(1-methyl-1H-[1,2,3]triazol-4-yl)-ethyl]-pyrrolidin-2-yl}-phenyl)-acrylamide (75) was prepared from azidomethane and (E)-3-[4-(1-but-3-ynyl-pyrrolidin-2-yl)-phenyl]-acrylic acid methyl ester. LCMS (m/z): 342.4 (M+1).

Example 87

Preparation of (E)-3-[4-((S)-1-{2-[1-(2-benzyloxy-ethyl)-1H-[1,2,3]triazol-4-yl]-ethyl}-pyrrolidin-2-yl)-phenyl]N-hydroxy-acrylamide (76)

Following procedures analogous to those described in Examples 85 and 2, (E)-3-[4-((S)-1-{2-[1-(2-benzyloxy-ethyl)-1H-[1,2,3]triazol-4-yl]-ethyl}-pyrrolidin-2-yl)-phenyl]-N-hydroxy-acrylamide (76) was prepared from (2-azido-ethoxymethyl)-benzene and (E)-3-[4-(1-but-3-ynyl-pyrrolidin-2-yl)-phenyl]-acrylic acid methyl ester. LCMS (m/z): 462.5 (M+1).

Example 88

Preparation of (E)-N-hydroxy-3-(4-{(S)-1-[2-(1-trimethylsilanylmethyl-1H-[1,2,3]triazol-4-yl)-ethyl]-pyrrolidin-2-yl}-phenyl)-acrylamide (77)

Following procedures analogous to those described in Examples 85 and 2, (E)-N-hydroxy-3-(4-{(S)-1-[2-(1-trimethylsilanylmethyl-1H-[1,2,3]triazol-4-yl)-ethyl]-pyrrolidin-2-yl}-phenyl)-acrylamide (77) was prepared from azidomethyl-trimethyl-silane and (E)-3-[4-(1-but-3-ynyl-pyrrolidin-2-yl)-phenyl]-acrylic acid methyl ester. LCMS (m/z): 414.3 (M+1).

Example 89

Preparation of (E)-3-(4-{(S)-1-[2-(1-benzyl-1H-[1,2,3]triazol-4-yl)-ethyl]-pyrrolidin-2-yl}-phenyl)-N-hydroxy-acrylamide (78)

Following procedures analogous to those described in Examples 85 and 2, (E)-3-(4-{(S)-1-[2-(1-benzyl-1H-[1,2,3]triazol-4-yl)-ethyl]-pyrrolidin-2-yl}-phenyl)-N-hydroxy-acrylamide (78) was prepared from azidomethyl-benzene and (E)-3-[4-(1-but-3-ynyl-pyrrolidin-2-yl)-phenyl]-acrylic acid methyl ester. LCMS (m/z): 418.5 (M+1).

Example 90

Preparation of (E)-3-[4-((S)-1-{2-[1-(4-Amino-phenyl)-1H-[1,2,3]triazol-4-yl]-ethyl}-pyrrolidin-2-yl)-phenyl]-N-hydroxy-acrylamide (79)

Following procedures analogous to those described in Examples 85 and 2, (E)-3-[4-((S)-1-{2-[1-(4-Amino-phenyl)-1H-[1,2,3]triazol-4-yl]-ethyl}-pyrrolidin-2-yl)-phenyl]-N-hydroxy-acrylamide (79) was prepared from 4-azido-phenylamine and (E)-3-[4-(1-but-3-ynyl-pyrrolidin-2-yl)-phenyl]-acrylic acid methyl ester. LCMS (m/z): 419.2 (M+1).

Example 91

Typical Procedure for Synthesis of Tetrazole Analogs

Step a: Preparation of (E)-3-{4-[1-(2-cyano-ethyl)-pyrrolidin-2-yl]-phenyl}-acrylic acid methyl ester

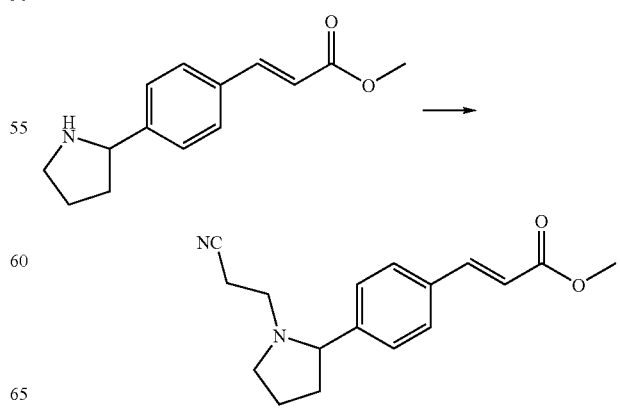

A mixture of (E)-3-(4-pyrrolidin-2-yl-phenyl)-acrylic acid methyl ester (1.0 g, 4.3 mmol), acrylonitrile (1.1 g, 22 mmol) and silica gel (4 g, grade 62 60-200 mesh 150 Å) was stirred at room temperature for 24 h. The reaction mixture was purified via silica gel column chromatography to give (E)-3-{4-[1-(2-cyano-ethyl)-pyrrolidin-2-yl]-phenyl}-acrylic acid methyl ester (1.2 g, 98%) as a colorless oil. LCMS (m/z): 285.1 (M+1).

Step b: Preparation of (E)-3-(4-{1-[2-(1H-tetrazol-5-yl)-ethyl]-pyrrolidin-2-yl}-phenyl)-acrylic acid methyl ester

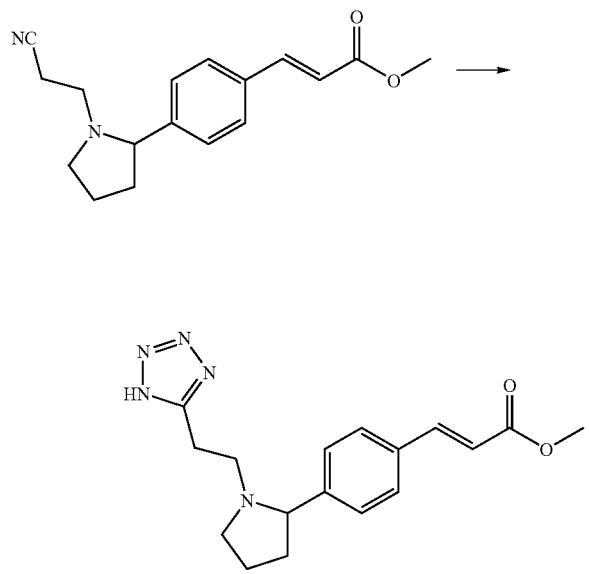

To a solution of (E)-3-{4-[1-(2-cyano-ethyl)-pyrrolidin-2-yl]-phenyl}-acrylic acid methyl ester (1.0 g, 3.5 mmol) in xylene (35 mL) was added azidotrimethyltin (1.09 g, 5.30 mmol) and the reaction solution was stirred at 130° C. for 16 h. The solvent was removed under reduced pressure and the residue was dissolved in an aqueous sodium hydroxide solution, washed with ethyl acetate, and neutralized with 1 N hydrochloride. A yellow oil was separated from the aqueous layer which was extracted with methylene chloride:ethanol (4:1) several times. The organic layers were combined with the yellow oil, dried over sodium sulfate, filtrated and concentrated in vacuo to give 1.6 g of a yellow oil, which was used to the next step without further purification. LCMS (m/z): 328.0 (M+1).

Example 92

Preparation of (E)-N-hydroxy-3-(4-{1-[2-(1H-tetrazol-5-yl)-ethyl]-pyrrolidin-2-yl}-phenyl)-acrylamide (80)

Following procedures analogous to those described in Example 2, (E)-3-(4-{1-[2-(1H-tetrazol-5-yl)-ethyl]-pyrrolidin-2-yl}-phenyl)-acrylic acid methyl ester (100 mg) was converted to (E)-N-hydroxy-3-(4-{1-[2-(1H-tetrazol-5-yl)-ethyl]-pyrrolidin-2-yl}-phenyl)-acrylamide (80, 76 mg, 76% yield). LCMS (m/z): 329.1721 (M+1)

Example 93

Typical Procedure for Alkylation of Tetrazoles

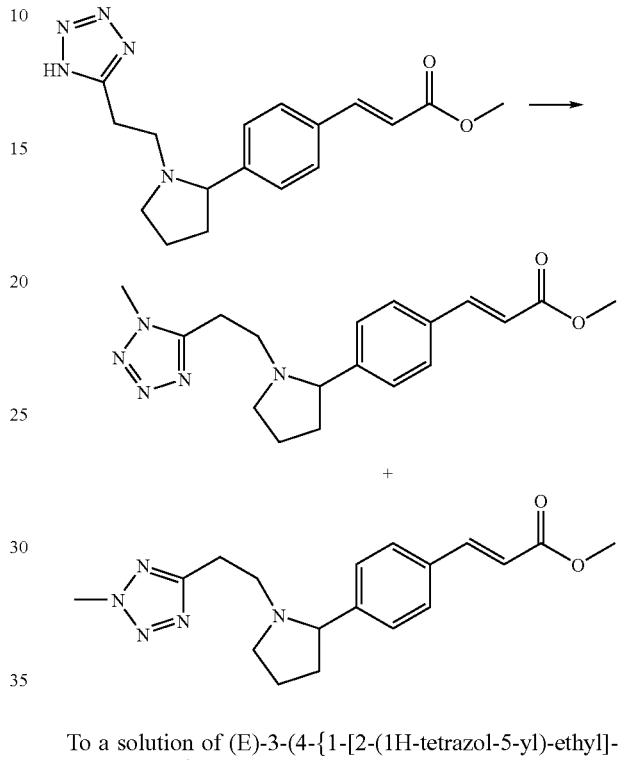

To a solution of (E)-3-(4-{1-[2-(1H-tetrazol-5-yl)-ethyl]-pyrrolidin-2-yl}-phenyl)-acrylic acid methyl ester (1.0 g, 2.1 mmol) in dimethylformamide (5 mL) was added iodomethane (1.91 mL, 30.6 mmol) and sodium hydroxide (1.64 g, 30.7 mmol). The reaction was stirred at room temperature for 2 h, ice water was added, and the resulting mixture was extracted several times with ethyl acetate. The combined organic layers were washed with a saturated aqueous solution of sodium chloride, dried over sodium sulfate, filtered and concentrated in vacuo. The residue was purified via silica gel column chromatography to give (E)-3-(4-{1-[2-(2-methyl-2H-tetrazol-5-yl)-ethyl]-pyrrolidin-2-yl}-phenyl)-acrylic acid methyl ester (0.15 g, 21%, LCMS (m/z): 342.1 (M+1)) and (E)-3-(4-{1-[2-(1-methyl-1H-tetrazol-5-yl)-ethyl]-pyrrolidin-2-yl}-phenyl)-acrylic acid methyl ester (0.20 g, 27%, LCMS (m/z): 342.1 (M+1)).

Example 94

Preparation of (E)-N-hydroxy-3-(4-{1-[2-(2-methyl-2H-tetrazol-5-yl)-ethyl]-pyrrolidin-2-yl}-phenyl)-acrylamide (81)

Following procedures analogous to those described in Example 2, (E)-3-(4-{1-[2-(2-methyl-2H-tetrazol-5-yl)-ethyl]-pyrrolidin-2-yl}-phenyl)-acrylic acid methyl ester (130 mg) was converted to (E)-N-hydroxy-3-(4-{1-[2-(2-methyl-2H-tetrazol-5-yl)-ethyl]-pyrrolidin-2-yl}-phenyl)-acrylamide (81, 77 mg, 59% yield). LCMS (m/z): 343.1881 (M+1).

Example 95

Preparation of (E)-N-hydroxy-3-(4-{1-[2-(1-methyl-1H-tetrazol-5-yl)-ethyl]-pyrrolidin-2-yl}-phenyl)-acrylamide (82)

Following procedures analogous to those described in Example 2, (E)-3-(4-{1-[2-(1-methyl-1H-tetrazol-5-yl)-ethyl]-pyrrolidin-2-yl}-phenyl)-acrylic acid methyl ester (140 mg) was converted to (E)-N-hydroxy-3-(4-{1-[2-(1-methyl-1H-tetrazol-5-yl)-ethyl]-pyrrolidin-2-yl}-phenyl)-acrylamide (82, 61 mg, 43% yield). LCMS (m/z): 343.1886 (M+1).

Example 96

Preparation of (E)-N-hydroxy-3-[4-(1-{2-[3-phenyl-1-(3-trifluoromethyl-phenyl)-1H-pyrazol-4-yl]-ethyl}-pyrrolidin-2-yl)-phenyl]-acrylamide (83)

Following procedures analogous to those described in Example 6, [3-phenyl-1-(3-trifluoromethyl-phenyl)-1H-pyrazol-4-yl]-acetaldehyde (0.57 g) was prepared from 3-phenyl-1-(3-trifluoromethyl-phenyl)-1H-pyrazole-4-carbaldehyde.

Following procedures analogous to those described in Example 3, (E)-3-[4-(1-{2-[3-phenyl-1-(3-trifluoromethyl-phenyl)-1H-pyrazol-4-yl]-ethyl}-pyrrolidin-2-yl)-phenyl]-acrylic acid methyl ester (0.49 g, 0.9 mmol, 69% yield) was prepared from [3-phenyl-1-(3-trifluoromethyl-phenyl)-1H-pyrazol-4-yl]-acetaldehyde (0.35 g, 1.31 mmol).

Following procedures analogous to those described in Example 2, (E)-N-hydroxy-3-[4-(1-{2-[3-phenyl-1-(3-trifluoromethyl-phenyl)-1H-pyrazol-4-yl]-ethyl}-pyrrolidin-2-yl)-phenyl]-acrylamide was prepared (83, 0.14 g, 0.25 mmol) as a brown solid. LCMS (m/z): 547.1 (M+1).

Example 97

Preparation of (E)-N-hydroxy-3-(4-{(S)-1-[2-[(Z)-hydroxyimino]-2-(5-methyl-1-phenyl-1H-pyrazol-4-yl)-ethyl]-pyrrolidin-2-yl}-phenyl)-acrylamide (84)

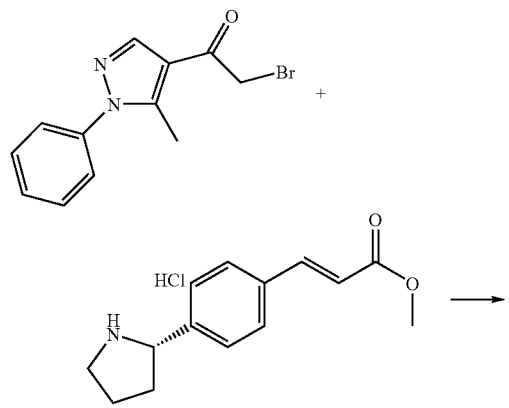

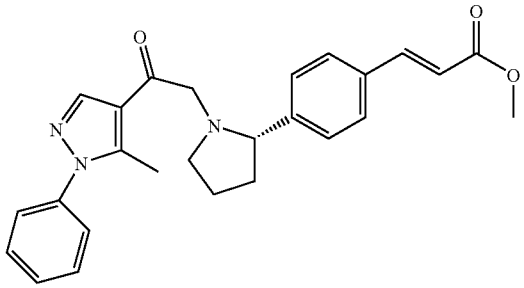

To a stirred solution of (E)-3-((S)-4-pyrrolidin-2-yl-phenyl)-acrylic acid methyl ester (45 mg, 0.17 mmol) in N,N-dimethylformamide (1 mL) was added triethylamine (0.074 mL, 0.537 mmol) and 2-bromo-1-(5-methyl-1-phenyl-1H-pyrazol-4-yl)-ethanone (50 mg, 0.179 mmol). Water was added and the resulting material was extracted repeatedly with dichloromethane. The combined organic layers were dried over sodium sulfate, filtered, and concentrated in vacuo, and the residue was purified via basic alumina chromatography (0-20% methanol in dichloromethane) to yield the title compound (65% yield) as a yellow oil.

Following procedures analogous to those described in Example 2, (E)-N-hydroxy-3-(4-{(S)-1-[2-[(Z)-hydroxyimino]-2-(5-methyl-1-phenyl-1H-pyrazol-4-yl)-ethyl]-pyrrolidin-2-yl}-phenyl)-acrylamide (84) was prepared. LCMS (m/z): 446.1 (M+1).

Example 98

Preparation of (E)-N-hydroxy-3-{4-[(S)-1-(2-pyrazolo[1,5-a]pyridin-3-yl-ethyl)-piperidin-2-yl]-phenyl}-acrylamide (85)

Following procedures analogous to those described in Example 3, (E)-3-{4-[(S)-1-(2-pyrazolo[1,5-a]pyridin-3-yl-ethyl)-piperidin-2-yl]-phenyl}-acrylic acid methyl ester (0.086 g, 0.221 mmol) was prepared from pyrazolo[1,5-a]pyridin-3-yl-acetaldehyde and (E)-3-((S)-4-piperidin-2-yl-phenyl)acrylic acid methyl ester in 47% yield.

Following procedures analogous to those described in Example 2, (E)-N-hydroxy-3-{4-[(S)-1-(2-pyrazolo[1,5-a]pyridin-3-yl-ethyl)-piperidin-2-yl]-phenyl}-acrylamide was prepared (85, 0.04 g, 0.102 mmol, 68% yield) as a yellow solid. LCMS (m/z): 391.2 (M+1).

Example 99

Preparation of (E)-N-hydroxy-3-{4-[(S)-1-(2-pyrazolo[1,5-a]pyridin-3-yl-ethyl)-azepan-2-yl]-phenyl}-acrylamide (86)

Following procedures analogous to those described in Example 3, (E)-3-{4-[(S)-1-(2-pyrazolo[1,5-a]pyridin-3-yl-ethyl)-azepan-2-yl]-phenyl}-acrylic acid methyl ester (0.042 g, 0.104 mol) was prepared from pyrazolo[1,5-a]pyridin-3-yl-acetaldehyde and (E)-3-((S)-4-azepan-2-yl-phenyl)-acrylic acid methyl ester as a yellow oil in 22% yield.

Following procedures analogous to those described in Example 2, (E)-N-hydroxy-3-{4-[(S)-1-(2-pyrazolo[1,5-a]pyridin-3-yl-ethyl)-azepan-2-yl]-phenyl}-acrylamide was prepared (86, 0.021 g, 0.052 mmol, 50% yield) as a yellow solid. LCMS (m/z): 405.2 (M+1).

Example 100

Typical Procedure for Synthesis of Phenyl-Piperazine Analogs

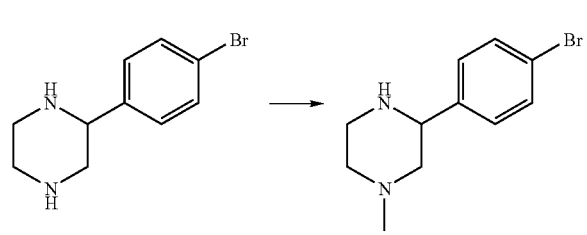

To a cooled (0° C.) solution of 2-(4-bromophenyl)piperazine (4.07 g, 16.0 mmol) and triethylamine (17 mL, 122 mmol) in acetone (50 mL) was added a solution of methyl iodide (1.4 mL, 22 mmol) in acetone (20 mL) over 50 min and the reaction mixture was stirred at 0° C. for 15 minutes, warmed to room temperature, and stirred for 16 h. The reaction mixture was slowly treated with saturated ammonium chloride (150 mL) and extracted with ethyl acetate (200 mL×3). The organic layers were combined, dried over magnesium sulfate, filtered and concentrated in vacuo. Purification via flash silica gel column chromatography (heptane/ethyl acetate) gave 3-(4-bromo-phenyl)-1-methyl-piperazine (1.89 g, 46% yield). LCMS (m/z): 257.00 (M+1).

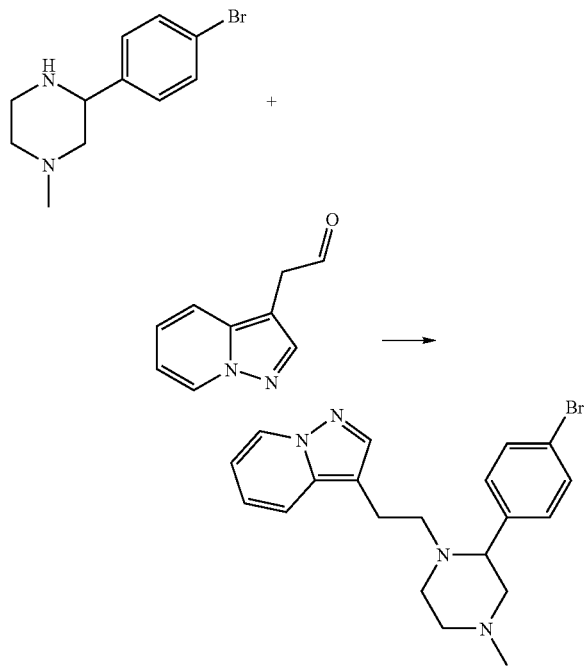

To a solution of 3-(4-bromo-phenyl)-1-methyl-piperazine (1.0 g, 3.92 mmol), pyrazolo[1,5-a]pyridin-3-yl-acetaldehyde (753 mg, 4.70 mmol) and acetic acid (1.2 mg) in tetrahydrofuran (15 mL) was added sodium triacetoxyborohydride (1.92 g, 8.62 mmol) and the resulting mixture was stirred at room temperature for 4 h. The reaction mixture was diluted with ethyl acetate, washed with a saturated aqueous sodium bicarbonate solution, a saturated aqueous solution of sodium chloride, dried over magnesium sulfate, filtered and concentrated in vacuo. Purification via flash silica gel column chromatography (heptane/ethyl acetate) gave 3-{2-[2-(4-bromo-phenyl)-4-methyl-piperazin-1-yl]-ethyl}-pyrazolo[1,5-a]pyridine (786 mg, 50% yield). LCMS (m/z): 401.00 (M+1).

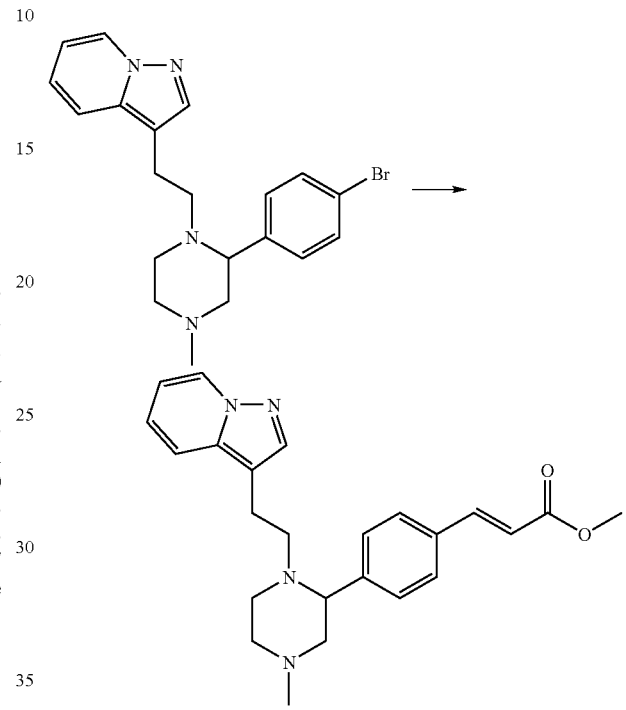

A mixture of 3-{2-[2-(4-bromo-phenyl)-4-methyl-piperazin-1-yl]-ethyl}-pyrazolo[1,5-a]pyridine (1.0 g, 2.49 mmol), methyl acrylate (0.458 mL, 4.98 mmol), N-methyl-dicyclohexylamine (584 mg, 2.99 mmol), tri-(tert-butyl) phosphine-tetrafluoroborate (28.9 mg, 0.0997 mmol) and Pd$_2$(dba)$_3$ (22.8 mg, 0.02 mmol) in 1,4-dioxane (10 mL) was flushed with nitrogen and heated at 100° C. for 1 h and at 135° C. for 1 h under microwave irradiation. The reaction mixture was cooled to room temperature, filtered through Celite pad, and concentrated in vacuo. Purification via flash silica gel column chromatography (heptane/ethyl acetate) gave (E)-3-{4-[4-methyl-1-(2-pyrazolo[1,5-a]pyridin-3-yl-ethyl)-piperazin-2-yl]-phenyl}-acrylic acid methyl ester (0.978 g, 97% yield). LCMS (m/z): 405.30 (M+1).

Example 101

Preparation of 3-[4-((E)-2-hydroxycarbamoyl-vinyl)-phenyl]-4-[2-(2-methyl-1H-indol-3-yl)-ethyl]-piperazine-1-carboxylic acid tert-butyl ester (87)

Following procedures analogous to those described in Example 100, 3-[4-((E)-2-methoxycarbonyl-vinyl)-phenyl]-4-[2-(2-methyl-1H-indol-3-yl)-ethyl]-piperazine-1-carboxylic acid tert-butyl ester was prepared. LCMS (m/z): 504.32 (M+1).

Following procedures analogous to those described in Example 2, 3-[4-((E)-2-hydroxycarbamoyl-vinyl)-phenyl]-4-[2-(2-methyl-1H-indol-3-yl)-ethyl]-piperazine-1-carboxylic acid tert-butyl ester (87, 65 mg, 57%) was prepared from 3-[4-((E)-2-methoxycarbonyl-vinyl)-phenyl]-4-[2-(2-methyl-1H-indol-3-yl)-ethyl]-piperazine-1-carboxylic acid tert-butyl ester (113 mg). LCMS (m/z): 505.3 (M+1).

Example 102

Preparation of (E)-N-hydroxy-3-(4-{4-methyl-1-[2-(2-methyl-1H-indol-3-yl)-ethyl]-piperazin-2-yl}-phenyl)-acrylamide (88)

Following procedures analogous to those described in Example 2, (E)-N-hydroxy-3-(4-{4-methyl-1-[2-(2-methyl-1H-indol-3-yl)-ethyl]-piperazin-2-yl}-phenyl)-acrylamide (88, 51 mg, 65%) was prepared from (E)-3-{4-[4-methyl-1-(2-pyrazolo[1,5-a]pyridin-3-yl-ethyl)-piperazin-2-yl]-phenyl}-acrylic acid methyl ester (78 mg). LCMS (m/z): 419.3 (M+1).

Example 103

Preparation of (E)-N-hydroxy-3-(4-{1-[2-(2-methyl-1H-indol-3-yl)-ethyl]-piperazin-2-yl}-phenyl)-acrylamide (89)

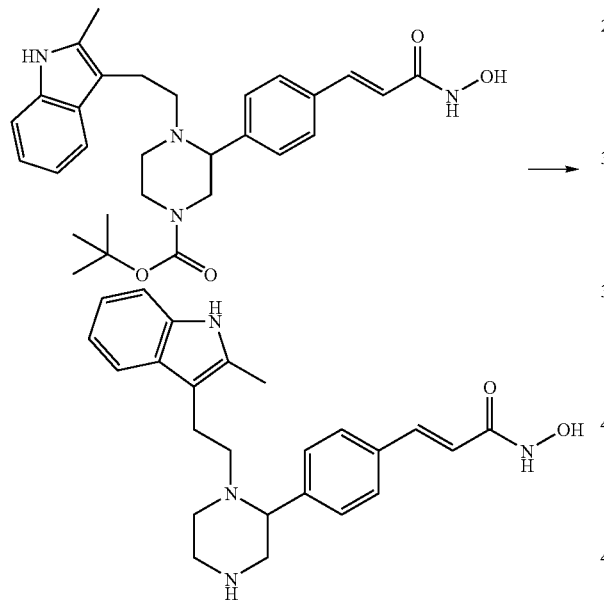

A solution of 3-[4-((E)-2-hydroxycarbamoyl-vinyl)-phenyl]-4-[2-(2-methyl-1H-indol-3-yl)-ethyl]-piperazine-1-carboxylic acid tert-butyl ester (55.8 mg, 0.111 mmol) in dioxane (5 mL) was treated with a solution of hydrochloric acid in dioxane (0.03 mL, 4 M) and the resulting mixture was stirred at room temperature. A brown precipitate was collected and dissolved in water. The aqueous solution was washed with diethyl ether and concentrated to give (E)-N-hydroxy-3-(4-{1-[2-(2-methyl-1H-indol-3-yl)-ethyl]-piperazin-2-yl}-phenyl)-acrylamide (89, 49 mg, 99% yield). LCMS (m/z): 405.1 (M+1).

Example 104

Preparation of (E)-N-hydroxy-3-{4-[4-methyl-1-(2-pyrazolo[1,5-a]pyridin-3-yl-ethyl)-piperazin-2-yl]-phenyl}-acrylamide (90)

Following procedures analogous to those described in Example 100, (E)-3-{4-[4-methyl-1-(2-pyrazolo[1,5-a]pyridin-3-yl-ethyl)-piperazin-2-yl]-phenyl}-acrylic acid methyl ester was prepared. LCMS (m/z): 405.23 (M+1).

Following procedures analogous to those described in Example 2, (E)-N-hydroxy-3-{4-[4-methyl-1-(2-pyrazolo[1,5-a]pyridin-3-yl-ethyl)-piperazin-2-yl]-phenyl}-acrylamide (90, 32 mg, 65%) was prepared from (E)-3-{4-[4-methyl-1-(2-pyrazolo[1,5-a]pyridin-3-yl-ethyl)-piperazin-2-yl]-phenyl}-acrylic acid methyl ester (50 mg). LCMS (m/z): 406.22 (M+1).

Example 105

Preparation of (E)-3-{3-fluoro-4-[(S)-1-(2-pyrazolo[1,5-a]pyridin-3-yl-ethyl)-pyrrolidin-2-yl]-phenyl}-N-hydroxy-acrylamide (91)

Following procedures analogous to those described in Example 3, (E)-3-{3-fluoro-4-[(S)-1-(2-pyrazolo[1,5-a]pyridin-3-yl-ethyl)-pyrrolidin-2-yl]-phenyl}-acrylic acid methyl ester (0.07 g, 0.178 mmol, 18% yield) was prepared from pyrazolo[1,5-a]pyridin-3-yl-acetaldehyde and (E)-3-((S)-3-fluoro-4-pyrrolidin-2-yl-phenyl)-acrylic acid methyl ester as a yellow oil.

Following procedures analogous to those described in Example 2, (E)-3-{3-fluoro-4-[(S)-1-(2-pyrazolo[1,5-a]pyridin-3-yl-ethyl)-pyrrolidin-2-yl]-phenyl}-N-hydroxy-acrylamide was prepared (91, 0.029 g, 0.074 mmol, 66% yield) as a solid. LCMS (m/z): 394.9 (M+1).

Example 106

Preparation of (E)-3-{3-chloro-4-[(S)-1-(2-pyrazolo[1,5-a]pyridin-3-yl-ethyl)-pyrrolidin-2-yl]-phenyl}-N-hydroxy-acrylamide (92)

Following procedures analogous to those described in Example 3, (E)-3-{3-chloro-4-[(S)-1-(2-pyrazolo[1,5-a]pyridin-3-yl-ethyl)-pyrrolidin-2-yl]-phenyl}-acrylic acid methyl ester (0.045 g, 0.083 mmol) was prepared from pyrazolo[1,5-a]pyridin-3-yl-acetaldehyde and (E)-3-((S)-3-chloro-4-pyrrolidin-2-yl-phenyl)-acrylic acid methyl ester as a yellow oil in 18% yield.

Following procedures analogous to those described in Example 2, (E)-3-{3-chloro-4-[(S)-1-(2-pyrazolo[1,5-a]pyridin-3-yl-ethyl)-pyrrolidin-2-yl]-phenyl}-N-hydroxy-acrylamide was prepared (92, 0.033 g, 0.08 mmol, 73% yield) as an off-white solid. LCMS (m/z): 411.1 (M+1).

Example 107

Preparation of (E)-3-{2-fluoro-4-[(S)-1-(2-pyrazolo[1,5-a]pyridin-3-yl-ethyl)-pyrrolidin-2-yl]-phenyl}-N-hydroxy-acrylamide (93)

Following procedures analogous to those described in Example 3, (E)-3-{2-fluoro-4-[(S)-1-(2-pyrazolo[1,5-a]pyridin-3-yl-ethyl)-pyrrolidin-2-yl]-phenyl}-acrylic acid methyl ester (0.123 g, 0.313 mmol, 26% yield) was prepared from pyrazolo[1,5-a]pyridin-3-yl-acetaldehyde and (E)-3-((S)-2-fluoro-4-pyrrolidin-2-yl-phenyl)-acrylic acid methyl ester as a yellow oil.

Following procedures analogous to those described in Example 2, (E)-3-{2-fluoro-4-[(S)-1-(2-pyrazolo[1,5-a]pyridin-3-yl-ethyl)-pyrrolidin-2-yl]-phenyl}-N-hydroxy-acrylamide was prepared (93, 0.073 g, 0.198 mmol, 63% yield) as a yellow solid. LCMS (m/z): 395.0 (M+1).

Example 108

Preparation of (E)-3-{3,5-difluoro-4-[(S)-1-(2-pyrazolo[1,5-a]pyridin-3-yl-ethyl)-pyrrolidin-2-yl]-phenyl}-N-hydroxy-acrylamide (94)

Following procedures analogous to those described in Example 3, (E)-3-{3,5-difluoro-4-[(S)-1-(2-pyrazolo[1,5-a]pyridin-3-yl-ethyl)-pyrrolidin-2-yl]-phenyl}-acrylic acid methyl ester (0.082 g, 0.199 mmol) was prepared from pyrazolo[1,5-a]pyridin-3-yl-acetaldehyde and (E)-3-((S)-3,5-difluoro-4-pyrrolidin-2-yl-phenyl)-acrylic acid methyl ester as a colorless solid in 24% yield.

Following procedures analogous to those described in Example 2, (E)-3-{3,5-difluoro-4-[(S)-1-(2-pyrazolo[1,5-a]pyridin-3-yl-ethyl)-pyrrolidin-2-yl]-phenyl}-N-hydroxy-acrylamide was prepared (94, 0.055 g, 0.133 mmol, 57% yield) as a yellow solid. LCMS (m/z): 413.0 (M+1).

Example 109

Preparation of (E)-3-(4-{(S)-1-[2-(3,5-dimethyl-1H-pyrazol-4-yl)-ethyl]-pyrrolidin-2-yl}-phenyl)-N-hydroxy-acrylamide (95)

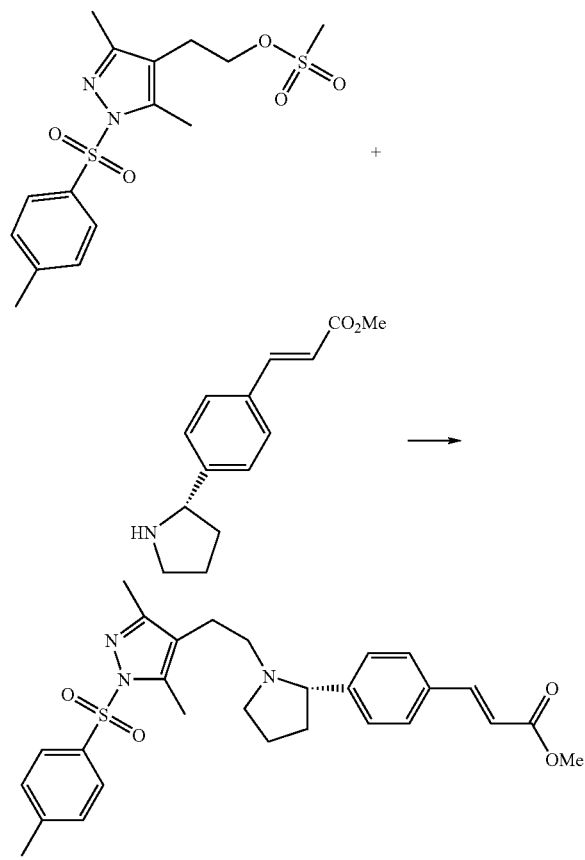

To a mixture of methanesulfonic acid 2-[3,5-dimethyl-1-(toluene-4-sulfonyl)-1H-pyrazol-4-yl]-ethyl ester (600 mg, 1.61 mmol) and (E)-3-((S)-4-pyrrolidin-2-yl-phenyl)-acrylic acid methyl ester (317 mg, 1.37 mmol) in 10 mL acetonitrile-N,N-dimethylacetamide (3:1 v/v) was added potassium carbonate (334 mg, 2.42 mmol). The mixture was subjected to microwave irradiation for 15 minutes and the crude mixture was filtered through a plug of Celite, which was washed with dichloromethane. The combined filtrates were partially concentrated and partitioned between ethyl acetate and aqueous ammonium chloride solution. The organic layer was washed three times with the same salt solution, which was back extracted once. The combined organic layers were dried over magnesium sulfate and concentrated in vacuo to give a yellow oil, which was purified via silica gel column chromatography (0-50% ethyl acetate in heptane) to give ((E)-3-[4-((S)-1-{2-[3,5-dimethyl-1-(toluene-4-sulfonyl)-1H-pyrazol-4-yl]-ethyl}-pyrrolidin-2-yl)-phenyl]-acrylic acid methyl ester (423 mg, 0.833 mmol, 52% yield) as a colorless solid.

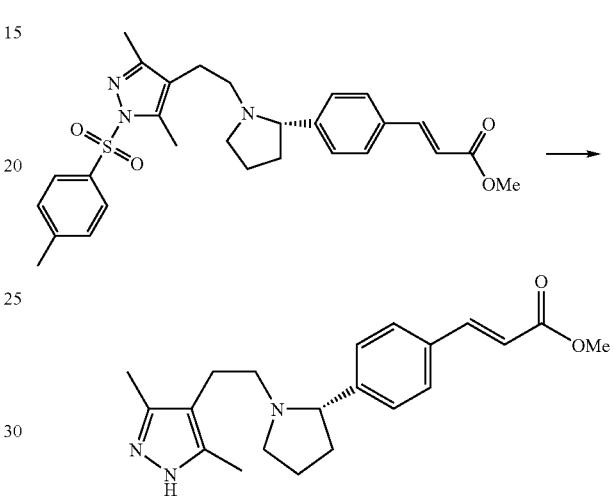

To a solution of (E)-3-[4-((S)-1-{2-[3,5-dimethyl-1-(toluene-4-sulfonyl)-1H-pyrazol-4-yl]-ethyl}-pyrrolidin-2-yl)-phenyl]-acrylic acid methyl ester (200 mg, 0.394 mmol) in methanol (10 mL) was added sodium methoxide in methanol (25 wt %, 1.0 mL). The mixture was subjected to microwave irradiation for 10 minutes, neutralized with 1 N HCl, and concentrated in vacuo. The remaining aqueous layer was extracted with ethyl acetate and dichloromethane, and the organic extracts were combined, dried over magnesium sulfate and concentrated in vacuo to give (E)-3-(4-{(S)-1-[2-(3,5-dimethyl-1H-pyrazol-4-yl)-ethyl]-pyrrolidin-2-yl}-phenyl)-acrylic acid methyl ester as a yellow crude oil (126 mg) that was directly used in the next step.

Following procedures analogous to those described in Example 2, (E)-3-(4-{(S)-1-[2-(3,5-dimethyl-1H-pyrazol-4-yl)-ethyl]-pyrrolidin-2-yl}-phenyl)-N-hydroxy-acrylamide was prepared (95, 26 mg, 0.073 mmol, 30% yield) as off-white solid. LCMS (m/z): 355.3 (M+1). 1H NMR (400 MHz, DMSO-$d_6$) δ 11.82 (br. s., 1 H), 10.73 (s, 1 H), 9.04 (s, 1 H), 7.44 (m, 3 H), 7.29 (d, J=7.5 Hz, 2 H), 6.42 (d, J=16.1 Hz, 1 H), 3.36 (m, 4 H), 2.41 (m, 2 H), 2.30 (m, 2 H), 2.09 (m, 2 H), 1.94 (s, 6 H), 1.81 (m, 2 H). 13C NMR (101 MHz, DMSO-$d_6$) δ 162.72, 145.58, 138.10, 133.26, 127.49, 127.31, 118.23, 112.32, 68.52, 54.39, 52.87, 34.63, 22.12. HRMS calcd for $C_{20}H_{26}N_4O_2$ [M+1]$^+$ 355.2134, found 355.2128.

Example 110

Preparation of (E)-3-(4-{(S)-1-[2-(1-ethyl-3,5-dimethyl-1H-pyrazol-4-yl)-ethyl]-pyrrolidin-2-yl}-phenyl)-N-hydroxy-acrylamide (96)

Following procedures analogous to those described in Example 4, (E)-3-(4-{(S)-1-[2-(1-ethyl-3,5-dimethyl-1H- pyrazol-4-yl)-ethyl]-pyrrolidin-2-yl}-phenyl)-acrylic acid methyl ester (37 mg, 0.102 mmol, 61% yield) was prepared from methanesulfonic acid 2-(1-ethyl-3,5-dimethyl-1H-pyrazol-4-yl)-ethyl ester (53 mg, 0.194 mmol, 90% pure) as a yellow oil.

Following procedures analogous to those described in Example 2, (E)-3-(4-{(S)-1-[2-(1-ethyl-3,5-dimethyl-1H-pyrazol-4-yl)-ethyl]-pyrrolidin-2-yl}-phenyl)-N-hydroxy-acrylamide was prepared (96, 42 mg, 0.110 mmol, 65% yield) as a light yellow solid. LCMS (m/z): 383.3 (M+1).

Example 111

Preparation of (E)-3-(4-{(S)-1-[2-(1-butyl-3,5-dimethyl-1H-pyrazol-4-yl)-ethyl]-pyrrolidin-2-yl}-phenyl)-N-hydroxy-acrylamide (97)

Following procedures analogous to those described in Example 4, (E)-3-(4-{(S)-1-[2-(1-butyl-3,5-dimethyl-1H-pyrazol-4-yl)-ethyl]-pyrrolidin-2-yl}-phenyl)-acrylic acid methyl ester (78 mg, 0.190 mmol) was prepared from methanesulfonic acid 2-(1-butyl-3,5-dimethyl-1H-pyrazol-4-yl)-ethyl ester (206 mg, 0.751 mmol, 25% yield) as a yellow oil.

Following procedures analogous to those described in Example 2, (E)-3-(4-{(S)-1-[2-(1-butyl-3,5-dimethyl-1H-pyrazol-4-yl)-ethyl]-pyrrolidin-2-yl}-phenyl)-N-hydroxy-acrylamide was prepared (97, 73 mg, 0.178 mmol, 74% yield) as a white solid. LCMS (m/z): 411.4 (M+1).

Example 112

Preparation of (E)-3-{4-[(S)-1-(2-benzenesulfonyl-ethyl)-pyrrolidin-2-yl]-phenyl}-N-hydroxy-acrylamide (98)

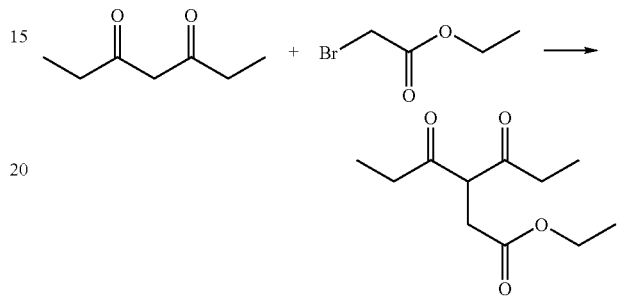

A mixture of (2-bromo-ethylsulfanyl)-benzene (273 mg, 1.26 mmol) and 3-chlorobenzenecarboperoxoic acid (650 mg, 3.77 mmol) in methylene chloride (5 mL) were stirred at room temperature for 16 h. A saturated sodium sulfite solution was added and the mixture was extracted with methylene chloride. The organic layers were washed by saturated sodium bicarbonate solution, dried over sodium sulfate, and concentrated in vacuo to provide (2-bromo-ethanesulfonyl)-benzene (0.24 g, 76%).

Following procedures analogous to those described in Example 4, (E)-3-{4-[(S)-1-(2-benzenesulfonyl-ethyl)-pyrrolidin-2-yl]-phenyl}-acrylic acid methyl ester (0.31 g, 0.78 mmol, 90% yield) was prepared from (2-bromo-ethanesulfonyl)-benzene (0.20 g, 0.87 mmol).

Following procedures analogous to those described in Example 2, (E)-3-{4-[(S)-1-(2-benzenesulfonyl-ethyl)-pyrrolidin-2-yl]-phenyl}-N-hydroxy-acrylamide was prepared (98, 0.17 g, 0.42 mol, 56% yield) as a white solid. LCMS (m/z): 401.1530 (M+1).

Example 113

Preparation of (E)-3-(4-{(S)-1-[2-(3,5-diethyl-1H-pyrazol-4-yl)-ethyl]-pyrrolidin-2-yl}-phenyl)-N-hydroxy-acrylamide (99)

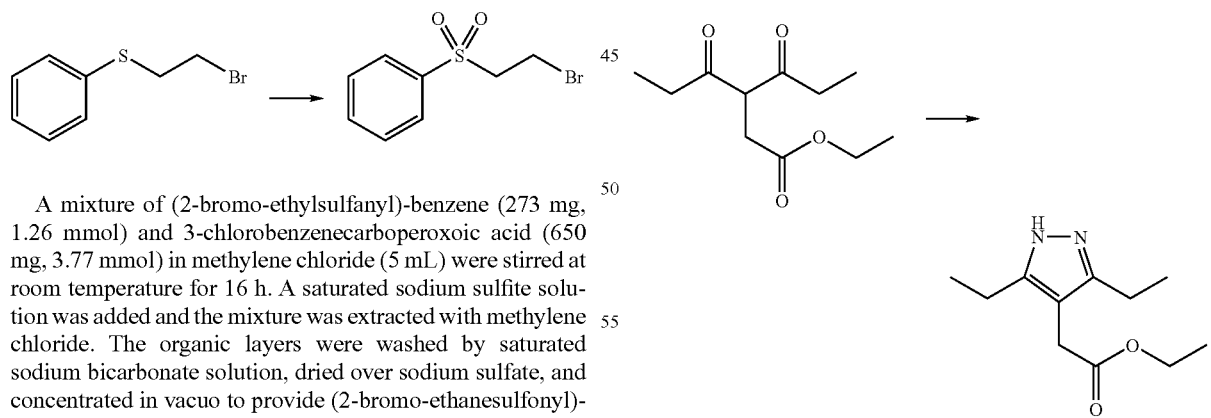

To a suspension of sodium hydride (5.2 g, 130 mmol, 60% in mineral oil) in tetrahydrofuran (100 mL) at 0° C. was added dropwise a solution of heptane-3,5-dione (16.6 g, 130 mmol) in tetrahydrofuran (30 mL). After 15 minutes, bromo-acetic acid ethyl ester (14.4 mL, 130 mmol) was added and the reaction mixture was stirred for 16 h at room temperature. The reaction mixture was poured into an aqueous ammonium chloride solution and extracted several times with ethyl acetate. The combined ethyl acetate layers were washed with water and a saturated aqueous solution of sodium chloride, dried over sodium sulfate, and concentrated under reduced pressure. The crude product was purified by silica gel column chromatography (0-30% ethyl acetate in heptane) to obtain 4-oxo-3-propionyl-hexanoic acid ethyl ester (19 g, 68%) as yellow oil.

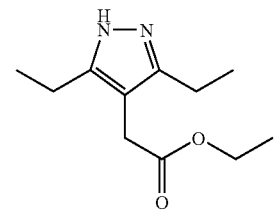

A mixture of 4-oxo-3-propionyl-hexanoic acid ethyl ester (15 g, 70 mmol) and hydrazine hydrate (3.5 mL, 71 mmol) in absolute ethanol (150 mL) was refluxed for 16 h. Solvent was removed under reduced pressure and the residue was purified by silica gel column chromatography (methanol in methylene chloride) to provide (3,5-diethyl-1H-pyrazol-4-yl)-acetic acid ethyl ester as yellow oil (11 g, 51 mmol).

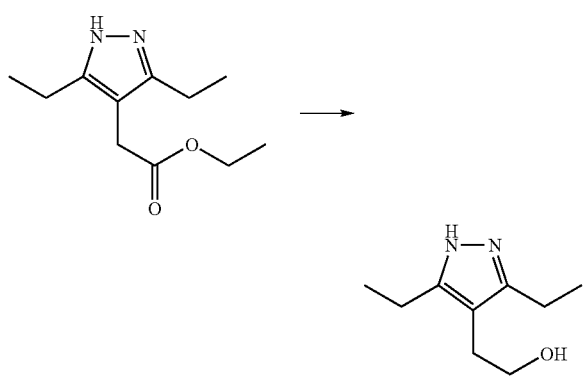

Lithium aluminum hydride (190 mg, 4.8 mmol) was added slowly to tetrahydrofuran (10 mL) under 0° C. (3,5-Diethyl-1H-pyrazol-4-yl)-acetic acid ethyl ester (1.0 g, 4.8 mol) in tetrahydrofuran (5 mL) was slowly added under nitrogen atmosphere. The reaction was allowed to slowly warm to room temperature and stirred for 16 h. After the reaction was cooled at 0° C., water (0.3 mL) was added slowly and the reaction was stirred for 30 minutes, filtered through a short silica gel column, which was rinsed with ethyl acetate followed by 20% methanol/methylene chloride. The solution was concentrated in vacuo to provide 2-(3,5-diethyl-1H-pyrazol-4-yl)-ethanol (0.8 g, 100% yield).

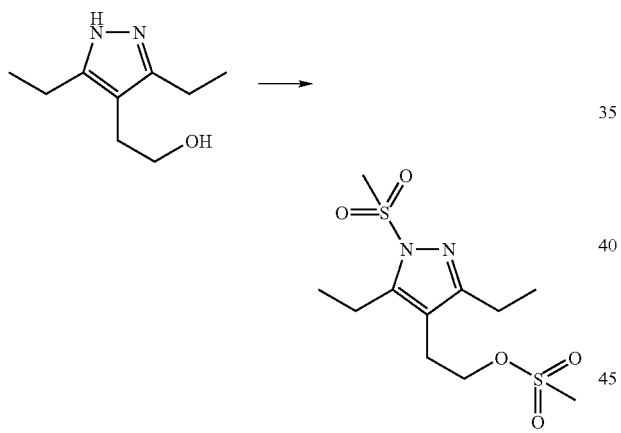

To a solution of 2-(3,5-diethyl-1H-pyrazol-4-yl)-ethanol (0.8 g, 4.8 mmol) in methylene chloride (20 mL) was added methanesulfonyl chloride (0.92 mL, 12 mmol) and triethylamine (2.0 mL, 14 mmol). The mixture was stirred at room temperature for 16 h and was loaded directly on to a silica gel column and eluted (methylene chloride/heptane followed by ethyl acetate/methylene chloride) to provide methanesulfonic acid 2-(3,5-diethyl-1-methanesulfonyl-1H-pyrazol-4-yl)-ethyl ester (940 mg, 41% yield).

Following procedures analogous to those described in Example 4, ((E)-3-(4-{(S)-1-[2-(3,5-diethyl-1-methanesulfonyl-1H-pyrazol-4-yl)-ethyl]-pyrrolidin-2-yl}-phenyl)-N-hydroxy-acrylamide (0.18 g, 0.31 mmol) was prepared from methanesulfonic acid 2-(3,5-diethyl-1-methanesulfonyl-1H-pyrazol-4-yl)-ethyl ester (940 mg, 1.94 mmol) in 16% yield.

Following procedures analogous to those described in Example 2, (E)-3-(4-{(S)-1-[2-(3,5-diethyl-1H-pyrazol-4-yl)-ethyl]-pyrrolidin-2-yl}-phenyl)-N-hydroxy-acrylamide was obtained (99, 55 mg, 0.14 mmol, 46% yield) as a white solid. LCMS (m/z): 383.2 (M+1).

Example 114

Preparation of (E)-3-(4-{(S)-1-[2-(3-tert-butyl-5-methyl-1H-pyrazol-4-yl)-ethyl]-pyrrolidin-2-yl}-phenyl)-N-hydroxy-acrylamide (100)

Following procedures analogous to those described in Examples 113 and 2, (E)-3-(4-{(S)-1-[2-(3-tert-butyl-5-methyl-1H-pyrazol-4-yl)-ethyl]-pyrrolidin-2-yl}-phenyl)-N-hydroxy-acrylamide (100) was prepared. LCMS (m/z): 397.3 (M+1).

Example 115

Preparation of (E)-N-hydroxy-3-(4-{(S)-1-[2-(2-isopropyl-2H-tetrazol-5-yl)-ethyl]-pyrrolidin-2-yl}-phenyl)-acrylamide (101)

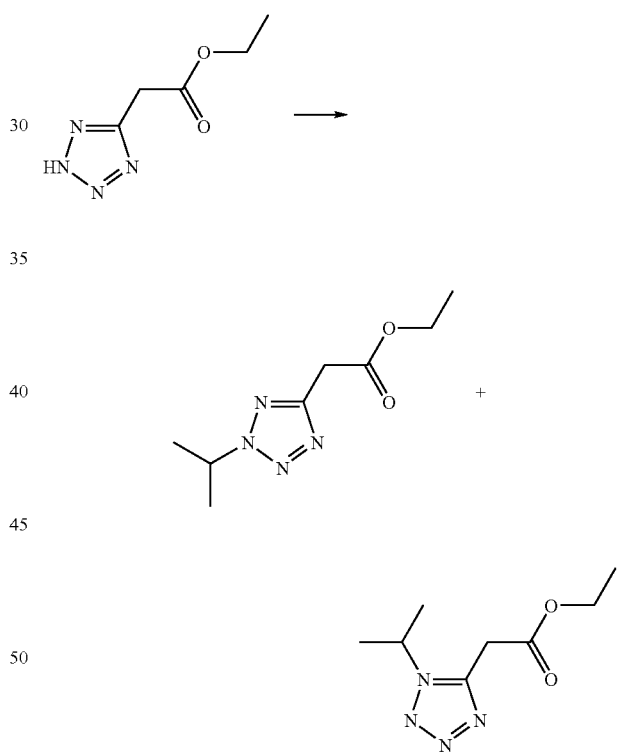

To a solution of (2H-tetrazol-5-yl)-acetic acid ethyl ester (2.0 g, 13 mmol) in dimethylformamide (5 mL) was added 2-iodo-propane (11 g, 64 mmol) and sodium hydroxide (2.6 g, 64 mmol) and the solution was stirred at room temperature for 2 h. Ice water was added and the solution was extracted several times with ethyl acetate. The combined organic layers were washed with a saturated aqueous solution of sodium chloride, dried over sodium sulfate, filtered and concentrated in vacuo. The residue was purified via silica gel column chromatography to provide a mixture of (2-isopropyl-2H-tetrazol-5-yl)-acetic acid ethyl ester and (1-isopropyl-1H-tetrazol-5-yl)-acetic acid ethyl ester (2 g, 79% yield).

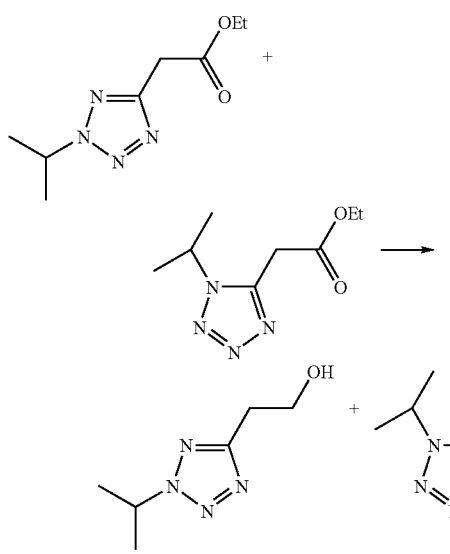

Lithium aluminum hydride (2.1 g, 10 mmol) was added slowly to tetrahydrofuran (30 mL) at 0° C. and a mixture of (2-isopropyl-2H-tetrazol-5-yl)-acetic acid ethyl ester and (1-isopropyl-1H-tetrazol-5-yl)-acetic acid ethyl ester (2 g, 10 mmol) in tetrahydrofuran (20 mL) was added under a nitrogen atmosphere. The reaction was allowed to warm to room temperature and stirred for 16 h. After the resulting mixture was cooled at 0° C., water (0.3 mL) was added slowly, and the reaction was stirred for 30 minutes and filtered through a short silica gel column, which was rinsed with ethyl acetate followed by 20% methanol/methylene chloride. The solution was concentrated in vacuo to provide 2-(2-isopropyl-2H-tetrazol-5-yl)-ethanol and 2-(1-isopropyl-1H-tetrazol-5-yl)-ethanol (1.5 g, 95% yield).

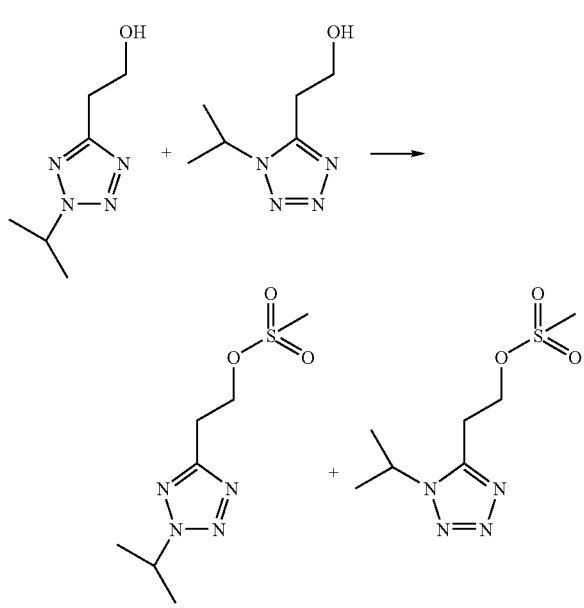

To a mixture of 2-(2-isopropyl-2H-tetrazol-5-yl)-ethanol and 2-(1-isopropyl-1H-tetrazol-5-yl)-ethanol (1.5 g, 9.6 mmol) in methylene chloride (40 mL) was added methanesulfonyl chloride (0.82 mL, 11 mmol) and triethylamine (2.67 mL, 19.2 mmol). The solution was stirred at room temperature for 6 h, loaded on to a silica gel column, and eluted using methylene chloride/heptane followed by ethyl acetate/methylene chloride to provide methanesulfonic acid 2-(2-isopropyl-2H-tetrazol-5-yl)-ethyl ester (370 mg, 17% yield) and methanesulfonic acid 2-(1-isopropyl-1H-tetrazol-5-yl)-ethyl ester (80 mg, 4% yield).

Following procedures analogous to those described in Example 4, (E)-3-(4-{(S)-1-[2-(2-isopropyl-2H-tetrazol-5-yl)-ethyl]-pyrrolidin-2-yl}-phenyl)-acrylic acid methyl ester (0.20 g, 0.85 mmol, 88% yield) was prepared from methanesulfonic acid 2-(2-isopropyl-2H-tetrazol-5-yl)-ethyl ester (0.36 g, 0.75 mmol).

Following procedures analogous to those described in Example 2, (E)-N-hydroxy-3-(4-{(S)-1-[2-(2-isopropyl-2H-tetrazol-5-yl)-ethyl]-pyrrolidin-2-yl}-phenyl)-acrylamide was prepared (101, 0.19 g, 0.38 mmol, 54% yield) as a white solid. LCMS (m/z): 371.2180 (M+1).

Example 116

Preparation of (E)-N-hydroxy-3-(4-{(S)-1-[2-(1-isopropyl-1H-tetrazol-5-yl)-ethyl]-pyrrolidin-2-yl}-phenyl)-acrylamide (102)

Following procedures analogous to those described in Examples 115, 4, and 2, (E)-N-hydroxy-3-(4-{(S)-1-[2-(1-isopropyl-1H-tetrazol-5-yl)-ethyl]-pyrrolidin-2-yl}-phenyl)-acrylamide (102) was prepared from (E)-3-((S)-4-pyrrolidin-2-yl-phenyl)-acrylic acid methyl ester and 2-(1-isopropyl-1H-tetrazol-5-yl)-ethyl ester. LCMS (m/z): 371.2183 (M+1).

Example 117

Preparation of (E)-N-hydroxy-3-[4-(1-{2-[2-(3,3,3-trifluoro-propyl)-2H-tetrazol-5-yl]-ethyl}-pyrrolidin-2-yl)-phenyl]-acrylamide (103)

Following procedures analogous to those described in Examples 115, 4, and 2, (E)-N-hydroxy-3-[4-(1-{2-[2-(3,3,3-trifluoro-propyl)-2H-tetrazol-5-yl]-ethyl}-pyrrolidin-2-yl)-phenyl]-acrylamide (103) was prepared from (E)-3-((S)-4-pyrrolidin-2-yl-phenyl)-acrylic acid methyl ester and 3-bromo-1,1,1-trifluoro-propane. LCMS (m/z): 425.1912 (M+1).

Example 118

Preparation of (E)-3-(4-{(S)-1-[2-(2-tert-butyl-2H-tetrazol-5-yl)-ethyl]-pyrrolidin-2-yl}-phenyl)-N-hydroxy-acrylamide (104)

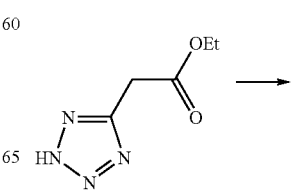

-continued

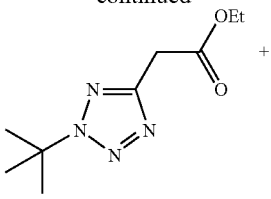

+

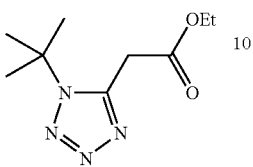

To a solution of (2H-tetrazol-5-yl)-acetic acid ethyl ester (2.0 g, 13 mmol) in 2-methyl-propan-2-ol (2.6 mL) and trifluoroacetic acid (6 mL) was added concentrated sulfuric acid (0.35 mL, 6.4 mmol) and the reaction was stirred at room temperature for 12 h. Ethyl acetate was added and the solution was neutralized by addition of an aqueous sodium hydroxide solution (2 N). The solution was extracted several times with ethyl acetate, and the organic layers were combined, dried over sodium sulfate, filtered, and concentrated in vacuo. The residue was purified via silica gel column chromatography to provide (2-tert-butyl-2H-tetrazol-5-yl)-acetic acid ethyl ester (2.0 g, 52% yield).

Following procedures analogous to those described in Examples 3 and 2, (E)-3-(4-{(S)-1-[2-(2-tert-butyl-2H-tetrazol-5-yl)-ethyl]-pyrrolidin-2-yl}-phenyl)-N-hydroxy-acrylamide (104) was prepared from (E)-3-((S)-4-pyrrolidin-2-yl-phenyl)-acrylic acid methyl ester and (2-tert-butyl-2H-tetrazol-5-yl)-acetic acid ethyl ester. LCMS (m/z): 385.2334 (M+1).

Example 119

Preparation of (E)-3-(4-{(S)-1-[2-(2-cyclobutyl-2H-tetrazol-5-yl)-ethyl]-pyrrolidin-2-yl}-phenyl)-N-hydroxy-acrylamide (105)

Following procedures analogous to those described in Examples 115, 4, and 2, (E)-3-(4-{(S)-1-[2-(2-cyclobutyl-2H-tetrazol-5-yl)-ethyl]-pyrrolidin-2-yl}-phenyl)-N-hydroxy-acrylamide (105) was prepared from (E)-3-((S)-4-pyrrolidin-2-yl-phenyl)-acrylic acid methyl ester and bromocyclobutane. LCMS (m/z): 383.2200 (M+1).

Example 120

Preparation of (E)-N-hydroxy-3-[4-((S)-1-{2-[2-(4-nitro-phenyl)-2H-tetrazol-5-yl]-ethyl}-pyrrolidin-2-yl)-phenyl]-acrylamide (106)

Following procedures analogous to those described in Examples 115, 4, and 2, (E)-N-hydroxy-3-[4-((S)-1-{2-[2-(4-nitro-phenyl)-2H-tetrazol-5-yl]-ethyl}-pyrrolidin-2-yl)-phenyl]-acrylamide (106) was prepared from (E)-3-((S)-4-pyrrolidin-2-yl-phenyl)-acrylic acid methyl ester and 1-fluoro-4-nitro-benzene. LCMS (m/z): 450.1881 (M+1).

Example 121

Preparation of (E)-N-hydroxy-3-[4-((S)-1-{2-[1-(4-nitro-phenyl)-1H-tetrazol-5-yl]-ethyl}-pyrrolidin-2-yl)-phenyl]-acrylamide (107)

Following procedures analogous to those described in Examples 115, 4, and 2, (E)-N-hydroxy-3-[4-((S)-1-{2-[1-(4-nitro-phenyl)-1H-tetrazol-5-yl]-ethyl}-pyrrolidin-2-yl)-phenyl]-acrylamide (107) was prepared from (E)-3-((S)-4-pyrrolidin-2-yl-phenyl)-acrylic acid methyl ester and 1-fluoro-4-nitro-benzene. LCMS (m/z): 450.1891 (M+1).

Example 122

Preparation of (E)-3-(4-{(S)-1-[2-(5-tert-butyl-1H-[1,2,3]triazol-4-yl)-ethyl]-pyrrolidin-2-yl}-phenyl)-N-hydroxy-acrylamide (108)

Following procedures analogous to those described in Examples 4 and 2, (E)-3-(4-{(S)-1-[2-(5-tert-butyl-1H-[1,2,3]triazol-4-yl)-ethyl]-pyrrolidin-2-yl}-phenyl)-N-hydroxy-acrylamide (108) was prepared from (E)-3-((S)-4-pyrrolidin-2-yl-phenyl)-acrylic acid methyl ester.

Example 123

Preparation of (E)-3-(4-{(S)-1-[2-(1,5-dimethyl-3-oxo-2-phenyl-2,3-dihydro-1H-pyrazol-4-yl)-ethyl]-pyrrolidin-2-yl}-phenyl)-N-hydroxy-acrylamide (116)

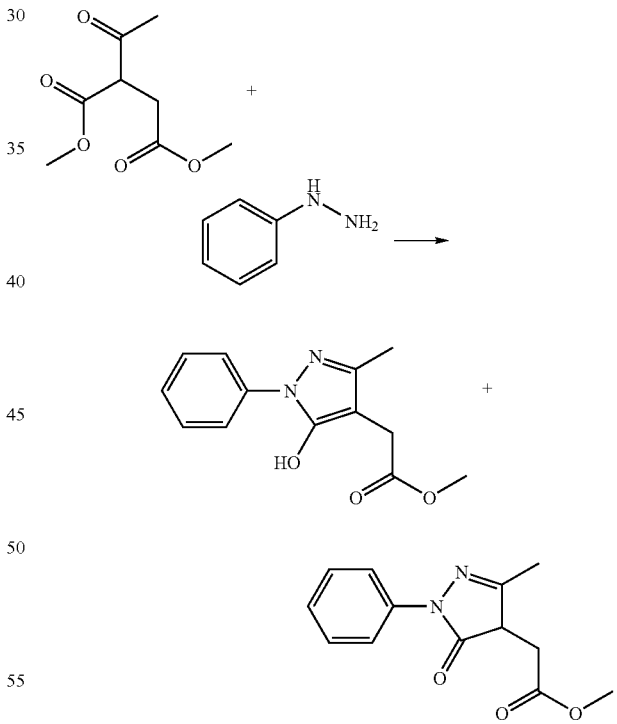

Phenylhydrazine (5.2 mL, 50 mmol) was added to a solution of dimethyl acetylsuccinate (8.1 mL, 50 mmol) in toluene (80 mL) and the mixture was heated to reflux using a Dean-Stark water separation apparatus for 8 h. The solid formed upon cooling was collected and rinsed with hexane to give a mixture of isomers (5-hydroxy-3-methyl-1-phenyl-1H-pyrazol-4-yl)-acetic acid methyl ester and (3-methyl-5-oxo-1-phenyl-4,5-dihydro-1H-pyrazol-4-yl)-acetic acid methyl ester in 91% yield (11.7 g). LCMS 247.2 (M+1).

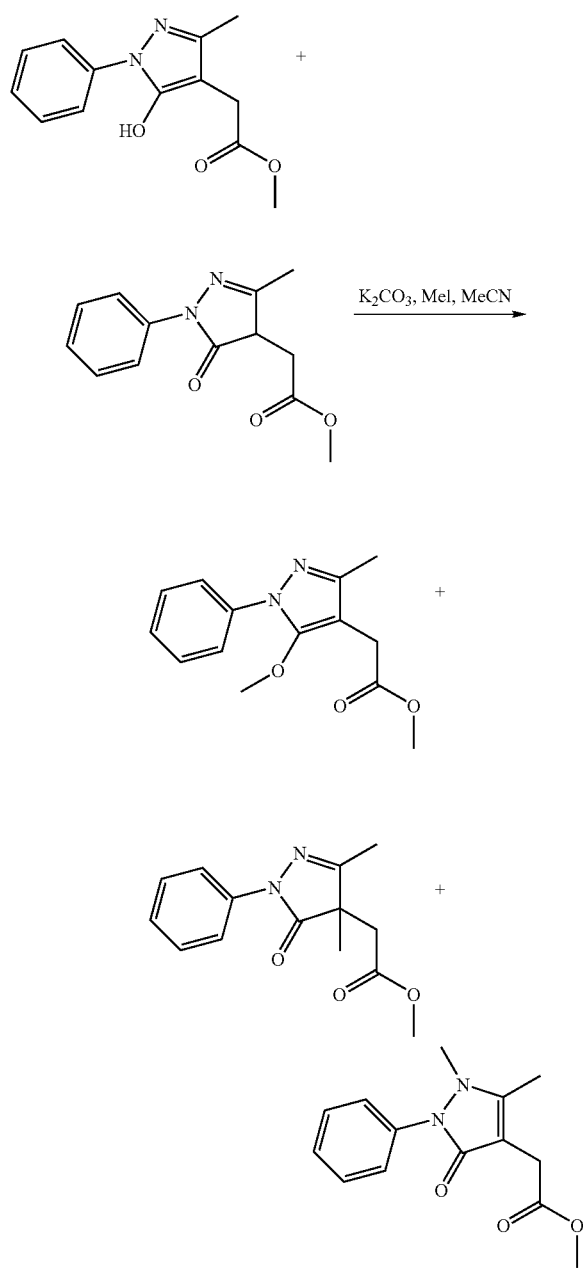

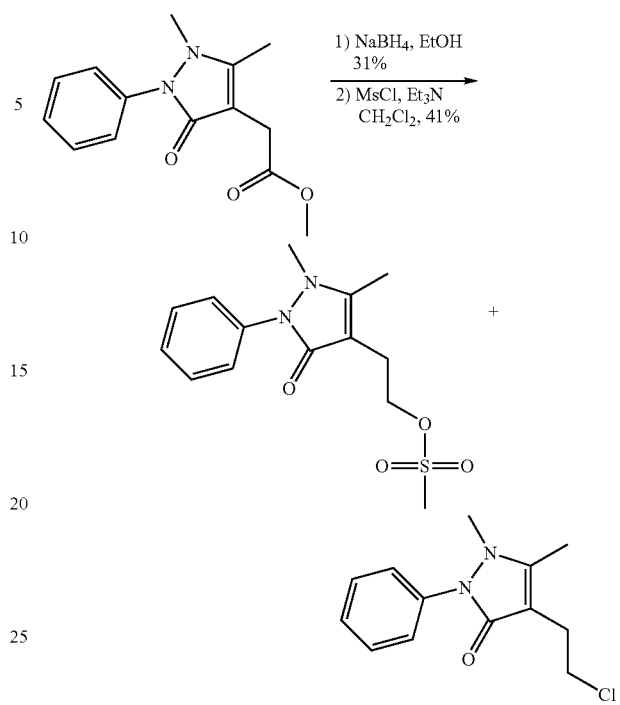

A mixture of (5-hydroxy-3-methyl-1-phenyl-1H-pyrazol-4-yl)-acetic acid methyl ester and (3-methyl-5-oxo-1-phenyl-4,5-dihydro-1H-pyrazol-4-yl)-acetic acid methyl ester (678 mg, 2.75 mmol), $K_2CO_3$ (pulverized, 1.45 g, 10.5 mmol), and methyl iodide (0.7 mL, 11 mmol) in acetonitrile 10 mL) was refluxed for 1 h and cooled to room temperature. The reaction mixture was diluted with water (40 mL) and extracted with ethyl acetate (3×100 mL). The combined organics were washed with brine, dried over $MgSO_4$, filtered and concentrated in vacuo. The residue was purified via silica gel column chromatography to give (5-methoxy-3-methyl-1-phenyl-1H-pyrazol-4-yl)-acetic acid methyl ester (86.5 mg, 12%), (3,4-dimethyl-5-oxo-1-phenyl-4,5-dihydro-1H-pyrazol-4-yl)-acetic acid methyl ester (161 mg, 22%) and (1,5-dimethyl-3-oxo-2-phenyl-2,3-dihydro-1H-pyrazol-4-yl)-acetic acid methyl ester (417 mg, 58%). LCMS 261.2 (M+1).

To a cooled (0° C.) solution of (1,5-dimethyl-3-oxo-2-phenyl-2,3-dihydro-1H-pyrazol-4-yl)-acetic acid methyl ester (122 mg, 0.479 mmol) in ethanol (5 mL) were added $CaCl_2.2H_2O$ (68.9 mg, 0.469 mmol) and sodium borohydride (37.4 mg, 0.937 mmol) and the resulting mixture was stirred at room temperature for 1 h. The reaction mixture was diluted with ethyl acetate, washed with water and brine, dried over $MgSO_4$, filtered, and concentrated in vacuo. The residue was purified by silica gel column chromatography to give 4-(2-hydroxy-ethyl)-1,5-dimethyl-2-phenyl-1,2-dihydro-pyrazol-3-one (33.7 mg, 31% yield). LCMS 233.3 (M+1).

A mixture of 4-(2-hydroxy-ethyl)-1,5-dimethyl-2-phenyl-1,2-dihydro-pyrazol-3-one (700 mg, 3.01 mmol), triethylamine (0.84 mL, 6.0 mmol), and methyl sulfonyl chloride (0.28 mL, 3.6 mmol) in dichloromethane (5.0 mL) was stirred at room temperature for 4 h. The reaction mixture was treated with saturated ammonium chloride and extracted with ethyl acetate. The combined organics were dried over $Na_2SO_4$, filtered and concentrated in vacuo. Purification via silica gel column chromatography provided methanesulfonic acid 2-(1,5-dimethyl-3-oxo-2-phenyl-2,3-dihydro-1H-pyrazol-4-yl)-ethyl ester (384 mg) and 4-(2-chloro-ethyl)-1,5-dimethyl-2-phenyl-1,2-dihydro-pyrazol-3-one (310 mg) in 41% combined yield. LCMS 311.3 (M+1) and LCMS 251.3 (M+1), respectively.

Following procedures analogous to those described in Example 4, methanesulfonic acid 2-(1,5-dimethyl-3-oxo-2-phenyl-2,3-dihydro-1H-pyrazol-4-yl)-ethyl ester (384 mg) and 4-(2-chloro-ethyl)-1,5-dimethyl-2-phenyl-1,2-dihydro-pyrazol-3-one (310 mg) was converted to (E)-3-(4-{(S)-1-[2-(1,5-dimethyl-3-oxo-2-phenyl-2,3-dihydro-1H-pyrazol-4-yl)-ethyl]-pyrrolidin-2-yl}-phenyl)-acrylic acid (86 mg, 31%).

Following procedures analogous to those described in Example 2, (E)-3-(4-{(S)-1-[2-(1,5-dimethyl-3-oxo-2-phenyl-2,3-dihydro-1H-pyrazol-4-yl)-ethyl]-pyrrolidin-2-yl}-phenyl)-acrylic acid (100 mg, 0.224 mmol) was converted to (E)-3-(4-{(S)-1-[2-(1,5-dimethyl-3-oxo-2-phenyl-2,3-dihydro-1H-pyrazol-4-yl)-ethyl]-pyrrolidin-2-yl}-phenyl)-N-hydroxy-acrylamide (15 mg, 15%). LCMS 447.5 (M+1).

Example 124

Preparation of (E)-N-hydroxy-3-(4-{(R)-1-[2-(1,3,5-trimethyl-1H-pyrazol-4-yl)-ethyl]-pyrrolidin-2-yl}-phenyl)-acrylamide (110)

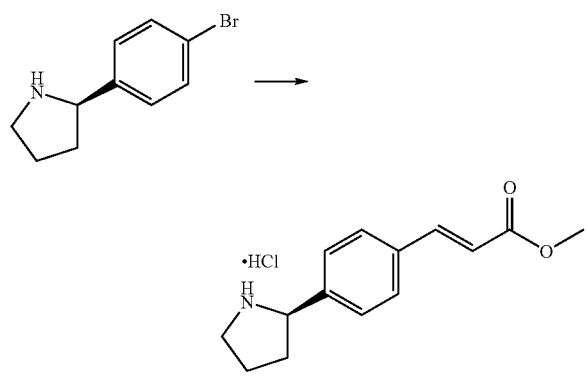

Following procedures analogous to those described in Example 1, (E)-3-((R)-4-pyrrolidin-2-yl-phenyl)-acrylic acid methyl ester hydrochloride was prepared from (R)-2-(4-bromo-phenyl)-pyrrolidine.

Following procedures analogous to those described in Example 113, methanesulfonic acid 2-(1,3,5-trimethyl-1H-pyrazol-4-yl)-ethyl ester was prepared from 2-(1,3,5-trimethyl-1H-pyrazol-4-yl)-ethanol.

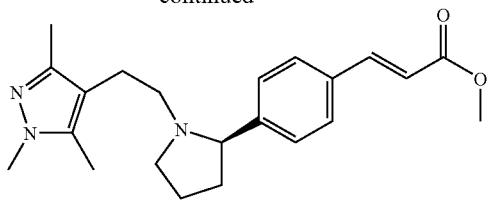

Following procedures analogous to those described in Example 4, (E)-3-(4-{(R)-1-[2-(1,3,5-trimethyl-1H-pyrazol-4-yl)-ethyl]-pyrrolidin-2-yl}-phenyl)-acrylic acid methyl ester was prepared from methanesulfonic acid 2-(1,3,5-trimethyl-1H-pyrazol-4-yl)-ethyl ester and (E)-3-((R)-4-pyrrolidin-2-yl-phenyl)-acrylic acid methyl ester hydrochloride.

Following procedures analogous to those described in Example 2, (E)-N-hydroxy-3-(4-{(R)-1-[2-(1,3,5-trimethyl-1H-pyrazol-4-yl)-ethyl]-pyrrolidin-2-yl}-phenyl)-acrylamide was prepared (110, 0.034 g, 0.09 mmol, 10% yield) as a white solid. LC/MS (m/z): 369.3 (M+1). $^1$H-NMR (d$_6$-dmso) δ 8.90 (br s, 1H); 7.58 (d, 1H); 7.34 (d, 2H); 7.15 (d, 2H); 6.31 (m, 1H); 3.56 (s, 3H); 3.40 (t, 1H); 3.22 (t, 1H); 2.50-2.20 (m, 4H); 2.09 (m, 2H); 1.94 (d, 6H); 1.90 (m, 1H); 1.79 (m, 1H); 1.60 (m, 1H).

Example 125

Preparation of N-hydroxy-3-(4-{(R)-1-[2-(1,3,5-trimethyl-1H-pyrazol-4-yl)-ethyl]-pyrrolidin-2-yl}-phenyl)-propionamide (111)

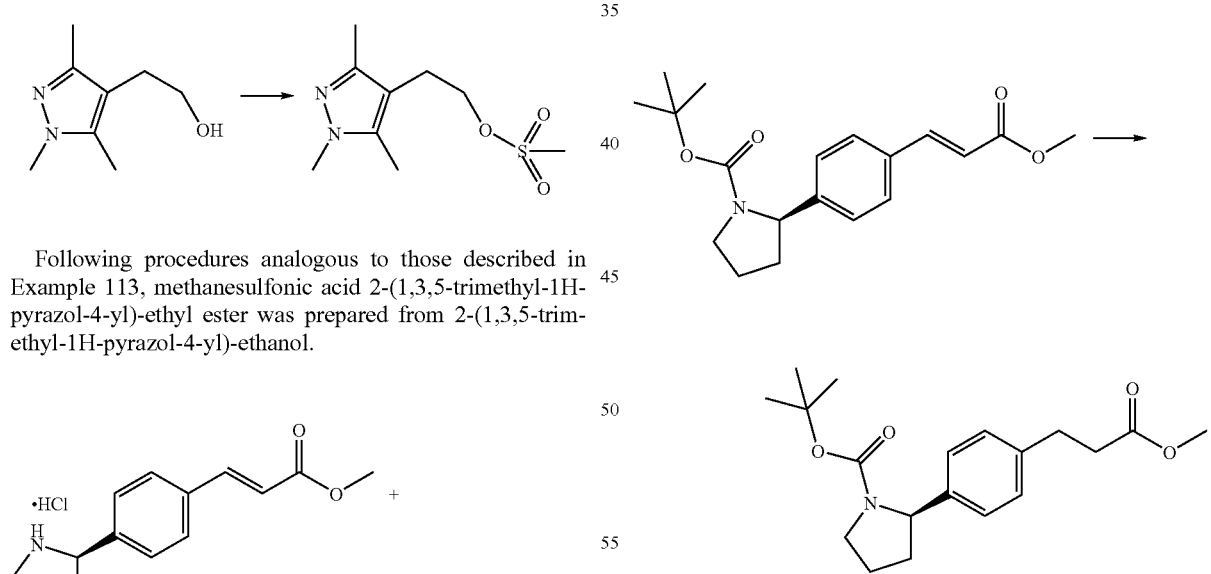

(R)-2-[4-((E)-2-Methoxycarbonyl-vinyl)-phenyl]-pyrrolidine-1-carboxylic acid tert-butyl ester (2.4 g, 7.242 mmol) was dissolved in ethanol (100 mL), and wet 10% Pd/C added. The reaction mixture was placed under an atmosphere of hydrogen for 4 hrs (Parr apparatus, 25 psi) then filtered through a plug of celite and concentrated to dryness to give (R)-2-[4-(2-methoxycarbonyl-ethyl)-phenyl]-pyrrolidine-1-carboxylic acid tert-butyl ester as a colorless oil (2.4 g, 7.2 mmol, >99% yield).

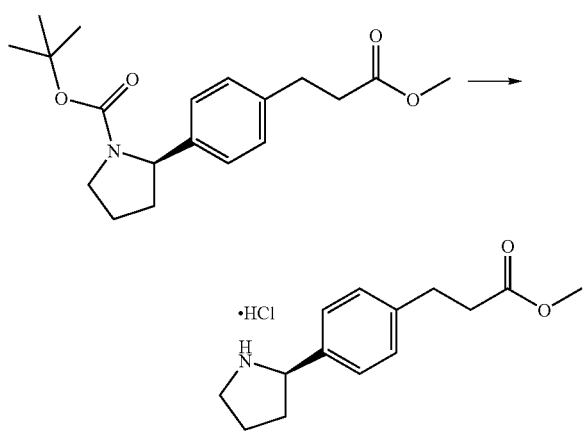

Following procedures analogous to those described in Example 1c, 3-((R)-4-pyrrolidin-2-yl-phenyl)-propionic acid methyl ester hydrochloride was prepared from (R)-2-[4-(2-methoxycarbonyl-ethyl)-phenyl]-pyrrolidine-1-carboxylic acid tert-butyl ester.

Following procedures analogous to those described in Example 4,3-(4-{(R)-1-[2-(1,3,5-trimethyl-1H-pyrazol-4-yl)-ethyl]-pyrrolidin-2-yl}-phenyl)-propionic acid methyl ester was prepared from methanesulfonic acid 2-(1,3,5-trimethyl-1H-pyrazol-4-yl)-ethyl ester and 3-((R)-4-pyrrolidin-2-yl-phenyl)-propionic acid methyl ester hydrochloride.

Following procedures analogous to those described in Example 2, N-hydroxy-3-(4-{(R)-1-[2-(1,3,5-trimethyl-1H-pyrazol-4-yl)-ethyl]-pyrrolidin-2-yl}-phenyl)-propionamide was prepared (111, 0.07 g, 0.19 mmol, 19% yield) as a white solid. LC/MS (m/z): 371.2 (M+1). $^1$H-NMR (MeOD) δ 7.17 (d, 2H), 7.12 (d, 2H), 3.73 (s, 3H), 3.47-3.4 (m, 1H), 3.28-3.21 (m, 1H), 2.88 (t, 2H), 2.52-2.4 (m, 2H), 2.4-2.3 (m, 4H), 2.18-2.07 (m, 2H), 2.01 (s, 3H), 1.96 (s, 3H), 1.95-1.82 (m, 2H), 1.75-1.6 (m, 1H).

Example 126

Preparation of N-hydroxy-3-(4-{(S)-1-[2-(1,3,5-trimethyl-1H-pyrazol-4-yl)-ethyl]-pyrrolidin-2-yl}-phenyl)-propionamide (112)

Following procedures analogous to those described in Example 125, (S)-2-[4-(2-methoxycarbonyl-ethyl)-phenyl]-pyrrolidine-1-carboxylic acid tert-butyl ester, 3-((S)-4-pyrrolidin-2-yl-phenyl)-propionic acid methyl ester hydrochloride, and 3-(4-{(S)-1-[2-(1,3,5-trimethyl-1H-pyrazol-4-yl)-ethyl]-pyrrolidin-2-yl}-phenyl)-propionic acid methyl ester were prepared.

Following procedures analogous to those described in Example 2, N-hydroxy-3-(4-{(S)-1-[2-(1,3,5-trimethyl-1H-pyrazol-4-yl)-ethyl]-pyrrolidin-2-yl}-phenyl)-propionamide was prepared (112, 1.15 g, 3.1 mmol) as a white solid. LC/MS (m/z): 371.0 (M+1). $^1$H-NMR (CDCl$_3$) δ 8.2 (br s, 1H), 7.26 (s, 1H), 6.94 (d, 2H), 6.9 (d, 2H), 3.55 (s, 3H), 3.48-3.42 (m, 1H), 3.18 (t, 1H), 3.08-2.98 (m, 1H), 2.85-2.75 (m, 1H), 2.58-2.48 (m, 1H), 2.42-2.28 (m, 4H), 2.24-2.15 (m, 1H), 2.15 (s, 3H), 2.15-2.03 (m, 1H), 1.95-1.78 (m, 1H), 1.78 (s, 3H), 1.70-1.52 (m, 3H).

Example 127

Preparation of (E)-3-(4-{(R)-1-[2-(3,5-dimethyl-1H-pyrazol-4-yl)-ethyl]-pyrrolidin-2-yl}-phenyl)-N-hydroxy-acrylamide (117)

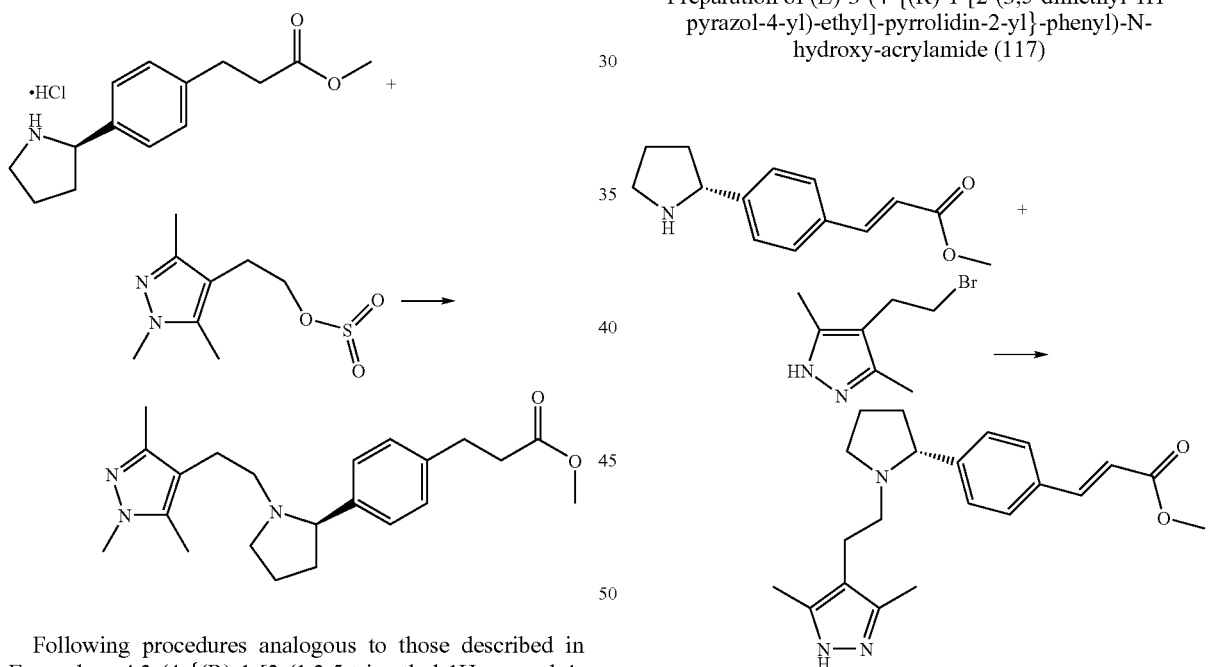

(E)-3-((R)-4-Pyrrolidin-2-yl-phenyl)-acrylic acid methyl ester (697 mg, 3 mmol) and 4-(2-bromo-ethyl)-3,5-dimethyl-1H-pyrazole (734 mg, 3.62 mmol) were dissolved in acetonitrile, potassium carbonate (833 mg, 6 mmol) was added, and the reaction mixture heated under nitrogen at 85° C. for 14 h. Cooled to room temperature, diluted with DCM (20 mL) and filtered through a plug of celite. Wash plug with DCM (30 mL). Filtrate was concentrated to 110 mL and columned on silica with EtOAc/hexane. Product elutes with neat EtOAc, and after concentrating gave (E)-3-(4-{(R)-1-[2-(3,5-dimethyl-1H-pyrazol-4-yl)-ethyl]-pyrrolidin-2-yl}-phenyl)-acrylic acid methyl ester as a tacky, pale yellow solid (804 mg, 2.275 mmol, 75%).

Following procedures analogous to those described in Example 2, (E)-3-(4-{(R)-1-[2-(3,5-dimethyl-1H-pyrazol-4-yl)-ethyl]-pyrrolidin-2-yl}-phenyl)-N-hydroxy-acrylamide was prepared (117, 0.095 g, 0.27 mmol, 24%) as a white solid. LC/MS (m/z): 355.0 (M+1). $^1$H-NMR (MeOD) δ 7.60 (d, 2H); 7.53 (d, 1H), 7.47 (d, 2H), 6.52 (d, 1H), 4.0 (br s, 1H), 3.73 (br s, 1H), 3.1-2.9 (br m, 1H), 2.9-2.75 (br m, 1H), 2.75-2.6 (br m, 2H), 2.6-2.5 (br m, 1H), 2.5-2.33 (br m, 1H), 2.25-2.1 (br m, 3H), 2.04 (s, 6H).

Example 128

Preparation of N-hydroxy-3-[4-((R)-1-{2-[2-(1-hydroxy-1-methyl-ethyl)-pyrazolo[1,5-a]pyridin-3-yl]-ethyl}-pyrrolidin-2-yl)-phenyl]-propionamide (120)

Following procedures analogous to those described in Examples 58, 125 & 2, N-hydroxy-3-[4-((R)-1-{2-[2-(1-hydroxy-1-methyl-ethyl)-pyrazolo[1,5-a]pyridin-3-yl]-ethyl}-pyrrolidin-2-yl)-phenyl]-propionamide was prepared as a white solid (120, 0.045 mg, 0.1 mmol, 13% yield). LC/MS (m/z): 437.2 (M+1).

Example 129

Preparation of (E)-3-[4-((S)-1-{2-[1-(2-Ethyl-4-hydroxy-butyl)-3,5-dimethyl-1H-pyrazol-4-yl]-ethyl}-pyrrolidin-2-yl)-phenyl]-N-hydroxy-acrylamide (109)

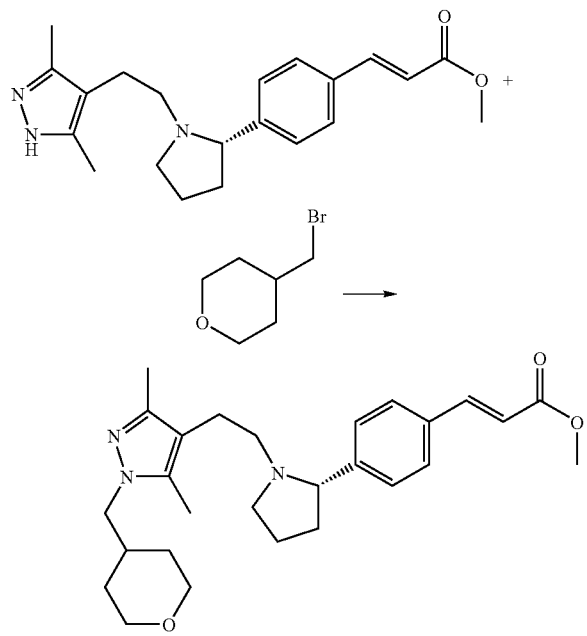

To an ice cold mixture of (E)-3-(4-{(S)-1-[2-(3,5-dimethyl-1H-pyrazol-4-yl)-ethyl]-pyrrolidin-2-yl}-phenyl)-acrylic acid methyl ester (0.85 g, 2.4 mmol) and potassium hydride (115 mg, 2.88 mmol) in 4.0 mL tetrahydrofuran:dimethyl sulfoxide (9:1 v/v) was added 4-bromomethyltetrahydropyran (945 mg, 5.28 mmol). The mixture was slowly warmed to room temperature and stirred under nitrogen for 16 h. It was then quenched with aqueous ammonium chloride and added with ethyl acetate. The layers were separated and the organic layer was washed with more aqueous ammonium chloride. The aqueous layers were then washed with more ethyl acetate and the combined organic extracts were dried over magnesium sulfate and concentrated to a yellow oil. The oil was then purified via silica gel column chromatography (100:0 to 0:100 heptane:ethyl acetate) to give (E)-3-[4-((S)-1-{2-[3,5-dimethyl-1-(tetrahydro-pyran-4-ylmethyl)-1H-pyrazol-4-yl]-ethyl}-pyrrolidin-2-yl)-phenyl]-acrylic acid methyl ester (160 mg, 0.35 mmol, 14% yield) as a yellow oil. LC/MS (m/z): 452.5 (M+1).

Following procedures analogous to those described in Example 2, (E)-3-[4-((S)-1-{2-[3,5-dimethyl-1-(tetrahydro-pyran-4-ylmethyl)-1H-pyrazol-4-yl]-ethyl}-pyrrolidin-2-yl)-phenyl]-N-hydroxy-acrylamide was prepared (109, 34 mg, 0.075 mmol, 28% yield) as an off-white solid. LC/MS (m/z): 453.4 (M+1).

Example 130

HDAC Inhibition Assay

The baculovirus donor vector pFB-GSTX3 was used to generate a recombinant baculovirus that can express the HDAC polypeptide. Transfer vectors containing the HDAC coding region were transfected into the DH10Bac cell line (GIBCO) and plated on selective agar plates. Colonies without insertion of the fusion sequence into the viral genome (carried by the bacteria) were blue. Single, white colonies were picked and viral DNAs (bacmid) were isolated from the bacteria by standard plasmid purification procedures. Sf9 cells or Sf21 (American Type Culture Collection) cells were then transfected in 25 cm$^3$ flasks with the viral DNA using Cellfectin reagent.

Determination of Small Scale Protein Expression in Sf9 Cells

Virus-containing media was collected from the transfected cell culture and used for infection to increase its titer. Virus-containing media obtained after two rounds of infection was used for large-scale protein expression. For large-scale protein expression 100 cm$^2$ round tissue culture plates were seeded with 5×10$^7$ cells/plate and infected with 1 mL of virus-containing media (at an approximately MOI of 5). After 3 days, the cells were scraped off the plate and centrifuged at 500 rpm for 5 minutes. Cell pellets from 10-20, 100 cm$^2$ plates, were re-suspended in 50 mL of ice-cold lysis buffer (25 mM tris-HCl, pH 7.5, 2 mM EDTA, 1% NP-40, 1 mM DTT, 1 mM P MSF). The cells were stirred on ice for 15 minutes and then centrifuged at 5,000 rpms for 20 minutes.

Purification of GST-Tagged Proteins

The centrifuged cell lysate was loaded onto a 2 mL glutathione-sepharose column (Pharmacia) and was washed thrice with 10 mL of 25 mM tris-HCl, pH 7.5, 2 mM EDTA, 1 mM DTT, 200 mM NaCl. The GST-tagged proteins were then eluted by 10 applications (1 mL each) of 25 mM tris-HCl, pH 7.5, 10 mM reduced-glutathione, 100 mM NaCl, 1 mM DTT, 10% glycerol and stored at −70° C.

Enzyme Activity Measurement

HDAC assays with purified GST-HDAC protein were carried out in a final volume of 30 μL containing 15 ng of GST-HDAC protein, 20 mM tris-HCl, pH 7.5, 1 mM MnCl$_2$, 10 mM MgCl$_2$, 1 mM DTT, 3 μg mL poly(Glu,Tyr) 4:1, 1% DMSO, 2.0 μM ATP (γ-[$^{33}$P]-ATP 0.1 μCi). The activity was assayed in the presence or absence of inhibitors. The assay was carried out in 96-well plates at ambient temperature for 15 minutes under conditions described below and terminated by the addition of 20 μL of 125 mM EDTA. Subsequently, 40 μL of the reaction mixture were transferred onto EMMOBILON-PVDF membrane (Millipore) previously soaked for 5 minutes with methanol, rinsed with water, then soaked for 5 minutes with 0.5% $H_3PO_4$ and mounted on vacuum manifold with disconnected vacuum source. After spotting all samples, a vacuum was connected and each well rinsed with 200 μL 0.5% $H_3PO_4$. Membranes were removed and washed four times on a shaker with 1.0% $H_3PO_4$, once with ethanol. Membranes were counted after drying at ambient temperature, mounting in Packard TopCount 96-well frame, and addition of 10 μL/well of MICROSCINT™ (Packard). IC50 values were calculated by linear regression analysis of the percentage inhibition of each compound in duplicate, at 4 concentrations (usually 0.01, 0.1, 1 and 10 μM).

$IC_{50}$ Calculations

| Input: | 3 × 4 μL stopped assay on IMMOBILON membrane, not washed |
|---|---|
| Background (3 wells): | assay with $H_2O$ instead of enzyme |
| Positive control (4 wells): | 3% DMSO instead of compound |
| Bath control (1 well): | no reaction mix |

IC50 values were calculated by logarithmic regression analysis of the percentage inhibition of each compound at 4 concentrations (usually 3- or 10-fold dilution series starting at 10 μM). In each experiment, the actual inhibition by reference compound was used for normalization of IC50 values to the basis of an average value of the reference inhibitor:

Normalized IC50=measured IC50 average ref IC50/measured ref IC50

Example: Reference inhibitor in experiment 0.4 μM, average 0.3 μM,

Test compound in experiment 1.0 μM, normalization: 0.3/0.4=0.75 μM

For example, known HDAC inhibitors or a synthetic derivative thereof may be used as reference compounds.

Using this protocol, the compounds of the present teachings were found to show IC50 values for HDAC inhibition in the range from about 0.0003 μM to about 100 μM, or about 0.0003 μM to about 50 μM, including, for example, the range from about 0.0003 μM to about 2 μM or less.

Table 2 provides assay results of exemplified compounds.

TABLE 2

| Compound No. | HDAC-1 $IC_{50}$ (nM) | HCT116 $IC_{50}$ (nM) |
|---|---|---|
| 1 | 3 | 1 |
| 2 | 10 | 50 |
| 3 | 1 | 1.2 |
| 4 | 10 | 10 |
| 5 | 6 | 10 |
| 6 | 2 | 1.2 |
| 7 | 12 | 3 |
| 8 | 5 | 0.9 |
| 9 | 7 | 0.5 |
| 10 | 3 | 2 |
| 12 | 4 | 96 |
| 19 | 3 | 7 |
| 20 | 3 | 11 |
| 21 | 8 | 21 |
| 22 | 7 | 13 |
| 23 | 19 | 97 |
| 24 | 8 | 43 |
| 25 | 5 | 7 |
| 26 | 7 | 29 |
| 27 | 6 | 11 |
| 28 | 25 | 85 |
| 29 | 8 | 40 |
| 30 | 14 | 46 |
| 31 | 5 | 67 |
| 33 | 5 | 39 |
| 34 | 21 | 77 |
| 35 | 5 | 9 |
| 36 | 10 | 40 |
| 40 | 9 | 42 |
| 41 | 7 | 48 |
| 42 | 32 | 53 |
| 43 | 1 | 1.1 |
| 44 | 0.6 | 0.38 |
| 45 | 2.4 | 8 |
| 46 | 3 | 0.6 |
| 47 | 1 | 0.35 |
| 48 | 2 | 3 |
| 49 | 3 | 3 |
| 50 | 1 | 0.4 |
| 51 | 1.2 | 4 |
| 52 | 2.7 | 4.3 |
| 53 | 0.9 | 1 |
| 54 | 3 | 4 |
| 55 | 2 | 1.1 |
| 56 | 1.7 | 5 |
| 57 | 1.4 | 1 |
| 58 | 7 | 36 |
| 59 | 8 | 35 |
| 60 | 1.8 | 4 |
| 61 | 7 | 8 |
| 62 | 2 | 2 |
| 63 | 42 | 180 |
| 64 | 62 | 190 |
| 65 | 35 | 180 |
| 66 | 28 | 61 |
| 67 | 17 | 39 |
| 68 | 40 | 160 |
| 69 | 25 | 170 |
| 70 | 30 | 96 |
| 71 | 55 | 110 |
| 72 | 19 | 31 |
| 73 | 71 | 230 |
| 76 | 31 | 210 |
| 77 | 25 | 110 |
| 78 | 22 | 120 |
| 79 | 6 | 43 |
| 81 | 67 | 230 |
| 85 | 4 | 9 |
| 86 | 10 | 42 |
| 87 | 35 | 58 |
| 88 | 9 | 24 |
| 89 | 7 | 200 |
| 90 | 8 | 34 |
| 91 | 4 | 2 |
| 92 | 4 | 3 |
| 93 | 1.4 | 1.1 |
| 94 | 1.4 | 5 |
| 95 | 1.6 | 3 |
| 96 | 1.7 | 2 |
| 97 | 1.7 | 1.7 |
| 98 | 36 | 50 |
| 99 | 0.8 | 1.4 |
| 100 | 1 | 0.5 |
| 101 | 58 | 160 |
| 102 | 25 | 32 |
| 104 | 42 | 360 |
| 105 | 120 | 160 |
| 106 | 67 | 180 |
| 107 | 170 | 540 |
| 108 | 7 | 10 |
| 109 | 3.2 | |
| 110 | 100 | 180 |
| 112 | 10 | 30 |
| 113 | 75 | |
| 115 | 25 | 32 |
| 116 | 20 | 49 |
| 117 | 12 | |
| 119 | 155 | |
| 120 | 75 | 510 |
| 121 | 31 | 180 |

As those skilled in the art will appreciate, numerous changes and modifications can be made to the above-described embodiments of the present teachings without departing from the spirit of the present teachings. It is intended that all such variations fall within the scope of the present teachings.

What is claimed is:

1. A compound of Formula I:

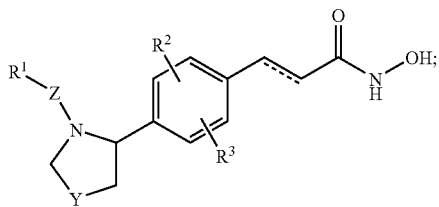

I or a pharmaceutically acceptable salt or ester thereof, wherein:

═══ is a) a single bond or b) a double bond;

Y and Z independently are a) -L-, b) -L-O-L-, c) -L-S(O)$_m$-L-, or d) -L-NR$^4$-L-;

L, at each occurrence, is a) a divalent C$_{1-10}$ alkyl group, b) a divalent C$_{2-10}$ alkenyl group, c) a divalent C$_{2-10}$ alkynyl group, or d) a covalent bond, wherein each of a)-c) optionally is substituted with 1-4-L'-R$^5$;

R$^1$ is a) H, b) a C$_{1-10}$ alkyl group, c) a C$_{2-10}$ alkenyl group, d) a C$_{2-10}$ alkynyl group, e) a C$_{3-14}$ cycloalkyl group, f) a C$_{6-14}$ aryl group, g) a 3-14 membered cycloheteroalkyl group, or h) a 5-14 membered heteroaryl group, wherein each of b)-h) optionally is substituted with 1-4-L'-R$^5$ groups;

R$^2$ and R$^3$ independently are a) H or b) halogen c) —NO$_2$, d) —CN, e) a C$_{1-10}$ alkyl group, f) a C$_{2-10}$ alkenyl group, g) a C$_{2-10}$ alkynyl group, h) a C$_{3-14}$ cycloalkyl group, i) a C$_{6-14}$ aryl group, j) a 3-14 membered cycloheteroalkyl group, k) a 5-14 membered heteroaryl group, l) a C$_{1-10}$ alkoxy group, m) —NC$_{1-10}$ alkyl, n) C(O)C$_{1-10}$ alkyl, and o) C(O)OC$_{1-10}$ alkyl, wherein each of e)-o) optionally is substituted with 1-4-L'-R$^7$ groups;

R$^4$ is a) H, b) —C(O)OR$^6$, or c) a C$_{1-10}$ alkyl group;

R$^5$, at each occurrence, is a) halogen, b) —CN, c) —NO$_2$, d) oxo, e) =N-L'-R$^6$, f) —O-L'-R$^6$, g) —S(O)$_m$R$^7$, h) a C$_{1-10}$ alkyl group, i) a C$_{2-10}$ alkenyl group, j) a C$_{2-10}$ alkynyl group, k) a C$_{3-14}$ cycloalkyl group, l) a C$_{6-14}$ aryl group, m) a 3-14 membered cycloheteroalkyl group, or n) a 5-14 membered heteroaryl group, wherein each of h)-n) optionally is substituted with 1-4-L'-R$^{10}$ groups;

R$^6$, at each occurrence, is a) H, b) —OR$^8$, c) —S(O)$_m$R$^8$, or d) a C$_{1-10}$ alkyl group optionally substituted with 1-4-L'-R$^{10}$ groups;

R$^7$ is a) H, b) —OR$^8$, c) —NR$^8$R$^9$, d) a C$_{1-10}$ alkyl group, e) a C$_{2-10}$ alkenyl group, f) a C$_{2-10}$ alkynyl group, g) a C$_{3-14}$ cycloalkyl group, h) a C$_{6-14}$ aryl group, i) a 3-14 membered cycloheteroalkyl group, or) a 5-14 membered heteroaryl group, wherein each of d)-j) optionally is substituted with 1-4-L'-R$^{10}$ groups;

R$^8$ and R$^9$, at each occurrence, independently are a) H, b) a C$_{1-10}$ alkyl group, c) a C$_{2-10}$ alkenyl group, d) a C$_{2-10}$ alkynyl group, e) a C$_{3-14}$ cycloalkyl group, f) a C$_{6-14}$ aryl group, g) a 3-14 membered cycloheteroalkyl group, or h) a 5-14 membered heteroaryl group, wherein each of b)-h) optionally is substituted with 1-4-L'-R$^{10}$ groups;

R$^{10}$, at each occurrence, is a) halogen, b) —CN, c) —NO$_2$, d) oxo, e) —OH, f) —NH$_2$, g) —NH(C$_{1-10}$ alkyl), h) —N(C$_{1-10}$ alkyl)$_2$, i) —CHO, j) —C(O)—C$_{1-10}$ alkyl, k) —C(O)OH, l) —C(O)—OC$_{1-10}$ alkyl, m) —C(O)SH, n) —C(O)—SC$_{1-10}$ alkyl, o) —C(O)NH$_2$, p) —C(O)NH(C$_{1-10}$ alkyl), q) —C(O)N(C$_{1-10}$ alkyl)$_2$, r) —C(S)H, s) —C(S)—C$_{1-10}$ alkyl, t) —C(S)NH$_2$, u) —C(S)NH(C$_{1-10}$ alkyl), v) —C(S)N(C$_{1-10}$ alkyl)$_2$, w) —C(NH)H, x) —C(NH)C$_{1-10}$ alkyl, y) —C(NH)NH$_2$, z) —C(NH)NH(C$_{1-10}$ alkyl), aa) —C(NH)N(C$_{1-10}$ alkyl)$_2$, ab) —C(NC$_{1-10}$ alkyl)H, ac) —C(NC$_{1-10}$ alkyl)-C$_{1-10}$ alkyl, ad) —C(NC$_{1-10}$ alkyl)NH(C$_{1-10}$ alkyl), ae) —C(NC$_{1-10}$ alkyl)N(C$_{1-10}$ alkyl)$_2$, af) —S(O)$_m$H, ag) —S(O)$_m$—C$_{1-10}$ alkyl, ah) —S(O)$_2$OH, ai) —S(O)$_m$—OC$_{1-10}$ alkyl, aj) —S(O)$_m$NH$_2$, ak) —S(O)$_m$NH(C$_{1-10}$ alkyl), al) —S(O)$_m$N(C$_{1-10}$ alkyl)$_2$, am) —Si(C$_{1-10}$ alkyl)$_3$, an) a C$_{1-10}$ alkyl group, ao) a C$_{2-10}$ alkenyl group, ap) a C$_{2-10}$ alkynyl group, aq) a C$_{1-10}$ alkoxy group, ar) a C$_{1-10}$ haloalkyl group, as) a C$_{3-14}$ cycloalkyl group, at) a C$_{6-14}$ aryl group, au) a 3-14 membered cycloheteroalkyl group, or av) a 5-14 membered heteroaryl group;

L', at each occurrence, is a) a divalent C$_{1-10}$ alkyl group, b) a divalent C$_{2-10}$ alkenyl group, c) a divalent C$_{2-10}$ alkynyl group, d) a divalent C$_{1-10}$ haloalkyl group, d) a divalent C$_{1-10}$ alkoxy group, or f) a covalent bond; and m, at each occurrence, is 0, 1, or 2.

2. The compound of claim 1, or a pharmaceutically acceptable salt or ester thereof, wherein R$^1$ is H, a C$_{2-10}$ alkenyl group, a C$_{3-14}$ cycloalkyl group, or a 3-14 membered cycloheteroalkyl group, wherein each of the C$_{2-10}$ alkenyl group, the C$_{3-14}$ cycloalkyl group, and the 3-14 membered cycloheteroalkyl group optionally is substituted with 1-4-L'-R$^5$ groups, and L' and R$^5$ are as defined in claim 1.

3. The compound of claim 1 or a pharmaceutically acceptable salt or ester thereof, wherein R$^1$ is a C$_{2-10}$ alkenyl group optionally substituted with 1-4 groups independently selected from the group consisting of halogen, —CN, —NO$_2$, and —CF$_3$.

4. The compound of claim 1 or a pharmaceutically acceptable salt or ester thereof, wherein R$^1$ is 2,2-dichloroethenyl.

5. The compound of claim 1 or a pharmaceutically acceptable salt or ester thereof, wherein R$^1$ is a C$_{3-14}$ cycloalkyl group or a 3-14 membered cycloheteroalkyl group, each of which optionally is substituted with 1-4-L'R$^5$ groups, wherein L' and R$^5$ are as defined in claim 1.

6. The compound of claim 5, or a pharmaceutically acceptable salt or ester thereof, wherein the C$_{3-14}$ cycloalkyl group or the 3-14 membered cycloheteroalkyl group is selected from the group consisting of a cyclopropyl group, a cyclobutyl group, a cyclopentyl group, a cyclohexyl group, a cycloheptyl group, a pyrrolidyl group, a piperidyl group, a tetrahydrofuranyl group, and a tetrahydropyranyl group.

7. The compound of claim 1, or a pharmaceutically acceptable salt or ester thereof, wherein R$^1$ is a C$_{6-14}$ aryl group or a 5-14 membered heteroaryl group, each of which optionally is substituted with 1-4-L'-R$^5$ groups, wherein L' and R$^5$ are as defined in claim 1.

8. The compound of claim 1 or a pharmaceutically acceptable salt or ester thereof, wherein R$^1$ is a phenyl group optionally substituted with 1-4 groups independently selected from the group consisting of halogen, —CN, —NO$_2$, a C$_{1-10}$ alkyl group, a C$_{3-14}$ cycloalkyl group, and a C$_{6-14}$ aryl group, wherein each of the C$_{1-10}$ alkyl group, the C$_{3-14}$ cycloalkyl group, and the C$_{6-14}$ aryl group optionally is substituted with 1-4-L'-R$^{10}$ groups, and L' and R$^{10}$ are as defined in claim 1.

9. The compound of any one of claim 1 or a pharmaceutically acceptable salt or ester thereof, wherein R$^1$ is a phenyl group optionally substituted with 1-4 groups independently selected from the group consisting of F, Cl, —NO$_2$, —OH, —OCH$_3$, and methyl.

10. The compound of claim 1 or a pharmaceutically acceptable salt or ester thereof, wherein R$^1$ is a 5-14 membered heteroaryl group optionally substituted with 1-4-L'-R$^5$ groups, wherein L' and R$^5$ are as defined in claim 1.

11. The compound of claim 10 or a pharmaceutically acceptable salt or ester thereof, wherein the 5-14 membered heteroaryl group is selected from the group consisting of:

i
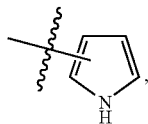

ii
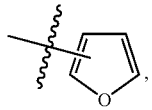

iii
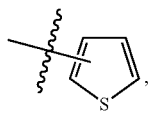

iv
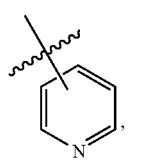

v
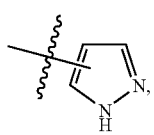

vi
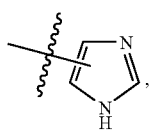

vii
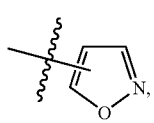

viii
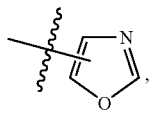

ix
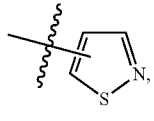

x
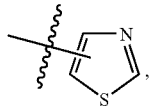

-continued xi
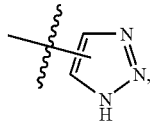

xii
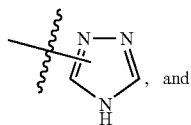, and xiii
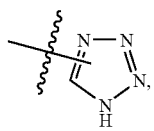, wherein each of i-xiii optionally is fused to a phenyl group or a 5-6 membered heteroaryl group, and optionally substituted with 1-4-L'-R$^5$ groups.

12. The compound of claim 11 or pharmaceutically acceptable salt or ester thereof, wherein R$^1$ is

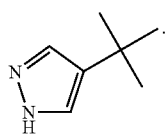

13. The compound of claim 11 or a pharmaceutically acceptable salt or ester thereof, wherein R$^1$ is selected from i-xiii, each of which optionally is substituted with 1-4 groups independently selected from the group consisting of halogen, —NO$_2$, —S(O)$_m$R$^7$,
—(C$_{1-10}$ alkyl)-(C$_{3-14}$ cycloalkyl), —(C$_{1-10}$ alkyl)-(C$_{6-14}$ aryl), —(C$_{1-10}$ alkyl)-(3-14 membered cycloheteroalkyl), —(C$_{1-10}$ alkyl)-(5-14 heteroaryl), —(C$_{1-10}$ alkoxy)-(C$_{3-14}$ cycloalkyl), —(C$_{1-10}$ alkoxy)-(C$_{6-14}$ aryl), —(C$_{1-10}$ alkoxy)-(3-14 membered cycloheteroalkyl), —(C$_{1-10}$ alkoxy)-(5-14 heteroaryl), a C$_{1-10}$ alkyl group, a C$_{2-10}$ alkenyl group, a C$_{2-10}$ alkynyl group, a C$_{3-14}$ cycloalkyl group, a C$_{6-14}$ aryl group, a 3-14 membered cycloheteroalkyl group, and a 5-14 membered heteroaryl group, wherein each of the C$_{1-10}$ alkyl groups, the C$_{2-10}$ alkenyl group, the C$_{2-10}$ alkynyl group, the C$_{1-10}$ alkoxy groups, the C$_{3-14}$ cycloalkyl groups, the C$_{6-14}$ aryl groups, the 3-14 membered cycloheteroalkyl groups, and the 5-14 membered heteroaryl groups optionally is substituted with 1-4-L'-R$^{10}$ groups.

14. The compound of claim 1 or a pharmaceutically acceptable salt or ester thereof, wherein R$^1$ is a pyrazolyl group optionally substituted with 1-4 groups independently selected from the group consisting of F, Cl, Br, —OH, —CF$_3$, methyl, ethyl, n-propyl, i-propyl, n-butyl, t-butyl, 2-methylpropyl, 2,2-dimethyl-propyl, propynyl, cyanomethyl, 2-cyanoethyl, 3-cyanopropyl, cyclopropylmethyl, tetrahydropyranylmethyl, phenyl, and trifluorophenyl.

15. The compound of claim 1 or a pharmaceutically acceptable salt or ester thereof, wherein R$^1$ is a pyrazolyl group disubstituted with methyl.

16. The compound of claim 1 or a pharmaceutically acceptable salt or ester thereof, wherein R$^1$ is a thienyl group, a pyridyl group, an imidazolyl group, an oxazolyl group, an isoxazolyl group, a thiazolyl group, a triazolyl group, or a tetrazolyl group, each of which optionally is substituted with 1-4 groups independently selected from the group consisting of F, Cl, Br, —$CF_3$, methyl, ethyl, i-propyl, t-butyl, (trimethylsilyl)methyl, benzyl, 2-benzoxyethyl, phenyl, and 4-aminophenyl.

17. The compound of claim 1 or a pharmaceutically acceptable salt or ester thereof, wherein $R^1$ is an indolyl group, a pyrazolo[1,5-a]pyridyl group, a pyrrolo[2,3-b]pyridyl group, or an imidazo[1,2-a]pyridyl group, each of which optionally is substituted with 1-4 groups independently selected from the group consisting of F, Cl, Br, $NO_2$, —$CF_3$, methyl, ethyl, i-propyl, t-butyl, 1-hydroxy-1-methylethyl, phenyl, pyridyl, and pyrazinyl.

18. The compound of claim 1 or a pharmaceutically acceptable salt or ester thereof, wherein $R^2$ and $R^3$ independently are H, F, Cl, or Br.

19. The compound of any one of claims 1-18, or a pharmaceutically acceptable salt or ester thereof, wherein Y is -L- or -L-$NR^4$-L-.

20. The compound of claim 1 or a pharmaceutically acceptable salt or ester thereof, wherein Y is -L-$NR^4$-L-, wherein $R^4$ is selected from the group consisting of H, —$C(O)OR^6$, and a $C_{1-10}$ alkyl group, and L and $R^6$ are as defined in claim 1.

21. The compound of claim 1 or a pharmaceutically acceptable salt or ester thereof, wherein Y is selected from the group consisting of —$CH_2$—, —$CH_2CH_2$—, —$CH_2CH_2CH_2$—, —$NHCH_2$—, —$N(CH_3)CH_2$—, and —$N(C(O)O$-t-$Bu)CH_2$—.

22. The compound of claim 1 or a pharmaceutically acceptable salt or ester thereof, wherein Z is a divalent $C_{1-10}$ alkyl group optionally substituted with 1-4 groups independently selected from the group consisting of oxo, =N—$R^6$, and —OH, wherein $R^6$ is as defined in claim 1.

23. The compound of claim 1 or a pharmaceutically acceptable salt or ester thereof, wherein Z is selected from the group consisting of —$CH_2$—, —$CH_2CH_2$—, —$CH_2CH_2CH_2$—, —$C(O)CH_2$—, —$CH_2CH(OH)$—, —$CH_2CH_2CH(CH_3)$—, and —$CH_2C(=NOH)$—.

24. A compound, or a pharmaceutically acceptable salt or ester thereof, the compound selected from the group consisting of:
- (E)-N-hydroxy-3-(4-{1-[2-(2-methyl-1H-indol-3-yl)-ethyl]-pyrrolidin-2-yl}-phenyl)-acrylamide,
- (E)-N-hydroxy-3-(4-{1-[3-(1H-indol-3-yl)-propyl]-pyrrolidin-2-yl}-phenyl)-acrylamide,
- (E)-N-hydroxy-3-(4-{1-[2-(1H-indol-3-yl)-ethyl]-pyrrolidin-2-yl}-phenyl)-acrylamide,
- (E)-N-hydroxy-3-(4-{1-[2-(2-methyl-indol-1-yl)-ethyl]-pyrrolidin-2-yl}-phenyl)-acrylamide,
- (E)-N-hydroxy-3-{4-[1-(2-indol-1-yl-ethyl)-pyrrolidin-2-yl]-phenyl}-acrylamide
- (E)-N-hydroxy-3-(4-{1-[2-(5-methoxy-2-methyl-1H-indol-3-yl)-ethyl]-pyrrolidin-2-yl}-phenyl)-acrylamide,
- (E)-N-hydroxy-3-(4-{1-[2-(2-phenyl-1H-indol-3-yl)-ethyl]-pyrrolidin-2-yl}-phenyl)-acrylamide,
- (E)-N-hydroxy-3-[4-(1-{2-[2-(5-methyl-isoxazol-3-yl)-1H-indol-3-yl]-ethyl}-pyrrolidin-2-yl)-phenyl]-acrylamide,
- (E)-3-(4-{1-[2-(2-tert-butyl-6-nitro-1H-indol-3-yl)-ethyl]-pyrrolidin-2-yl}-phenyl)-N-hydroxy-acrylamide,
- (E)-3-(4-{1-[2-(2-tert-butyl-6-methanesulfonylamino-1H-indol-3-yl)-ethyl]-pyrrolidin-2-yl}-phenyl)-N-hydroxy-acrylamide,
- (E)-3-(4-{1-[2-(2-tert-butyl-1-methanesulfonyl-6-methanesulfonylamino-1H-indol-3-yl)-ethyl]-pyrrolidin-2-yl}-phenyl)-N-hydroxy-acrylamide,
- (E)-N-hydroxy-3-(4-{1-[2-(2-methyl-1H-indol-3-yl)-acetyl]-pyrrolidin-2-yl}-phenyl)-acrylamide,
- (E)-3-[4-(1-benzyl-pyrrolidin-2-yl)-phenyl]-N-hydroxy-acrylamide,
- (E)-N-hydroxy-3-{4-[1-(2-phenyl-2H-pyrazol-3-ylmethyl)-pyrrolidin-2-yl]-phenyl}-acrylamide,
- (E)-N-hydroxy-3-[4-(1-pyrazolo[1,5-a]pyridin-3-ylmethyl-pyrrolidin-2-yl)-phenyl]-acrylamide,
- (E)-3-{4-[1-(3,5-dimethyl-1-phenyl-1H-pyrazol-4-ylmethyl)-pyrrolidin-2-yl]-phenyl}-N-hydroxy-acrylamide,
- (E)-N-hydroxy-3-{4-[(S)-1-(3-pyrazol-1-yl-propyl)-pyrrolidin-2-yl]-phenyl}-acrylamide,
- (E)-N-hydroxy-3-[4-((S)-1-phenylacetyl-pyrrolidin-2-yl)-phenyl]-acrylamide,
- (E)-N-hydroxy-3-[4-(1-phenethyl-pyrrolidin-2-yl)-phenyl]-acrylamide,
- (E)-N-hydroxy-3-(4-{1-[2-(4-hydroxy-phenyl)-ethyl]-pyrrolidin-2-yl}-phenyl)-acrylamide,
- (E)-3-(4-{(S)-1-[2-(4-fluoro-phenyl)-ethyl]-pyrrolidin-2-yl}-phenyl)-N-hydroxy-acrylamide,
- (E)-3-(4-{(S)-1-[2-(4-chloro-phenyl)-ethyl]-pyrrolidin-2-yl}-phenyl)-N-hydroxy-acrylamide,
- (E)-3-(4-{1-[2-(3,4-dichloro-phenyl)-ethyl]-pyrrolidin-2-yl}-phenyl)-N-hydroxy-acrylamide,
- (E)-N-hydroxy-3-(4-{1-[2-(4-nitro-phenyl)-ethyl]-pyrrolidin-2-yl}-phenyl)-acrylamide,
- (E)-3-(4-{1-[2-(2-chloro-phenyl)-ethyl]-pyrrolidin-2-yl}-phenyl)-N-hydroxy-acrylamide,
- (E)-3-(4-{1-[2-(2,4-dichloro-phenyl)-ethyl]-pyrrolidin-2-yl}-phenyl)-N-hydroxy-acrylamide,
- (E)-3-(4-{1-[2-(2-fluoro-phenyl)-ethyl]-pyrrolidin-2-yl}-phenyl)-N-hydroxy-acrylamide,
- (E)-N-hydroxy-3-{4-[1-(2-hydroxy-2-phenyl-ethyl)-pyrrolidin-2-yl]-phenyl}-acrylamide,
- (E)-N-hydroxy-3-{4-[1-(2-hydroxy-2-p-tolyl-ethyl)-pyrrolidin-2-yl]-phenyl}-acrylamide,
- (E)-N-hydroxy-3-(4-{1-[2-hydroxy-2-(4-methoxy-phenyl)-ethyl]-pyrrolidin-2-yl}-phenyl)-acrylamide,
- (E)-3-(4-{1-[2-(4-chloro-phenyl)-2-hydroxy-ethyl]-pyrrolidin-2-yl}-phenyl)-N-hydroxy-acrylamide,
- (E)-3-(4-{1-[2-(3,4-dichloro-phenyl)-2-hydroxy-ethyl]-pyrrolidin-2-yl}-phenyl)-N-hydroxy-acrylamide,
- (E)-N-hydroxy-3-{4-[1-(3-phenyl-propyl)-pyrrolidin-2-yl]-phenyl}-acrylamide,
- (E)-N-hydroxy-3-{4-[1-(2-pyridin-2-yl-ethyl)-pyrrolidin-2-yl]-phenyl}-acrylamide,
- (E)-N-hydroxy-3-{4-[(S)-1-(2-thiophen-3-yl-ethyl)-pyrrolidin-2-yl]-phenyl}-acrylamide,
- (E)-N-hydroxy-3-{4-[1-(3-methyl-butyl)-pyrrolidin-2-yl]-phenyl}-acrylamide,
- (E)-3-{4-[1-(3,3-dichloro-allyl)-pyrrolidin-2-yl]-phenyl}-N-hydroxy-acrylamide,
- (E)-3-[4-((S)-1-cyclopropylmethyl-pyrrolidin-2-yl)-phenyl]-N-hydroxy-acrylamide,
- (E)-3-[4-((S)-1-cyclobutylmethyl-pyrrolidin-2-yl)-phenyl]-N-hydroxy-acrylamide,
- (E)-3-[4-(1-cyclopentylmethyl-pyrrolidin-2-yl)-phenyl]-N-hydroxy-acrylamide,
- (E)-3-{4-[(S)-1-(2-cyclohexyl-ethyl)-pyrrolidin-2-yl]-phenyl}-N-hydroxy-acrylamide,
- (E)-N-hydroxy-3-(4-{(S)-1-[2-(tetrahydro-pyran-4-yl)-ethyl]-pyrrolidin-2-yl}-phenyl)-acrylamide, (E)-N-hydroxy-3-{4-[(S)-1-(2-pyrazolo[1,5-a]pyridin-3-yl-ethyl)-pyrrolidin-2-yl]-phenyl}-acrylamide,
(E)-N-hydroxy-3-(4-{(S)-1-[2-(2-methyl-pyrazolo[1,5-a]pyridin-3-yl)-ethyl]-pyrrolidin-2-yl}-phenyl)-acrylamide,
(E)-N-hydroxy-3-(4-{(R)-1-[2-(2-methyl-pyrazolo[1,5-a]pyridin-3-yl)-ethyl]-pyrrolidin-2-yl}-phenyl)-acrylamide,
(E)-N-hydroxy-3-(4-{(S)-1-[2-(2-trifluoromethyl-pyrazolo[1,5-a]pyridin-3-yl)-ethyl]-pyrrolidin-2-yl}-phenyl)-acrylamide,
(E)-3-(4-{(S)-1-[2-(2-ethyl-pyrazolo[1,5-a]pyridin-3-yl)-ethyl]-pyrrolidin-2-yl}-phenyl)-N-hydroxy-acrylamide,
(E)-N-hydroxy-3-[4-((S)-1-{2-[2-(1-hydroxy-1-methyl-ethyl)-pyrazolo[1,5-a]pyridin-3-yl]-ethyl}-pyrrolidin-2-yl)-phenyl]-acrylamide,
(E)-N-hydroxy-3-(4-{(S)-1-[2-(2-pyrazin-2-yl-pyrazolo[1,5-a]pyridin-3-yl)-ethyl]-pyrrolidin-2-yl}-phenyl)-acrylamide,
(E)-N-hydroxy-3-(4-{(S)-1-[2-(2-pyridin-3-yl-pyrazolo[1,5-a]pyridin-3-yl)-ethyl]-pyrrolidin-2-yl}-phenyl)-acrylamide,
(E)-N-hydroxy-3-(4-{(S)-1-[2-(1H-pyrrolo[2,3-b]pyridin-3-yl)-ethyl]-pyrrolidin-2-yl}-phenyl)-acrylamide,
(E)-3-(4-{(S)-1-[2-(2-tert-butyl-1H-pyrrolo[2,3-b]pyridin-3-yl)-ethyl]-pyrrolidin-2-yl}-phenyl)-N-hydroxy-acrylamide,
(E)-N-hydroxy-3-{4-[1-(2-imidazo[1,2-a]pyridin-3-yl-ethyl)-pyrrolidin-2-yl]-phenyl}-acrylamide,
(E)-N-hydroxy-3-(4-{(S)-1-[2-(2-methyl-imidazo[1,2-a]pyridin-3-yl)-ethyl]-pyrrolidin-2-yl}-phenyl)-acrylamide,
(E)-3-(4-{(S)-1-[2-(3,5-dimethyl-1-phenyl-1H-pyrazol-4-yl)-ethyl]-pyrrolidin-2-yl}-phenyl)-N-hydroxy-acrylamide,
(E)-N-hydroxy-3-(4-{(S)-1-[2-(3-methyl-5-phenyl-isoxazol-4-yl)-ethyl]-pyrrolidin-2-yl}-phenyl)-acrylamide,
(E)-N-hydroxy-3-(4-{(S)-1-[2-(5-methyl-2-phenyl-oxazol-4-yl)-ethyl]-pyrrolidin-2-yl}-phenyl)-acrylamide,
(E)-N-hydroxy-3-(4-{(S)-1-[2-(1H-pyrazol-4-yl)-ethyl]-pyrrolidin-2-yl}-phenyl)-acrylamide,
(E)-N-hydroxy-3-(4-{(S)-1-[2-(1-methyl-1H-pyrazol-4-yl)-ethyl]-pyrrolidin-2-yl}-phenyl)-acrylamide,
(E)-N-hydroxy-3-(4-{(S)-1-[2-(1,3,5-trimethyl-1H-pyrazol-4-yl)-ethyl]-pyrrolidin-2-yl}-phenyl)-acrylamide,
(E)-3-(4-{(S)-1-[2-(1-tert-butyl-3,5-dimethyl-1H-pyrazol-4-yl)-ethyl]-pyrrolidin-2-yl}-phenyl)-N-hydroxy-acrylamide,
(E)-3-(4-{(S)-1-[2-(1-cyclopropylmethyl-3,5-dimethyl-1H-pyrazol-4-yl)-ethyl]-pyrrolidin-2-yl}-phenyl)-N-hydroxy-acrylamide,
(E)-N-hydroxy-3-{4-[(S)-1-(2-pyrazol-1-yl-ethyl)-pyrrolidin-2-yl]-phenyl}-acrylamide,
(E)-N-hydroxy-3-(4-{(S)-1-[2-(4-methyl-pyrazol-1-yl)-ethyl]-pyrrolidin-2-yl}-phenyl)-acrylamide,
(E)-3-(4-{(S)-1-[2-(4-bromo-pyrazol-1-yl)-ethyl]-pyrrolidin-2-yl}-phenyl)-N-hydroxy-acrylamide,
(E)-3-(4-{(S)-1-[2-(3,5-dimethyl-pyrazol-1-yl)-ethyl]-pyrrolidin-2-yl}-phenyl)-N-hydroxy-acrylamide,
(E)-N-hydroxy-3-(4-{1-[2-(3,4,5-trimethyl-pyrazol-1-yl)-ethyl]-pyrrolidin-2-yl}-phenyl)-acrylamide,
(E)-3-[4-((S)-1-{2-[3-(2,2-dimethyl-propyl)-5-hydroxy-4-methyl-pyrazol-1-yl]-ethyl}-pyrrolidin-2-yl)-phenyl]-N-hydroxy-acrylamide,
(E)-3-(4-{(S)-1-[2-(4-bromo-3,5-dimethyl-pyrazol-1-yl)-ethyl]-pyrrolidin-2-yl}-phenyl)-N-hydroxy-acrylamide,
(E)-3-(4-{(S)-1-[2-(4-bromo-3-methyl-pyrazol-1-yl)-ethyl]-pyrrolidin-2-yl}-phenyl)-N-hydroxy-acrylamide,
(E)-N-hydroxy-3-(4-{(S)-1-[2-(3-methyl-pyrazol-1-yl)-ethyl]-pyrrolidin-2-yl}-phenyl)-acrylamide,
(E)-N-hydroxy-3-(4-{(S)-1-[2-(5-methyl-pyrazol-1-yl)-ethyl]-pyrrolidin-2-yl}-phenyl)-acrylamide,
(E)-N-hydroxy-3-(4-{(S)-1-[2-(3-trifluoromethyl-pyrazol-1-yl)-ethyl]-pyrrolidin-2-yl}-phenyl)-acrylamide,
(E)-N-hydroxy-3-{4-[1-(2-imidazol-1-yl-ethyl)-pyrrolidin-2-yl]-phenyl}-acrylamide,
(E)-N-hydroxy-3-(4-{(S)-1-[2-(1-methyl-1H-[1,2,3]triazol-4-yl)-ethyl]-pyrrolidin-2-yl}-phenyl)-acrylamide,
(E)-3-[4-((S)-1-{2-[1-(2-benzyloxy-ethyl)-1H-[1,2,3]triazol-4-yl]-ethyl}-pyrrolidin-2-yl)-phenyl]N-hydroxy-acrylamide,
(E)-N-hydroxy-3-(4-{(S)-1-[2-(1-trimethylsilanylmethyl-1H-[1,2,3]triazol-4-yl)-ethyl]-pyrrolidin-2-yl}-phenyl)-acrylamide,
(E)-3-(4-{(S)-1-[2-(1-benzyl-1H-[1,2,3]triazol-4-yl)-ethyl]-pyrrolidin-2-yl}-phenyl)-N-hydroxy-acrylamide,
(E)-3-[4-((S)-1-{2-[1-(4-amino-phenyl)-1H-[1,2,3]triazol-4-yl]-ethyl}-pyrrolidin-2-yl)-phenyl]-N-hydroxy-acrylamide,
(E)-N-hydroxy-3-(4-{(S)-1-[2-(2H-tetrazol-5-yl)-ethyl]-pyrrolidin-2-yl}-phenyl)-acrylamide,
(E)-N-hydroxy-3-(4-{(S)-1-[2-(2-methyl-2H-tetrazol-5-yl)-ethyl]-pyrrolidin-2-yl}-phenyl)-acrylamide,
(E)-N-hydroxy-3-(4-{(S)-1-[2-(1-methyl-1H-tetrazol-5-yl)-ethyl]-pyrrolidin-2-yl}-phenyl)-acrylamide,
(E)-N-hydroxy-3-[4-(1-{2-[3-phenyl-1-(3-trifluoromethyl-phenyl)-1H-pyrazol-4-yl]-ethyl}-pyrrolidin-2-yl)-phenyl]-acrylamide,
(E)-N-hydroxy-3-(4-{(S)-1-[2-[(Z)-hydroxyimino]-2-(5-methyl-1-phenyl-1H-pyrazol-4-yl)-ethyl]-pyrrolidin-2-yl}-phenyl)-acrylamide,
(E)-N-hydroxy-3-{4-[(S)-1-(2-pyrazolo[1,5-a]pyridin-3-yl-ethyl)-piperidin-2-yl]-phenyl}-acrylamide,
(E)-N-hydroxy-3-{4-[(S)-1-(2-pyrazolo[1,5-a]pyridin-3-yl-ethyl)-azepan-2-yl]-phenyl}-acrylamide,
3-[4-((E)-2-hydroxycarbamoyl-vinyl)-phenyl]-4-[2-(2-methyl-1H-indol-3-yl)-ethyl]-piperazine-1-carboxylic acid tert-butyl ester,
(E)-N-hydroxy-3-(4-{4-methyl-1-[2-(2-methyl-1H-indol-3-yl)-ethyl]-piperazin-2-yl}-phenyl)-acrylamide,
(E)-N-hydroxy-3-(4-{1-[2-(2-methyl-1H-indol-3-yl)-ethyl]-piperazin-2-yl}-phenyl)-acrylamide,
(E)-N-hydroxy-3-{4-[4-methyl-1-(2-pyrazolo[1,5-a]pyridin-3-yl-ethyl)-piperazin-2-yl]-phenyl}-acrylamide,
(E)-3-{3-fluoro-4-[(S)-1-(2-pyrazolo[1,5-a]pyridin-3-yl-ethyl)-pyrrolidin-2-yl]-phenyl}-N-hydroxy-acrylamide,
(E)-3-{3-chloro-4-[(S)-1-(2-pyrazolo[1,5-a]pyridin-3-yl-ethyl)-pyrrolidin-2-yl]-phenyl}-N-hydroxy-acrylamide,
(E)-3-{2-fluoro-4-[(S)-1-(2-pyrazolo[1,5-a]pyridin-3-yl-ethyl)-pyrrolidin-2-yl]-phenyl}-N-hydroxy-acrylamide,
(E)-3-{3,5-difluoro-4-[(S)-1-(2-pyrazolo[1,5-a]pyridin-3-yl-ethyl)-pyrrolidin-2-yl]-phenyl}-N-hydroxy-acrylamide, (E)-3-(4-{(S)-1-[2-(3,5-dimethyl-1H-pyrazol-4-yl)-ethyl]-pyrrolidin-2-yl}-phenyl)-N-hydroxy-acrylamide, (E)-3-(4-{(S)-1-[2-(1-ethyl-3,5-dimethyl-1H-pyrazol-4-yl)-ethyl]-pyrrolidin-2-yl}-phenyl)-N-hydroxy-acrylamide, (E)-3-(4-{(S)-1-[2-(1-butyl-3,5-dimethyl-1H-pyrazol-4-yl)-ethyl]-pyrrolidin-2-yl}-phenyl)-N-hydroxy-acrylamide, (E)-3-{4-[(S)-1-(2-benzenesulfonyl-ethyl)-pyrrolidin-2-yl]-phenyl}-N-hydroxy-acrylamide, (E)-3-(4-{(S)-1-[2-(3,5-diethyl-1H-pyrazol-4-yl)-ethyl]-pyrrolidin-2-yl}-phenyl)-N-hydroxy-acrylamide, (E)-3-(4-{(S)-1-[2-(3-tert-butyl-5-methyl-1H-pyrazol-4-yl)-ethyl]-pyrrolidin-2-yl}-phenyl)-N-hydroxy-acrylamide, (E)-N-hydroxy-3-(4-{(S)-1-[2-(2-isopropyl-2H-tetrazol-5-yl)-ethyl]-pyrrolidin-2-yl}-phenyl)-acrylamide, (E)-N-hydroxy-3-(4-{(S)-1-[2-(1-isopropyl-1H-tetrazol-5-yl)-ethyl]-pyrrolidin-2-yl}-phenyl)-acrylamide, (E)-N-hydroxy-3-[4-(1-{2-[2-(3,3,3-trifluoro-propyl)-2H-tetrazol-5-yl]-ethyl}-pyrrolidin-2-yl)-phenyl]-acrylamide, (E)-3-(4-{(S)-1-[2-(2-tert-butyl-2H-tetrazol-5-yl)-ethyl]-pyrrolidin-2-yl}-phenyl)-N-hydroxy-acrylamide, (E)-3-(4-{(S)-1-[2-(2-cyclobutyl-2H-tetrazol-5-yl)-ethyl]-pyrrolidin-2-yl}-phenyl)-N-hydroxy-acrylamide, (E)-N-hydroxy-3-[4-((S)-1-{2-[2-(4-nitro-phenyl)-2H-tetrazol-5-yl]-ethyl}-pyrrolidin-2-yl)-phenyl]-acrylamide, (E)-N-hydroxy-3-[4-((S)-1-{2-[1-(4-nitro-phenyl)-1H-tetrazol-5-yl]-ethyl}-pyrrolidin-2-yl)-phenyl]-acrylamide, (E)-3-(4-{(S)-1-[2-(5-tert-butyl-1H-[1,2,3]triazol-4-yl)-ethyl]-pyrrolidin-2-yl}-phenyl)-N-hydroxy-acrylamide, (E)-3-[4-((S)-1-{2-[3,5-dimethyl-1-(tetrahydro-pyran-4-ylmethyl)-1H-pyrazol-4-yl]-ethyl}-pyrrolidin-2-yl)-phenyl]-N-hydroxy-acrylamide, (E)-N-hydroxy-3-(4-{(R)-1-[2-(1,3,5-trimethyl-1H-pyrazol-4-yl)-ethyl]-pyrrolidin-2-yl}-phenyl)-acrylamide, N-hydroxy-3-(4-{(R)-1-[2-(1,3,5-trimethyl-1H-pyrazol-4-yl)-ethyl]-pyrrolidin-2-yl}-phenyl)-propionamide, N-hydroxy-3-(4-{(S)-1-[2-(1,3,5-trimethyl-1H-pyrazol-4-yl)-ethyl]-pyrrolidin-2-yl}-phenyl)-propionamide, N-hydroxy-3-[4-((S)-1-{2-[2-(1-hydroxy-1-methyl-ethyl)-pyrazolo[1,5-a]pyridin-3-yl]-ethyl}-pyrrolidin-2-yl)-phenyl]-propionamide, N-hydroxy-3-{4-[(S)-1-(2-pyrazolo[1,5-a]pyridin-3-yl-ethyl)-pyrrolidin-2-yl]-phenyl}-propionamide, N-hydroxy-3-(4-{(S)-1-[2-(1-isopropyl-1H-tetrazol-5-yl)-ethyl]-pyrrolidin-2-yl}-phenyl)-propionamide, and (E)-3-(4-{(S)-1-[2-(1,5-dimethyl-3-oxo-2-phenyl-2,3-dihydro-1H-pyrazol-4-yl)-ethyl]-pyrrolidin-2-yl}-phenyl)-N-hydroxy-acrylamide.

25. The compound of claim 1 or a pharmaceutically acceptable salt or ester thereof, wherein the compound or the pharmaceutically acceptable salt or ester thereof is in the form of an enantiomer or a diastereomer.

26. A composition comprising a therapeutically effective amount of a compound of claim 1 or a pharmaceutically acceptable salt or ester thereof, and a pharmaceutically acceptable carrier or excipient.

27. A compound which is (E)-N-Hydroxy-3-[4-((S)-1-{2-[2-(1-hydroxy-1-methyl-ethyl)-pyrazolo[1,5-a]pyridin-3-yl]-ethyl}-pyrrolidin-2-yl)-phenyl]-acrylamide or a pharmaceutically acceptable salt thereof.

28. A pharmaceutical composition comprising a compound according to claim 27, or a pharmaceutically acceptable salt thereof, and a pharmaceutically acceptable carrier or excipient.

29. A compound which is (E)-N-Hydroxy-3-[4-((S)-1-{2-[2-(1-hydroxy-1-methyl-ethyl)-pyrazolo[1,5-a]pyridin-3-yl]-ethyl}-pyrrolidin-2-yl)-phenyl]-acrylamide.

30. A pharmaceutical composition comprising a compound according to claim 29 and a pharmaceutically acceptable carrier or excipient.

31. A compound which is (E)-N-Hydroxy-3-{4-[(S)-1-(2-pyrazolo[1,5-a]pyridin-3-yl-ethyl)-pyrrolidin-2-yl]-phenyl}-acrylamide or a pharmaceutically acceptable salt thereof.

32. A pharmaceutical composition comprising a compound according to claim 31, or a pharmaceutically acceptable salt thereof, and a pharmaceutically acceptable carrier or excipient.

33. A compound which is (E)-N-Hydroxy-3-{4-[(S)-1-(2-pyrazolo[1,5-a]pyridin-3-yl-ethyl)-pyrrolidin-2-yl]-phenyl}-acrylamide.

34. A pharmaceutical composition comprising a compound according to claim 33 and a pharmaceutically acceptable carrier or excipient.

35. A compound which is (E)-3-(4-{(S)-1-[2-(3,5-Dimethyl-1H-pyrazol-4-yl)-ethyl]-pyrrolidin-2-yl}-phenyl)-N-hydroxy-acrylamide or a pharmaceutically acceptable salt thereof.

36. A pharmaceutical composition comprising a compound according to claim 35, or a pharmaceutically acceptable salt thereof, and a pharmaceutically acceptable carrier or excipient.

37. A compound which is (E)-3-(4-{(S)-1-[2-(3,5-Dimethyl-1H-pyrazol-4-yl)-ethyl]-pyrrolidin-2-yl}-phenyl)-N-hydroxy-acrylamide.

38. A pharmaceutical composition comprising a compound according to claim 37 and a pharmaceutically acceptable carrier or excipient.

39. A compound which is (E)-N-Hydroxy-3-(4-{(S)-1-[2-(1,3,5-trimethyl-1H-pyrazol-4-yl)-ethyl]-pyrrolidin-2-yl}-phenyl)-acrylamide or a pharmaceutically acceptable salt thereof.

40. A pharmaceutical composition comprising a compound according to claim 39, or a pharmaceutically acceptable salt thereof, and a pharmaceutically acceptable carrier or excipient.

41. A compound which is (E)-N-Hydroxy-3-(4-{(S)-1-[2-(1,3,5-trimethyl-1H-pyrazol-4-yl)-ethyl]-pyrrolidin-2-yl}-phenyl)-acrylamide.

42. A pharmaceutical composition comprising a compound according to claim 41 and a pharmaceutically acceptable carrier or excipient.

* * * * *